(12) United States Patent
Cornish et al.

(10) Patent No.: US 10,725,036 B2
(45) Date of Patent: Jul. 28, 2020

(54) DETECTION OF ANALYTES USING LIVE CELLS

(71) Applicant: THE TRUSTEES OF COLUMBIA UNIVERSITY IN THE CITY OF NEW YORK, New York, NY (US)

(72) Inventors: Virginia Wood Cornish, New York, NY (US); Nili Ostrov, Boston, MA (US); Miguel Jimenez, New York, NY (US); Sonja Billerbeck, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 114 days.

(21) Appl. No.: 15/596,837

(22) Filed: May 16, 2017

(65) Prior Publication Data
US 2017/0336407 A1    Nov. 23, 2017

Related U.S. Application Data

(63) Continuation-in-part of application No. PCT/US2015/061373, filed on Nov. 18, 2015.
(Continued)

(51) Int. Cl.
*G01N 33/566* (2006.01)
*C12Q 1/02* (2006.01)
(Continued)

(52) U.S. Cl.
CPC .......... *G01N 33/566* (2013.01); *C12Q 1/005* (2013.01); *C12Q 1/02* (2013.01); *C12Q 1/025* (2013.01);
(Continued)

(58) Field of Classification Search
CPC .......... G01N 33/566; G01N 33/56961; G01N 33/5695; G01N 33/56916;
(Continued)

(56) References Cited

U.S. PATENT DOCUMENTS 6,406,856 B1   6/2002   Glover et al.
6,692,696 B1   2/2004   Alberte
(Continued)

FOREIGN PATENT DOCUMENTS

WO   WO 2005/042695 A2   5/2005
WO   WO 2010/127111 A1   11/2010

OTHER PUBLICATIONS

Extended European Search Report dated Apr. 30, 2018 in Application No. EP 15861179.
(Continued)

*Primary Examiner* — Ruixiang Li
(74) *Attorney, Agent, or Firm* — Baker Botts L.L.P.

(57) ABSTRACT

The present invention provides sensor cells comprising a receptor that binds to an analyte indicative of the presence of an agent, where binding of the analyte to the receptor triggers a detection event that is indicative of the presence of the agent. In certain embodiments, the detection event is appearance of a reporter detectable by the naked eye. The present invention also provides uses of such sensor cells for detecting the presence of an agent in a sample.

Figure 1A:
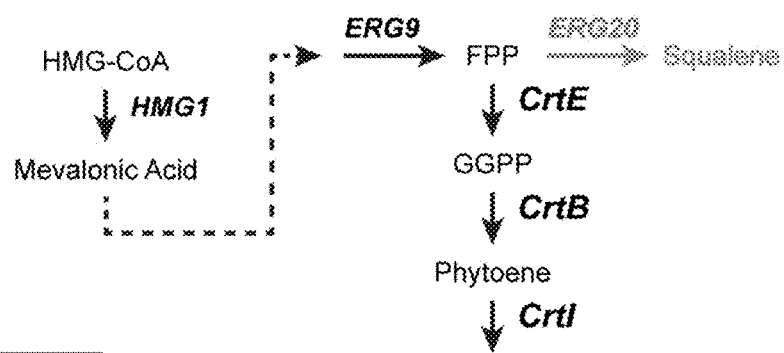

32 Claims, 22 Drawing Sheets
(20 of 22 Drawing Sheet(s) Filed in Color)
Specification includes a Sequence Listing.

Related U.S. Application Data

(60) Provisional application No. 62/081,441, filed on Nov. 18, 2014.

(51) Int. Cl.

| | | |
|---|---|---|
| *C12Q 1/00* | (2006.01) | |
| *C12Q 1/06* | (2006.01) | |
| *G01N 33/569* | (2006.01) | |
| *G01N 33/74* | (2006.01) | |
| *G01N 33/50* | (2006.01) | |

(52) U.S. Cl.
CPC ............ *C12Q 1/06* (2013.01); *G01N 33/5023* (2013.01); *G01N 33/5038* (2013.01); *G01N 33/569* (2013.01); *G01N 33/5695* (2013.01); *G01N 33/56911* (2013.01); *G01N 33/56916* (2013.01); *G01N 33/56961* (2013.01); *G01N 33/74* (2013.01); *G01N 2333/726* (2013.01)

(58) Field of Classification Search
CPC ........... G01N 33/56911; G01N 33/569; G01N 33/5038; G01N 2333/726; C12Q 1/025; C12Q 1/02; C12Q 1/06; C12Q 1/005
See application file for complete search history.

(56) References Cited

U.S. PATENT DOCUMENTS

| 7,223,550 | B2 | 5/2007 | Dhanasekaran et al. |
|---|---|---|---|
| 9,809,862 | B2* | 11/2017 | Peralta-Yahya ...... C12Q 1/6897 |
| 2003/0008331 | A1 | 1/2003 | Lerner |
| 2010/0221817 | A1 | 9/2010 | Ostermann et al. |
| 2012/0135497 | A1 | 5/2012 | Schofield et al. |
| 2017/0205401 | A1* | 7/2017 | Tyo ...................... C07K 14/395 |

OTHER PUBLICATIONS

Wingler et al., "Reiterative Recombination for the in vivo assembly of libraries of multigene pathways," PNAS 108(37):15135-15140 (2011).
Abramoff et al., "Image processing with ImageJ," Biophotonics International 11:36-42 (2004).
Ali et al., "Expression of plant cyclic nucleotide-gated cation channels in yeast," J. Exp. Botany 57:125-138 (2006).
Alper et al., "Identifying gene targets for the metabolic engineering of lycopene biosynthesis in *Escherichia coli*," Metab Eng 7:155-164 (2005).
Anderson et al., "Unique Phenotype of Opaque Cells in the White-Opaque Transition of *Candida albicans*," J. Bacterial. 169(12):5579-5588 (1987).
Andreatta et al., "Simultaneous alignment and clustering of peptide data using a Gibbs sampling approach," Bioinformatics 29(1):8-14 (2013).
Armbruster et al., "Evolving the lock to fit the key to create a family of G protein-coupled receptors potently activated by an inert ligand," PNAS USA 104(12):5163-5168 (2007).
Armstrong, "Genetics of eubacterial carotenoid biosynthesis: a Colorful Tale," Annu Rev Microbiol 51:629-659 (1997).
Ault et al., "Creation of GPCR-based chemical sensors by directed evolution in yeast," Protein Eng Des Sel 19(1):1-8 (2006).
Bashor et al., "Using Engineered Scaffold Interactions to Reshape MAP Kinase Pathway Signaling Dynamics," Science 319:1539-1543 (2008).
Belkin et al., "Oxidative Stress Detection with *Escherichia coli* Harboring a katG' ::lux Fusion," Appl Environ Microbiol 62(7):2252-2256 (1996).
Bellin et al., "Integrated circuit-based electrochemical sensor for spatially resolved detection of redox-active metabolites in biofilms," Nat. Commun. 5:3256 (2014).
Berman et al., "*Candida albicans*: A molecular revolution built on lessons from budding yeast," Nat Rev Genet 3:918-932 (2002).
Blignaut et al., "Ca3 Fingerprinting of *Candida albicans* Isolates from Human Immunodeficiency Virus-Positive and Healthy Individuals Reveals a New Clade in South Africa," J. Clin. Microbial. 40(3):826-836 (2002).
Bourbonnais et al., "Secretion of Somatostatin by *Saccharomyces cerevisiae* Correct Proteolytic Processing of pro-α-Factor-Somatostatin Hybrids Requires the Products of the KEX2 and STE13 Genes," J. Biol. Chem. 263(30):15342-15347 (1988).
Brown et al., "Hidden Killers: Human Fungal Infections," Sci Transl Med 4:165rv13 (2012).
Cairns et al., "Order of action of components in the yeast pheromone response pathway revealed with a dominant allele of the STE11 kinase and the multiple phosphorylation of the STE7 kinase," Genes Dev 6:1305-1318 (1992).
Celic et al., "Sequences in the Intracellular Loops of the Yeast Pheromone Receptor Ste2p Required for G Protein Activation," Biochemistry 42:3004-3017 (2003).
Chemler et al., "Biosynthesis of isoprenoids, polyunsaturated fatty acids and flavonoids in *Saccharomyces cerevisiae*," Microbiol Cell Fact 5:20 (2006).
Cloak et al., "Quorum Sensing and Production of Autoinducer-2 in *Campylobacter* spp., *Escherichia coli* O157:H7, and *Salmonella enterica* Serovar Typhimurium in Foods," Appl Environ Microbiol 68(9):4666-4671 (2002).
Conklin et al., "Engineering GPCR signaling pathways with RASSLs," Nat Methods 5(8):673-678 (2008).
De Nobel et al., "Passage of Molecules Through Yeast Cell Walls: A Brief Essay-Review," Yeast 7:313-323 (1991).
De Nobel et al., "An Assay of Relative Cell Wall Porosity in *Saccharomyces cerevisiae*, *Kluyveromyces lactis* and *Schizosaccharomyces pombe*," Yeast 6:483-490 (1990).
Dong et al., "Directed molecular evolution of DREADDs: a generic approach to creating next-generation RASSLs," Nat Protocols 5(3):561-573 (2010).
Dumitru et al., "In Vivo and In Vitro Anaerobic Mating in *Candida albicans*," Eukaryotic Cell 6(3):465-472 (2007).
Ebert et al., "Identification of Gastric Cancer Patients by Serum Protein Profiling," J Proteome Res 3:1261-1266 (2004).
Eilam et al., "Nystatin Effects on Cellular Calcium in *Saccharomyces cerevisiae*," Biochim. Biophys. Acta 692:238-243 (1982).
Erickson et al., "Edg-2/Vzg-1 Couples to the Yeast Pheromone Response Pathway Selectively in Response to Lysophosphatidic Acid," J Biol Chem 273(3):1506-1510 (1998).
Erlenbach et al., "Functional expression of M(1), M(3) and M(5) muscarinic acetylcholine receptors in yeast," J Neurochem 77:1327-1337 (2001).
Felipe et al., "Functional genome of the human pathogenic fungus *Paracoccidioides brasiliensis*," FEMS Immunol. Med. Microbiol. 45:369-381 (2005).
Findlay et al., "Yeast-Based Biosensors and Their Incorporation of Mammalian Protein Receptors for High-Throughput Screening," Handbook of Biosensors and Biochips, Chapter 13 (2007).
Fukuda et al., "Amplification of agonist stimulation of human G-protein-coupled receptor signaling in yeast," Anal Biochem 417:182-187 (2011).
Garjonyte et al., "Amperometric biosensors for lactic acid based on baker's and wine yeast," Microchim Acta 164:177-183 (2009).
Gomes-Rezende et al., "Functionality of the *Paracoccidioides* Mating α-Pheromone-Receptor System," PLoS One 7(10):e47033 (2012).
Goughenour et al., "Quantitative Microplate-Based Growth Assay for Determination of Antifungal Susceptibility of *Histoplasma capsulatum* Yeasts," J. Clin. Microbiol. 53(10):3286-3295 (2015).
Gu et al., "Some observations in freeze-drying of recombinant bioluminescent *Escherichia coli* for toxicity monitoring," J Biotechnol 88:95-105 (2001).
Gujraty et al., "Functional Characterization of Peptide-Based Anthrax Toxin Inhibitors," Mol. Pharm 2(5):367-372 (2005).
Hagen et al., "Pheromone Response Elements are Necessary and Sufficient for Basal and Pheromone-Induced Transcription of the FUS1 Gene of *Saccharomyces cerevisiae*," Mol Cell Biol. 11(6):2952-2961 (1991).
Hansen et al., "Versatile biosensor vectors for detection and quantification of mercury," FEMS Microbial Lett 193:123-127 (2000).

(56) References Cited

OTHER PUBLICATIONS

Harris et al., "Field evaluation of Crystal VC Rapid Dipstick test for cholera during a cholera outbreak in Guinea-Bissau," Trop Med Int Health 14(9):1117-1121 (2009).
Hauser et al., "The First Extracellular Loop of the *Saccharomyces cerevisiae* G Protein-coupled Receptor Ste2p Undergoes a Conformational Change upon Ligand Binding," J Biol Chem 282(14):10387-10397 (2007).
Higashijima et al., "Physiological activities of peptides are correlated with the conformations of membrane-bound molecules: α-Mating factor from *Saccharomyces cerevisiae* and analog peptides," FEBS Letters 159(1,2):229-232 (1983).
Higgins et al., "The major *Vibrio cholerae* autoinducer and its role in virulence factor production," Nature 450:883-886 (2007).
Hingorani et al., "Preinvasive and invasive ductal pancreatic cancer and its early detection in the mouse," Cancer Cell 4:437-450 (2003).
Hollis et al., "Design and Application of a Biosensor for Monitoring Toxicity of Compounds to Eukaryotes," Appl. Environ. Microbiol. 66(4):1676-1679 (2000).
Hotez et al., "The Neglected Tropical Diseases of Latin America and the Caribbean: A Review of Disease Burden and Distribution and a Roadmap for Control and Elimination," PLoS Negl. Trop. Dis. 2(9):e300 (2008).
Huang et al., "N-Acetylglucosamine Induces White to Opaque Switching, a Mating Prerequisite in *Candida albicans*," PLoS Pathog 6(3):e1000806 (2010).
Huat et al., "*Entamoeba histolytica* acetyl-CoA synthetase: biomarker of acute amoebic liver abscess," Asian Pac J Trop Biomed 4(6):446-450 (2014).
Hull et al., "Evidence for Mating of the 'Asexual' Yeast *Candida albicans* in a Mammalian Host," Science 289:307-310 (2000).
Huzarewich et al., "Application of "omics" to Prion Biomarker Discovery," J. Biomed Biotechnol, Article ID 613504 (2010).
Han et al., "Optimization of bio-indigo production by recombinant *E. coli* harboring fmo gene," Enzyme and Microbial Technology 42:617-623 (2008).
Ignatovica et al., "Identification and analysis of functionally important amino acids in human purinergic 12 receptor using a *Saccharomyces cerevisiae* expression system," FEBS J 279:180-191 (2012).
International Search Report dated Apr. 1, 2016 in International Application No. PCT/US15/61373.
Janbon et al., "Monosomy of a specific chromosome determines L-sorbose utilization: A novel regulatory mechanism in *Candida albicans*," PNAS USA 95:5150-5155 (1998).
Janiak et al., "Functional expression of the *Candida albicans* α-factor receptor in *Saccharomyces cerevisiae*," Fungal Genetics and Biology 42:328-338 (2005).
King et al., "Control of Yeast Mating Signal Transduction by a Mammalian β-2-Adrenergic Receptor and Gs α Subunit," Science 250:121-123 (1990).
Krogh et al., "Predicting Transmembrane Protein Topology with a Hidden Markov Model: Application to Complete Genomes," J. of Mol. Biol. 305:567-580 (2001).
Kyte et al., "A Simple Method for Displaying the Hydropathic Character of a Protein," J. Mol. Biol. 157:105-132 (1982).
Lachke et al., "Skin Facilitates *Candida albicans* Mating," Infect. Immun. 71(9):49704976 (2003).
LaRocque et al., "Proteomic Analysis of *Vibrio cholerae* in Human Stool," Infect. Immun. 76(9):4145-4151 (2008).
Leavitt et al., "Dominant negative mutations in the α-factor receptor, a G protein-coupled receptor encoded by the STE2 gene of the yeast *Saccharomyces cerevisiae*," Mol Gen Genet 261:917-932 (1999).
Lee et al., "Expression-level optimization of a multi-enzyme pathway in the absence of a high-throughput assay," Nucleic Acids Research 41(22):10668-10678 (2013).
Lequin, "Enzyme Immunoassay (EIA)/Enzyme-Linked Immunosorbent Assay (ELISA)," Clinical Chemistry 51(12):2415-2418 (2005).

Levskaya et al., "Engineering *Escherichia coli* to see light," Nature 438:441-442 (2005).
Lin et al., "Aromatic Residues at the Extracellular Ends of Transmembrane Domains 5 and 6 Promote Ligand Activation of the G Protein-Coupled α-Factor Receptor," Biochemistry 42:293-301 (2003).
Lin et al., "DJ-1 isoforms in whole blood as potential biomarkers of Parkinson disease," Sci Rep 2:954 (2012).
Ma et al., "A cyclic peptide-polymer probe for the detection of *Clostridium botulinum* neurotoxin serotype A," Toxicon 47:901-908 (2006).
MacKay et al., "Gene Expression Analyzed by High-resolution State Array Analysis and Quantitative Proteomics: Response of Yeast to Mating Pheromone," Mol Cell Proteomics 3:478-489 (2004).
Magee et al., "Induction of Mating in *Candida albicans* by Construction of MTLa and MTLα Strains," Science 289:310-313 (2000).
Martin et al., "Causes and Consequences of Variability in Peptide Mating Pheromones of Ascomycete Fungi," Molecular Biology and Evolution 28(7):1987-2003 (2011).
Martin et al., "Mate-recognition and species boundaries in the ascomycetes," Fungal Diversity 58:1-12 (2013).
Martin et al., "Mutagenic Mapping of Helical Structures in the Transmembrane Segments of the Yeast α-Factor Receptor," J. Mol. Biol. 317:765-788 (2002).
Mathew et al., "Differential Interactions of Fluorescent Agonists and Antagonists with the Yeast G Protein Coupled Receptor Ste2p," J. Mol. Biol. 409(4):513-528 (2011).
Mavrodi et al., "Functional Analysis of Genes for Biosynthesis of Pyocyanin and Phenazine-1-Carboxamide from *Pseudomonas aeruginosa* PAO1," J. Bacteriology 183(21):6454-6465 (2001).
Mayrhofer et al., "Functional Characterization of an α-Factor-Like *Sordaria macrospora* Peptide Pheromone and Analysis of Its Interaction with Its Cognate Receptor in *Saccharomyces cerevisiae*," Eukaryot Cell 4(4):661-672 (2005).
Minic et al., "Functional expression of olfactory receptors in yeast and development of a bioassay for odorant screening," FEBS J 272:524-537 (2005).
Miret et al., "Functional Expression of Heteromeric Calcitonin Gene-related Peptide and Adrenomedullin Receptors in Yeast," J. Biol. Chem. 277(9):6881-6887 (2002).
Mischak et al., "Capillary Electrophoresis-Mass Spectrometry As a Powerful Tool in Biomarker Discovery and Clinical Diagnosis: An Update of Recent Developments," Mass Spectrom Rev 28:703-724 (2009).
Miyajima et al., "Secretion of mature mouse interleukin-2 by *Saccharomyces cerevisiae*: use of a general secretion vector containing promoter and leader sequences of the mating pheromone α-factor," Gene 37:155-161 (1985).
Myers et al., "Improving accuracy of cell and chromophore concentration measurements using optical density," BMC Biophys. 6:4 (2013).
Naider et al., "The α-factor mating pheromone of *Saccharomyces cerevisiae*: a model for studying the interaction of peptide hormones and G protein-coupled receptors," Peptides 25:1441-1463 (2004).
Niwa, "Biomarker discovery for kidney diseases by mass spectrometry," J. Chromatogr. B 870:148-153 (2008).
Olivo et al., "Detection and Quantitation of Human Respiratory Syncytial Virus (RSV) Using Minigenome cDNA and a Sindbis Virus Replicon: A Prototype Assay for Negative-Strand RNA Viruses," Virology 251:198-205 (1998).
Pausch, "G-protein-coupled receptors in *Saccharomyces cerevisiae*: high-throughput screening assays for drug discovery," Trends Biotechnol 15:487-494 (1997).
Pei et al., "Engineered GPCRs as Tools to Modulate Signal Transduction," Physiology 23:313-321 (2008).
Pfaller et al., "Epidemiology of Invasive Candidiasis: a Persistent Public Health Problem," Clin. Microbiol. Rev. 20:133-163 (2007).
Pi et al., "Transcriptional Activation upon Pheromone Stimulation Mediated by a Small Domain of *Saccharomyces cervisiae* Ste12p," Molecular and Cellular Biology 17(11):6410-6418 (1997).
Pierce et al., "Seven-Transmembrane Receptors," Nat Rev Mol. Cell Biol. 3:639-650 (2002).

(56) References Cited

OTHER PUBLICATIONS

Pisa et al., "Different Brain Regions are Infected with Fungi in Alzheimer's Disease," Sci Rep 5:15015 (2015).
Price et al., "Functional Coupling of a Mammalian Somatostatin Receptor to the Yeast Pheromone Response Pathway," Mol. Cell Biol. 15(11):6188-6195 (1995).
Price et al., "Pharmacological Characterization of the Rat A2a Adenosine Receptor Functionally Coupled to the Yeast Pheromone Response Pathway," Mol. Pharmacol 50:829-837 (1996).
Ptitsyn et al., "A Biosensor for Environmental Genotoxin Screening Based on an SOS lux Assay in Recombinant *Escherichia coli* Cells," Appl Environ Microbiol 63(11):4377-4384 (1997).
Radhika et al., "Chemical sensing of DNT by engineered olfactory yeast strain," Nat Chem Biol 3(6):325-330 (2007).
Rafati et al., "Amastin Peptide-Binding Antibodies as Biomarkers of Active Human Visceral Leishmaniasis," Clin Vaccine Immunol 13(10):1104-1110 (2006).
Ramirez-Zavala et al., "Environmental Induction of White-Opaque Switching in *Candida albicans*," PLoS Pathog 4(6):e1000089 (2008).
Ramirez-Zavaleta et al., "Subtelomeric Silencing of the MTL3 Locus of *Candida glabrata* Requires yKu70, yKu80, and Rif1 Proteins," Eukaryotic Cell 9(10):1602-1611 (2010).
Restrepo et al., "Growth of *Paracoccidioides brasiliensis* Yeast Phase in a Chemically Defined Culture Medium," J. Clin. Microbiol. 12(2):279-281 (1980).
Rider et al., "A B Cell-Based Sensor for Rapid Identification of Pathogens," Science 301:213-215 (2003).
Ro et al., "Production of the antimalarial drug precursor artemisinic acid in engineered yeast," Nature 440:940-943 (2006).
Sanchez et al., "Reevaluation of the Violacein Biosynthetic Pathway and its Relationship to Indolocarbazole Biosynthesis," ChemBioChem 7:1231-1240 (2006).
Sander et al., "Heterologous expression of the human D2S dopamine receptor in protease-deficient *Saccharomyces cerevisiae* strains," Eur. J. Biochem 226:697-705 (1994).
Santos et al., "Melanin-Based High-Throughput Screen for L-Tyrosine Production in *Escherichia coli*," Appl. Environ. Microbiol. 74(4):1190-1197 (2008).
Sauer et al., "Mass spectrometry tools for the classification and identification of bacteria," Nat Rev Microbiol 8:74-82 (2010).
Schofield et al., "Development of a yeast biosensor—biocatalyst for the detection and biodegradation of the organophosphate paraoxon," Applied Microbiology and Biotechnology 76:1382-1394 (2007).
Sherwood et al., "Mutations in GSF1 and GSF2 Alter Glucose Signaling in *Saccharomyces cerevisiae*," Genetics 147:557-566 (1997).
Shin et al., "Freeze-dried recombinant bacteria for on-site detection of phenolic compounds by color change," J Biotechnol 119:36-43 (2005).
Sievers et al., "Fast, scalable generation of high-quality protein multiple sequence alignments using Clustal Omega," Molecular Systems Biology 7:539-539 (2011).
Son et al., "Identification of Ligand Binding Regions of the *Saccharomyces cerevisiae* α-Factor Pheromone Receptor by Photoaffinity Cross-Linking," Biochemistry 43:13193-13203 (2004).
Spira et al., "Multi-electrode array technologies for neuroscience and cardiology," Nat. Nanotechnol. 8:83-94 (2013).
Stocker et al., "Development of a Set of Simple Bacterial Biosensors for Quantitative and Rapid Measurements of Arsenite and Arsenate in Potable Water," Environ. Sci. Technol. 37:4743-4750 (2003).
Struss et al., "Chapter 14: Biosensing Systems Based on Genetically Engineered Whole Cells," in Recognition Receptors in Biosensors (ed. M. Zourob) pp. 565-598 (Springer New York, 2010).
Su et al., "Microbial biosensors: A review," Biosens. Bioelectron. 26:1788-1799 (2011).
Takahashi et al., "Membrane localization of scaffold proteins promotes graded signaling in the yeast MAP kinase cascade," Curr Biol 18(16):1184-1191 (2008).
Toine et al., "A new highly specific and robust yeast androgen bioassay for the detection of agonists and antagonists," Analytical and Bioanalytical Chemistry 389:1549-1558 (2007).
Tones et al., "Presence and expression of the mating type locus in *Paracoccidioides brasiliensis* isolates," Fungal Genet. Biol. 47:373-380 (2010).
Tracewell et al., "Directed enzyme evolution: climbing fitness peaks one amino acid at a time," Curr Opin Chem Biol 13:3-9 (2009).
Umanah et al., "Changes in Conformation at the Cytoplasmic Ends of the Fifth and Sixth Transmembrane Helices of a Yeast G Protein-Coupled Receptor in Response to Ligand Binding," Biochemistry 50:6841-6854 (2011).
Umanah et al., "Identification of Residue-to-residue Contact between a Peptide Ligand and its G Protein-coupled Receptor Using Periodate-mediated Dihydroxyphenylalanine Cross-linking and Mass Spectrometry," J Biol Chem 285(50):39425-39436 (2010).
Van der Meer et al., "Where microbiology meets microengineering: design and applications of reporter bacteria," Nat Rev Microbiol 8:511-522 (2010).
Van Dyk et al., "Rapid and Sensitive Pollutant Detection by Induction of Heat Shock Gene-Bioluminescence Gene Fusions," Appl Environ Microbiol 60(5):1414-1420 (1994).
Van Everbroeck et al., "Cerebrospinal fluid biomarkers in Creutzfeldt-Jakob disease," Clin Neural Neurosurg 107:355-360 (2005).
Van Holten et al., "Circulating Biomarkers for Predicting Cardiovascular Disease Risk; a Systematic Review and Comprehensive Overview of Meta-Analyses," PLoS One 8(4):e62080 (2013).
Verwaal et al., "High-Level Production of Beta-Carotene in *Saccharomyces cerevisiae* by Successive Transformation with Carotenogenic Genes from *Xanthophyllomyces dendrorhous*," Appl Environ Microbiol 73(13):4342-4350 (2007).
Villanueva et al., "Differential exoprotease activities confer tumor-specific serum peptidome patterns," J Clin Invest 116:271-284 (2006).
Villanueva et al., "Serum Peptide Profiling by Magnetic Particle-Assisted, Automated Sample Processing and MALDI-TOF Mass Spectrometry," Anal. Chem. 76:1560-1570 (2004).
Wang et al., "Pheromone-regulated Sumoylation of Transcription Factors That Mediate the Invasive to Mating Developmental Switch in Yeast," J Biol Chem 281(4):1964-1969 (2006).
Wang et al., "Pheromone Signaling Mechanisms in Yeast: A Prototypical Sex Machine," Science 306:1508-1509 (2004).
Wendland et al., "Characterization of α-factor pheromone and pheromone receptor genes of *Ashbya gossypii*," FEMS Yeast Res 11:418-429 (2011).
Werlen et al., "Measurement of Biologically Available Naphthalene in Gas and Aqueous Phases by Use of a *Pseudomonas putida* Biosensor," Appl Environ Microbiol 70:43-51 (2004).
Worsham et al., "Quantitative plating of *Histoplasma capsulatum* without addition of conditioned medium or siderophores," J. Med. Vet. Mycol. 26:137-143 (1988).
Xu et al., "Yeast That Smell," J Biochem Tech 1(1):06-08 (2008).
Yagi, "Applications of whole-cell bacterial sensors in biotechnology and environmental science," Appl Microbial Biotechnol 73:1251-1258 (2007).
Yang et al., "Prognostic Polypeptide Blood Plasma Biomarkers of Alzheimer's Disease Progression," J Alzheimer's Dis 40:659-666 (2014).

\* cited by examiner

Induction of lycopene biosynthesis by the natural yeast peptide, α-factor.

Improvement of lycopene readout speed in optimal laboratory conditions.

FIG. 9A
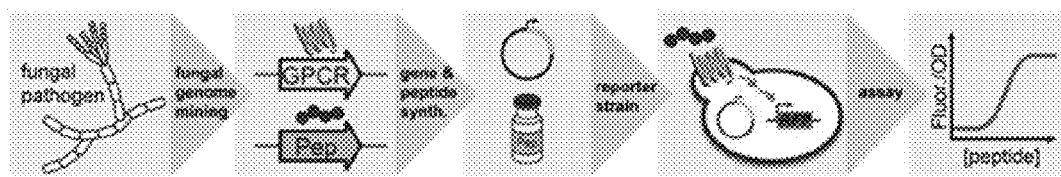
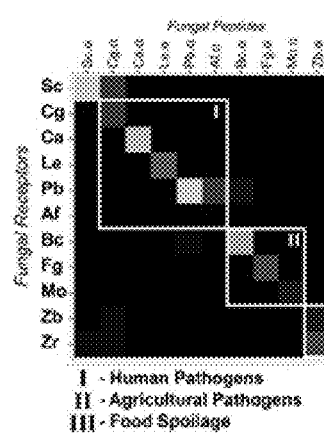
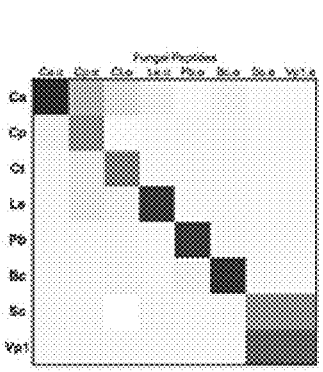
FIG. 9B
FIG. 9C

FIG. 11A
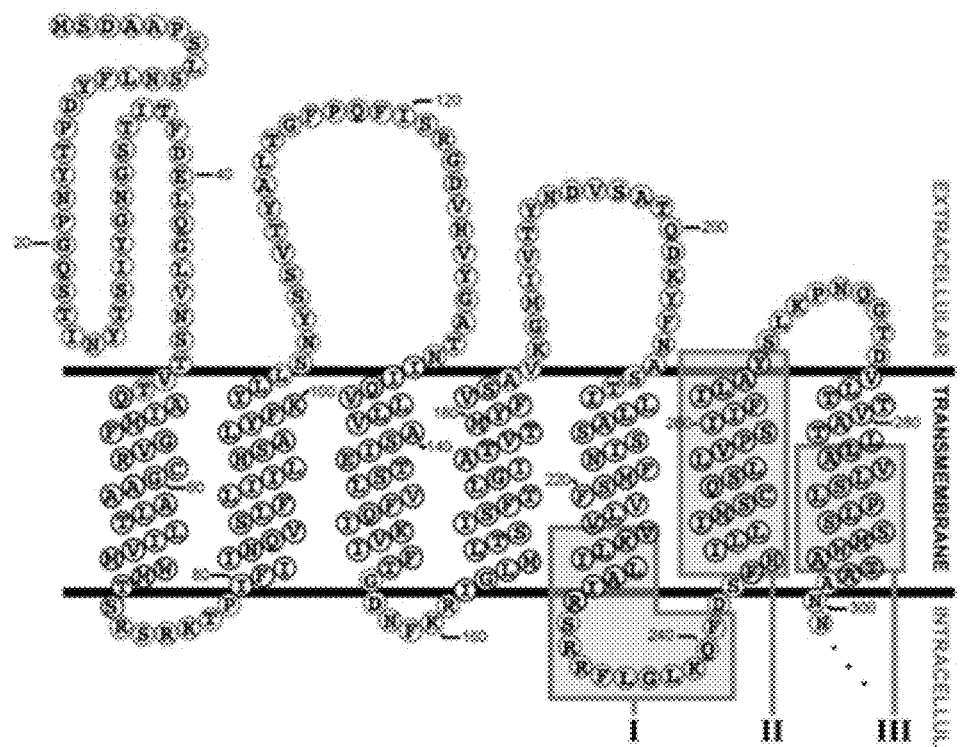
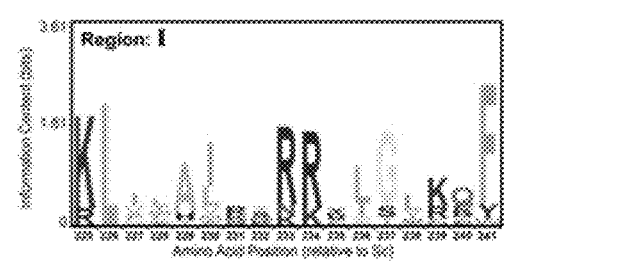
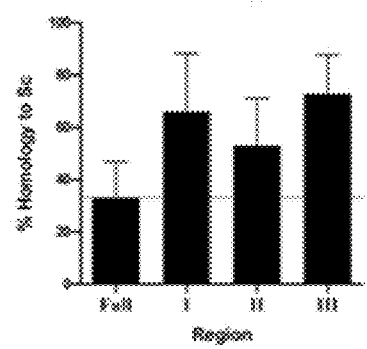
FIG. 11C
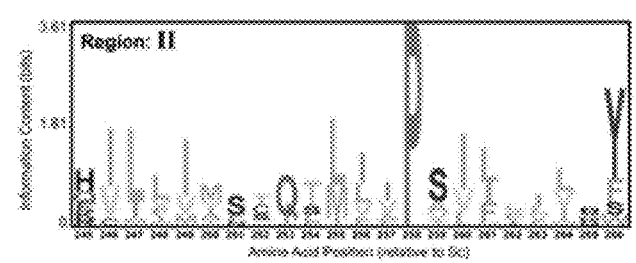
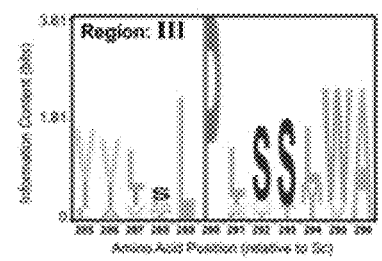
FIG. 11B FIG. 12A
FIG. 12B
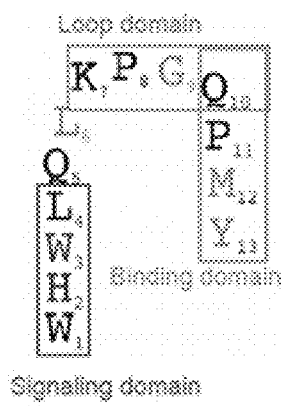
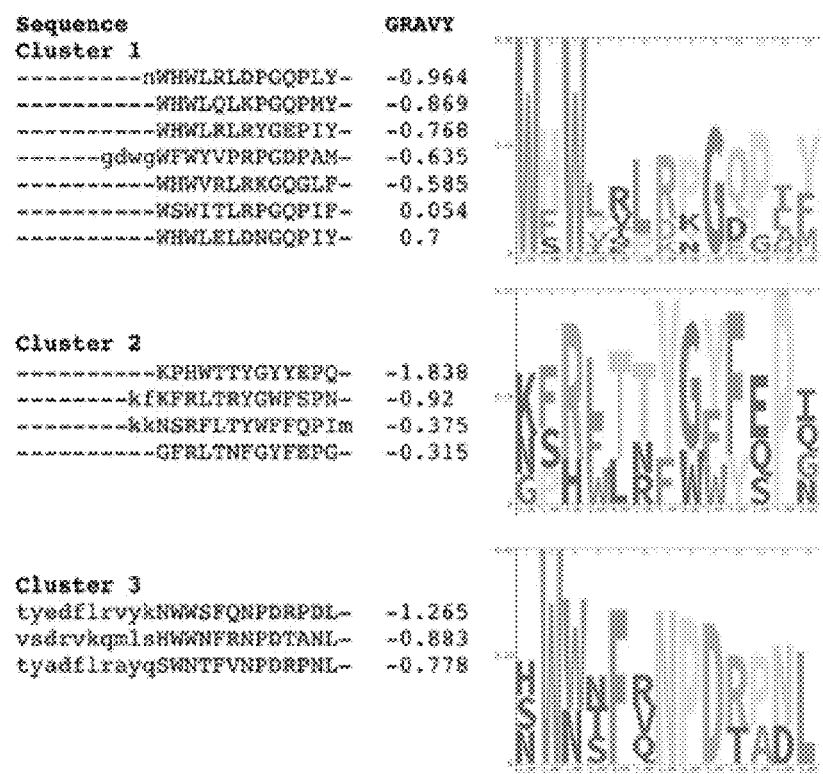

FIG. 13A
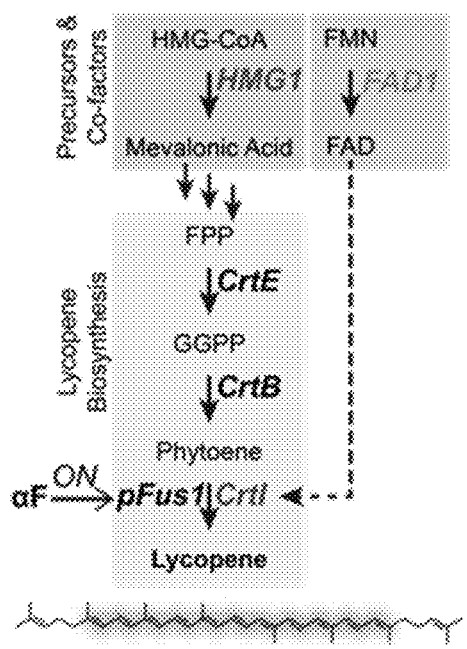
FIG. 13B
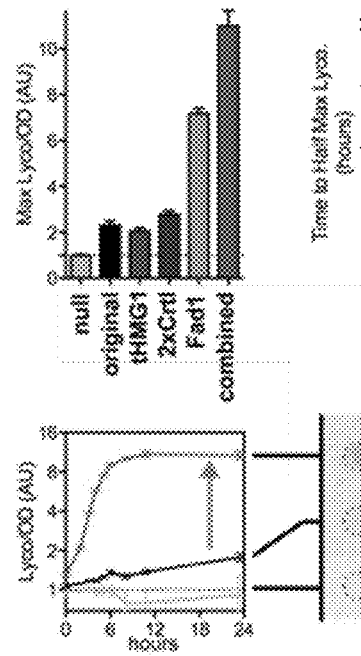
FIG. 13C
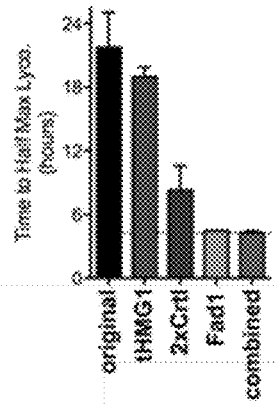
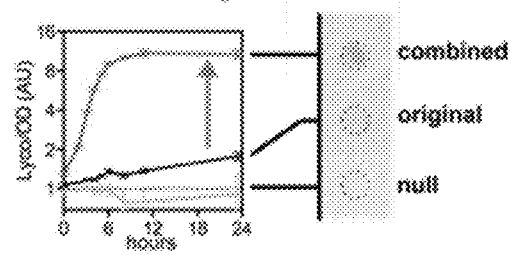
FIG. 13D

FIG. 14A
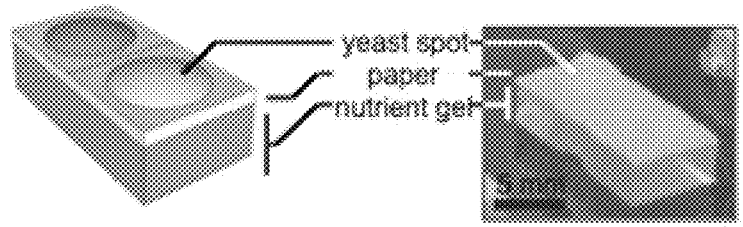
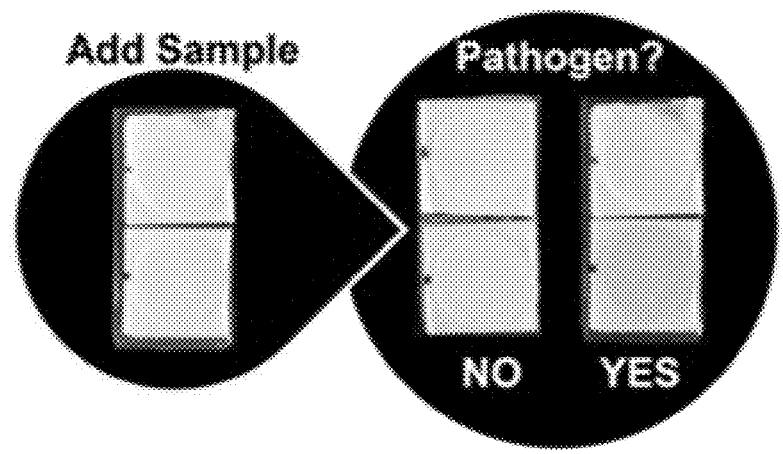
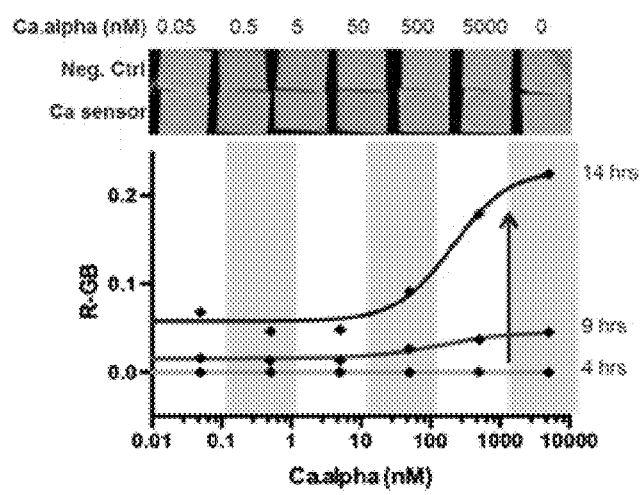
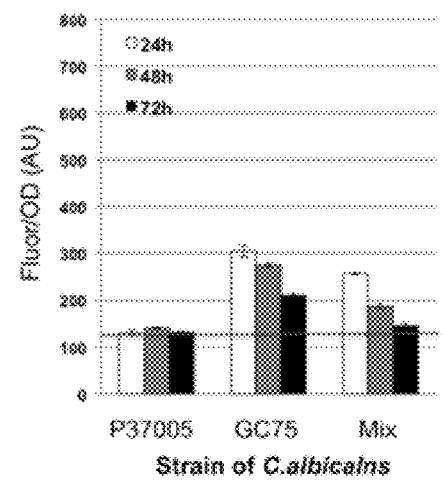
FIG. 14B
FIG. 14C

FIG. 17A              FIG. 17B
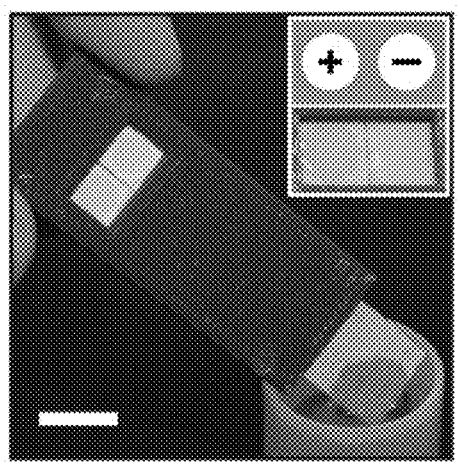 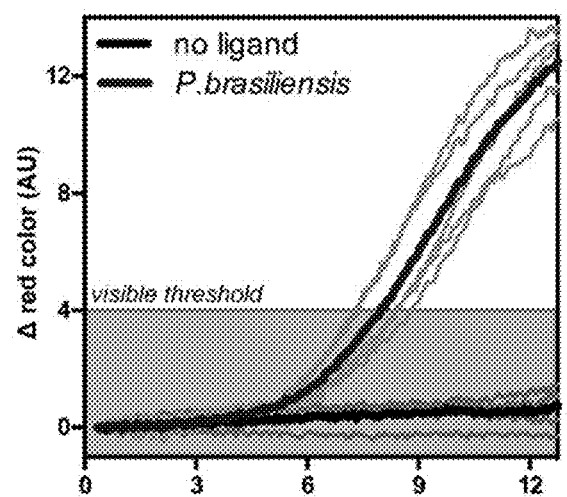
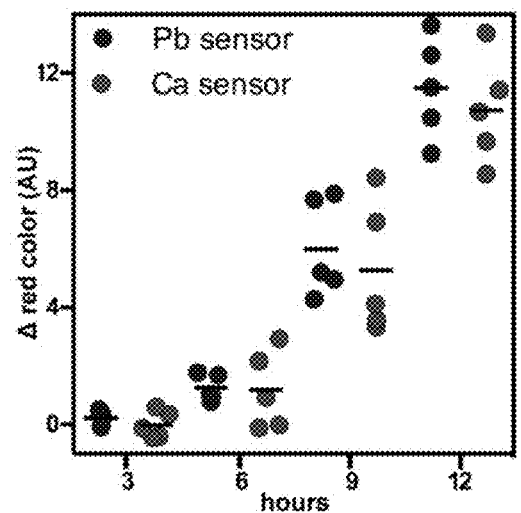 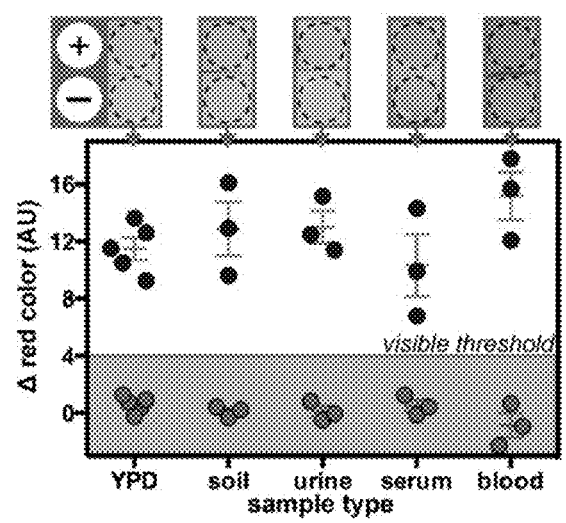
FIG. 17C              FIG. 17D

FIG. 18A   FIG. 18B   FIG. 18C
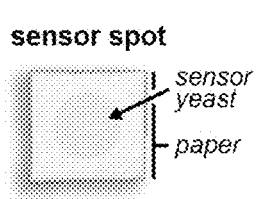
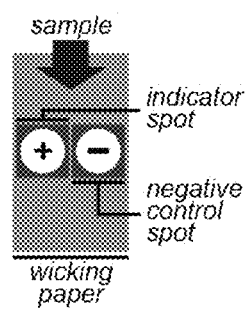
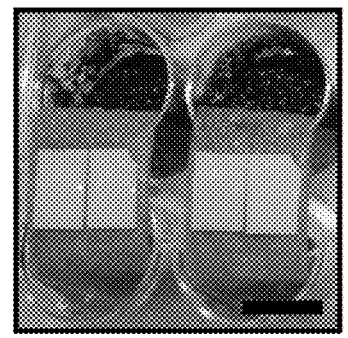
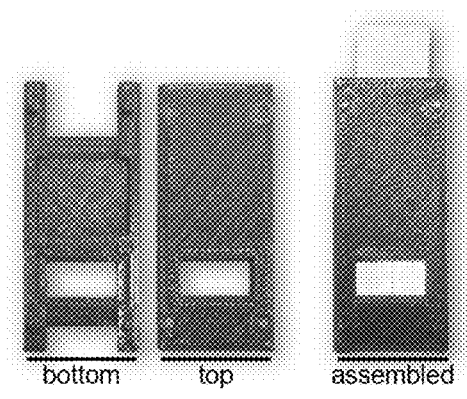
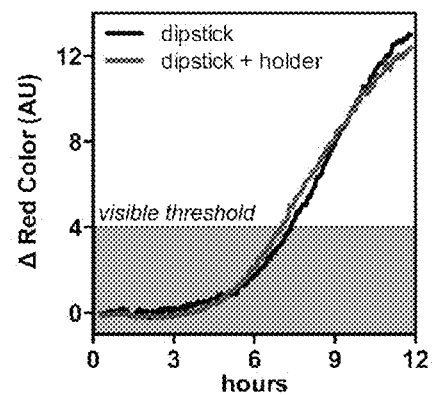
FIG. 18D   FIG. 18E FIG. 19A
FIG. 19B
FIG. 19C
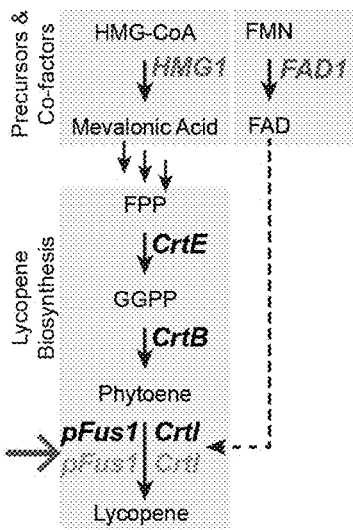
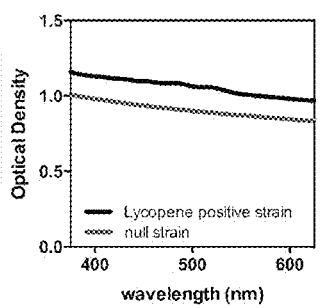
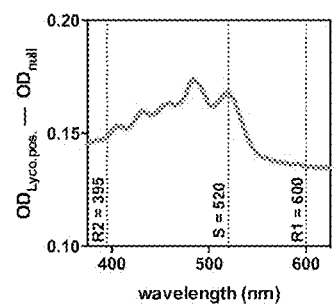
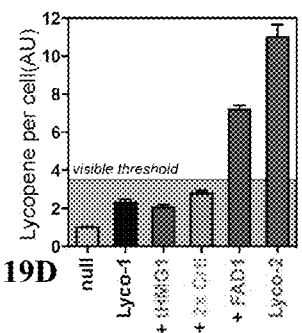
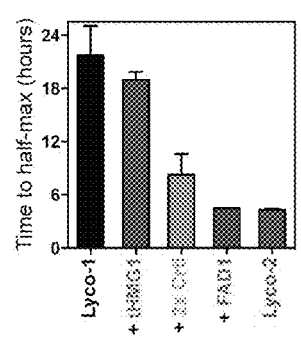
FIG. 19D
FIG. 19E
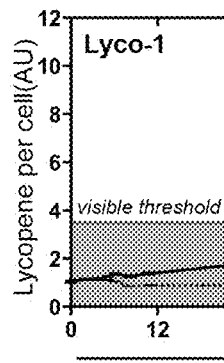
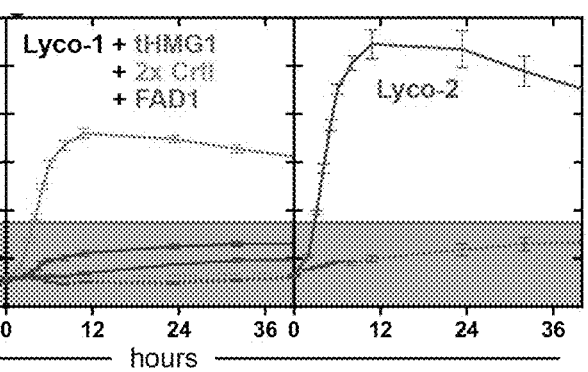
FIG. 19F
FIG. 19G
FIG. 19H

FIG. 20A
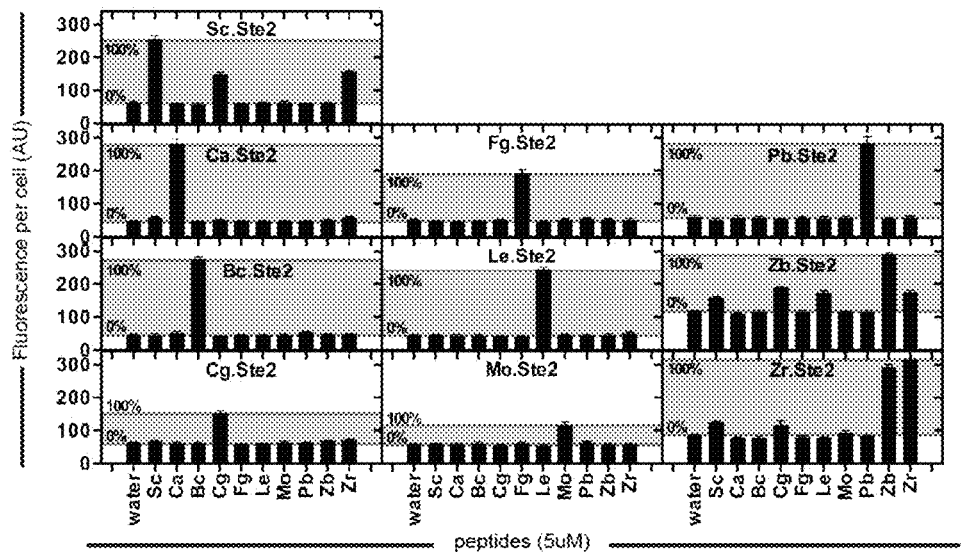
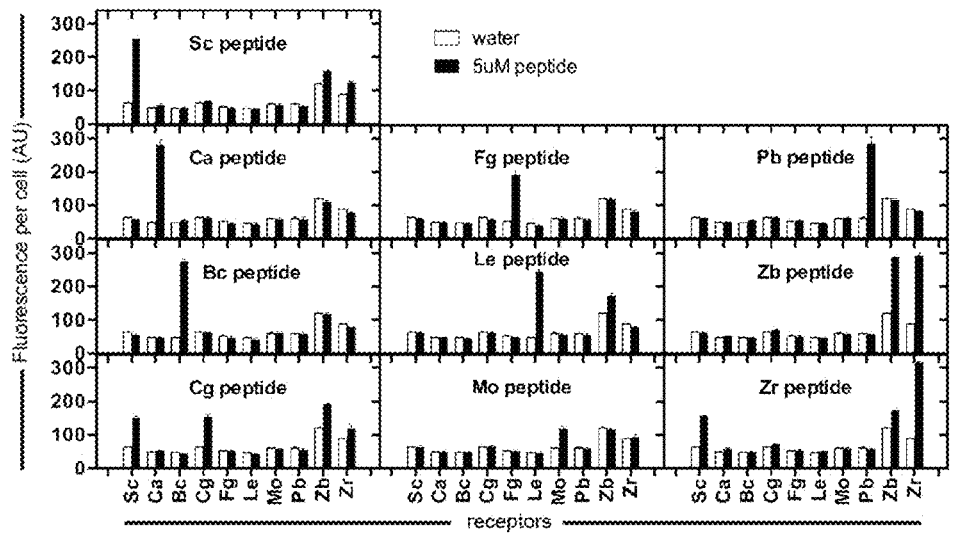
FIG. 20B

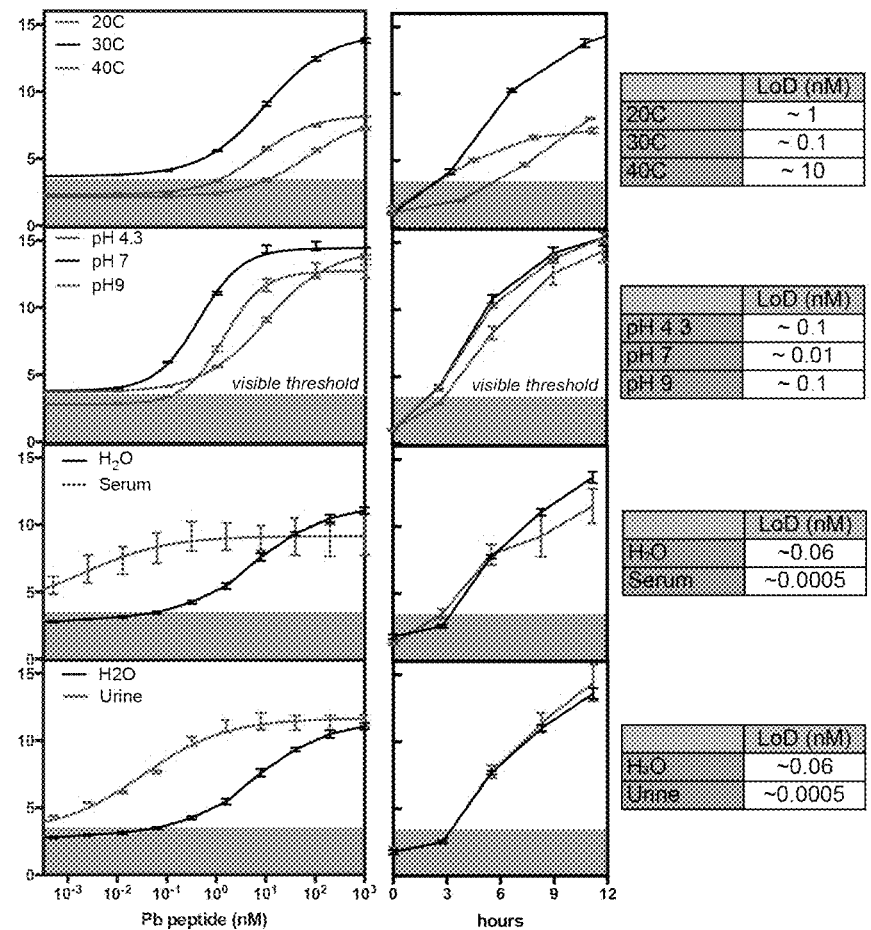

FIG. 22A

```
Pb - M SFDPF Q VVFHKADGTPFNVSIH LD FVQY     VCINY  QLGA VIA  MLA L    60
Hc - M SFDPF Q VVFHKADGTPFNVSIH LD FVQY     VCINY  QLGA VIA  MLA L    60

Pb - T S KRR PVFFLNT AL MNFARLLCMTIYFTTGFN YA F  DYS VPGSAYA S L    120
Hc - T S KRR PVFFLNT AL MNFARLLCMTIYFTTGFN YA F  DYS VPGSAYA S L    120

Pb - G  F T LVI MEMSL IQT VVC TL IQR LL  VS  I L AIGFR GLMVENCIA    180
Hc - G  F T LVI MEMSL IQT VVC TL IQR LL  VS  I L AIGFR GLMVENCIA    180

Pb - I  ASNF PFIWLQSASNI ITISTCFFSAVFVTKL YALVTR RLG TRFGAMQVMFI    240
Hc - I  ASNF PFIWLQSASNI ITISTCFFSAVFVTKL YALVTR RLG TRFGAMQVMFI    240

Pb - S QTMVIPAIFSI QYP P YEMNSN FTLVAIFLPLSSLWA AT  SFET  SG HQY    300
Hc - S QTMVIPAIFSI QYP P YEMNSN FTLVAIFLPLSSLWA AT  SFET  SG HQY    300

Pb - LW SE SN  T S   Q S  QN  T RSGGSVAT LSPD LD  Y    VFA  KA      356
Hc - LW SE SN  T S   Q S  QN  T RSGGSVAT LSPD LD  Y  DF A  KA       357
```

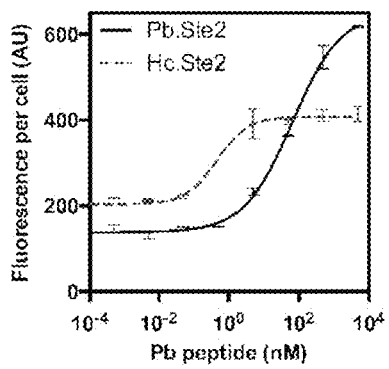

FIG. 22B

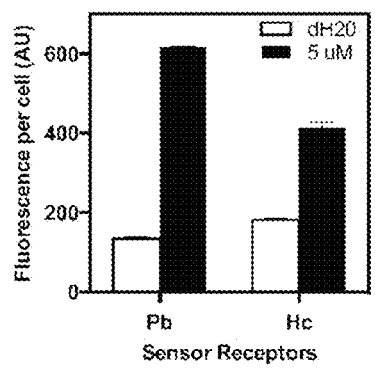

FIG. 22C

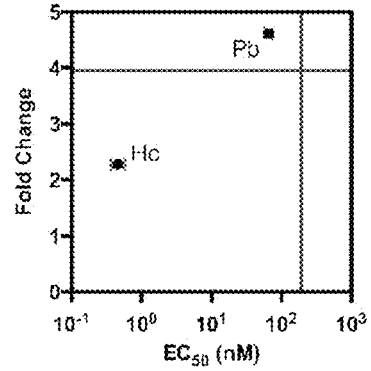

FIG. 22D

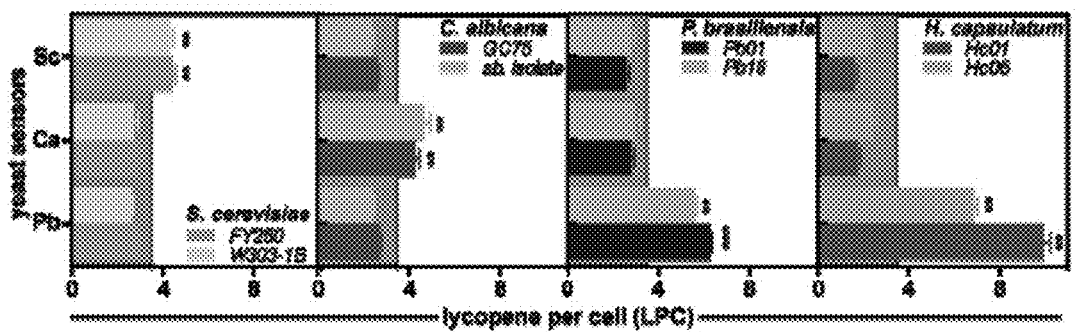

FIG. 22E

DETECTION OF ANALYTES USING LIVE CELLS

CROSS-REFERENCE TO RELATED APPLICATIONS

This application is a continuation-in-part of International Patent Application No. PCT/US2015/061373, filed Nov. 18, 2015, which claims priority to U.S. Provisional Patent Application Ser. No. 62/081,441, filed Nov. 18, 2014, priority to both of which is claimed, and the contents of both of which are incorporated by reference in their entireties herein. International Patent Application No. PCT/US2015/061373 includes a Sequence Listing which is incorporated by reference herein.

GRANT INFORMATION

This invention was made with government support under grant AI110794 awarded by the National Institutes of Health, grant HR0011-15-2-0032 awarded by the Department of Defense/Defense Advanced Research Projects Agency, and grant 1144155 awarded by the National Science Foundation. The government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 8, 2017, is named 070050_5943_SL.txt and is 276,956 bytes in size.

1. INTRODUCTION

The present invention relates to methods and compositions for detecting the presence of an agent in a test sample using a whole cell reporter. In certain embodiments, detection can be performed without the aid of instrumentation, for example outside of a laboratory setting, permitting home and field tests for interrogating the status of biological systems. The present invention may be used, for example, to identify pathogens and thereby limit the dissemination of disease.

2. BACKGROUND

2.1. Whole-Cell Biosensors

Microbial whole-cell bio-reporters present unique advantages for environmental sensing, such as the probing of complex biochemical processes, compatibility with aqueous media, self-renewal by replication, portability by freeze-drying, availability of numerous natural sensing pathways, and ease of engineering new functions (e.g., by directed evolution).[1,2] Bacterial whole cell sensors have previously been demonstrated for detection of DNA damage,[3] heat shock,[4] oxidative stress,[5] heavy metals,[6-8] viruses,[9] and light.[10] Yeast and mammalian whole cell sensors have also been reported. For yeast whole cell sensors, see Hollis (2000) and Radhika (2007). For mammalian whole cell sensors, see Rider, (2003).

2.2. Peptides as Analytes

While natural receptors can be utilized for detection of a broad range of analytes, proteins and their peptide epitopes present a ubiquitous pool of natural biomarkers which are highly characteristic of the organisms that produce them. Peptides can thus be used as targets for detection of pathogenic organisms, food born toxins, immunogens and bioterrorism agents. For example, see the recent development of mass spectrometry of proteolized samples as a diagnostic tool for various diseases.[11,12]

2.3. Using GPCRs for Detection

G-protein coupled receptors (GPCR) constitute a large family of seven-transmembrane receptors for hormones, neurotransmitters, chemokines, calcium, odorants, taste molecules and even light.[19] GPCR signaling pathways are highly conserved among diverse species. Furthermore, GPCR-activation of the Mitogen-activated protein kinase (MAPK) phosphorylation cascade is conserved from yeast to mammals,[19] with different MAPK families activated by multiple different GPCRs.

It was shown that yeast pheromone receptors can be functionally replaced by expressing mammalian GPCRs that couple to the endogenous MAPK signaling pathway, so that the corresponding mammalian agonist activates the yeast pheromone response using different reporter genes[21-23] beta-galactosidase[24-26] or auxotrophic markers.[27-29]

G-protein coupled receptors (GPCRs) have previously been implemented in yeast to develop high-throughput drug discovery assays based around mammalian receptors by using a growth based reporter.[13,14] Additionally, yeast has also been used to functionally express native fungal receptors to study the biology of the respective fungi.[15-18] These previous studies coupled the GPCRs to the endogenous pheromone response pathway by using laboratory assays requiring instrumentation.

3. SUMMARY OF THE INVENTION

The present invention relates to methods and compositions for detecting the presence of an agent, for example, but not limited to, a human disease agent (e.g., a pathogenic agent), an agricultural agent, an industrial and model organism agent, a bioterrorism agent, or a heavy metal contaminant, by detecting the presence of an analyte indicative of the presence of the agent in a test sample. In certain embodiments, the analyte is the agent itself, a portion of the agent (e.g., a portion generated by proteolysis), or a product of the agent. The methods utilize a sensor cell bearing a receptor that is specific for the analyte, where binding of the receptor to the analyte triggers a detection event that is indicative of the presence of the agent. The reporter can be coupled to the receptor. In certain embodiments, the sensor cell is a microbe that is easy and quick to propagate, for example a yeast cell, and the reporter gene product is detectable to the naked eye, for example a pigmented compound such as (red) lycopene. In certain non-limiting embodiments, the present disclosure provides an engineered baker's yeast that uses G-protein coupled receptors (GPCRs) to detect a range of peptide ligands associated with specific target agents and uses the red plant pigment lycopene as a fast, non-technical, visual readout. In certain non-limiting embodiments, the present disclosure provides methods of engineering peptide-activated GPCRs to detect non-cognate agent-specific peptides and to improve performance (e.g., sensitivity and/or specificity) against peptide ligands, using directed evolution.

The present invention provides methods of detecting the presence of an agent of interest in a sample. In certain embodiments, the method comprises: contacting the sample with a sensor cell comprising a non-native G-protein coupled receptor (GPCR) that binds to an analyte indicative of the presence of the agent, wherein binding of the analyte to the receptor triggers appearance of a reporter detectable by the naked eye, wherein the increased expression is indicative of the presence of the agent. The agent can be selected from the group consisting of human disease agents, agricultural agents, industrial and model organism agents, bioterrorism agents, and heavy metal contaminants. In certain embodiments, the non-native GPCR receptor is engineered to bind to the analyte. In certain embodiments, the non-native GPCR receptor is engineered by directed evolution. In certain embodiments, the non-native GPCR receptor is a fungal pheromone GPCR. In certain embodiments, the non-native GPCR receptor is selected from the group consisting of the GPCRs listed in Tables 2 and 6.

In certain embodiments, the sensor cell is a microbe. In certain embodiments, the sensor cell is a fungal cell. In certain embodiments, the sensor cell is a yeast cell. In certain embodiments, the sensor cell is *S. cerevisiae*. In certain embodiments, the sensor cell comprises a nucleic acid encoding the receptor. In certain embodiments, the nucleic acid is linked to a promoter.

In certain embodiments, the analyte is a cognate ligand for the non-native GPCR receptor. In certain embodiments, the analyte is a non-cognate ligand for the non-native GPCR receptor.

In certain embodiments, the analyte is a peptide. In certain embodiments, the peptide is a fungal mating pheromone. The fungal mating pheromone can be selected from the group consisting of human fungal mating pheromones (meaning mating pheromones of fungi that can colonize or infect humans), non-human animal fungal mating pheromones (meaning mating pheromones of fungi that colonize or infect a non-human animal), plant fungal mating pheromones (meaning mating pheromones of fungi that colonize or infect a plant), food fungal mating pheromones (meaning mating pheromones of fungi that colonize or infect human or non-human animal food items), and industrial/model fungal mating pheromone. In non-limiting examples, the human fungal mating pheromone can be selected form the group consisting of the mating pheromones of *C. albicans, C. glabrata, P. brasiliensis, L. elongisporous, P. rubens, C. guillermondi, C. tropicalis, C. parapsilosis, C. lusitaniae, S. scheckii*, and *Candida krusei*. An example of a non-human animal fungal mating pheromone is the mating pheromone of *P. destructans*. In non-limiting examples, the plant fungal mating pheromone can be selected from the group consisting of the mating pheromones of *F. graminearum, M. oryzea, B. cinerea, G. candidum,* and *C. purpurea*. In non-limiting examples, the food fungal mating pheromone can be selected from the group consisting of the mating pheromones of *Zygosaccharomyces bailii, Zygosaccharomyces rouxii*, and *N. fischeri*. In non-limiting examples, the industrial/model fungal mating pheromone can be selected from the group consisting of the mating pheromones of *S. cerevisiae, K. lactis, S. pombe, V. polyspora* (receptor 1), *V. polyspora* (receptor 2), *S. stipitis, S. japonicas, S. castellii,* and *S. octosporus, A. oryzae, T. melanosporum, D. haptotyla, C. tenuis, Y. lipolytica, T. delbrueckii, B. bassiana, K. pastoris, A. nidulans, N. crassa,* and *H. jecorina*.

In non-limiting examples, the peptide can be selected from the group consisting of the peptides listed in Table 5. In certain embodiments, the peptide has a length of about 5-25 residues. In certain embodiments, the peptide has a length of about 9-23 residues.

In certain embodiments, the peptide is associated with a bacterial infection. In certain embodiments, the peptide is associated with *Vibrio cholera*. In non-limiting examples, the peptide associated with *Vibrio cholerae* can be selected from the group consisting of a peptide having an amino acid sequence set forth in VEVPGSQHIDSQKKA (SEQ ID NO: 26), a peptide having an amino acid sequence that is at least 80%, at least 90% or at least 95% about homologous to SEQ ID NO: 26, a peptide having an amino acid sequence set forth in VPGSQHIDS (SEQ ID NO: 27), and a peptide having an amino acid sequence that is at least about 80%, at least 90% or at least 95% homologous to SEQ ID NO: 27. In certain embodiments, the peptide is derived from cholera toxin. The peptide derived from cholera toxin can be selected from the group consisting of the peptides listed in Table 7.

In certain embodiments, the non-native GPCR receptor is coupled to the reporter. In certain embodiments, the method further comprises culturing the sensor cell for an effective period of time; and determining expression of the reporter gene.

In certain embodiments, determining expression of the reporter gene does not comprise instrumentation. In certain embodiments, the reporter is a biosynthesized visible-light pigment. In certain embodiments, the reporter is lycopene. In certain embodiments, the sensor cell is engineered to express the receptor.

In certain embodiments, the sample is selected from the group consisting of water samples and body fluid samples. The water sample can be selected from the group consisting of fresh water, sea water, and sewage samples. The body fluid sample can be selected from the group consisting of intestinal fluids, diarrhea, mucus, blood, cerebrospinal fluid, lymph, pus, saliva, vomit, urine, bile, and sweat.

Additionally, the present invention provides a sensor cell comprising a non-GPCR receptor that binds to an analyte indicative of the presence of the agent, wherein binding of the analyte to the receptor triggers appearance of a reporter detectable by the naked eye, wherein the increased expression is indicative of the presence of the agent.

Furthermore, the present invention provides a kit for detecting the presence of an agent of interest, comprising a sensor cell as described above. In certain embodiments, the kit further comprises a negative control. In certain embodiments, the kit further comprises a substrate that comprises the sensor cell. In certain embodiments, the substrate is comprised in a dipstick. In certain embodiments, the kit further comprises a nutrient source.

4. BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 1B:
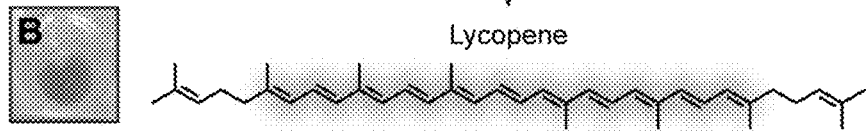

FIGS. 1A and 1B depict biosynthesis of lycopene. (A) Introduction of *E. herbicola* carotenoid enzymes (CrtEBI) result in biosynthesis of lycopene from endogenous yeast farnesyl pyrophosphate. (B) A lycopene-producing yeast strain becomes visibly colored.

Figure 2:
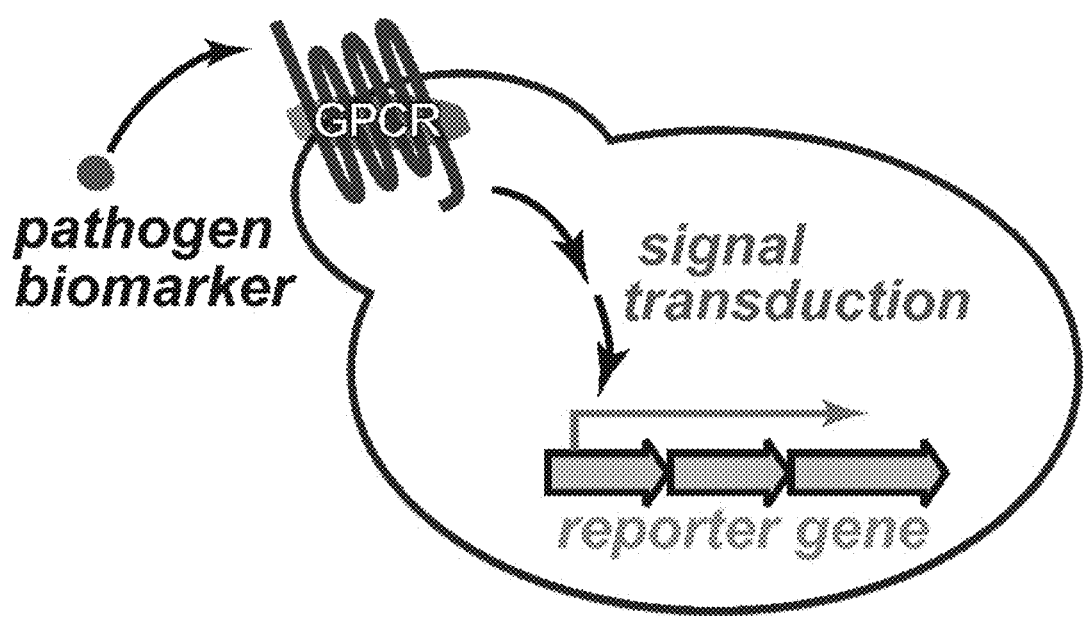

FIG. 2 depicts eukaryotic biosensor design. Binding of one or more agent-specific analyte (e.g., a peptide) to a receptor triggers a signal transduction cascade, resulting in induction of CrtI (or other Crt) gene responsible for a reporter (e.g., lycopene) biosynthesis or other reporter genes. The G-protein coupled receptor operates via the mating signaling pathway in yeast.

Figure 3:
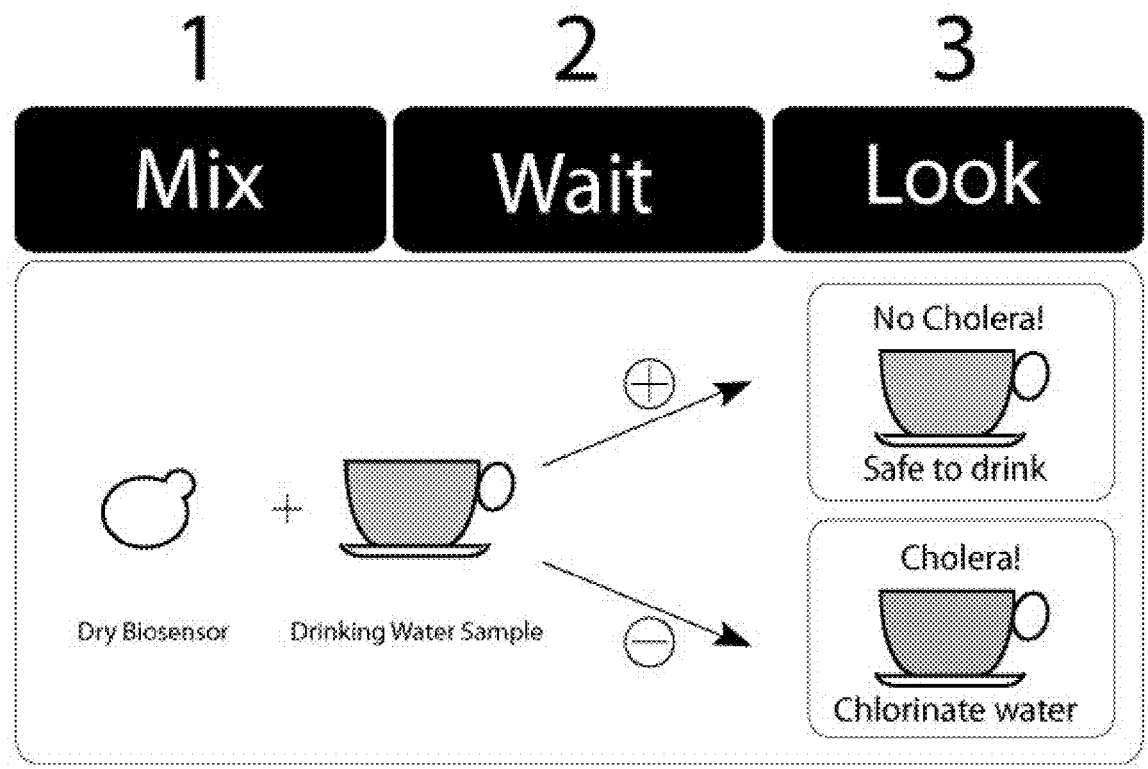

FIG. 3 depicts one embodiment of cell-based detection of cholera pathogen in drinking water. Engineered sensor is added to cholera-contaminated water or a clinical sample. Binding of the cholera pathogen-specific peptide induces a signal cascade in the sensor cell, resulting in amplification of a color reporter gene colorimetric signal.

Figure 4A:
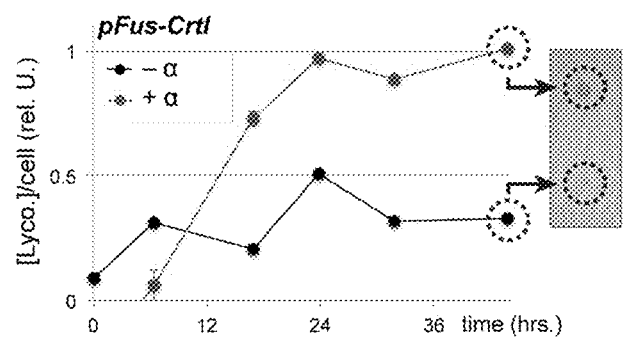
Figure 4B:
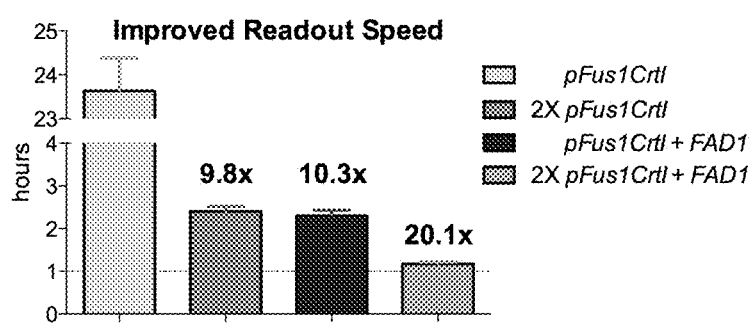

FIGS. 4A and 4B depict experimental results with yeast strains that produced lycopene in response to activation of the endogenous GPCR Ste2. FIG. 4A shows induction of lycopene biosynthesis by the natural yeast peptide, α-factor. FIG. 4B shows improvement of lycopene readout speed with modification of the yeast strain, in laboratory conditions.

Figure 5:
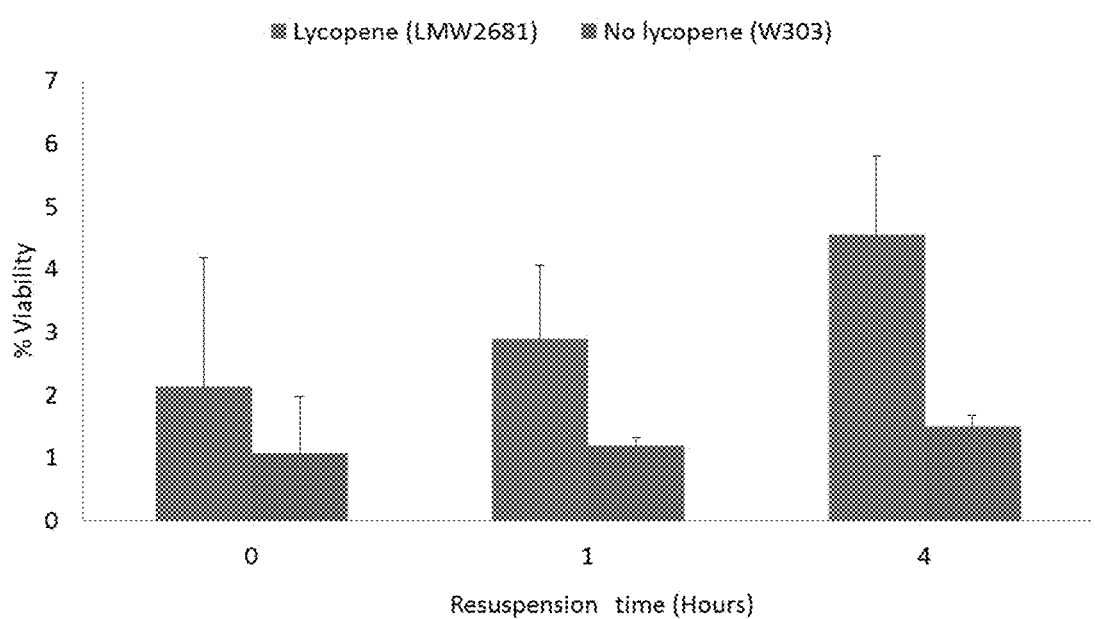

FIG. 5 depicts viability of yeast after freeze-drying. $10^8$ cells were freeze dried and resuspended in YPD. Cell was then plated to quantify survival after 0, 1 or 4 hours in YPD media.

Figure 6:
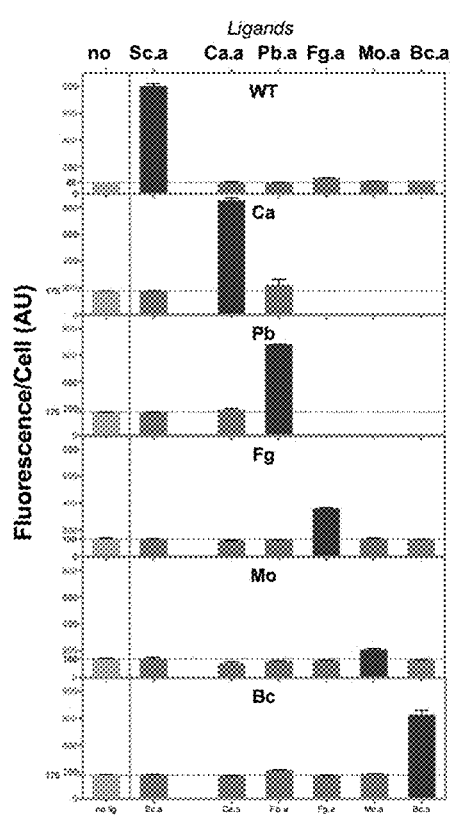

FIG. 6 depicts functional and specific response of fungal GPCRs measured by fluorescence. "Xx.a" denotes peptide pheromones derived from species Xx. Species abbreviations: Sc, *S. cereviseae*; Ca, *C. albicans*; Pb, *P. brasiliensis*; Fg, *F. graminearum*; Mo, *M. oryzea*; Bc, *B. cinerea*.

Figure 7:
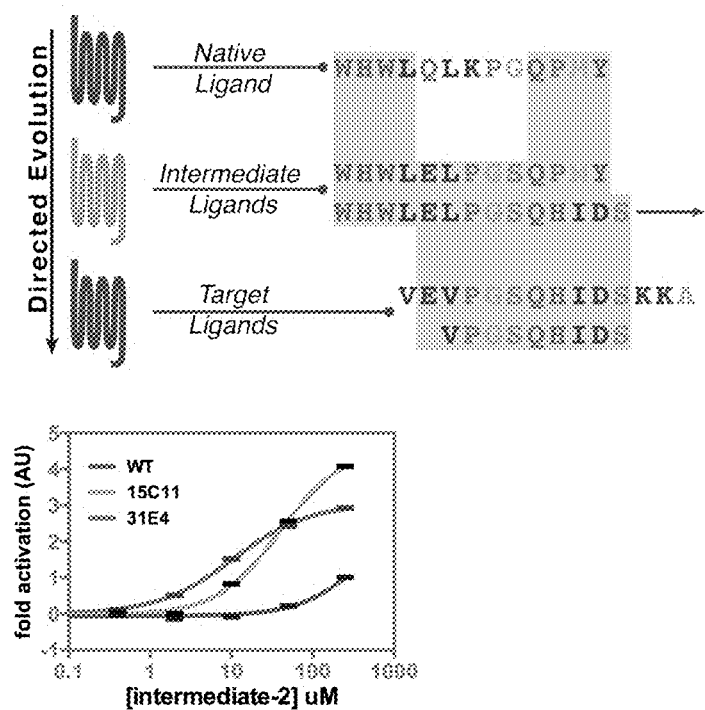

FIG. 7 depicts a peptide-centric directed evolution (DE) approach. The peptide-centric DE approach permitted direct use of hybrid peptides that march from αF to the target peptide analytes. After rounds of DE, mutant engineered receptors gained activity to an intermediate peptide and then further increased EC50.

Figure 8:
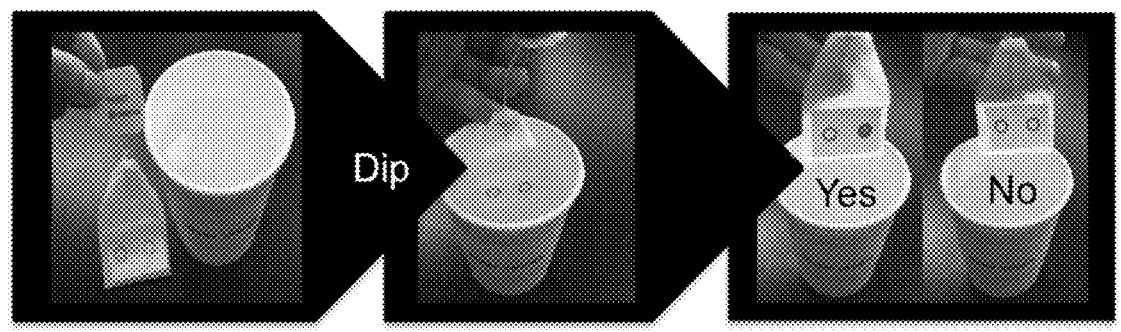

FIG. 8 depicts one embodiment of cell-based detection of an agent of interest. A yeast-based biosensor constructed around engineered baker's yeast is extremely cheap to produce, portable as a freeze-dried product, and simple to use. A non-technical user simply adds a sample and waits for a color change signaling the presence of the agent.

FIGS. 9A-9C depict specific detection of fungal peptides. (A) Mining of fungal receptor-pheromone pairs. Fungal receptor gene was cloned into *S. cerevisiae* sensor strain, and tested using a synthetic fungal peptide pheromone, using a fluorescent readout. (B) Orthogonality matrices of fungal receptors, measured in biosensor strain using fungal GPCR-peptide pairs. (C) EC50 values for fungal receptors.

Figure 10:
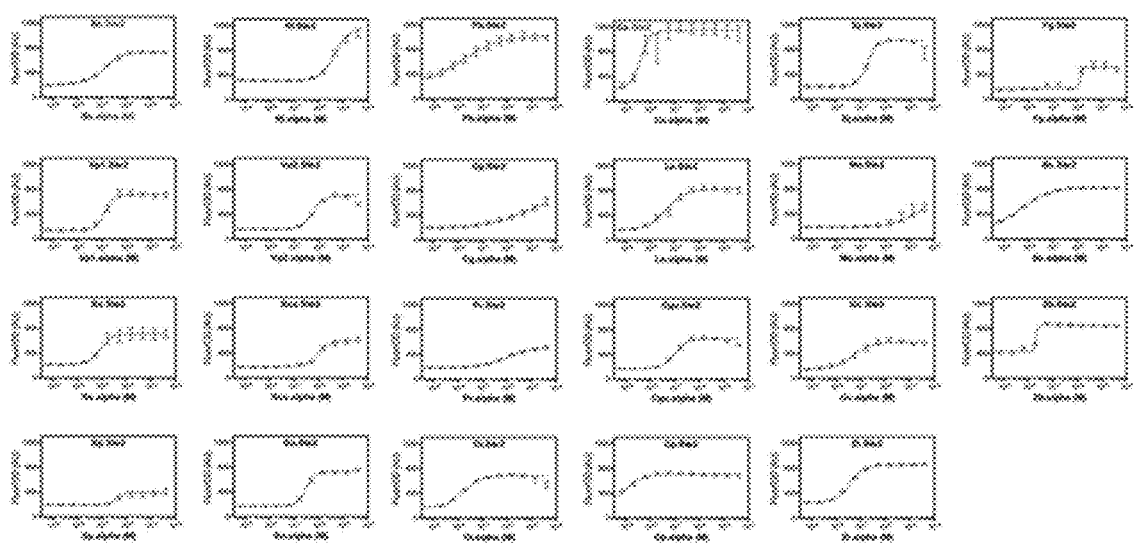

FIG. 10 depicts functional characterization of fungal GPCR-peptide pairs. GPCR was engineered into *S. cerevisiae* sensor cell, and induced using its native fungal peptide (synthetic peptide). Induction of fluorescent marker was monitored in culture.

FIGS. 11A-11C depict common topology of fungal GPCRs. (A) Topological model of the *S. cerevisiae* Ste receptor was predicted by TMHMM v2.0. All the GPCRs characterized have similar topological profile which includes three key regions of higher homology to *S. cerevisiae* Ste2 (gray boxes). Region I corresponds to the third intracellular loop and shows two positively charged residues with high conservation at positions 233 and 234 relative to the *S. cerevisiae* Ste2. Region II corresponds to the sixth transmembrane helix and contains an essential proline that is conserved across all the receptors at position 258 relative to the *S. cerevisiae* Ste2. Region III shows the highest level of conservation and also includes an essential proline conserved across all the receptors at position 290 relative to the *S. cerevisiae* Ste2. (B) Sequence logo results after alignment of the 23 characterized receptors. These three key regions have higher density of conserved residues with some residues conserved across all receptors. (C) Percent homology of different regions the 23 receptors when compared to the corresponding region of the *S. cerevisiae* Ste2.

FIGS. 12A and 12B depict characteristics of peptide ligands. (A) Functional domains within *S. cerevisiae* alpha factor. Residues in blue were shown to have a strong impact on binding when changed to alanine, while residues in purple were shown to be involved in signaling. [Naider et al. (2004)]. These findings led to the simplified designation of the N-terminus of alpha factor as the signaling domain and the C-terminus as the binding domain, with internal residues $L_6$ and $G_9$ strongly contributing to peptide binding. (B) Functional peptide ligands were aligned and clustered according to [Andreatta et al. (2013)]. Positive and negative charges (red and green, respectively) were indicated in colored bolt. Sequences within each of the clusters were shown along with the resulting sequence logos. Logos only highlight the identified 13-residue motifs.

FIGS. 13A-13D depict enhancement of lycopene output. (A) Detailed lycopene pathway w/co-factors and improved yield lycopene yield & time of visible detection. (B and C) Lycopene yield (B) and response time (C) were optimized using the natural *S. cerevisiae* alpha factor response. Overexpression of genes tHMG1, CrtI and Fad1 showed gradual increase in lycopene yield allowing faster visible response. (D) Characterization of lycopene output in response to alpha factor peptide of pathogenic fungi *C. Albicans*.

FIGS. 14A-14C depict direct detection of pheromone-producing *C. albicans* strain via biosensor strain. (A) Design of "Yeast Block" product and functional demonstration of integrated biosensor. (B) Dose-response curve of lycopene-producing biosensor using synthetic *C. Albians* alpha pheromone. (C) Biosensor response to different pheromone-producing *C. albicans* strains, as measured using fluorescence output. Each of the *C. albicans* were grown first on Phloxine B stained agar and opaque colonies were selected. These opaques colonies were cultured and their supernatants were assayed.

Figure 15:
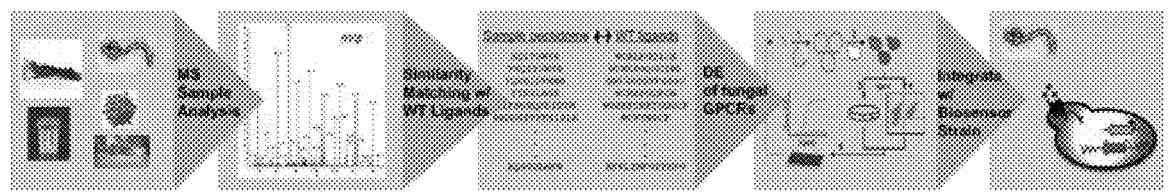

FIG. 15 depicts a process from biomarker identification to a novel biosensor. Workflow starts with identification of potential peptide biomarkers by mass spectrometry, leading to identification of parent GPCR used for directed evolution. The resulting GPCR which binds the selected biomarker is incorporated into the biosensor cell.

Figure 16:
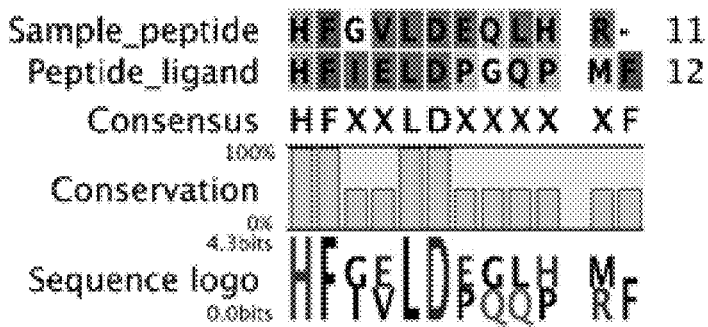

FIG. 16 depicts best matching fungal library member/ peptidome member pair. The sample peptide HFGVLD-EQLHR (SEQ ID NO:132) is similar in length and sequence (36% identity) to the natural mating pheromone activating the mating GPCR of *Zygosaccharomyces rouxii*.

FIGS. 17A-17D. (A) Dipstick device. Inset: positive readout, "+" biosensor strain. "−" negative control cells. (B) Quantitative analysis of lycopene production using dipstick assay, as scored by time-lapse photography for detection of 1 µM synthetic *P. brasiliensis* mating peptide. Individual runs shown in light color, average response shown in dark color. Shading indicates visible threshold. (C) *P. brasiliensis* and *C. albicans* mating peptides were reproducibly detected using the dipstick assay. Maximal response was achieved by 12 hours after exposure to the respective peptides (1 µM). (D) Detection of *P. brasiliensis* mating peptide in complex samples. Liquid samples were supplemented with synthetic *P. brasiliensis* mating peptide (blue) or water (grey), and scored as in B. YPD—media only, Soil—standard potting soil, Urine—50% pooled human urine Serum—50% human serum, Blood—2% whole blood. All experiments were performed using 1 µM peptide and supplemented with YPD media.

FIGS. 18A-18E. Paper-based dipstick assay. (A) Engineered *S. cerevisiae* biosensor cells spotted on paper are the only active component required for the dipstick assay. Spot diameter-5 mm. (B) Dipstick assay includes two spots, indicator biosensor strain and control strain, placed on top of a strip of paper towel that acts as wicking paper. The indicator biosensor spot detects the target ligand and the negative control spot contains a strain with an off-target receptor. This design enables easy visual interpretation of the results as well as quantification by calculating the difference in the pixel color values between the two spots (see Supplementary Methods). (C) Representative photograph of the dipstick for detection of the fungal pathogen *P. brasiliensis* in soil. Left—no mating peptide in soil. Right—mating peptide added to soil. Scale bar-1 cm. (D) A simple plastic holder was designed to enable easy use of the dipstick assay. Thin black bars-2 cm. (E) Dipstick holder does not affect biosensor performance as shown by time course measurement of the *P. brasiliensis* dipstick test response using 1 μM cognate peptide. FIGS. 19A-19H. Optimization of peptide-induced lycopene production.

(A) Lycopene biosynthetic pathway. Lycopene production is induced (red arrow) by mating-signal dependent activation of the FUS1 promoter. Biosynthetic enzymes shown in bold. Genes targeted for optimization shown in colors. HMG-CoA: 3-hydroxy-3-methylglutaryl-coenzyme A, FMN: flavin mononucleotide, FAD: flavin adenine dinucleotide, FPP: farnesyl pyrophosphate, GGPP: geranylgeranyl pyrophosphate. (B) Optical density spectrum of constitutive lycopene producing and lycopene null strains. (C) The spectrum of lycopene in yeast cells calculated from B. This spectrum allows selection of wavelengths for spectroscopic measurement of lycopene per cell (see Supplementary Methods). (D) Maximal lycopene yield per cell calculated from time course data in F-H. "Null" (grey)—parental strain (no lycopene genes); "Lyco-1" (black)—parental strain with single copy CrtE, CrtB and CrtI; "tHMG1" (green)—Lyco-1 with plasmid-borne truncated copy of Hmg1; "2×CrtI" (orange)—Lyco-1 with plasmid-borne copy of CrtI; "Fad1" (blue)—Lyco-1 with plasmid-borne copy of Fad1; "Lyco-2" (red)—Lyco-1 with additional genes genomically integrated. (E) The time to half-maximal lycopene yield was used to compare readout speed. Strains as in D. (F-H), Time course of lycopene strains induced with 10 μM of *S. cerevisiae* peptide (solid line) or water (dotted line). Strains as in D.

FIGS. 20A-20B. Specificity of fungal mating receptors. (A) Heterologous receptors ('species.Ste2') were induced with 5 μM of the indicated fungal mating peptide. mCherry fluorescence was measured after 9 hours. Basal (0%) and maximal (100%) fluorescence used indicated in grey. (B) Data as in A. Activation of heterologous mating receptors shown here grouped by mating peptide.

FIGS. 21A-21D. *P. brasiliensis* biosensor characterization in liquid culture. Dose-response and time-course data shown for *S. cerevisiae* strain carrying *P. brasiliensis* Ste2 receptor (Ca.Ste2) under different conditions: (A)-temperatures, (B)-pH, (C)-50% human serum and (D)-50% human urine. Lycopene yield was determined by absorbance after 9 hours. All experiments were performed using 1 μM synthetic peptide. The limit of detection (LoD, lowest peptide concentration producing significant signal over background, **P≤0.01) is shown for each sample conditions. N=3.

FIGS. 22A-22E. Comparison of mating receptors from human pathogens *P. brasiliensis* and *H. capsulatum*. (A) Protein sequence comparison of the *P. brasiliensis* (Pb. Ste2) and *H. capsulatum* (Hc. Ste2) receptors. Positions that differ highlighted in grey. (B) Dose response curve using Pb.Ste2 and Hc.Ste2 receptors cloned in *S. cerevisiae* and induced with the common cognate ligand (see Table 9, below). Measurement was taken after 12 hours. All measurements were performed in duplicate. (C) Comparison of basal (dH2O) and maximum (5 μM) activation level for Pb and Hc mating receptor using the same synthetic ligand, as shown in B. (D) Comparison of Pb.Ste2 and Hc.Ste2 receptors fold-activation and EC50 values calculated from panel B. Grey cross lines mark the equivalent values for *S. cerevisiae* wild type mating receptor Ste2 activated by its own cognate peptide. While Hc.Ste2 exhibited higher sensitivity to the common mating peptide than Pb.Ste2, it also had higher basal level and lower maximal activation making it less effective for detection using the visible lycopene readout. (E) Lycopene production induced by culture supernatant from clinically isolated fungal pathogens. Lycopene per cell measured by spectroscopy at 9 hours P≤0.01, *P≤0.001, N=3.

5. DETAILED DESCRIPTION OF THE INVENTION

The present invention relates to methods and compositions for detecting the presence of an agent of interest in a test sample.

For clarity and not by way of limitation, the detailed description is divided into the following subsections:
(i) Agents of Interest
(ii) Sensor cells;
(iii) Receptors and coupling systems;
(iv) Detection events;
(v) Analytes;
(vi) Methods of use; and
(vii) Kits

5.1. Agents of Interest

Presently disclosed sensor calls can be used to detect the presence of a variety of agents. Non-limiting examples of suitable agents include human disease agents (human pathogenic agents), agricultural agents, industrial and model organism agents, bioterrorism agents, and heavy metal contaminants.

Human disease agents include, but are not limited to infectious disease agents, oncological disease agents, neurodegenerative disease agents, kidney disease agents, cardiovascular disease agents, clinical chemistry assay agents, and allergen and toxin agents.

Infectious disease agents include, but are not limited to, fungal pathogens, bacterial pathogens, viral pathogens, and protozoan pathogens, as well as toxins produced by same. Non-limiting examples of fungal pathogens include *C. albicans, C. glabrata, P. brasiliensis, L. elongisporous, P. rubens, C. guillermondi, C. tropicalis, C. parapsilosis, C. lusitaniae, S. scheckii*, and *Candida krusei*.

Non-limiting examples of bacterial pathogens include *Vibrio cholerae, Staphylococcus aureus* and Methicillin-resistant *Staphylococcus aureus* (MRSA) strains, *Bacillus subtilis, Streptococcus pneumonia*, Group B *Streptococcus, Salmonella* sp., *Listeria monocytogenes, Chlamydia trachomatis, Neisseria gonorrhoeae, Clostridium difficile, Yersinia enterocolitica, Legionella* sp., *Mycobacterium tuberculosis, Klebsiella pneumoniae, Klebsiella oxytoca, Serratia marcescens, Neisseria meningitis, Streptococcus pneumoniae, Pseudomonas aeruginosa, Streptococcus pyogenes*, botulinum toxin of *Clostridium botulinum*, Shigella/Enteroinvasive *E.coli*, Shiga toxin from the Shiga toxin-producing *Escherichia coli* (STEC), and Verotoxin derived from *Shigella dysenteriae*. Analytes that are indicative of the presence of bacterial pathogens include, but are not limited to, quorum sensing small molecules such as the Vibrio Cholera CAI-1,[69] inter-species bacterial quorum sensing AL-2,[70] or components of the bacterial LPS.

Non-limiting examples of viral pathogens include Ebola virus, HPV, HIV, influenza, Hepatitis C Virus, Hepatitis B Virus. Cytomegalovirus (CMV), Epstein-Barr virus (EBV), Respiratory syncytial virus (RSV), Norovirus, Sapovirus, and measles virus. Analytes that are indicative of the presence of viral pathogens include, but are not limited to, capsid protein or peptides, and other viral particles.

Non-limiting examples of protozoan pathogens include *Trichomonas vaginalis, Cryptosporidium, Cyclospora cayetanensis, Giardia lamblia*, and biomarkers for Amoebiasis derived from *Entamoeba histolytica* such as *E. histolytica* ADP-forming acetyl-CoA synthetase (EhACS) or related peptides [Huat (2014)], Leishmaniasis biomarkers such as the amastin signature peptide [Rafati (2006)].

Oncological disease agents include, but are not limited to, lung, breast, colorectum, prostate, stomach, liver, kidney or cervix cancer, leukemia, Kaposi sarcoma, Testis, Ovary, thyroid, and other cancer peptide biomarkers unique for certain cancer types, which can be identified by mass spectrometry.[60-63]

Neurodegenerative disease agents include, but are not limited to, peptide biomarkers indicated in Alzheimer's,[64] [notably fungal biomarker for Alzheimer's were recently suggested in Pisa (2015)], the protein DJ-1 or peptides thereof as biomarkers for Parkinson disease,[65] and biomarkers for prion disease such as proteins or peptides of the 14-3-3 family in cerebrospinal fluid for detection of Creutzfeldt-Jakob disease [Van Everbroeck (2005) and Huzarewich (2010)].

Clinical chemistry assay (for general health diagnostics) agents include, but are not limited to, peptide hormones. Peptide hormones include, but are not limited to, neurohypophysial hormones (e.g., oxytocin and vasopressin) and pancreatic hormones (e.g., glucagon, insulin and somatostatin).

Allergen and toxin agents include, but are not limited to, peptide derived from immunogenic wheat peptide (e.g., gluten), and carcinogen aflatoxin B1 derived from the fungi *A. flavus*.

Kidney disease agents include, but are not limited to, proteins and peptides identified as urinary biomarkers for kidney disease, such as β2-microglobulin, and differential patterns of peptides in type 2 diabetis[66].

Cardiovascular disease agents include, but are not limited to, proteins and peptides indicative for atherothrombosis or risk markers for stroke. Markers for primary cardiovascular events include peptides derived from C-reactive protein, fibrinogen, cholesterol, apolipoprotein B, high density lipoprotein, and small molecules like vitamin D. Markers for secondary cardiovascular events include peptides derived from cardiac troponins I and T, C-reactive protein, serum creatinine, and cystatin C. Risk markers for primary stroke, include peptides derived from fibrinogen and serum uric acid [Van Holten et al. (2013)]

Agricultural agents include, but are not limited to, fungal pathogens of animals and plants, and fungal agents causing food spoilage. Fungal pathogens of animals and plants include, but are not limited, to animal fungal pathogens and plant fungal pathogens. Animal fungal pathogens include, but is not limited to, *P. destructans*. Non-limiting examples of plant fungal pathogens include *F. graminearum, M oryzea, B. cinerea, G. candidum*, and *C. purpurea*. Non-limiting examples of fungal agents causing food spoilage include *Z. bailii, Z. rouxii*, and *N. fischeri*.

Industrial and model organism agents include, but are not limited to, fungal agents used for genetic studies and industrial applications such as food production, pharmaceutical production, fine chemical production, bioremediation, including, but not limited to, *S. cerevisiae, K. lactis, S. pombe, V. polyspora* (receptor 1), *V. polyspora* (receptor 2), *S. stipitis, S. japonicus, S. castellii*, and *S. octosporus*.

Bioterrorism agents include, but are not limited to, peptide biomarkers for *Bacillus anthracis* (causative agent of anthrax—e.g., one of three polypeptides that comprise the anthrax toxin secreted by the pathogen: protective antigen (PA), lethal factor (LF) and edema factor (EF)),[67] *Clostridium botulinum* (causative agent of botulism—e.g., Botulinum neurotoxin peptides such as the cyclic peptide C11-019),[68] viral agents such as smallpox (Variola virus) and Viral encephalitis, Ebola virus.

Heavy metal contaminant include, but are not limited to, cadmium, mercury, lead or arsenic, as bound to biological receptors.

In certain embodiments, the agent is the same as the analyte, as disclosed herein. In certain embodiments, the agent is different from the analyte.

5.2. Sensor Cells

The sensor cell can be engineered to comprise one or more component of the assay system disclosed herein. As used herein, the term "engineered" means that one or more component is introduced into a sensor cell or its parent cell by a method selected from the group consisting of recombinant DNA techniques (e.g., Reiterative Recombination and CRISPR), natural genetic events, conjugation, and a combination thereof. Sensor cells can be prokaryotic cells or eukaryotic cells. In certain embodiments, a presently disclosed sensor cell is a microbe, including, but not limited to, bacteria, fungi, and slime molds. In certain embodiments, the sensor cell is a fungal cell. In certain embodiments, the fungal cell is a yeast cell. Non-limiting examples of yeast cells include *Saccharomyces cerevisiae, Pichia pastoris* and *Schizosaccharomyces pombe*. In one non-limiting embodiment, the sensor cell is *Saccharomyces cerevisiae*. Additional non-limiting examples of fungal cells include *Candida albicans, Paracoccidioides brasiliensis, Fusarium graminearum, Magnaporthe oryzae*, and *Botrytis cinerea*. In certain embodiments, the sensor cell is a bacterial cell. Non-limiting examples of bacterial cells include *Escherichia coli, Bacillus subtilis*, and *Lactobacillus acidophilus*.

5.3 Receptors and Coupling Systems

The present invention provides for receptors and coupling systems wherein a sensor cell comprises (e.g., bears) a receptor that binds to an analyte, where binding of the analyte triggers a detection event that is indicative of the presence of the agent (e.g., expression of a detectable reporter gene, including increased or decreased expression), release of a therapeutic molecule that directly remediates the agent, production of a redox active molecule, or a change in the membrane potential of the sensor cell). In certain embodiments, the sensor cell is engineered to bind to the analyte.

As used herein, the term "receptor" means a molecule (e.g., a ligand) that binds to a presently disclosed analyte that is indicative of the presence of an agent of interest. A presently disclosed receptor is positioned, either inherently or by association with a membrane protein, at the cell surface exposed to the extracellular environment. In certain embodiments, the receptor is a protein. In certain embodiment, the receptor is a naturally occurring (native) protein or a portion thereof. In certain embodiments, the receptor is a portion of a naturally occurring protein comprised in a fusion protein with one or more heterologous proteins. In certain embodiments, the receptor is a mutated version of a naturally occurring protein. In certain embodiments, the receptor is a synthetic protein. In certain embodiments, the receptor is a partly-synthetic protein. In certain embodiments, the receptor comprises one or more non-protein element.

In certain embodiments, the receptor is a non-protein molecule. In one non-limiting embodiment, the receptor is an aptamer or a riboswitch. The receptor may be comprised of a single element or may be comprised of a plurality of elements/subunits.

In certain non-limiting embodiments, the sensor cell comprises a receptor that binds to an analyte, wherein the receptor is coupled to a detectable reporter gene such that when the analyte binds to the receptor, expression of the reporter gene is increased or induced. In certain embodiments, the receptor is coupled to a detectable reporter gene such that when an analyte binds to the receptor, expression of the reporter gene is inhibited (for example, by binding of a transcriptional repressor). In certain embodiments, the analyte is a peptide, e.g., an agent-specific peptide.

As used herein, the term "coupled to" means that binding of an analyte to a receptor is causally linked, directly or indirectly, to and triggers a detection event that is indicative of the presence of the agent (e.g., expression of a detectable reporter gene (induced or inhibited expression), release of a therapeutic molecule that directly remediates the agent, production of a redox active molecule, or a change in the membrane potential of the sensor cell). In certain embodiments, the detection event is expression of a detectable reporter gene. In certain embodiments, the detection event is induced expression of a detectable reporter gene. The receptor may be linked to expression level of the reporter gene through, for example, a pathway of interacting molecules. This pathway may be host-endogenous or engineered.

In certain embodiments, the sensor cell is engineered to express the receptor, for example, by the introduction of a nucleic acid encoding the receptor. In certain embodiments, the nucleic acid is operably linked to a promoter element. In certain embodiments, the promoter element is constitutively active. In certain embodiments, the promoter element is inducibly active. In certain embodiments, the receptor is expressed on the surface of the sensor cell. In certain embodiments, the receptor is expressed on internal membranes of the sensor cell. In certain embodiments, the receptor is expressed in the cytoplasm of the sensor cell.

In certain embodiments, the analyte is a natural (cognate) ligand of the receptor; the coupled analyte-receptor system utilizes a receptor and its natural (cognate) ligand as the analyte. In certain embodiments, the coupled analyte-receptor system is a receptor engineered to bind a different non-cognate ligand as analyte, by way of directed evolution detailed below.

In certain non-limiting embodiments, the sensor cell expresses a single species of analyte receptor. In certain non-limiting embodiments, the sensor cell expresses a plurality of species of analyte receptor.

In certain non-limiting embodiments, the sensor cell comprises an analyte-specific receptor which is coupled to a detectable reporter gene by a G-protein signaling pathway. Hence, in certain embodiments, the receptor is a G-protein coupled receptor (GPCR) polypeptide or protein. In certain embodiments, the receptor is a non-native GPCR receptor.

In certain non-limiting embodiments, a yeast pheromone sensing system is used for analyte detection. The yeast pheromone signaling pathway is well studied structurally and is functionally similar to hormone and neurotransmitter signaling pathways in mammals.[20] In certain non-limiting embodiments, the receptor is a variant of the yeast Ste2 receptor or Ste3 receptor, wherein the receptor is modified so that it binds to the analyte rather than yeast pheromone. In certain embodiments, the receptor or portion thereof is a polypeptide that is at least about 40%, at least about 50%, at least about 60%, at least about 70%, at least about 80%, at least about 90%, at least about 95%, at least about 98% homologous, or at least about 99% homologous to the native yeast Ste2 or yeast Ste3 receptor. "Homologous" or "homology" can mean sequence (nucleotide sequence or amino acid sequence) homology or structural homology. In certain embodiments, "homology" or "homologous" refers to sequence (nucleotide sequence or amino acid sequence) homology. The sequence homology can be determined by standard software such as BLAST or FASTA. The receptor binds specifically to the analyte (e.g., agent-specific peptide) under assay conditions or under natural conditions (for example, but not limited to, at room temperature (e.g., 20-25° C., at or around body temperature (e.g., 30-40° C.), field temperature (e.g., 5-40° C.) or between about 20-40° C.). In certain non-limiting embodiments, the receptor is a chimeric protein comprising one or more fragment originating from other receptor proteins, or evolved from non-homologous receptor protein to bind to the analyte (e.g., agent-specific peptide) and interface with a signaling pathway. In certain non-limiting embodiments the receptor is a yeast GPCR polypeptide other than a pheromone binding receptor, such as Gpr1 putative sugar binding receptor and the cognate Gα protein Gpa2.

The present invention also provides a nucleic acid encoding the receptor and a host cell comprising said nucleic acid. The nucleic acid can be used to produce a presently disclosed sensor cell. The nucleic acid can be introduced into the host cell such that it is operably linked to an inducible or constitutively active promoter element. In certain embodiments, the sensor cell is a yeast cell, and a nucleic acid encoding a receptor is introduced into the yeast cell either as a construct or a plasmid in which it is operably linked to a promoter active in the yeast cell or such that it is inserted into the yeast cell genome at a location where it is operably linked to a suitable promoter. Non-limiting examples of suitable yeast promoters include, but are not limited to, constitutive promoters pTef1, pPgk1, pCyc1, pAdh1, pKex1, pTdh3, pTpi1, pPyk1, and pHxt7 and inducible promoters pGal1, pCup1, pMet15, and pFus1.

In certain non-limiting embodiments, receptor activation induces reporter gene expression under a FUS1 promoter, which allows for a convenient screen using reporter gene activation. In one non-limiting example, a GPCR polypeptide is expressed in a yeast cell and is coupled to the yeast pheromone mating system such that GPCR binding activates the yeast Fus1 promoter to express a downstream reporter gene.[27] The GPCR DNA sequence can then be varied, and this library of altered receptors may be screened for binding of an analyte (e.g., an agent-specific peptide) using production of reporter gene as an indicator of binding.[13,26]

In certain non-limiting embodiments, where the pathway includes the yeast pheromone sensing pathway, a nucleic acid encoding the reporter is operably linked to at least a transcription controlling portion of the Fus1 promoter, for example, but not limited to, an activating sequence located in the region (−300) to (+400) of the Fus1 gene (Gene ID: 850330). In certain non-limiting embodiments, where the pathway includes the yeast pheromone sensing pathway, a nucleic acid encoding the reporter is operably linked to a Ste12-binding element [(A/T)GAAACA], such that binding of Ste12 acts as a transactivator of the expression of the reporter. In certain non-limiting embodiments, where the pathway includes the yeast pheromone sensing pathway, a nucleic acid encoding the reporter is alternatively linked to one or more inducible promoter other than pFus1, e.g., pFus2, pFig2, and/or pAga1. In certain embodiments, receptor-activation is linked to an engineered pheromone-responsive transcription factor, which binds a synthetic transcription controlling element distinct from the Ste12-binding element. The transcription factor Ste12 is composed of a DNA-binding domain, a pheromone responsive domain and an activation domain. The feasibility of engineering Ste12 to bind to non-natural control elements but remain to activate transcription in a pheromone-responsive manner has been shown

[Pi et al (1997)].

In certain embodiments, a GPCR is engineered by directed evolution (DE) to alter its stability, specificity, and/or sensitivity. Hence, a receptor that is activated by a desired analyte can be generated by mutagenesis and selection in the laboratory. Several research groups have established DE in yeast as tool for changing mammalian GPCR ligand specificity.[13,14,30-32] Non-limiting examples of such engineered GPCRs include mammalian tachykinin receptors, secretin receptors, opioid receptors, and calcitonin receptors. Non-limiting examples of DE to develop a stable reporter strain are provided in the Examples section.

In certain embodiments, the GPCR is a fungal GPCR. In certian embodiments, the GPCR is a fungal phermone GPCR. In certain non-limiting embodiments, a fungal Ste2-type or Ste3-type GPCR derived from one or more fungus is engineered into S. cerevisiae or other yeast cells to serve as areceptor for detecting an agent of interest. While any peptide-sensing GPCR can be repurposed as a detection element in a yeast cell, fungal pheromone GPCRs have several key advantages for biosensor engineering. First, this type of GPCRs (GPCRs homologous to the S cerevisiae Ste2) couple robustly to the host/native pheromone pathway (see FIGS. 9 and 10), and several have been expressly validated in S. cerevisiae with little to no further modifications.[15-18]. Second, fungal pheromone GPCRs from related fungi recognize different peptides based on the natural evolution of this class of GPCR.[33] For example, as shown in FIG. 12 and Table 1, these fungal GPCRs recognize a diverse set of peptide ligands. Third, fungal pheromone GPCRs are highly specific for their respective peptides (see FIG. 9), since they must mediate the species-specific mating reaction while preventing interspecies breeding.[34] Furthermore, though there is no crystal structure of these GPCRs, extensive biochemical characterization and mutagenesis data indicates that the S. cerevisiae GPCR has a large binding interface across the seven transmembrane helices and the extracellular loops modulating ligand binding.[35-40]

Based on these characteristics, fungal pheromone GPCRs offer a highly viable platform for DE towards binding of novel peptide ligands (e.g., non-cognate peptide ligands) through mutagenesis of specific portions of the receptor, the peptide or both.

In certain embodiments, the receptors are identified by searching protein and genomic databases (e.g., NCBI, UniProt) for proteins and/or genes with homology (structural or sequence homology) to S. cerevisiae Ste2 receptor. In certain embodiments, the receptor has an average amino acid sequence homology of 33% to S. cerevisiae Ste2, ranging from 66% to 15% as calculated with Clustal Omega [Sievers (2014)].

In certain embodiments, the receptors have seven transmembrane helices, an extracellular N-terminus, an intracellular C-terminus, three extracellular loops and three intracellular loops when analyzed by TMHMM v2.0 [Krogh et al. (2001)]. As shown in FIG. 11, there are three key regions that have higher density of conserved residues with some residues conserved across all receptors: Region I, Region II, and Region III. Region I corresponds to the third intracellular loop and shows two positively charged residues with high conservation at positions 233 and 234 relative to the S. cerevisiae Ste2. Region II corresponds to the sixth transmembrane helix and contains an essential proline that is conserved across all the receptors at position 258 relative to the S. cerevisiae Ste2. Region III shows the highest level of conservation and also includes an essential proline conserved across all the receptors at position 290 relative to the S. cerevisiae Ste2. Based on previous mutational studies of the S. cerevisiae Ste2 receptor, these three regions are important in mediating signal transduction and interactions with the downstream G-protein. [Ćelić et al. (2003); Martin et al. (2002)]. In certain embodiments, the receptor has at least about >30%, at least about 40%, at least about 50%, at least about 60%, at least about 70%, at least about 80%, at least about 85%, at least about 90%, at least about 95%, at least about 99%, or least about 100% homologous to Region 1 and/or Region 2 and/or Region 3. The receptor functions in a S. cerevisiae biosensor.

In certain embodiments, when coupled to a lycopene reporter system, as described below, a fungal-derived GPCR, optionally further modified by directed evolution, generates lycopene in the sensor cell in response to the peptide pheromones produced by an agent of interest. Pheromone GPCRs from related fungi can naturally recognize different peptide pheromones based on the highly specific characteristics of this class of GPCRs, which mediate the species-specific mating reaction while preventing interspecies breeding. As described in the Example section, putative GPCRs can be cloned and screened against their putative cognate peptide pheromones using a detector gene, e.g., a fluorescent reporter gene.

The present invention provides a sensor cell (e.g., a yeast cell) comprising a receptor, which is a fungal receptor modified to bind to a bacterial pathogen-specific analyte, such as one from V. cholerae. In certain embodiments, this modification is achieved via directed evolution. The natural yeast pheromone mating receptors Ste2 or Ste3, evolved to bind to a peptide pheromone ligand, are not necessarily likely to adjust to bacterial pathogen-specific analyte and therefore can be deleted from the strain to prevent false activation of reporter gene. A mammalian or hybrid G-protein can be used to enhance GPCR signal transduction in a yeast cell. The remaining genes in the pathway may be endogenous to the yeast sensor cell, or may be engineered for improved performance.

One or more rounds of DE can be performed to generate a GPCR responsive to the natural cholera analytes and peptides. In certain embodiments, cholera-specific peptides can be generated by adding sequence-specific proteases (e.g., trypsin, chymotrypsin, LysN, or GluC) to a given sample. Also, using available computational methods, a peptide database of in-silico proteolized proteomes from bacterial pathogens (e.g., Vibrio cholerae, Staphylococcus

*aureus, Bacillus subtilis, Streptococcus pneumonia, Salmonella* sp., *Listeria monocytogenes*), fungal pathogens (e.g., *Aspergillus niger, Candida albicans, Cryptococcus neoformans, Cryptococcus gattii, Histoplasma capsulatum, Pneumocystis jirovecii* and *Stachybotrys*) viral pathogens (e.g., Ebola virus, HPV, HIV, influenza viruses), or proteolysis pattern of any single protein of interst e.g. produced during an industrial process, can be generated. This peptide database can be searched using peptide motifs derived from analysis of the natural diversity of fungal pheromones.

A computational approach can also be used to discover target peptide analytes that are amenable to detection by an engineered fungal GPCR. This computational method generates a pool of high priority targets that can be highly amenable to a DE approach. Engineered receptors such as 15C11 and 31E4, that show increased ligand promiscuity as starting points to generate engineered GPCRs, can be used to detect these new target peptide ligands from a diverse set of bacterial pathogens. Additionally, some of the natural peptide pheromones produced by bacterial pathogens can be targeted.

DE can be implemented to optimize any engineered GPCR for improved signal levels, enhanced EC50 and/or signal transduction kinetics. Of the six GPCR families, the secretin and fungal pheromone receptor families naturally sense peptides. Moreover, the rhodopsin receptor family also contains members with peptide ligands. Representative members of each of these families have been heterologously expressed in yeast and functionally coupled to the pheromone response pathway: neurotensin NT1 (rhodopsin-like), growth-hormone-releasing-hormone receptor (secretin-like), *Sordaria macrospora* pheromone receptor (fungal pheromone-like). These GPCRs can be engineered into a yeast cell as a method for detecting their cognate peptide ligands, e.g., growth hormone or neurotensin, for monitoring or quantification.

Fungal Ste2-type or Ste3-type GPCRs as well as other peptide-specific GPCRs mentioned above can be used as a platform for developing engineered peptide-activated GPCRs to generically detect agent-specific analytes. In certain embodiments, the present disclosure provides a stepwise Directed Evolution (DE) strategy based on intermediate hybrid peptides to change the ligand specificity of the parent GPCRs to bind the target peptides.

In certain embodiments, the engineered GPCR is an engineered receptor for the detection of *Vibrio cholerae*. The receptor can detect a peptide derived from the Cholera toxin (CTx). Additionally, there is a reservoir of biochemical and mutational data of the yeast Ste2 and Ste3 receptor in the literature.[35-37,39,40,43] The same strategy can be used for detection of other fungal, viral or bacterial analytes described below.

GPCRs constitute a large class of cell-surface receptors that can be activated by a variety of other ligands, e.g., full proteins, small molecules (e.g., nucleotides and lipids), or light. A variety of these non-peptide sensing receptors have been functionally expressed in yeast.[44] These receptors can be employed and engineered into the biosensor to sense analytes other than peptides, e.g., small molecules, proteins or heavy metals.

Non-limiting examples of DNA encoding certain GPCRs of the invention are set forth in Tables 2 and 6 below; the invention further provides for proteins encoded by said DNA sequences.

5.4. Detection Events

Being of the analyte to the receptor triggers a detection event that is indicative of the presence of the agent. The detection events include, but are not limited to, appearance of a reporter (including expression (increased or decreased expression) of a detectable reporter gene), release of a therapeutic molecule that directly remediates the agent, production of a redox active molecule, and a change in the membrane potential of the sensor cell.

In certain embodiments, the detection event is appearance of a reporter. The reporter can be a result of expression of a reporter gene. A reporter can include an enzyme that can produce chromogenic product on a substrate. In certain embodiments, the detection event is increased expression of a reporter gene.

In certain embodiments, the reporter is a laboratory reporter. A "laboratory reporter" means a reporter that cannot be detected by the naked eye (e.g., the change or appearance of the color cannot be detected by the naked eye), and/or a reporter whose detection requires instrumentation. Suitable laboratory reporters include, but are not limited to, bioluminescent, fluorescent, and certain chromogenic reporters. Bioluminescent reporters include, but are not limited to, luciferase. Fluorescent reporters include, but are not limited to, various fluorescent proteins (e.g., a green fluorescent protein, a red fluorescent protein, a yellow fluorescent protein, a blue fluorescent protein). Non-laboratory chromogenic reporters include, but are not limited to, beta-galactosidase, beta-glucoronidase, and horse-radish peroxidase. In certain embodiments, the reporter is a fluorescent protein.

In certain embodiments, the reporter does not comprise a laboratory reporter. In certain embodiments, the reporter is a non-laboratory reporter. A "non-laboratory reporter" means a reporter that can be detected by the naked eye (e.g., the change or appearance of the color can be detected by the naked eye), and/or whose detection does not require instrumentation (e.g., reporters that are not conventionally used as research tools). Non-laboratory reporters include, but are not limited to, enzymes in the biosynthetic pathways of pigments (biosynthesized pigments that absorb in the visible light spectrum, also referred to as "biosynthesized visible-light pigments"), electrochemical, and reporters which constitute release of one or more therapeutic molecule. Certain chromogenic reporters are non-laboratory reporters, e.g., lycopene.

Biosynthesized visible-light pigments include, but are not limited to, terpenoids, carotenoids, lycopene, violacein and its precursors, melanin, and indigo. In certain embodiments, the reporter is a terpenoid. In certain embodiments, the reporter is a carotenoid. In certain embodiments, the reporter is lycopene. In certain embodiments, the receptor does not comprise a fluorescent protein.

Binding of analyte can induce or alternatively repress reporter gene expression. In the absence of an analyte, there may be essentially no reporter gene expression, reporter gene expression may occur at an undetectable level (e.g., undetectable by the naked eye), or reporter gene expression may occur at a baseline level that detectably increases upon analyte binding.

Violacein and deoxyviolacein are blue pigments isolated from several bacteria. [Sánchez (2006)]. Heterologous expression of the involved genes vioABCDE and optimization of production yields has been shown in *E. coli* and *S. cerevisiae*. [Lee (2013)].

Melanin is a black diffusible macromolecule whose overproduction has been achieved from L-tyrosine as precursor by heterologous co-expression of a tyrosinase in *E. coli* [Santos (2008)].

Production of the blue pigment bio-indigo from tryptophan as a precursor using a bacterial flavin-containing monooxygenase from the methylotrophic bacteria *Methylophaga aminisulfidivorans* has been achieved and optimized in *E. coli* [Hwan Han (2008)].

Carotenoids are a class of terpenoids composed of 8 isoprene units totaling 40 carbon atoms. Lycopene is a specific naturally produced carotenoid pigment whose heterologous expression in *E. coli* using the genes CrtE, CrtB and CrtI has been extensively studied.[45] If lycopene is used as a reporter, a presently disclosed sensor cell can be engineered to contain the genes required for synthesis and at least one of said genes can be the detectable reporter gene coupled to activation by peptide receptor binding (e.g., at least a portion of the Fus1 promoter). As a non-limiting example, the gene coupled may be CrtI, CrtE or CrtB.

Lycopene can be visualized by the naked eye, is widely validated in yeast metabolic engineering, and is non-toxic. Lycopene is the first intermediate in carotenoid biosynthesis that has a sufficiently conjugated π-system to absorb in the visible region.[46] Thus, unlike standard laboratory reporters like lacZ that require exogenously added caged dyes (X-gal) or fluorescent proteins that require specialized equipment (fluorimeter), lycopene can be directly observed by a non-technical person. Additionally, the biosynthesis of lycopene from endogenous yeast farnesyl pyrophosphate is well established in yeast, requiring only three heterologous genes (FIG. 1).[47]

Use of a biosynthesized visible-light pigment as a simple visual readout has a number of advantages. Use of a biosynthesized visible-light pigment readout requires no complex equipment since it can be seen by the naked eye and requires no expensive externally added reagent, since it can be biosynthesized from endogenous substrates. In contrast, most whole-cell biosensors reported in the literature use laboratory readouts such as fluorescent proteins, lacZ, or luciferase, which require the use of expensive equipment, externally added chromogenic reagents or both.[48-51]

In certain embodiments, lycopene is modified to achieve better response times, signal-to-noise and robustness. For example, in certain embodiments, one or more alternate pheromone-responsive promoter is used.[52] In certain embodiments, one or more synthetic Fus1-like promoter is used.[53] In certain embodiments, one or more variant of the transcription factor Ste12 is used.[54] In certain embodiments, one or more enhancement to the pheromone response pathway is made.[55-58] In certain embodiments, one or more variant of the Crt genes including homologues is used.[59] In certain embodiments, one or more codon optimized version and engineered version with enhanced activity or activation modality is used.

Additional biosynthesized visible-light pigments include mutants of CrtI disclosed in Schmidt-Dannert, C., Umeno, D. & Arnold, F. H. Molecular breeding of carotenoid biosynthetic pathways. Nat Biotech 18, 750-753 (2000), biosynthetic enzymes that generate alternate carotenoid pigments disclosed in Umeno, D. & Arnold, F. H. Evolution of a Pathway to Novel Long-Chain Carotenoids. J. Bacteriol. 186, 1531-1536 (2004), and lycopene enzymes from alternate organism disclosed in Verwaal, R. et al. High-Level Production of Beta-Carotene in Saccharomyces cerevisiae by Successive Transformation with Carotenogenic Genes from *Xanthophyllomyces dendrorhous*. Appl. Environ. Microbiol. 73, 4342-4350 (2007).

A presently disclosed sensor cell may also report in a non-measurable, non-visible way by releasing a therapeutic molecule that directly remediates the detected agent. In general, microbial cells have been used to produce therapeutic molecules such as peptides, proteins and other bioactive small-molecules. [Bourbonnais (1988); Miyajima (1985); Ro (2006)]. Similar to the generation of lycopene, a presently disclosed sensor cell can be coupled to the biosynthesis and secretion of such therapeutic molecule.

In certain embodiments, the detection event is release of a therapeutically relevant molecule, which can be reported through an electronic device. Interfacing to an electronic device can allow reporting to occur much more rapidly and produce a quantitative result. Additionally or alternatively, the release of a therapeutic molecule can be used to directly remediate the agent detected by a presently disclosed sensor cell.

In certain embodiments, the detection event is production of a redox active molecule. Others have in general coupled whole cells electrochemically to electrodes. This is usually done by mixing the cells with a redox-active molecule (a mediator) that couples a redox-active enzymatic process within the cell to a redox reaction on the electrode surface. [Su (2011); Eilam (1982); Garjonyte (2009)].

In certain embodiments, the production or release of a redox active molecule is detected by a redox reaction on an electrode. The redox active molecule can be biosynthesized in an analogous way as lycopene, e.g., by introducing the relevant biosynthetic enzymes into a presently disclosed sensor cell. Similarly, the production of this redox active molecule can be triggered by coupling one of the relevant biosynthetic enzymes to the pheromone signaling pathway. In certain embodiments, the redox active molecule is phenazine. The relevant biosynthetic enzymes are known [Mavrodi (2001)], and their secretion from a bacteria has been measured through the use of an electronic device [Bellin (2014)].

In certain embodiments, the detection event is a change in the membrane potential of the sensor cell. Electronic device that can measure changes in the membrane potential of cells are very common in neuroscience (e.g., multi electrode arrays). [Spira (2013)]. Such a device can be used to measure changes in membrane potential in our biosensor. In certain embodiments, the, a change in the membrane potential of the sensor cell is expression of a cAMP-activated ion channel in the sensor cell (e.g., a yeast cell). This type of channel has been shown to be functional in yeast. [Ali (2006)]

Signal amplification: In order to improve the robustness of the reporter signal, quorum sensing signal amplification strategy can be used. Specifically, binding of analyte not only induces expression of visible reporter gene but also induces the expression of enzymes responsible for synthesis of quorum sensing molecules in yeast, or alternative GPCR ligands such as α-factor or alpha-factor. Thus, enhanced sensitivity can be achieved by signal amplification using a positive feedback loop. Signal amplification in this form naturally exists in *S. cerevisiae* and other fungi using the same GPCRs described below such as Ste2

5.5. Analytes

Suitable analytes can be any ligand which is capable of binding to a receptor, where such binding triggers a detection event that is indicative of the presence of the agent, including triggering a cellular response by the sensor receptor. Suitable analytes include, but are not limited to, proteins, polypeptides (including amino acid polymers), and peptides. "Protein" generally refers to molecules having a particular defined 3-dimensional (3D) structure, whereas "polypeptide" refers to any polymers of amino acids, regardless of length, sequence, structure, and function. "Peptide" is generally reserved for a short oligomer that often but not necessarily lacks a stable conformation. [Creighton Proteins: Structures and Molecular Properties 2$^{nd}$ Edition, ISBN-10: 071677030X]. Proteins can be longer than 50 amino acid residues and peptides can be between 3 and 50 amino acid residues or longer.

In certain embodiments, an analyte is a peptide epitope. As used herein, the term a "peptide epitope" refers to a sub-region of amino acids within a larger polypeptide or protein. A peptide epitope can be composed of about 3-50 residues that are either continuous within the larger polypeptide or protein, or can also be a group of 3-50 residues that are discontinuous in the primary sequence of the larger polypeptide or protein but that are spatially near in three-dimensional space. The recognized peptide epitope can stretch over the complete length of the polypeptide or protein, the peptide epitope can be part of a peptide, the peptide epitope can be part of a full protein and can be released from that protein by proteolytic treatment or can remain part of the protein molecule.

Some sensor cells (e.g., yeast cells, e.g. *S. cerevisiae* or *Candida albicans*) are surrounded by a thick cell wall, which can cause a permeability barrier to large molecules. The permeability of the *S. cerevisiae* cell wall was shown to be strongly growth phase-dependent, being most porous and plastic during exponential phase. [Nobel et al. (1991)]. The cell wall was shown to be permeable to molecules of a hydrodynamic radius of 5.8 nm, corresponding to a globular protein of 400 kDa. [Nobel (1990)]. Similar sized proteins are functionally secreted from yeast cells like *S. cerevisiae*, *C. albicans*, *C. glabrata* by passaging the cell wall [Nobel (1991)]. Therefore, polypeptides or proteins of up to at least 400 kDa may be accessible to the cell surface receptor as analytes. However, proteins or polypeptides beyond this range can also be detected. In certain embodiments, proteolysis are used to fragment the polypeptide or protein to release smaller polypeptides that can serve as the analyte and be accessible to the cell surface receptors.

The analytes can be natural, engineered or synthetic analytes. Virtually any peptide and modified peptide can be assayed using the composition and methods of this invention, including secreted peptides or fragments of proteins which may be released from the protein by a protease. Proteolysis can be induced by one or more host-specific proteases and/or by addition to a given sample of sequence-specific proteases such as trypsin, chymotrypsin, Gluc, and LysN. Modifications of peptides include but are not limited to post-translational farnesylation, glycosylation, deamination, and proteolytic processing.

In certain embodiments, the peptide is a fungal mating pheromone, e.g., a peptide specific to a fungal pathogen. Non-limiting examples of fungal mating pheromones include human fungal mating pheromones (meaning mating pheromones of fungi that can colonize or infect humans), non-human fungal mating pheromones (meaning mating pheromones of fungi that colonize or infect a non-human animal), plant fungal mating pheromones (meaning mating pheromones of fungi that colonize or infect a plant), food fungal mating pheromones (e.g., food safety/spoilage) (meaning mating pheromones of fungi that colonize or infect human or non-human animal food items), and industrial/model fungal mating pheromones. In certain embodiments, the industrial/model fungal mating pheromones are fungi species that are used for making food (e.g., fermentation of alcohol). In certain embodiments, the industrial/model fungal mating pheromones are fungi species that are used for industrial microbiology, e.g., production of drugs, or pesticides in agriculture. In certain embodiments, the industrial/model fungal mating pheromones are fungi species that are used for academic research.

Non-limiting examples of human fungal mating pheromones include the mating pheromones of *C. albicans*, *C. glabrata*, *P. brasiliensis*, *L. elongisporous*, *P. rubens*, *C. guillermondi*, *C. tropicalis*, *C. parapsilosis*, *C. lusitaniae*, *S. scheckii*. and *Candida krusei*.

Non-limiting examples of non-human animal fungal mating pheromones include the mating pheromone of *P. destructans*.

Non-limiting examples of plant fungal mating pheromones include the mating pheromones of *F. graminearum*, *M. oryzea*, *B. cinerea*, *G. candidum*, and *C. purpurea*.

Non-limiting exmaples of food fungal mating pheromones include the mating pheromones of *Zygosaccharomyces bailii*, *Zygosaccharomyces rouxii*, and *N. fischeri*.

Non-limiting exmaples of industrial/model fungal mating pheromones include the mating pheromones of *S. cerevisiae*, *K. lactis*, *S. pombe*, *V. polyspora* (receptor 1), *V. polyspora* (receptor 2), *S. stipitis*, *S. japonicas*, *S. castellii*, and *S. octosporus*, *A. oryzae*, *T. melanosporum*, *D. haptotyla*, *C. tenuis*, *Y. lipolytica*, *T. delbrueckii*, *B. bassiana*, *K. pastoris*, *A. nidulans*, *N. crassa*, and *H. jecorina*.

In certain embodiments, the peptide is a peptide disclosed in Table 5.

In certain embodiments, the physicochemical properties, e.g., peptide length, overall charge, charge distribution and hydrophobicity/hydrophilicity, of a peptide are determined by using the program ProtParam on the Expasy server [Walker (2005) ISBN 978-1-59259-890-8]. In certain embodiments, the peptide has a length of 3 residues or more, a length of 4 residues or more, a length of 5 residues or more, 6 residues or more, 7, residues or more, 8 residues or more, 9 residues or more, 10 residues or more, 11 residues or more, 12 residues or more, 13 residues or more, 14 residues or more, 15 residues or more, 16 residues or more, 17 residues or more, 18 residues or more, 19 residues or more, 20 residues or more, 21 residues or more, 22 residues or more, 23 residues or more, 24 residues or more, 25 residues or more, 26 residues or more, 27 residues or more, 28 residues or more, 29 residues or more, 30 residues or more, 31 residues or more, 32 residues or more, 33 residues or more, 34 residues or more, 35 residues or more, 36 residues or more, 37 residues or more, 38 residues or more, 39 residues or more, 40 residues or more, 41 residues or more, 42 residues or more, 43 residues or more, 44 residues or more, 45 residues or more, 46 residues or more, 47 residues or more, 48 residues or more, 49 residues or more, or 50 residues or more. In certain embodiments, the peptide has a length of 3-50 residues, 5-50 residues, 3-45 residues, 5-45 residues, 3-40 residues, 5-40 residues, 3-35 residues, 5-35 residues, 3-30 residues, 5-30 residues, 3-25 residues, 5-25 residues, 3-20 residues, 5-20 residues, 3-15 residues, 5-15 residues, 3-10 residues, 3-10 residues, 5-10 residues, 10-15 residues, 15-20 residues, 20-25 residues, 25-30 residues, 30-35 residues, 35-40 residues, 40-45 residues, or 45-50 residues. In certain embodiments, the peptide has a length of 9-25 residues. In certain embodiments, the peptide has a length of 9-23 residues. In one non-limiting embodiments, the peptide has a length of 9 residues. In one non-limiting embodiments, the peptide has a length of 10 residues. In one non-limiting embodiments, the peptide has a length of 11 residues. In one non-limiting embodiments, the peptide has a length of 12 residues. In one non-limiting embodiments, the peptide has a length of 13 residues. In one non-limiting embodiments, the peptide has a length of 14 residues. In one non-limiting embodiments, the peptide has a length of 15 residues. In one non-limiting embodiments, the peptide has a length of 16 residues. In one non-limiting embodiments, the peptide has a length of 17 residues. In one non-limiting embodiments, the peptide has a length of 18 residues. In one non-limiting embodiments, the peptide has a length of 19 residues. In one non-limiting embodiments, the peptide has a length of 20 residues. In one non-limiting embodiments, the peptide has a length of 21 residues. In one non-limiting embodiments, the peptide has a length of 22 residues. In one non-limiting embodiments, the peptide has a length of 23 residues.

In certain embodiments, the peptide is hydrophobic. In certain embodiments, the peptide is mildly hydrophilic.

In certain embodiments, the peptide is a *S. cerevisiae* pheromone alpha-factor. The C-terminus of the *S. cerevisiae* pheromone alpha-factor is involved in binding to the receptor. The N-terminus of the *S. cerevisiae* pheromone alpha-factor contributes to signaling due to receptor activation.

Non-limiting examples of classes of peptide analytes include the following.

5.5.1. Peptides as Analytes in Diseases 5.5.1.1. Peptides in Fungal Infections

Suitable analyte peptides associated with fungal infections include, but are not limited to, a peptide from *Aspergillus* (e.g., *Aspergillus niger*), *Candida* (e.g., *C. albicans* or *C. glabrata*), *Cryptococcus* (e.g., *Cryptococcus neoformans* or *Cryptococcus gattii*), *Histoplasma* (e.g., *Histoplasma capsulatum*), *Pneumocystis* (e.g., *Pneumocystis jirovecii*), or *Stachybotrys* (e.g., *Stachybotrys chartarum*).

In certain embodiments, the agent-specific peptide is a peptide pheromone produced by a pathogenic fungus or a proteolytic product from a pathogenic fungus.

5.5.1.2. Peptides in Bacterial Infections

Suitable analyte peptides associated with bacterial infections include, but are not limited to, a peptide from *V. cholera* (e.g., Cholera toxin), *Staphylococcus aureus* (e.g., staphylococcal auto-inducing peptide or portion of beta toxin), and *Salmonella* spec. (e.g., *Salmonella* Exotoxins). In certain embodiments, an agent-specific analyte is a peptide derived from the cholera toxin or a proteolytic product from cholera. The proteolytic product from cholera can be generated by a host-specific protease and/or by an exogenous protease. In certain embodiments, an agent-specific analyte is a small molecule secreted or derived from *Vibrio cholera*. In certain embodiments, an agent-specific peptide is *Vibrio cholerae* specific or at least specific to a small group of bacteria including *Vibrio cholerae* (for example a group of up to 10 known species or up to 5 known species).

In certain embodiments, the peptide derived from the cholera toxin is selected from the group consisting of the peptides disclosed in Table 7.

In certain embodiments, the peptide associated with *V. cholera* is selected from the group consisting of a peptide having an amino acid sequence set forth in VEVPGSQHIDSQKKA (SEQ ID NO: 26), a peptide having an amino acid sequence that is at least about 80% (e.g., at least about 85%, at least about 90%, at least about 95%, at least about 98%, or at least about 99%) homologous to SEQ ID NO: 26, a peptide having an amino acid sequence set forth in VPGSQHIDS (SEQ ID NO: 27), and a peptide having an amino acid sequence that is at least 80% (e.g., at least about 85%, at least about 90%, at least about 95%, at least about 98%, or at least about 99%) homologous to SEQ ID NO: 27.

5.5.1.3. Peptides in Viral Infections

Suitable analyte peptides associated with viral infections include, but are not limited to, a peptide from Ebola virus (e.g., secreted glycoprotein), Influenza virus (e.g., Hemagglutinin), or HIV (e.g., HIV glycoprotein)

5.5.1.4. Peptides in Non-Infectious Disease

Patterns of peptide biomarkers unique for certain cancer types have been identified by mass spectrometry.[60-63] Suitable analyte peptides associated with cancer include, but are not limited to, protein portions released from human endogenous proteins by tumor-specific exopeptidases or antibody-derived peptide biomarkers for well characterized disease states.

Peptide or protein biomarkers have been identified in other diseases, e.g., Alzheimers,[64] Parkinson,[65] or different kidney diseases.[66] Such peptides and proteins may also function as analytes.

5.5.2. Peptides as Analytes in Food Safety 5.5.2.1. Toxins

Suitable analyte peptides associated with food toxins include, but are not limited to, a peptide from *Clostridium botulinum* (e.g., Botulinum toxin), Shiga toxin-producing *Escherichia coli* (STEC) (e.g., Shiga toxin), and *Shigella dysenteriae* (e.g., Verotoxin).

5.5.2.2. Immunogens and Allergens

Suitable analyte peptides associated with food immunogens and allergens include, but are not limited to, immunogenic wheat peptide (e.g., gluten).

5.5.3. Peptides in Plant & Crop Infections

Suitable analyte peptides associated with plant and crop infections include, but are not limited to, a peptide of *Fusarium graminearum, Botrytis cinerea, Magnaporthe oryzae*, and *Geotrichum candidum*.

5.5.4. Peptides in Bioterrorism

Suitable analyte peptides associated with bioterrorism include, but are not limited to, peptides of *Bacillus anthracis* (anthrax), e.g., one of three polypeptides that comprise the anthrax toxin secreted by the pathogen: protective antigen (PA), lethal factor (LF) and edema factor (EF),[67] or *Clostridium botulinum* (botulism), e.g., Botulinum neurotoxin peptides such as the cyclic peptide C11-019.[68]

5.5.5. Other Analytes

Non-peptide analytes can include, but are not limited to, quorum sensing small molecules such as the Vibrio Cholera CAI-1,[69] inter-species bacterial quorum sensing AL-2,[70] aflatoxin B1 produced by Aspergillus flavus, components of the bacterial LPS, or heavy metals contaminants such as cadmium, mercury, lead or arsenic.

5.6. Methods of Use

The present invention provides for a method of detecting the presence of an agent of interest in a sample using the sensor cell disclosed herein. In certain embodiments, the method comprises contacting the sample with a sensor cell (e.g., a yeast sensor cell) comprising (e.g., bearing) a receptor (e.g., a non-native GPCR receptor) that binds to an analyte indicative of the presence of the agent, wherein binding of the analyte to the receptor triggers a detection event that is indicative of the presence of the agent (e.g., increased expression of a reporter gene).

In certain embodiments, the receptor is coupled to the reporter gene. The method further comprises culturing the sensor cell for an effective period of time; and determining expression of the reporter gene. In certain embodiments, determining whether expression of the reporter gene comprises detecting the expression of the reporter gene by the naked eye and does not require instrumentation. In certain non-limiting embodiments, the reporter is lycopene.

In certain embodiments, the detection event is release of a therapeutic molecule that directly remediates the agent.

In certain embodiments, the detection event is production of a redox active molecule. The method further comprises measuring the production of the redox active molecule. In certain embodiments, measuring the production of the redox active molecule comprises an electronic device. The redox active molecule can be phenazine.

In certain embodiments, the detection event is a change in the membrane potential of the sensor cell. The change in the membrane potential of the sensor cell comprises expression of a cAMP-activated ion channel in the sensor cell.

The particulars of the receptor, coupling, and reporter gene are described in the sections above.

The method for determining whether the reporter gene is or has been expressed depends upon the particular reporting gene used. If the reporter gene produces a visibly detectable product, such as lycopene, it can be detected with the naked eye or colorimetrically. Means of detection of reporter genes known in the art can be used.

In certain non-limiting embodiments, the receptor is a G-protein coupled receptor (GPCR) engineered to bind to the analyte.

By way of non-limiting example, a method of detecting the presence of *Vibrio cholerae* in a water sample can include detecting the presence of a peptide associated with *Vibrio cholerae* in the water sample by a method comprising:

contacting the water sample with a sensor yeast cell bearing a GPCR polypeptide that binds to the analyte coupled to a CrtI gene such that when the peptide binds to the receptor, expression of the CrtI gene is induced and lycopene is produced;

culturing the sensor yeast cell for an effective period of time; and determining whether lycopene has been produced.

The analyte associated with *Vibrio cholerae* can be a peptide having at least about 80%, at least about 85%, at least about 90%, at least about 95%, at least about 98%, or at least about 99% homologous to VEVPGSQHIDSQKKA (SEQ ID NO: 26) or VPGSQHIDS (SEQ ID NO: 27). The effective period of time can be hours (e.g., about 24 hours, about 18 hours, about 12 hours, about 8 hours, about 6 hours, about 4 hours, about 3 hours, or about 2 hours) or minutes (e.g., about 90 minutes, about 60 minutes, about 45 minutes, about 30 minutes, about 20 minutes, about 15 minutes, about 10 minutes, about 5 minutes, about 3 minutes, about 2 minutes, or about 1 minute).

In certain non-limiting embodiments, the present invention provides for a method of detecting the presence of a fungus or a fungal pathogen, comprising detecting the presence of an analyte associated with said fungus or a fungal pathogen in a sample by a method comprising:

contacting the sample with a sensor cell comprising (e.g., bearing) a receptor that binds to the analyte coupled to a reporter gene such that when the analyte binds to the receptor, expression of a detectable reporter gene is induced;

culturing the sensor cell for an effective period of time; and determining whether the reporter gene is expressed. In certain non-limiting embodiments, the receptor is a G-protein coupled yeast receptor engineered to bind to the analyte. In certain non-limiting embodiments, the reporter gene expression is detected by the naked eye and does not require instrumentation. In certain non-limiting embodiments, the reporter gene product is lycopene.

In certain embodiments, the sensor cell is a freeze-dried or other dried cell, e.g., a freeze-dried yeast cell. The cell can be activated for use by addition of a food source, e.g., sugar or agar.

Non-limiting examples of samples can include a water sample and a sample of body fluid. Non-limiting examples of water samples include fresh water, sea water, and sewage samples. Non-limiting examples of body fluid samples include intestinal fluids, diarrhea or other feces, mucus (e.g., sputum), blood, cerebrospinal fluid, lymph, pus, saliva, vomit, urine, bile, and sweat. In certain embodiments, the agent to be detected is a plant fungal pathogen. A plant can be shaken in water to provide a water sample containing the fungal pathogen, or a soil sample can be mixed with water and tested for the fungal pathogen, or a portion of plant material (e.g., a fluid obtained from the plant) can be used as a sample.

5.7. Kits

The present invention provides kits for detecting the presence of an agent of interest, for example but not limited to a chemical or a pathogen, as described above. Kits can include one or more sensor cells, as described above, and can be used to perform methods of detecting the presence of an agent, as described above. Kits can further include one or more controls. Kits can include both a positive and a negative control. Kits can include a substrate that comprises the sensor cells and on which or in which detection can occur, e.g., a dish, cup, bowl, plate, paper, chip, gel, bag, stick, syringe, jar, or bottle. Kits can include a food or nutrient source, e.g., sugar or agar. Kits can include components to improve cell viability, including one or more carbon sources, one or more nitrogen sources, one or more trace nutrient sources, and one or more additional nutrient sources to improve response speed. Kits can include additional assay components, including proteases to release target peptides, dyes, filters, and/or cryo-protectants. Kits can be produced by combining all required assay components (e.g., nutrients, sensor cells, and proteases) and freeze-drying, air-drying, or binding this component mix to a substrate. In certain embodiments, the kit comprises a protease (e.g., a protease from prokaryote sources or a protease from eukaryote sources) for digestion of the agent into smaller detectable peptides.

FIG. 14A represents a kit ("Yeast Block") in accordance with one non-limiting embodiments. As shown in FIG. 14A, the kit comprises a yeast cell, a piece of paper, a negative control, and a nutrient source.

5.7.1 Dipstick Embodiments

In particular non-limiting embodiments, the invention provides for a kit comprising biosensor cells on a solid support comprised in a dipstick configuration. The solid support may be any natural and/or synthetic material, including but not limited to glass fiber, cellulose, quartz fiber, cellulose fiber, polytetrafluoroethylene, cotton, rayon, viscose, etc. In non-limiting examples, the support material may be configured such that the biosensor cells may be applied by filtration; for example, biosensor cells may be applied, by filtration, to a filter paper or disk, and then at least a portion of that paper or disk (e.g. a section of the filter paper or disk) may be incorporated into a dipstick configuration. Alternatively, the biosensor cells may be applied by direct application, for example, applying a volume of liquid culture. The solid support may be affixed, prior to or after (or concurrently with) application of biosensor cells, to a support strip to create a dipstick having a proximal end that may be directly or indirectly held by the user and a distal end bearing the solid support and biosensor cells, permitting dipping the biosensor into a sample to be tested. In certain embodiments, the support strip has liquid wicking activity (e.g., absorbent paper or other material). The proximal end of the dipstick may optionally fit into a holder (to form a dipstick device) that facilitates gripping the dipstick device. In certain non-limiting embodiments, the dipstick comprises a solid support having at least a portion of its surface bearing an amount of biosensor cells sufficient to generate detectable signal after contacting an analyte of interest, and optionally a portion bearing an amount of a negative control (e.g. cells that would not generate detectable signal after contact with the analyte of interest). In certain non-limiting embodiments, the dipstick comprises a solid support having at least several portions of its surface (e,g., an array) each bearing distinct biosensor cells with each type of biosensor cells present in an amount sufficient to generate detectable signal after contacting its corresponding analyte or analytes of interest. In certain non-limiting embodiments, the amount of biosensor is at least between about $1 \times 10^6$ and $5 \times 10^8$ cells, or between about $1 \times 10^7$ and $1 \times 10^8$ cells. Cells may be applied to the support, for example, by vacuum filtration. After application of biosensor to solid support, the composition may optionally be allowed to dry for at least about 20 minutes. The present invention provides for a kit comprising one or more dipstick, and optionally comprising one or more holder; in a particular embodiment, the kit comprises 1-3 holders, or one holder, and at least 3 or at least 5 or at least 10 dipsticks for testing for the same or different analytes. In certain non-limiting embodiments, a method is provided in which the dipstick described above may be used to detect an analyte of interest or an array of analytes of interest by dipping its distal end, bearing the biosensor cells and/or the negative control cells and/or the array of distinct biosensor cell types, into a sample such that the biosensor cells and/or the negative control cells and/or the array of distinct biosensor cell types contact the sample, and then incubating the dipstick at a temperature that is at least about 20° C., preferably greater than 20° C., and preferably greater than 25° C., for a period of time that allows signal to develop, for example, but not limited to, at least about 1 hour, at least about 3 hours, at least about 5 hours, at least about 7 hours, at least about 10 hours, at least about 12 hours or at least 15 hours. In certain situations, it may be desirable to add liquid (e.g. water, saline, or a medium that allows or promotes growth of biosensor cells) to a sample prior to testing; for example, where the biosensor is a yeast, a sample may be diluted with yeast growth medium. In certain exemplary non-limiting embodiments, urine or serum may be diluted 1:1 with yeast growth medium, and blood may be diluted about 2:98 with yeast growth medium. A solid sample, such as soil or stool, may be suspended in yeast growth medium prior to testing. In certain non-limiting embodiments, a kit is provided comprising at least one dipstick as described above, optionally a dipstick holder, and either liquid nutrient medium or powdered medium that can be reconstituted, by addition of water or other liquid, to form a liquid nutrient medium for growth of biosensor cells. In certain non-limiting embodiments, a kit is provided comprising at least one dipstick as described above, optionally a dipstick holder, and either liquid yeast nutrient medium or powdered medium that can be reconstituted, by addition of water or other liquid, to form a liquid yeast nutrient medium for growth of yeast biosensor cells, as described above.

6. EXAMPLES

6.1. Example 1: Yeast Strains that Produce Lycopene in Response to Activation of the Endogenous GPCR Ste2

A yeast strain producing lycopene in response to the activation of the endogenous GPCR, Ste2 was generated by the natural *S. cerevisiae* peptide pheromone, α-Factor (αF). A parental reporter strain was made by deleting the cyclin-dependent kinase inhibitor Far1 to prevent cell-cycle arrest and deleted the G-protein activating protein Sst2 to prevent signal attenuation. For general procedures, see Pausch, M. H. G-protein-coupled receptors in *Saccharomyces cerevisiae*: high-throughput screening assays for drug discovery. Trends Biotechnol. 15, 487-494 (1997). Then, the carotenoid genes derived from *E. herbicola*, CrtE, and CrtB were placed under the control of the constitutive promoters pTef1 and pPgk1, respectively. The final biosynthetic gene CrtI was placed under control of the Fus1 promoter, a downstream target of the pheromone response pathway. See Bardwell, L. A walk-through of the yeast mating pheromone response pathway. Peptides 26, 339-350 (2005). This lycopene reporter cassette was introduced into the parental reporter strain through Reiterative Recombination. See Wingler, L. M. & Cornish, V. W. Reiterative Recombination for the in vivo assembly of libraries of multigene pathways. Proc Natl Acad Sci USA 108, 15135-15140 (2011). This v1.0 reporter strain became visibly orange 36 hours after exposure to αF, as shown in FIG. 4A.

Through modification of the v1.0 strain, a lycopene response time of 2 hours under optimal culture conditions and less than 6 hours in a stringent product prototype assay was observed. To do so, the CrtI amount was increased with an additional chromosomal copy of the pFus1-CrtI construct. This led to a 9.8-fold improvement in response time. The catalytic activity of CrtI was improved by increasing FAD content in the cell through the overexpression of the FAD synthetase FAD1. See Schaub, P. et al. On the Structure and Function of the Phytoene Desaturase CRTI from Pantoea ananatis, a Membrane-Peripheral and FAD-Dependent Oxidase/Isomerase. PLoS ONE 7, e39550 (2012); Wu, M., Repetto, B., Glerum, D. M. & Tzagoloff, A. Cloning and characterization of FAD1, the structural gene for flavin adenine dinucleotide synthetase of *Saccharomyces cerevisiae*. Mol. Cell. Biol. 15, 264-271 (1995). This modification independently led to a 10.3-fold improvement in the response time, and to a 21.1-fold improvement when combined with the increased CrtI copy number. These results are shown in FIG. 4B.

TABLE 1

Key genes and sequences.

| Key Genes | Nucleotide Sequence |
|---|---|
| E. herbicola CrtI | ATGAAGAAAACCGTAGTGATTGGTGCAGGTTTTG GTGGTTTAGCTTTGGCTATACGTCTACAAGCTGC AGGTATTCCTACAGTGCTATTGGAGCAAAGAGAC AAACCAGGAGGAAGAGCTTATGTTTGGCACGATC AAGGCTTTACCTTTGATGCTGGTCCTACAGTCAT CACTGATCCTACTGCATTGGAAGCTTTGTTCACC TTAGCTGGTAGAAGAATGGAAGATTATGTCCGTC TATTGCCTGTCAAGCCGTTTTACAGATTGTGTTG GGAATCTGGTAAAACCCTAGATTACGCCAATGAC AGTGCTGAACTAGAAGCTCAGATTACGCAGTTTA ATCCCAGAGATGTCGAAGGTTACAGGAGATTCCT TGCCTATTCCCAAGCTGTTTTCCAAGAGGGTTAT |

TABLE 1-continued

Key genes and sequences.

| Key Genes | Nucleotide Sequence |
|---|---|
| | CTTCGTTTGGGTTCAGTTCCATTCCTGTCCTTTA
GGGATATGCTTAGAGCAGGTCCTCAGTTGTTGAA
GCTACAAGCATGGCAAAGTGTGTATCAGTCTGTT
TCGAGATTTATCGAGGATGAACATCTGAGACAAG
CATTCTCATTCCACAGTCTTCTAGTTGGAGGTAA
TCCCTTTACCACATCGAGCATATATACGTTGATT
CACGCTTTGGAAAGAGAATGGGGAGTTTGGTTTC
CTGAAGGTGGAACAGGTGCTTTGGTTAATGGTAT
GGTGAAGCTATTCACGGATTTGGGTGGAGAAATA
GAGCTGAATGCAAGAGTGGAAGAACTTGTTGTAG
CAGACAACAGAGTCTCACAAGTTAGACTTGCTGA
TGGTAGGATCTTCGATACAGATGCTGTAGCTTCA
AACGCAGATGTAGTGAACACTTATAAAAAGTTGT
TGGGACATCATCCTGTTGGACAAAAGAGAGCAGC
TGCTTTGGAGAGGAAATCTATGAGCAACTCGTTG
TTTGTCCTTTACTTTGGGCTGAATCAACCACACT
CACAACTAGCTCATCACACAATCTGCTTTGGTCC
TAGATACAGAGAGCTGATAGATGAAATTTTCACT
GGATCTGCTTTAGCAGACGATTTTTCCCTGTACT
TGCATTCACCATGTGTTACTGATCCCTCTTTAGC
ACCACCTGGTTGTGCTAGCTTCTATGTACTAGCA
CCTGTACCACATTTGGGTAATGCTCCATTAGATT
GGGCACAAGAAGGACCGAAATTGAGGGATAGGAT
CTTCGACTATTTGGAAGAACGTTACATGCCAGGT
TTGAGATCTCAGTTGGTTACACAGAGGATATTCA
CACCAGCTGATTTTCATGATACTCTAGATGCGCA
TTTAGGTAGCGCTTTTTCCATTGAGCCACTTTTG
ACGCAAAGTGCTTGGTTTAGACCACACAACAGAG
ATTCTGACATTGCCAATCTGCTACCTAGTAGGTGC
AGGAACTCATCCAGGAGCTGGTATTCCTGGAGTT
GTAGCTTCTGCTAAAGCTACTGCTAGTCTGATGA
TCGAGGATTTGCAGTAA (SEQ ID NO: 1) |
| E. herbicola CrtE | ATGGTTTCTGGTTCGAAAGCAGGAGTATCACCTC
ATAGGGAAATCGAAGTCATGAGACAGTCCATTGA
TGACCACTTAGCAGGATTGTTGCCAGAAACAGAT
TCCCAGGATATCGTTAGCCTTGCTATGAGAGAAG
GTGTTATGGCACCTGGTAAACGTATCAGACCTTT
GCTGATGTTACTTGCTGCAAGAGACCTGAGATAT
CAGGGTTCTATGCCTACACTACTGGATCTAGCTT
GTGCTGTTGAACTGACACATACTGCTTCCTTGAT
GCTGGATGACATGCCTTGTATGGACAATGCGGAA
CTTAGAAGAGGTCAACCAACAACCCACAAGAAAT
TCGGAGAATCTGTTGCCATTTTGGCTTCTGTAGG
TCTGTTGTCGAAAGCTTTTGGCTTGATTGCTGCA
ACTGGTGATCTTCCAGGTGAAAGGAGAGCACAAG
CTGTAAACGAGCTATCTACTGCAGTTGGTGTTCA
AGGTCTAGTCTTAGGACAGTTCAGAGATTTGAAT
GACGCAGCTTTGGACAGAACTCCTGATGCTATCC
TGTCTACGAACCATCTGAAGACTGGCATCTTGTT
CTCAGCTATGTTGCAAATCGTAGCCATTGCTTCT
GCTTCTTCACCATCTACTAGGGAAACGTTACACG
CATTCGCATTGGACTTTGGTCAAGCCTTTCAACT
GCTAGACGATTTGAGGGATGATCATCCAGAGACA
GGTAAAGACCGTAACAAAGACGCTGGTAAAAGCA
CTCTAGTCAACAGATTGGGTGCTGATGCAGCTAG
ACAGAAACTGAGAGAGCACATTGACTCTGCTGAC
AAACACCTGACATTTGCATGTCCACAAGGAGGTG
CTATAAGGCAGTTTATGCACCTATGGTTGGACA
CCATCTTGCTGATTGGTCTCCAGTGATGAAGATC
GCCTAA (SEQ ID NO: 2) |
| E. herbicola CrtB | ATGAGTCAACCACCTTTGTTGGATCATGCTACTC
AAACGATGGCTAATGGTTCCAAGTCCTTTGCTAC
AGCAGCTAAACTGTTTGACCCAGCTACTAGAAGA
TCAGTGCTTATGCTGTACACTTGGTGTAGACACT
GTGATGACGTTATAGATGACCAGACACATGGTTT
CGCATCTCGAAGCTGCTGCAGAAGAGGCTACT
CAGAGATTGGCTAGATTGAGAACGCTTACACTTG
CAGCTTTTGAAGGTGCTGAGATGCAAGATCCTGC
TTTTGCTGCATTCCAAGAAGTTGCACTAACACAC
GGTATTACGCCAAGAATGGCACTTGATCACTTGG
ATGGTTTCGCAATGGATGTTGCTCAAACTCGTTA
CGTGACCTTTGAAGACACCTTGAGATACTGCTAC
CATGTTGCTGGAGTAGTTGGTTTGATGATGGCAA
GAGTAATGGGTGTAAGAGACGAAAGGGTTTTGGA | | Key Genes | Nucleotide Sequence |
|---|---|
| | CAGAGCTTGTGATCTAGGTTTGGCTTTTCAGCTG
ACAAACATCGCGAGAGATATTATCGACGATGCAG
CTATTGACAGATGCTATCTACCTGCTGAATGGTT
GCAAGATGCTGGTCTAACTCCTGAGAATTACGCT
GCAAGAGAGAACAGAGCTGCATTAGCAAGAGTTG
CTGAAAGGCTGATAGACGCTGCTGAACCCTATTA
CATCTCAAGTCAAGCTGGATTGCATGATCTACCA
CCTAGATGTGCTTGGGCTATAGCTACTGCAAGAT
CTGTCTACAGAGAGATTGGCATCAAGGTAAAAGC
TGCAGGTGGTTCTGCTTGGGATAGACGTCAACAC
ACTAGCAAAGGAGAGAAGATTGCGATGCTTATGG
CTGCACCAGGACAAGTCATTCGTGCCAAAACAAC
CAGAGTTACACCAAGACCTGCTGGTTTTATGGCAA
AGACCTGTCTAA (SEQ ID NO: 3) |
| S. cerevisiae Fad1 | ATGCAGTTGAGCAAGGCTGCTGAGATGTGTTATG
AGATAACAAACTCTTACTTACACATAGACCAGAA
ATCTCAGATAATAGCAAGTACACAAGAAGCGATA
CGGTTGACAAGAAAATACTTACTAAGTGAAATTT
TTGTACGTTGGAGTCCACTGAATGGGAAATATC
ATTCTCGTACAACGGAGGAAAAGATTGCCAGGTA
TTACTACTGTTATATCTGAGTTGCTTATGGGAAT
ATTTCTTCATTAAGGCTCAAAATTCCCAATTCGA
TTTCGAGTTTCAAAGCTTCCCCATGCAAAGACTT
CCAACTGTTTTCATTGATCAAGAAGAAACTTTCC
CTACATTAGAGAATTTTGTACTGGAAACCTCAGA
GCGATATTGCCTTTCCTTATACGAATCACAAAGG
CAATCTGGTGCATCGGTCAATATGGCAGACGCAT
TTAGAGATTTTATAAAGATATACCCTGAGACCGA
AGCTATAGTGATAGGTATTAGACACACAGACCCA
TTTGGTGAAGCATTAAAGCCTATTCAAAGAACAG
ATTCTAACTGGCCTGATTTTATGAGGTTGCAACC
TCTCTTACACTGGGACTTAACCAATATATGGAGT
TTCTTACTGTATTCTAATGAGCCAATTTGTGAC
TATATGGTAAAGGTTTCACATCAATCGGCGGAAT
TAACAACTCATTGCCTAACCCACACTTGAGAAAG
GACTCCAATAATCCAGCCTTGCATTTTGAATGGG
AAATCATTCATGCATTTGGCAAGGACGCAGAAGG
CGAACGTAGTTCCGCTATAAACACGTCACCTATT
TCCGTGGTGGATAAGGAAAGATTCAGCAAATACC
ATGACAATTACTATCCTGGCTGGTATTTGGTTGA
TGACACTTTAGAGAGAGCAGGCAGGATCAAGAAT
TAA (SEQ ID NO: 4) |

6.2. Example 2: Cloning and Screening of Putative GPCRs Against Putative Cognate Fungal Peptide Hormones Several putative GPCRs were screened against their putative cognate peptide pheromones using a fluorescent reporter gene.[33] Recognition of pheromones from the following pathogenic fungi was shown in *S. cerevisiae:*

Human pathogens:
 *Candida albicans* (functional expression in yeast previously shown)[17]
 *Paracoccidioides brasiliensis* (functional expression in yeast previously shown)[16]
 *Candida glabrata*

Plant Pathogens:
 *Fusarium graminearum* (grain disease)
 *Magnaporthe oryzea* (Rice blast)
 *Botrytis cinerea* (Grey mould)

As shown in FIG. 6, these receptors were orthogonal to the endogenous *S. cerevisiae* pheromone receptor and demonstrated a high level of specificity. Their EC50 values were as follows: *C.albicans*, 51 nM; *P. brasiliensis*, 9 nM; *F. graminearum*, 230 nM; *M. oryzea*, 5 uM; *B. cinerea*, <1 nM. Additionally, the GPCR from *B. cinerea* showed activity against the putative pheromone from *Aspergillus flavus* and therefore may provide a useful diagnostic against this human pathogen. The results also demonstrated that these receptors succesfully generate lycopene in the disclosed reporter strain.

TABLE 2

Pathogens and associated sequences

| Pathogen | Amino acid sequence of peptide analyte used | Amino acid sequence of GPCRs used | DNA coding sequence of corresponding GPCRs that sense peptide analyte |
|---|---|---|---|
| Candida albicans | GFRLTNF GYFEPG (SEQ ID NO: 5) | MNINSTFIPDKPGDI IISYSIPGLDQPIQI PFHSLDSFQTDQAKI ALVMGITIGSCSMTL IFLISIMYKTNKLTN LKLKLKLKYILQWIN QKIFTKKRNDNKQQQ QQQQQQIESSSYNNT TTTLGGYKLFLFYLN SLILLIGIIRSGCYL NYNLGPLNSLSFVFT GWYDGSSFISSDVTN GFKCILYALVEISLG FQVYVMFKTSNLKIW GIMASLLSIGLGLIV VAFQINLTILSHIRF SRAISTNRSEEESSS SLSSDSVGYVINSIW MDLPTILFSISINIM TILLIGKLIIAIRTR RYLGLKQFDSFHILL IGFSQTLIIPSIILV VHYFYLSQNKDSLLQ QISLLLIILMLPLSS LWAQTANNTHNINSS PSLSFISRHHLSDSS RSGGSNTIVSNGGSN GGGGGGGNFPVSGID AQLPPDIEKILHEDN NYKLLNSNNESVNDG DIIINDEGMITKQIT IKRV (SEQ ID NO: 6) | ATGAATATCAATTCAACTTTCATACCTGAT AAACCAGGCGATATAATTATTAGTTATTCA ATTCCAGGATTAGATCAACCAATTCAAATT CCTTTCCATTCATTAGATTCATTTCAAACC GATCAAGCTAAAATAGCTTTAGTCATGGGG ATAACTATTGGGAGTTGTTCAATGACATTA ATTTTTTTGATTTCTATAATGTATAAAACT AATAAATTAACAAATTTAAAATTAAAATTA AAATTAAAATATATCTTGCAATGGATAAAT CAAAAAATCTTCACCAAAAAAAGGAATGAC AACAAACAACAACAACAACAACAACAACAA CAAATTGAATCATCATCATATAACAATACT ACTACTACGCTGGGGGGTTATAAATTATTT TTATTTTATCTTAATTCATTGATTTTATTA ATTGGTATTATTCGATCAGGTTGTTATTTA AATTATAATTTAGGTCCATTAAATTCACTT AGTTTTGTATTTACTGGTTGGTATGATGGA TCATCATTTATATCATCCGATGTAACTAAT GGATTTAAATGTATTTTATATGCTTTAGTG GAAATTTCATTAGGTTTCCAAGTTTATGTG ATGTTCAAAACTTCAAATTTAAAAATTTGG GGGATAATGGCATCATTATTATCAATTGGT TTAGGATTGATTGTTGTTGCCTTTCAAATC AATTTAACAATTTTATCTCATATTCGATTT TCCCGGGCTATATCAACTAACAGAAGTGAA GAAGAATCATCATCATCATTATCATCTGAT TCGGTTGGGTATGTGATTAATTCAATATGG ATGGATTTACCAACAATATTATTTTCCATT AGTATTAATATAATGACAATATTATTGATT GGTAAACTTATAATTGCTATTAGAACAAGA CGTTATTTAGGATTGAAACAATTTGATAGT TTCCATATTTTATTAATTGGTTTCAGTCAA ACATTAATTATTCCTTCAATTATTTTGGTG GTTCATTATTTTTATTTATCACAAAATAAA GATTCTTTATTACAACAAATTAGTCTTTTA TTGATTATTTTAATGTTACCATTAAGTTCT TTATGGGCTCAAACTGCTAATAATACTCAT AATATTAATTCATCTCCAAGTTTATCATTC ATATCTCGTCATCATCTGTCTGATAGTAGT CGTAGTGGTGGTTCCAATACAATTGTTAGT AATGGTGGTAGTAATGGTGGTGGTGGTGGT GGTGGGAATTTCCCTGTTTCAGGTATTGAT GCACAATTACCACCTGATATTGAAAAAATC TTACATGAAGATAATAATTATAAATTACTT AATAGTAATAATGAAAGTGTAAATGATGGA GATATTATCATTAATGATGAAGGTATGATT ACTAAACAAATCACCATCAAAAGAGTGTAG (SEQ ID NO: 7) |
| Candida glabrata | WHWVRLR KGQGLF (SEQ ID NO: 8) | MEMGYDPRMYNPRNE YLNFTSVYDVNDTIR FSTLDAIVKGLLRIA IVHGVRLGAIFMTLI IMFISSNTWKKPIFI INMVSLMLVMIHSAL SFHYLLSNYSSISYI LTGFPQLITSNNKRI QDAASIVQVLLVAAI EASLVFQIHVMFTIE NIKLIREIVLSISIA MGLATVATYLAAAIK LIRGLHDEVMPQTHL IFNLSIILLASSINF MTFILVIKLFFAIRS RRYLGLRQFDAFHIL LIMFCQSLLIPSVLY IIVYAVDSRSNQDYL | ATGGAGATGGGCTACGATCCAAGAATGTAT AATCCAAGAAATGAATACTTGAATTTCACG TCGGTATATGATGTAAATGACACAATCAGA TTTTCGACTCTGGACGCCATTGTAAAAGGA TTGCTTAGAATTGCCATTGTTCATGGAGTT AGATTGGGAGCAATATTCATGACGTTAATA ATAATGTTTATCTCATCAAATACATGGAAA AAACCCATATTTATAATTAACATGGTGTCG TTGATGTTAGTTATGATTCATTCCGCACTT AGCTTCCATTACCTTTTATCGAATTATTCT TCAATTTCTTATATACTGACAGGGTTTCCT CAGTTGATTACAAGCAATAATAAACGAATT CAAGATGCAGCGAGTATAGTCCAAGTTTTA TTGGTTGCTGCGATAGAAGCATCATTGGTA TTTCAGATTCATGTTATGTTTACGATTGAA AACATTAAGCTTATTAGAGAAATAGTACTC TCTATATCGATAGCAATGGGATTGCAACA GTGGCTACATATCTTGCTGCAGCAATAAAG |

TABLE 2-continued

Pathogens and associated sequences

| Pathogen | Amino acid sequence of peptide analyte used | Amino acid sequence of GPCRs used | DNA coding sequence of corresponding GPCRs that sense peptide analyte |
|---|---|---|---|
| | | IPIANLFVVLSLPLS<br>SIWANTSNNSSRSPK<br>YWKNSQTNKSNGSFV<br>SSISVNSDSQNPLYK<br>KIVRFTSKGDTTRSI<br>VSDSTLAEVGKYSMQ<br>DVSNSNFECRDLDFE<br>KVKHTCENFGRISET<br>YSELSTLDTTALNET<br>RLFWKQQSQCDK<br>(SEQ ID NO: 9) | CTGATAAGAGGACTGCATGATGAGGTAATG<br>CCACAAACACATCTTATTTTCAATTTATCT<br>ATAATATTGCTTGCATCCTCCATAAATTTT<br>ATGACATTTATATTGGTCATTAAACTTTTC<br>TTCGCTATTAGATCTAGAAGATATCTCGGT<br>CTTCGTCAATTCGATGCTTTTCATATTTTA<br>TTAATCATGTTCTGCCAGTCATTATTGATA<br>CCCTCAGTATTATATATTATAGTTTACGCG<br>GTTGATAGCAGATCTAATCAGGATTATCTG<br>ATTCCAATTGCCAATTTATTTGTTGTTTTA<br>TCTTTGCCATTATCCTCTATCTGGGCTAAC<br>ACATCAAATAACTCATCCAGATCTCCAAAA<br>TATTGGAAAAACTCTCAAACGAATAAGAGC<br>AATGGGTCTTTTGTCTCTTCAATATCTGTC<br>AATAGTGACTCACAAAACCCTTTGTACAAA<br>AAGATTGTACGTTTTACATCAAAAGGCGAC<br>ACTACCCGTAGTATTGTAAGTGATTCAACA<br>TTAGCAGAGGTGGGAAAATACTCTATGCAA<br>GACGTTAGCAATTCAAACTTTGAATGTCGA<br>GACCTTGATTTTGAGAAGGTAAAACATACT<br>TGCGAAAATTTTGGCAGAATATCTGAAACA<br>TATAGTGAGTTAAGTACTTTAGATACCACT<br>GCCCTCAATGAGACTCGGTTGTTTTGGAAA<br>CAACAAAGTCAGTGTGACAAATAG<br>(SEQ ID NO: 10) |
| Paracocci-<br>dioides<br>brasiliensis | WCTRPGQ<br>GC<br>(SEQ ID<br>NO: 11) | MAPSFDPFNQSVVFH<br>KADGTPFNVSIHELD<br>DFVQYNTKVCINYSS<br>QLGASVIAGLMLAML<br>THSEKRRLPVFFLNT<br>FALAMNFARLLCMTI<br>YFTTGFNKSYAYFGQ<br>DYSQVPGSAYAASVL<br>GVVFTTLLVISMEMS<br>LLIQTRVVCTTLPDI<br>QRYLLMAVSSAISLM<br>AIGFRLGLMVENCIA<br>IVQASNFAPFIWLQS<br>ASNITITISTCFFSA<br>VFVTKLAYALVTRIR<br>LGLTRFGAMQVMFIM<br>SCQTMVIPAIFSILQ<br>YPLPKYEMNSNLFTL<br>VAIFLPLSSLWASVA<br>TRSSFETSSSGRHQY<br>LWPSEQSNNVTNSEI<br>KYQVSFSQNHTTLRS<br>GGSVATTLSPDRLDP<br>VYCEVEAGTKA<br>(SEQ ID NO: 12) | ATGGCACCCTCATTCGACCCCTTCAACCAA<br>AGCGTGGTCTTCCACAAGGCCGACGGAACT<br>CCATTCAACGTCTCAATCCATGAACTAGAC<br>GACTTCGTGCAGTACAACACCAAAGTCTGC<br>ATCAACTACTCTTCCCAGCTCGGAGCATCT<br>GTCATTGCAGGACTCATGCTTGCCATGCTG<br>ACACACTCAGAAAAGCGTCGTCTGCCAGTT<br>TTCTTCCTAAACACATTCGCACTGGCCATG<br>AACTTTGCCCGCCTGCTCTGCATGACCATC<br>TACTTCACCACGGGCTTCAACAAGTCCTAT<br>GCCTACTTTGGTCAGGATTACTCCCAGGTG<br>CCTGGGAGCGCCTACGCAGCCTCTGTCTTG<br>GGCGTTGTCTTCACCACTCTCCTGGTAATC<br>AGCATGGAAATGTCCCTCCTGATCCAAACA<br>AGGGTTGTCTGCACGACCCTTCCGGATATC<br>CAACGTTATCTACTCATGGCAGTTTCCTCC<br>GCGATTTCCCTGATGGCCATCGGGTTCCGC<br>CTTGGCTTAATGGTTGAGAACTGCATTGCC<br>ATTGTGCAGGCGTCGAATTTCGCCCCTTTT<br>ATCTGGCTTCAAAGCGCCTCGAACATCACC<br>ATTACGATCAGCACATGTTTCTTCAGTGCC<br>GTCTTTGTTACGAAATTGGCATATGCACTC<br>GTCACTCGTATACGACTAGGCTTGACGAGG<br>TTTGGTGCTATGCAGGTTATGTTCATCATG<br>TCCTGCCAGACTATGGTGATTCCAGCCATC<br>TTCTCAATTCTCCAATACCCACTCCCCAAG<br>TACGAAATGAACTCCAACCTCTTTACGCTG<br>GTGGCCATTTTCCTCCCTCTTTCCTCGCTA<br>TGGGCTTCAGTTGCTACGAGATCCAGTTTC<br>GAGACGTCTTCTTCCGGCCGCCATCAGTAT<br>CTTTGGCCAAGCGAACAGAGCAATAACGTC<br>ACCAATTCGGAAATTAAGTATCAGGTCAGC<br>TTCTCTCAGAACCACACTACGTTGCGGTCT<br>GGAGGGTCTGTGGCCACGACACTCTCCCCG<br>GACCGGCTCGACCCGGTTTATTGTGAAGTT<br>GAAGCTGGCACAAAGGCCTAG<br>(SEQ ID NO: 13) |
| Fusarium<br>graminearum | WCWWKGQ<br>PCW<br>(SEQ ID<br>NO: 14) | MSKEVFDPFTQNVTF<br>FAPDGKTEISIPVAA<br>IDQVRRMMVNTTINY<br>ATQLGACLIMLVVLL<br>VMVPKEKFRRPFMIL<br>QITSLVISCCRMLLL<br>SIFHSSQFLDFYVFW<br>GDDHSRIPRSAYAPS<br>VAGNTMSLCLVISVE | ATGTCTAAGGAAGTTTTCGACCCATTCACT<br>CAAAACGTTACTTTCTTCGCTCCAGACGGT<br>AAGACTGAAATCTCTATCCCAGTTGCTGCT<br>ATCGACCAAGTTAGAAGAATGATGGTTAAC<br>ACTACTATCAACTACGCTACTCAATTGGGT<br>GCTTGTTTGATCATGTTGGTTGTTTTGTTG<br>GTTATGGTTCCAAAGGAAAAGTTCAGAAGA<br>CCATTCATGATCTTGCAAATCACTTCTTTG<br>GTTATCTCTTGTTGTAGAATGTTGTTGTTG |

TABLE 2-continued

Pathogens and associated sequences

| Pathogen | Amino acid sequence of peptide analyte used | Amino acid sequence of GPCRs used | DNA coding sequence of corresponding GPCRs that sense peptide analyte |
|---|---|---|---|
| | | TMLMSQAWTMVRLWP NVWKYIIAGVSLIVS IMAISVRLAYTIIQN NAVLKLEPAFHMFWL IKWTVIMNVASISWW CAIFNIKLVWHLISN RGILPSYKTFTPMEV LIMTNGILMIIPVIF ASLEWAHFVNFESAS LTLTSVAVILPLGTL AAQRIASSAPSSANS TGASSGIRYGVSGPS SFTGFKAPSFSTGTT DRPHVSIYARCEAGT SSREHINPQGVELAK LDPETDHHVRVDRAF LQREERIRAPL (SEQ ID NO: 15) | TCTATCTTCCACTCTTCTCAATTCTTGGAC TTCTACGTTTTCTGGGGTGACGACCACTCT AGAATCCCAAGATCTGCTTACGCTCCATCT GTTGCTGGTAACACTATGTCTTTGTGTTTG GTTATCTCTGTTGAAACTATGTTGATGTCT CAAGCTTGGACTATGGTTAGATTGTGGCCA AACGTTTGGAAGTACATCATCGCTGGTGTT TCTTTGATCGTTTCTATCATGGCTATCTCT GTTAGATTGGCTTACACTATCATCCAAAAC AACGCTGTTTTGAAGTTGGAACCAGCTTTC CACATGTTCTGGTTGATCAAGTGGACTGTT ATCATGAACGTTGCTTCTATCTCTTGGTGG TGTGCTATCTTCAACATCAAGTTGGTTTGG CACTTGATCTCTAACAGAGGTATCTTGCCA TCTTACAAGACTTTCACTCCAATGGAAGTT TTGATCATGACTAACGGTATCTTGATGATC ATCCCAGTTATCTTCGCTTCTTTGGAATGG GCTCACTTCGTTAACTTCGAATCTGCTTCT TTGACTTTGACTTCTGTTGCTGTTATCTTG CCATTGGGTACTTTGGCTGCTCAAAGAATC GCTTCTTCTGCTCCATCTTCTGCTAACTCT ACTGGTGCTTCTTCTGGTATCAGATACGGT GTTTCTGGTCCATCTTCTTTCACTGGTTTC AAGGCTCCATCTTTCTCTACTGGTACTACT GACAGACCACACGTTTCTATCTACGCTAGA TGTGAAGCTGGTACTTCTTCTAGAGAACAC ATCAACCCACAAGGTGTTGAATTGGCTAAG TTGGACCCAGAAACTGACCACCACGTTAGA GTTGACAGAGCTTTCTTGCAAAGAGAAGAA AGAATCAGAGCTCCATTGTAG (SEQ ID NO: 16) |
| Magnaporthe oryzae | QWCPRRG QPCW (SEQ ID NO: 17) | MDQTLSATGTATSPP GPALTVDPRFQTITM LTPALMGQGFEEVQT TPAEINDVYFLAFNT AIGYSTQIGACFIML LVLLTMTAKARFARI PTIINTAALVVSIIR CTLLVIFFTSTMMEF YTIFSDDFSFVHPND IRRSVAATVFAPLQL ALVEAALMVQAWAMV ELWPRAWKVSGIAFS LILATVTVAFKCASA AVTVKSALEPLDPRP YLWIRQTDLAFTTAM VTWFCFLFNVRLIMH MWQNRSILPTVKGLS PMEVLVMANGLLMVF PVLFAGLYYGNFGQF ESASLTITSVVLVLP LGTLVAQRLAVNNTV AGSSANTDMDDKLAF LGNATTVTSSAAGFA GSSASATRSRLASPR QNSQLSTSVSAGKPR ADPIDLELQRIDDED DDFSRSGSAGGVRVE RSIERREERL (SEQ ID NO: 18) | ATGGACCAAACTTTGTCTGCTACTGGTACT GCTACTTCTCCACCAGGTCCAGCTTTGACT GTTGACCCAAGATTCCAAACTATCACTATG TTGACTCCAGCTTTGATGGGTCAAGGTTTC GAAGAAGTTCAAACTACTCCAGCTGAAATC AACGACGTTTACTTCTTGGCTTTCAACACT GCTATCGGTTACTCTACTCAAATCGGTGCT TGTTTCATCATGTTGTTGGTTTTGTTGACT ATGACTGCTAAGGCTAGATTCGCTAGAATC CCAACTATCATCAACACTGCTGCTTTGGTT GTTTCTATCATCAGATGTACTTTGTTGGTT ATCTTCTTCACTTCTACTATGATGGAATTC TACACTATCTTCTCTGACGACTTCTCTTTC GTTCACCCAAACGACATCAGAAGATCTGTT GCTGCTACTGTTTTCGCTCCATTGCAATTG GCTTTGGTTGAAGCTGCTTTGATGGTTCAA GCTTGGGCTATGGTTGAATTGTGGCCAAGA GCTTGGAAGGTTTCTGGTATCGCTTTCTCT TTGATCTTGGCTACTGTTACTGTTGCTTTC AAGTGTGCTTCTGCTGCTGTTACTGTTAAG TCTGCTTTGGAACCATTGGACCCAAGACCA TACTTGTGGATCAGACAAACTGACTTGGCT TTCACTACTGCTATGGTTACTTGGTTCTGT TTCTTGTTCAACGTTAGATTGATCATGCAC ATGTGGCAAAACAGATCTATCTTGCCAACT GTTAAGGGTTTGTCTCCAATGGAAGTTTTG GTTATGGCTAACGGTTTGTTGATGGTTTTC CCAGTTTTGTTCGCTGGTTTGTACTACGGT AACTTCGGTCAATTCGAATCTGCTTCTTTG ACTATCACTTCTGTTGTTTTGGTTTTGCCA TTGGGTACTTTGGTTGCTCAAAGATTGGCT GTTAACAACACTGTTGCTGGTTCTTCTGCT AACACTGACATGGACGACAAGTTGGCTTTC TTGGGTAACGCTACTACTGTTACTTCTTCT GCTGCTGGTTTCGCTGGTTCTTCTGCTTCT GCTACTAGATCTAGATTGGCTTCTCCAAGA CAAAACTCTCAATTGTCTACTTCTGTTTCT GCTGGTAAGCCAAGAGCTGACCCAATCGAC TTGGAATTGCAAAGAATCGACGACGAAGAC GACGACTTCTCTAGATCTGGTTCTGCTGGT GGTGTTAGAGTTGAAAGATCTATCGAAAGA |

TABLE 2-continued

Pathogens and associated sequences

| Pathogen | Amino acid sequence of peptide analyte used | Amino acid sequence of GPCRs used | DNA coding sequence of corresponding GPCRs that sense peptide analyte |
|---|---|---|---|
| | | | AGAGAAGAAAGATTGTAG (SEQ ID NO: 19) |
| Botrytis cinerea | WCGRPGQ PC (SEQ ID NO: 20) | MASNSSNFDPLTQSI TILMADGITTVSFTP LDIDFFYYYNVACCI NYGAQAGACLLMFFV VVVLTKAVKRKTLLF VLNVLSLIFGFLRAM LYAIYFLQGFNDFYA AFTFDFSRVPRSSYA SSVAGSVIPLCMTIT VNMSLYLQAYTVCKN LDDIKRIILTTLSAI VALLAIGFRFAATVV NSVAILATSASSVPM QWLVKGTLVTETISI WFFSLIFTGKLVWTL YNRRRNGWRQWSAVR ILAAMGGCTMVIPSI FAILEYVTPVSFPEA GSIALTSVALLLPIS SLWAGMVTDEETSAI DVSNLTGSRTMLGSQ SGNFSRKTHASDITA QSSHLDFSSRKGSNA TMMRKGSNAMDQVTT IDCVVEDNQANRGLR DSTEMDLEAMGVRVN KSYGVQKA (SEQ ID NO: 21) | ATGGCTTCTAACTCTTCTAACTTCGACCCA TTGACTCAATCTATCACTATCTTGATGGCT GACGGTATCACTACTGTTTCTTTCACTCCA TTGGACATCGACTTCTTCTACTACTACAAC GTTGCTTGTTGTATCAACTACGGTGCTCAA GCTGGTGCTTGTTTGTTGATGTTCTTCGTT GTTGTTGTTTTGACTAAGGCTGTTAAGAGA AAGACTTTGTTGTTCGTTTTGAACGTTTTG TCTTTGATCTTCGGTTTCTTGAGAGCTATG TTGTACGCTATCTACTTCTTGCAAGGTTTC AACGACTTCTACGCTGCTTTCACTTTCGAC TTCTCTAGAGTTCCAAGATCTTCTTACGCT TCTTCTGTTGCTGGTTCTGTTATCCCATTG TGTATGACTATCACTGTTAACATGTCTTTG TACTTGCAAGCTTACACTGTTTGTAAGAAC TTGGACGACATCAAGAGAATCATCTTGACT ACTTTGTCTGCTATCGTTGCTTTGTTGGCT ATCGGTTTCAGATTCGCTGCTACTGTTGTT AACTCTGTTGCTATCTTGGCTACTTCTGCT TCTTCTGTTCCAATGCAATGGTTGGTTAAG GGTACTTTGGTTACTGAAACTATCTCTATC TGGTTCTTCTCTTTGATCTTCACTGGTAAG TTGGTTTGGACTTTGTACAACAGAAGAAGA AACGGTTGGAGACAATGGTCTGCTGTTAGA ATCTTGGCTGCTATGGGTGGTTGTACTATG GTTATCCCATCTATCTTCGCTATCTTGGAA TACGTTACTCCAGTTTCTTTCCCAGAAGCT GGTTCTATCGCTTTGACTTCTGTTGCTTTG TTGTTGCCAATCTCTTCTTTGTGGGCTGGT ATGGTTACTGACGAAGAAACTTCTGCTATC GACGTTTCTAACTTGACTGGTTCTAGAACT ATGTTGGGTTCTCAATCTGGTAACTTCTCT AGAAAGACTCACGCTTCTGACATCACTGCT CAATCTTCTCACTTGGACTTCTCTTCTAGA AAGGGTTCTAACGCTACTATGATGAGAAAG GGTTCTAACGCTATGGACCAAGTTACTACT ATCGACTGTGTTGTTGAAGACAACCAAGCT AACAGAGGTTTGAGAGACTCTACTGAAATG GACTTGGAAGCTATGGGTGTTAGAGTTAAC AAGTCTTACGGTGTTCAAAAGGCTTAG (SEQ ID NO: 22) |

6.3. Example 3: Reduction to Practice of Directed Evolution

6.3.1. Directed Evolution of Reporter Strain

A stable reporter strain to perform DE on plasmid-borne receptor variants based on previous methods for DE of GPCRs in yeast was established. This strain was analogous to the lycopene reporter with the lycopene biosynthetic genes replaced by the reporters: pFus1-mCherry (fluorescence), pFus1-His3 (growth advantage), pFus2-Ura3 (negative selection). The chromosomal copy of Ste2 was deleted.

6.3.2. Library Generation and Selection Scheme

The endogenous S. cerevisiae Ste2 pheromone receptor was mutated by error-prone PCR and selected for active mutants by fluorescence-activated cell sorting (FACS). The enriched libraries were screened in microtiter plates using a growth based assay using pFus1-His3 as previously reported.[30]

6.3.3. Peptide Ligand Design for Step-Wise DE

A stepwise selection framework that has been used to change substrate specificity of proteins and enzymes was used.[72] Peptide targets that allow generation of a wide range of intermediate hybrid ligands that march from the native peptide ligand (e.g. native yeast α-Factor) to the desired target ligand (e.g. peptides derived from Cholera Toxin) were used for directed evolution.

6.3.4. Successful Demonstration of DE Strategy

This DE strategy was applied to CTx and two intermediate peptides (as shown in FIG. 7) were designed. An

TABLE 3

Peptides used in directed evolution and associated sequences

| Name of peptides used in DE | Amino acid sequence |
|---|---|
| α-Factor, wild type S. cereviseae | WHWLQLKPGQPMY (SEQ ID NO: 24) |
| intermediate-1 (int-1) | WHWLEVPGSQPMY (SEQ ID NO: 25) |
| intermediate-2 (int-2) | WHWLEVPGSQHIDS (SEQ ID NO: 26) |
| cholera toxin epitope long (CTxL) | VEVPGSQHIDSQKKA (SEQ ID NO: 27) |
| cholera toxin epitope short (CTxS) | VPGSQHIDS (SEQ ID NO: 28) |

TABLE 4

GPCRs and associated sequences

| Name of hit GPCRs | Amino acid sequence of GPCR | Corresponding DNA coding sequence |
|---|---|---|
| Ste2, wild type S. cereviseae | MSDAAPSLSNLFYDPTYNPGQSTINYTSIYGNGSTITFDELQGLVNSTVTQAIMFGVRCGAAALTLIVMWMTSRSRKTPIFIINQVSLFLIILHSALYFKYLLSNYSSVTYALTGFPQFISRGDVHVYGATNIIQVLLVASIETSLVFQIKVIFTGDNFKRIGLMLTSISFTLGIATVTMYFVSAVKGMIVTYNDVSATQDKYFNASTILLASSINFMSFVLVVKLILAIRSRRFLGLKQFDSFHILLIMSCQSLLVPSIIFILAYSLKPNQGTDVLTTVATLLAVLSLPLSSMWATAANNASKTNTITSDFTTSTDRFYPGTLSSFQTDSINNDAKSSLRSRLYDLYPRRKETTSDKHSERTFVSETADDIEKNQFYQLPTPTSSKNTRIGPFADASYKEGEVEPVDMYTPDTAADEEARKFWTEDNNNL (SEQ ID NO: 29) | ATGTCTGATGCGGCTCCTTCATTGAGCAATCTATTTTAT GATCCAACGTATAATCCTGGTCAAAGCACCATTAACTAC ACTTCCATATATGGGAATGGATCTACCATCACTTTCGAT GAGTTGCAAGGTTTAGTTAACAGTACTGTTACTCAGGCC ATTATGTTTGGTGTCAGATGTGGTGCAGCTGCTTTGACT TTGATTGTCATGTGGATGACATCGAGAAGCAGAAAAACG CCGATTTTCATTATCAACCAAGTTTCATTGTTTTTAATC ATTTTGCATTCTGCACTCTATTTTAAATATTTACTGTCT AATTACTCTTCAGTGACTTACGCTCTCACCGGATTTCCT CAGTTCATCAGTAGAGGTGACGTTCATGTTTATGGTGCT ACAAATATAATTCAAGTCCTTCTTGTGGCTTCTATTGAG ACTTCACTGGTGTTTCAGATAAAAGTTATTTTCACAGGC GACAACTTCAAAAGGATAGGTTTGATGCTGACGTCGATA TCTTTCACTTTAGGGATTGCTACAGTTACCATGTATTTT GTAAGCGCTGTTAAAGGTATGATTGTGACTTATAATGAT CTGGTAGTTAAATTGATTTTAGCTATTAGATCAAGAAGA TTCCTTGGTCTCAAGCAGTTCGATAGTTTCCATATTTTA CTCATAATGTCATGTCAATCTTTGTTGGTTCCATCGATA ATATTCATCCTGCATACAGTTTGAAACCAAACCAGGGA ACAGATGTCTTGACTACTGTTGCAACATTACTTGCTGTA TTGTCTTTACCATTATCATCAATGTGGGCCACGGCTGCT AATAATGCATCCAAAACAAACACAATTACTTCAGACTTT ACAACATCCACAGATAGGTTTTATCCAGGCACGCTGTCT AGCTTTCAAACTGATAGTATCAACAACGATGCTAAAAGC AGTCTCAGAAGTAGATTATATGACCTATATCCTAGAAGG AAGGAAACAACATCGGATAAACATTCGGAAAGAACTTTT GTTTCTGAGACTGCAGATGATATAGAGAAAAATCAGTTT TATCAGTTGCCCACACCTACGAGTTCAAAAAATACTAGG ATAGGACCGTTTGCTGATGCAAGTTACAAGAGGGAGAA GTTGAACCCGTCGACATGTACACTCCCGATACGGCAGCT GATGAGGAAGCCAGAAAGTTCTGGACTGAAGATAATAAT AATTTA (SEQ ID NO: 30) |
| MClone: 15C11 | same as Ste2 with mutation: V276A | ATGTCTGATGCGGCTCCTTCATTGAGCAATCTATTTTAT GATCCAACGTATAATCCTGGTCAAAGCACCATTAACTAC ACTTCCATATATGGGAATGGATCTACCATCACTTTCGAT GAGTTGCAAGGTTTAGTTAACAGTACTGTTACTCAGGCC ATTATGTTTGGTGTCAGATGTGGTGCAGCTGCTTTGACT TTGATTGTCATGTGGATGACATCGAGAAGCAGAAAAACG CCGATTTTCATTATCAACCAAGTTTCATTGTTTTTAATC ATTTTGCATTCTGCACTCTATTTTAAATATTTACTGTCT AATTACTCTTCAGTGACTTACGCTCTCACCGGATTTCCT GTAGAGGTGACGTTCATGTTTATGGTGCTACAAATATAA CAGTTCATCATTCAAGTCCTTCTTGTGGCTTCTATTGAG ACTTCACTGGTGTTTCAGATAAAAGTTATTTTCACAGGC |

TABLE 4-continued

GPCRs and associated sequences

| Name of hit GPCRs | Amino acid sequence of GPCR | Corresponding DNA coding sequence |
|---|---|---|
| | | GACAACTTCAAAAGGATAGGTTTGATGCTGACGTCGATA<br>TCTTTCACTTTAGGGATTGCTACAGTTACCATGTATTTT<br>GTAAGCGCTGTTAAAGGTATGATTGTGACTTATAATGAT<br>GTTAGTGCCACCCAAGATAAATACTTCAATGCATCCACA<br>ATTTTACTTGCATCCTCAATAAACTTTATGTCATTTGTC<br>CTGGTAGTTAAATTGATTTTAGCTATTAGATCAAGAAGA<br>TTCCTTGGTCTCAAGCAGTTCGATAGTTTCCATATTTTA<br>CTCATAATGTCATGTCAATCTTTGTTGGTTCCATCGATA<br>ATATTCATCCTCGCATACAGTTTGAAACCAAACCAGGGA<br>ACAGATGCCTTGACTACTGTTGCAACATTACTTGCTGTA<br>TTGTCTTTACCATTATCATCAATGTGGGCCACGGCTGCT<br>AATAATGCATCCAAAACAAACACAATTACTTCAGACTTT<br>ACAACATCCACAGATAGGTTTTATCCAGGCACGCTGTCT<br>AGCTTTCAAACTGATAGTATCAACAACGATGCTAAAAGC<br>AGTCTCAGAAGTAGATTATATGACCTATATCCTAGAAGG<br>AAGGAAACAACATCGGATAAACATTCGGAAAGAACTTTT<br>GTTTCTGAGACTGCAGATGATATAGAGAAAAATCAGTTT<br>TATCAGTTGCCCACACCTACGAGTTCAAAAAATACTAGG<br>ATAGGACCGTTTGCTGATGCAAGTTACAAAGAGGGAGAA<br>GTTGAACCCGTCGACATGTACACTCCCGATACGGCAGCT<br>GATGAGGAAGCCAGAAAGTTCTGGACTGAAGATAATAAT<br>AATTTA (SEQ ID NO: 31) |
| MClone: 31E4 | same as Ste2 with mutation: V276A and Y193C | ATGTCTGATGCGGCTCCTTCATTGAGCAATCTATTTTAT<br>GATCCAACGTATAATCCTGGTCAAAGCACCATTAACTAC<br>ACTTCCATATATGGGAATGGATCTACCATCACTTTCGAT<br>GAGTTGCAAGGTTTAGTTAACAGTACTGTTACTCAGGCC<br>ATTATGTTTGGTGTCAGATGTGGTGCAGCTGCTTTGACT<br>TTGATTGTCATGTGGATGACATCGAGAAGCAGAAAAACG<br>CCGATTTTCATTATCAACCAAGTTTCATTGTTTTTAATC<br>ATTTTGCATTCTGCACTCTATTTTAAATATTTACTGTCT<br>AATTACTCTTCAGTGACTTACGCTCTCACCGGATTTCCT<br>CAGTTCATCAGTAGAGGTGACGTTCATGTTTATGGTGCT<br>ACAAATATAATTCAAGTCCTTCTTGTGGCTTCTATTGAG<br>ACTTCACTGGTGTTTCAGATAAAAGTTATTTTCACAGGC<br>GACAACTTCAAAAGGATAGGTTTGATGCTGACGTCGATA<br>TCTTTCACTTTAGGGATTGCTACAGTTACCATGTATTTT<br>GTAAGCGCTGTTAAAGGTATGATTGTGACTTATAATGAT<br>GTTAGTGCCACCCAAGATAAATACTTCAATGCATCCACA<br>ATTCTACTTGCATCCTCAATAAACTTTATGTCATTTGTC<br>CTGGTAGTTAAATTGATTTTAGCTATTAGATCAAGAAGA<br>TTCCTTGGTCTCAAGCAGTTCGATAGTTTCCATATTTTA<br>CTCATAATGTCATGTCAATCTTTGTTGGTTCCATCGATA<br>ATATTCATCCTCGCATACAGTTTGAAACCAAACCAGGGA<br>ACAGATGCCTTGACTACTGTTGCAACATTACTTGCTGTA<br>TTGTCTTTACCATTATCATCAATGTGGGCCACGGCTGCT<br>AATAATGCATCCAAAACAAACACAATTACTTCAGACTTT<br>ACAACATCCACAGATAGGTTTTATCCAGGCACGCTGTCT<br>AGCTTTCAAACTGATAGTATCAACAACGATGCTAAAAGC<br>AGTCTCAGAAGTAGATTATATGACCTATATCCTAGAAGG<br>AAGGAAACAACATCGGATAAACATTCGGAAAGAACTTTT<br>GTTTCTGAGACTGCAGATGATATAGAGAAAAATCAGTTT<br>TATCAGTTGCCCACACCTACGAGTTCAAAAAATACTAGG<br>ATAGGACCGTTTGCTGATGCAAGTTACAAAGAGGGAGAA<br>GTTGAACCCGTCGACATGTACACTCCCGATACGGCAGCT<br>GATGAGGAAGCCAGAAAGTTCTGGACTGAAGATAATAAT<br>AATTTA (SEQ ID NO: 32) |

6.3.5. Demonstration of Proteases to Release Target Ligands

A simple proteolytic degradation of commercially purified CTx was performed. CTx was specifically degraded with either Trypsin or a combination of LysN and GluC. The expected target peptide was successfully detected by mass spectrometry showing it to be released from the full protein. The experiment resulted in a list of released peptides of different length and physicochemical properties which can be used as additional target analytes. Analogous degradation of CTx in the gut or the environment may make target peptides available in field samples. Additionally and alternatively, these extremely robust and cheap proteases may be incorporated into a product formulation.

6.4. Example 4: Yeast Cholera Biosensor

The strain is engineered to respond to a cholera specific peptide by generating a color output.

To develop a cholera peptide binding receptor, the GPCR is subjected to mutagenesis and the resulting library is expressed in the same yeast host. All variants are screened against the peptide, which is synthetically synthesized or originates from bacterial cultures, and strains that show reporter gene expression are further investigated and optimized. Enhanced binding may be achieved by more stringent screening conditions such as lower concentration of target molecule or less copies of the receptor expressed on the cell surface. In certain embodiments, color change is rapid—for example 10 grams, 1 gram, 100 mg, 10 mg, or even 1 mg of freeze dried yeast may result in sufficient red color to be readily apparent to the naked eye, and the assay is desirably sensitive enough to detect low levels of peptide. Non-engineered yeast may be used as controls to test biosensor specificity and false-positive rate. Native alpha factor/Ste2 receptor activation can also be used as a control.

6.5. Example 5: Expressing GPCRs in Yeast

GPCRs were cloned into yeast using the Reiterative Recombination DNA assembly system. The desensitization of the receptor, where prolonged stimulation leads to an attenuated response, was eliminated by deletion of SST2, allowing cells to respond to doses of pheromone that are roughly two orders of magnitude lower than those detected by normal cells and prevent recovery from pheromone-induced growth arrest, even if the ligand was removed.[20] Deletion of Far1 also prevented pheromone-induced cell cycle arrest. The endogenous pheromone receptor Ste2 was deleted to avoid cross talk with yeast mating signal.

6.6. Example 6: Freeze-Drying Yeast

Viability of *S. cerevisiae* was determined after different freeze-drying treatments.[73] The results are shown in FIG. 5. Cell viability of ~1-2% was observed, in agreement with previously published literature.

6.7. Example 7: Detection of Pathogenic Fungi Pheromones Using an Integrated Lycopene Biosensor The engineering of *S. cerevisiae* as a specific and sensitive biosensor for the presence of pathogenic fungi that may be easily used outside the laboratory. The sensor may be used by non-experts, and thus consists of non-technical mixing and color change output that is visible to the naked eye.

Baker's yeast, a safe organism broadly used in the food industry for centuries and easily grown in a robust manner was reprogrammed to express the tomato red pigment lycopene in response to binding of natural pathogen-specific peptides by expressing natural fungal binding receptors. This user-friendly and equipment-free signal is compatible with household use at local communities at-risk for fungi infections.

Fungal pathogens have recently been identified as increasing cause of human disease as well as a cause of population decline in animals and crops. The annual number of cases of sepsis caused by fungal organisms in the U.S. increased by 207% between 1979 and 2000 [Pfaller, Diekema, (2007)]. Several factors contribute to the increase in fungal infections, among which are the increasing number of immunocompromised HIV, cancer and transplantation patients, aging population, and increased global mobility which expands the habitats of endemic opportunistic fungal strains [Pfaller, Diekema, (2007)].

*Candida* fungal species are the major cause of opportunistic mycoses worldwide with 72.8 million annual *candida* species infections cases worldwide and a 33.9% case/fatality ratio [Pfaller, Diekema, (2007)]. *Candida* infections are associated with a high crude mortality of 46% to 75% and a long hospital stay which causes tremendous health care burden. Two fungal species, *C. albicans* and *C. Glabrata*, were shown to be the causative agents of 62% and 12% of *Candidasis*, respectively. [Ramirez-Zavaleta (2010)]. *Candida albicans* is a fungi naturally found in human gastrointestinal, genitourinary tracts and skin, but under compromised immunity it could result in kidney, heart or brain infection [Berman, Sudbery (2002)].

It is difficult to diagnose and distinguish fungal infections. While several anti-fungal therapeutics are available, mortality rates of invasive fungal diseases remain extremely high, often exceeding 50%. This is due to a major clinical bottleneck in early treatment, rooted in significant lack of rapid diagnosis [Brown et al. (2012)]. For example, although several methods are currently available for detection of pathogenic fungi in the laboratory, the current gold standard for confirming candida infection in patients remains slow methods such as cultures or cost prohibitive methods such as coagulation assays which are often unavailable in high risk areas for fungal infections. In this Example, a non-technical biosensor that could be used outside of the laboratory for detection of pathogenic fungi was developed.

In order to detect fungal pathogens, fungal receptors that are naturally binding the fungal peptide mating pheromone were generated. *Candida albicans* cells are diploid (a/alpha) and both homothallic and heterothallic mating have been observed in clinical samples, making mating peptide a relevant biomarker for fungal detection. *C. albicans* must switch its phenotype from white to opaque before secretion of pheromones can occur to induce mating, a transition triggered by different environmental signals. The opaque "mating" phenotype was found to be stabilized by the presence of $CO_2$ and GlcNAc and observed during passage through mouse intestines, suggesting persistence of mating-compatible, pheromone producing *C. albicans* cells in the host [Ramirez-Zavala (2008); Huang (2010)]. Mating was also observed in systemic infections and colonization of the skin and intestines. [Hull et al. (2000), Lachke et al (2003), Dumitru (2007)]. *C. glabrata* population is mostly clonal, and while distinct mating types have been identified, pheromone genes are not expressed in most isolates and neither mating types responds to pheromone.

6.7.1. Fungal GPCRs as the Detection Element

Natural fungal GPCRs were cloned and tested for functionality with their respective natural ligands in *S. cerevisiae* biosensor strain. The results for GPCR activation experiments in biosensor strain are presented in FIGS. 9 and 10. Sequence analysis of receptor and peptides are presented in FIGS. 11 and 12 and further discussed in Example 6.8 below.

As shown in FIG. 9, fungal receptors were found to be highly specific for their respective peptide pheromones, with very little crosstalk between receptors. This is due to the critical role of pheromone recognition in fungal mating and conservation of species integrity. For example, species cohabitating a common host, *C. Glabrata* and *C. albicans* did not respond to the other species pheromone. However, *S. cerevisiae* native Ste2 receptor responded to *C. glabrata*, but not to *C. albicans* pheromone, reflecting the difference in phylogenetic distance between the three strains. Interestingly, the *P. brasiliensis* receptor seemed more promiscuous, showing moderate activity when induced with *A. fumigatus* or pheromone.

Most receptor-pheromone pairs were found to be highly sensitive to their ligand peptide, with EC50 values of 4 nM, 51 nM and 34 nM for *C. albicans*, *L. elongisporous*, and *P. brasiliensis*, respectively, notably higher than the natural activation of the *S. cerevisiae* GPCR-pheromone pair (EC50=190 nM). *C. glabrata* was less active EC50=3.6 µM) in biosensor settings (see FIG. 9).

6.7.2. Lycopene as a Simple, Low-Cost Readout

Having established fungal GPCRs as the detection element, the inventors then implemented and optimized a lycopene biosynthetic pathway as a direct, low-cost readout for the biosensor (see FIG. 13). By overexpressing key pathway genes (Crt1, tHMG1, Fad1), there was significant improvement in the maximal yield of lycopene produced after induction with α-factor. These changes also greatly reduced the time required to reach half maximal biosynthesis of lycopene after induction by α-factor (see FIG. 13C).

6.7.3. An Integrated Biosensor

A product profile that satisfies the unique requirements of a live yeast cell sensor as diagnostic device was developed. Specifically, a core product component, the "Yeast Reporter Tab", maintaining viable, functional yeast cells while enhancing color contrast and ease of use (see FIG. 14) was developed. Importantly, this kit design incorporates a nutrient gel, a white paper to enhance signal contrast, a concentrated yeast spot to enhance apparent color intensity of the produced lycopene and a control yeast spot to eliminate false positives. The design was viable and functioned.

The integrated biosensor properly responded to a synthetic peptide derived from the human pathogen *C. albicans*. Importantly, the biosensor retained a high level of sensitivity and speed while producing a signal visible to the naked eye (see FIG. 14B).

Furthermore, FIG. 14C shows observed dose-response of the biosensor strain (using fluorescent readout) when exposed to culture supernatants from the homozygous *C. albicans* strains P37005, GC75 or a mixture of the two pathogen strain.

6.8. Example 8: Peptide-Activated Receptors and Peptide Ligands

EXAMPLE 8 is an updated study of EXAMPLE 2. Whole-cell diagnostic device enables the use of integral membrane receptors to mediate highly specific and sensitive detection of biologically relevant ligands. Notably, membrane proteins such as GPCRs have not been amenable for in vitro diagnostics as they are notoriously difficult to express outside of their natural membrane environment. A whole-cell provides access to the untapped repertoire of molecular recognition of GPCRs in much the same way ELISAs allowed access to antibody recognition [Lequin (2005)].

The inventors focused on implementing the highly specific fungal peptide-activated GPCRs, such as Ste2 from *S. cerevisiea*, for detection of fungal peptides.

Fungal GPCRs have several key advantages for biosensor engineering. First, GPCRs homologous to the *S. cerevisiae* Ste2 robustly coupled to the host pheromone pathway. (see FIGS. 9 and 10). Second, these fungal GPCRs recognized a diverse set of peptide ligands (see FIG. 12, Table 5). Third, fungal GPCRs showed very highly specificity for their respective peptides (see FIG. 9). Furthermore, these fungal GPCRs offered a highly viable platform for directed evolution towards binding of novel peptide ligands through mutagenesis of either receptor or peptide.

TABLE 5

Physicochemical properties of functionally verified peptide ligands, ordered by peptide length

| Sequence | Length | MW | IP | Charge (−/+) | GRAVY[a] |
|---|---|---|---|---|---|
| WCGRPGQPC (SEQ ID NO: 20) | 9 | 1 | 8.07 | 0/1 | −0.878 |
| WCTRPGQGC (SEQ ID NO: 11) | 9 | 1.007 | 8.07 | 0/1 | −0.778 |
| WCGHIGQGC (SEQ ID NO: 33) | 9 | 0.960 | 6.72 | 0/0 | 0.078 |
| WCWWKGQPCW (SEQ ID NO: 14) | 10 | 1.379 | 8.06 | 0/1 | −0.800 |
| QWCPRRGQPCW (SEQ ID NO: 17) | 11 | 1.416 | 9.02 | 0/2 | −1.491 |
| WMWTRYGRFSPV (SEQ ID NO: 34) | 12 | 1.585 | 10.84 | 0/2 | −0.558 |
| HLVRLSPGAAMF (SEQ ID NO: 35) | 12 | 1.298 | 9.76 | 0/1 | 0.800 |
| HFIELDPGQPMF (SEQ ID NO: 36) | 12 | 1.430 | 4.35 | 2/0 | −0.125 |
| WHWTSYGVFEPG (SEQ ID NO: 37) | 12 | 1.465 | 5.24 | 1/0 | −0.558 |
| WHWLQLKPGQPMY (SEQ ID NO: 38) | 13 | 1.670 | 8.6 | 0/1 | −0.869 |
| GFRLTNFGYFEPG (SEQ ID NO: 5) | 13 | 1.500 | 6 | 1/2 | −0.315 |

TABLE 5-continued

Physicochemical properties of functionally verified peptide ligands, ordered by peptide length

| Sequence | Length | MW | IP | Charge (−/+) | GRAVY[a] |
|---|---|---|---|---|---|
| WHWVRLRKGQGLF (SEQ ID NO: 8) | 13 | 1.682 | 12.1 | 0/3 | −0.585 |
| WSWITLRPGQPIF (SEQ ID NO: 39) | 13 | 1.600 | 9.75 | 0/1 | 0.054 |
| WHWLELDNGQPIY (SEQ ID NO: 40) | 13 | 1.670 | 4.35 | 2/0 | 0.785 |
| WHWLRLRYGEPIY (SEQ ID NO: 41) | 13 | 1.789 | 8.6 | 1/2 | −0.769 |
| KPHWTTYGYYEPQ (SEQ ID NO: 42) | 13 | 1.669 | 6.75 | 1/1 | −1.838 |
| NWHWLRLDPGQPLY (SEQ ID NO: 43) | 14 | 1.795 | 6.74 | 1/1 | −0.964 |
| KFKFRLTRYGWFSPN (SEQ ID NO: 44) | 15 | 1.947 | 11.1 | 0/4 | −0.92 |
| KKNSRFLTYWFFQPIM (SEQ ID NO: 45) | 16 | 2.106 | 10.29 | 0/3 | −0.375 |
| GDWGWFWYVPRPGDPAM (SEQ ID NO: 46) | 17 | 2.037 | 4.21 | 2/1 | −0.635 |
| TYADFLRAYQSWNTFVNPDRPNL (SEQ ID NO: 47) | 23 | 2.789 | 5.63 | 2/2 | −0.778 |
| VSDRVKQMLSHWWNFRNPDTANL (SEQ ID NO: 48) | 23 | 2.815 | 8.72 | 2/3 | −0.883 |
| TYEDFLRVYKNWWSFQNPDRPDL (SEQ ID NO: 49) | 23 | 2.990 | 4.68 | 4/3 | −1.265 |

[a] The GRAVY value is the average hydropathy of the given sequence. Positive values indicate overall hydrophilicity of the sequence and negative values relative hydrophobicity. Index range is −4.5 to 4.5.

6.8.1. Key Characteristics of Fungal GPCRs

Candidate receptors for biosenosor engineering were identified by searching protein and genomic databases (NCBI, UniProt) for proteins and/or genes with homology to *S. cerevisiae* Ste2 receptor. Functionally characterized receptors (described below) had an average amino acid sequence homology of 33% to *S. cerevisiae* Ste2, ranging from 66% to 15% as calculated with Clustal Omega [Sievers (2014)].

Additionally, all receptors were predicted to have seven transmembrane helices, an extracellular N-terminus, an intracellular C-terminus, three extracellular loops and three intracellular loops when analyzed by TMHMM v2.0 [Krogh et al. (2001)]. Notably, while large portions of the extracellular loops and transmembrane helices had low conservation across receptors, three key regions with increased homology (see FIG. 11) were observed. Based on previous mutational studies of the *S. cerevisiae* Ste2 receptor, these three regions have been shown to be important in mediating signal transduction and interactions with the downstream G-protein. [Ćelić et al. (2003); Martin et al. (2002)]. Thus, cell surface receptors with homology to these key regions have a high likelihood of functioning in a *S. cerevisiae* biosensor.

6.8.2. List of Functionally Characterized Receptors

Twenty three receptor-peptide pairs were cloned and functionally characterized in sensor strain, as shown in FIGS. 9 and 10 (see Table 6 for sequences).

Human pathogen: *C. albicans, C. glabrata, P. brasiliensis, L. elongisporous, P. rubens, C. guillermondi, C. tropicalis, C. parapsilosis,*

Plant pathogen: *F. graminearum, M. oryzea, B. cinerea, G. candidum.*

Food Safety/Spoilage: *Z. bailii. Z. rouxii*

Industrial/Model fungi: *S. cerevisiae, K. lactis, S. pombe, V. polyspora* (receptor 1), *V. polyspora* (receptor 2), *S. stipitis, S. japonicas, S. castellii, S. octosporus.*

6.8.3. List of Additional Cloned Receptors (see Table 6 for Sequences)

*A. nidulans, A. oryzae, B. bassiana, C. lusitaniae, C. tenuis, N. fischeri, N. crassa, P. destructans, H. jecorina, T. melanosporum, D. haptotyla, S. scheckii, Y. lipolytica, T. delbrueckii, K. pastoris*

TABLE 6

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| Saccharomyces cerevisiae | WHWLQLK PGQPMY (SEQ ID NO: 38) | MSDAAPSLSNLFY DPTYNPGQSTINY TSIYGNGSTITFD ELQGLVNSTVTQA IMFGVRCGAAALT LIVMWMTSRSRKT PIFIINQVSLFLI ILHSALYFKYLLS NYSSVTYALTGFP QFISRGDVHVYGA TNIIQVLLVASIE TSLVFQIKVIFTG DNFKRIGLMLTSI SFTLGIATVTMYF VSAVKGMIVTYND VSATQDKYFNAST ILLASSINFMSFV LVVKLILAIRSRR FLGLKQFDSFHIL LIMSCQSLLVPSI IFILAYSLKPNQG TDVLTTVATLLAV LSLPLSSMWATAA NNASKTNTITSDF TTSTDRFYPGTLS SFQTDSINNDAKS SLRSRLYDLYPRR KETTSDKHSERTF VSETADDIEKNQF YQLPTPTSSKNTR IGPFADASYKEGE VEPVDMYTPDTAA DEEARKFWTEDNN NL (SEQ ID NO:50) | (wild type) ATGTCTGATGCGGCTCCTTCATTGAG CAATCTATTTTATGATCCAACGTATA ATCCTGGTCAAAGCACCATTAACTAC ACTTCCATATATGGGAATGGATCTAC CATCACTTTCGATGAGTTGCAAGGTT TAGTTAACAGTACTGTTACTCAGGCC ATTATGTTTGGTGTCAGATGTGGTGC AGCTGCTTTGACTTTGATTGTCATGT GGATGACATCGAGAAGCAGAAAAACG CCGATTTTCATTATCAACCAAGTTTC ATTGTTTTAATCATTTTGCATTCTG CACTCTATTTTAAATATTTACTGTCT AATTACTCTTCAGTGACTTACGCTCT CACCGGATTTCCTCAGTTCATCAGTA GAGGTGACGTTCATGTTTATGGTGCT ACAAATATAATTCAAGTCCTTCTTGT GGCTTCTATTGAGACTTCACTGGTGT TTCAGATAAAGTTATTTTCACAGGC GACAACTTCAAAAGGATAGGTTTGAT GCTGACGTCGATATCTTTTCACTTTAG GGATTGCTACAGTTACCATGTATTTT GTAAGCGCTGTTAAAGGTATGATTGT GACTTATAATGATGTTAGTGCCACCC AAGATAAATACTTCAATGCATCCACA ATTTTACTTGCATCCTCAATAAACTT TATGTCATTTGTCCTGGTAGTTAAAT TGATTTTAGCTATTAGATCAAGAAGA TTCCTTGGTCTCAAGCAGTTCGATAG TTTCCATATTTTACTCATAATGTCAT GTCAATCTTTGTTGGTTCCATCGATA ATATTCATCCTCGCATACAGTTTGAA ACCAAACCAGGGAACAGATGTCTTGA CTACTGTTGCAACATTACTTGCTGTA TTGTCTTTACCATTATCATCAATGTG GGCCACGGCTGCTAATAATGCATCCA AAACAAACACAATTACTTCAGACTTT ACAACATCCACAGATAGGTTTTATCC AGGCACGCTGTCTAGCTTTCAAACTG ATAGTATCAACAACGATGCTAAAAGC AGTCTCAGAAGTAGATTATATGACCT ATATCCTAGAAGGAAGGAAACAACAT CGGATAAACATTCGGAAAGAACTTTT GTTTCTGAGACTGCAGATGATATAGA GAAAAATCAGTTTTATCAGTTGCCCA CACCTACGAGTTCAAAAAATACTAGG ATAGGACCGTTTGCTGATGCAAGTTA CAAAGAGGGAGAAGTTGAACCCGTCG ACATGTACACTCCCGATACGGCAGCT GATGAGGAAGCCAGAAAGTTCTGGAC TGAAGATAATAATAATTTATAG (SEQ ID NO: 51) |
| Candida albicans | GFRLTNF GYFEPG (SEQ ID NO: 5) | MNINSTFIPDKPG DIIISYSIPGLDQ PIQIPFHSLDSFQ TDQAKIALVMGIT IGSCSMTLIFLIS IMYKTNKLTNLKL KLKLKYILQWINQ KIFTKKRNDNKQQ QQQQQQQIESSSY NNTTTTLGGYKLF LFYLNSLILLIGI IRSGCYLNYNLGP LNSLSFVFTGWYD GSSFISSDVTNGF KCILYALVEISLG FQVYVMPKTSNLK IWGIMASLLSIGL GLIVVAFQINLTI LSHIRFSRAISTN | (wild type) ATGAATATCAATTCAACTTTCATACC TGATAAACCAGGCGATATAATTATTA GTTATTCAATTCCAGGATTAGATCAA CCAATTCAAATTCCTTTCCATTCATT AGATTCATTTCAAACCGATCAAGCTA AAATAGCTTTAGTCATGGGGATAACT ATTGGGAGTTGTTCAATGACATTAAT TTTTTTGATTTCTATAATGTATAAAA CTAATAAATTAACAAATTTAAAATTA AAATTAAAATTAAAATATATCTTGCA ATGGATAAATCAAAAAATCTTCACCA AAAAAAGGAATGACAACAAACAACAA CAACAACAACAACAACAACAAATTGA ATCATCATCATATAACAATACTACTA CTACGCTGGGGGGTTATAAATTATTT TTATTTTATCTTAATTCATTGATTTT ATTAATTGGTATTATTCGATCAGGTT GTTATTTAAATTATAATTTAGGTCCA |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | RSEEESSSSLSSD SVGYVINSIWMDL PTILFSISININMT ILLIGKLIIAIRT RRYLGLKQFDSFH ILLIGFSQTLIIP SIILVVHYFYLSQ NKDSLLQQISLLL IILMLPLSSLWAQ TANNTHNINSSPS LSFISRHHLSDSS RSGGSNTIVSNGG SNGGGGGGNFPV SGIDAQLPPDIEK ILHEDNNYKLLNS NNESVNDGDIIIN DEGMITKQITIKR V | TTAAATTCACTTAGTTTTGTATTTAC TGGTTGGTATGATGGATCATCATTTA TATCATCCGATGTAACTAATGGATTT AAATGTATTTTATATGCTTTAGTGGA AATTTCATTAGGTTTCCAAGTTTATG TGATGTTCAAAACTTCAAATTTAAAA ATTTGGGGGATAATGGCATCATTATT ATCAATTGGTTTAGGATTGATTGTTG TTGCCTTTCAAATCAATTTAACAATT TTATCTCATATTCGATTTTCCCGGGC TATATCAACTAACAGAAGTGAAGAAG AATCATCATCATTATCATCTGAT TCGGTTGGGTATGTGATTAATTCAAT ATGGATGGATTTACCAACAATATTAT TTTCCATTAGTATTAATATAATGACA ATATTATTGATTGGTAAACTTATAAT TGCTATTAGAACAAGACGTTATTTAG GATTGAAACAATTTGATAGTTTCCAT ATTTTATTAATTGGTTTCAGTCAAAC ATTAATTATTCCTTCAATTATTTTGG TGGTTCATTATTTTTATTTATCACAA AATAAAGATTCTTTATTACAACAAAT TAGTCTTTTATTGATTATTTTAATGT TACCATTAAGTTCTTTATGGGCTCAA ACTGCTAATAATACTCATAATATTAA TTCATCTCCAAGTTTATCATTCATAT CTCGTCATCATCTGTCTGATAGTAGT CGTAGTGGTGGTTCCAATACAATTGT TAGTAATGGTGGTAGTAATGGTGGTG GTGGTGGTGGTGGGAATTTCCCTGTT TCAGGTATTGATGCACAATTACCACC TGATATTGAAAAAATCTTACATGAAG ATAATAATTATAAATTACTTAATAGT AATAATGAAAGTGTAAATGATGGAGA TATTATCATTAATGATGAAGGTATGA TTACTAAACAAATCACCATCAAAAGA GTGTAG |
| Candida glabrata | WHWVRLR KGQGLF | MEMGYDPRMYNPR NEYLNFTSVYDVN DTIRFSTLDAIVK GLLRIAIVHGVRL GAIFMTLIIMFIS SNTWKKPIFIINM VSLMLVMIHSALS FHYLLSNYSSISY ILTGFPQLITSNN KRIQDAASIVQVL LVAAIEASLVFQI HVMFTIENIKLIR EIVLSISIAMGLA TVATYLAAAIKLI RGLHDEVMPQTHL IFNLSIILLASSI NFMTFILVIKLFF AIRSRRYLGLRQF DAFHILLIMFCQS LLIPSVLYIIVYA VDSRSNQDYLIPI ANLFVVLSLPLSS IWANTSNNSSRSP KYWKNSQTNKSNG SFVSSISVNSDSQ NPLYKKIVRFTSK GDTTRSIVSDSTL AEVGKYSMQDVSN SNFECRDLDFEKV KHTCENFGRISET YSELSTLDTTALN ETRLFWKQQSQCD K | (wild type) ATGGAGATGGGCTACGATCCAAGAAT GTATAATCCAAGAAATGAATACTTGA ATTTCACGTCGGTATATGATGTAAAT GACACAATCAGATTTTCGACTCTGGA CGCCATTGTAAAAGGATTGCTTAGAA TTGCCATTGTTCATGGAGTTAGATTG GGAGCAATATTCATGACGTTAATAAT AATGTTTATCTCATCAAATACATGGA AAAAACCCATATTTATAATTAACATG GTGTCGTTGATGTTAGTTATGATTCA TTCCGCACTTAGCTTCCATTACCTTT TATCGAATTATTCTTCAATTTCTTAT ATACTGACAGGGTTTCCTCAGTTGAT TACAAGCAATAATAAACGAATTCAAG ATGCAGCGAGTATAGTCCAAGTTTTA TTGGTTGCTGCGATAGAAGCATCATT GGTATTTCAGATTCATGTTATGTTTA CGATTGAAAACATTAAGCTTATTAGA GAAATAGTACTCTCTATATCGATAGC AATGGGATTGGCAACAGTGGCTACAT ATCTTGCTGCAGCAATAAAGCTGATA AGAGGACTGCATGATGAGGTAATGCC ACAAACACATCTTATTTTCAATTTAT CTATAATATTGCTTGCCATCCTCCATA AATTTTATGACATTTATATTGGTCAT TAAACTTTCTTCGCTATTAGATCTA GAAGATATCTCGGTCTTCGTCAATTC GATGCTTTTCATATTTTATTAATCAT GTTCTGCCAGTCATTATTGATACCCT CAGTATTATATATTATAGTTTACGCG GTTGATAGCAGATCTAATCAGGATTA TCTGATTCCAATTGCCAATTTATTTG TTGTTTTATCTTTGCCATTATCCTCT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | | ATCTGGGCTAACACATCAAATAACTC ATCCAGATCTCCAAAATATTGGAAAA ACTCTCAAACGAATAAGAGCAATGGG TCTTTTGTCTCTTCAATATCTGTCAA TAGTGACTCACAAAACCCTTTGTACA AAAAGATTGTACGTTTTACATCAAAA GGCGACACTACCCGTAGTATTGTAAG TGATTCAACATTAGCAGAGGTGGGAA AATACTCTATGCAAGCGTTAGCAAT TCAAACTTTGAATGTCGAGACCTTGA TTTTGAGAAGGTAAAACATACTTGCG AAAATTTTGGCAGAATATCTGAAACA TATAGTGAGTTAAGTACTTTAGATAC CACTGCCCTCAATGAGACTCGGTTGT TTTGGAAACAACAAAGTCAGTGTGAC AAATAG |
| Paracoccidioides brasiliensis | WCTRPG QGC | MAPSFDPFNQSVV FHKADGTPFNVSI HELDDFVQYNTKV CINYSSQLGASVI AGLMLAMLTHSEK RRLPVFFLNTFAL AMNFARLLCMTIY FTTGFNKSYAYFG QDYSQVPGSAYAA SVLGVVFTTLLVI SMEMSLLIQTRVV CTTLPDIQRYLLM AVSSAISLMAIGF RLGLMVENCIAIV QASNFAPFIWLQS ASNITITISTCFF SAVFVTKLAYALV TRIRLGLTRFGAM QVMFIMSCQTMVI PAIFSILQYPLPK YEMNSNLFTLVAI FLPLSSLWASVAT RSSFETSSSGRHQ YLWPSEQSNNVTN SEIKYQVSFSQNH TTLRSGGSVATTL SPDRLDPVYCEVE AGTKA | (wild type) ATGGCACCCTCATTCGACCCCTTCAA CCAAAGCGTGGTCTTCCACAAGGCCG ACGGAACTCCATTCAACGTCTCAATC CATGAACTAGACGACTTCGTGCAGTA CAACACCAAAGTCTGCATCAACTACT CTTCCCAGCTCGGAGCATCTGTCATT GCAGGACTCATGCTTGCCATGCTGAC ACACTCAGAAAAGCGTCGTCTGCCAG TTTTCTTCCTAAACACATTCGCACTG GCCATGAACTTTGCCCGCCTGCTCTG CATGACCATCTACTTCACCACGGGCT TCAACAAGTCCTATGCCTACTTTGGT CAGGATTACTCCCAGGTGCCTGGGAG CGCCTACGCAGCCTCTGTCTTGGGCG TTGTCTTCACCACTCTCCTGGTAATC AGCATGGAAATGTCCCTCCTGATCCA AACAAGGGTTGTCTGCACGACCCTTC CGGATATCCAACGTTATCTACTCATG GCAGTTTCCTCCGCGATTTCCCTGAT GGCCATCGGGTTCCGCCTTGGCTTAA TGGTTGAGAACTGCATTGCCATTGTG CAGGCGTCGAATTTCGCCCCTTTTAT CTGGCTTCAAAGCGCCTCGAACATCA CCATTACGATCAGCACATGTTTCTTC AGTGCCGTCTTTGTTACGAAATTGGC ATATGCACTCGTCACTCGTATACGAC TAGGCTTGACGAGGTTTGGTGCTATG CAGGTTATGTTCATCATGTCCTGCCA GACTATGGTGATTCCAGCCATCTTCT CAATTCTCCAATACCCACTCCCCAAG TACGAAATGAACTCCAACCTCTTTAC GCTGGTGGCCATTTTCCTCCCTCTTT CCTCGCTATGGGCTTCAGTTGCTACG AGATCCAGTTTCGAGACGTCTTCTTC CGGCCGCCATCAGTATCTTTGGCCAA GCGAACAGAGCAATAACGTCACCAAT TCGGAAATTAAGTATCAGGTCAGCTT CTCTCAGAACCACACTACGTTGCGGT CTGGAGGGTCTGTGGCCACGACACTC TCCCCGGACCGGCTCGACCCGGTTTA TTGTGAAGTTGAAGCTGGCACAAAGG CCTAG |
| Fusarium graminearum | WCWWK GQPCW | MSKEVFDPFTQNV TFFAPDGKTEISI PVAAIDQVRRMMV NTTINYATQLGAC LIMLVVLLVMVPK EKFRRPFMILQIT SLVISCCRMLLLS IFHSSQFLDFYVF WGDDHSRIPRSAY APSVAGNTMSLCL VISVETMLMSQAW | (codon optimized) ATGTCTAAGGAAGTTTTCGACCCATT CACTCAAAACGTTACTTTCTTCGCTC CAGACGGTAAGACTGAAATCTCTATC CCAGTTGCTGCTATCGACCAAGTTAG AAGAATGATGGTTAACACTACTATCA ACTACGCTACTCAATTGGGTGCTTGT TTGATCATGTTGGTTGTTTTGTTGGT TATGGTTCCAAAGGAAAAGTTCAGAA GACCATTCATGATCTTGCAAATCACT TCTTTGGTTATCTCTTGTTGTAGAAT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | TMVRLWPNVWKYI IAGVSLIVSIMAI SVRLAYTIIQNNA VLKLEPAFHMFWL IKWTVIMNVASIS WWCAIFNIKLVWH LISNRGILPSYKT FTPMEVLIMTNGI LMIIPVIFASLEW AHFVNFESASLTL TSVAVILPLGTLA AQRIASSAPSSAN STGASSGIRYGVS GPSSFTGFKAPSF STGTTDRPHVSIY ARCEAGTSSREHI NPQGVELAKLDPE TDHHVRVDRAFLQ REERIRAPL | GTTGTTGTTGTCTATCTTCCACTCTT CTCAATTCTTGGACTTCTACGTTTTC TGGGGTGACGACCACTCTAGAATCCC AAGATCTGCTTACGCTCCATCTGTTG CTGGTAACACTATGTCTTTGTGTTTG GTTATCTCTGTTGAAACTATGTTGAT GTCTCAAGCTTGGACTATGGTTAGAT TGTGGCCAAACGTTTGGAAGTACATC ATCGCTGGTGTTTCTTTGATCGTTTC TATCATGGCTATCTCTGTTAGATTGG CTTACACTATCATCCAAAACAACGCT GTTTTGAAGTTGGAACCAGCTTTCCA CATGTTCTGGTTGATCAAGTGGACTG TTATCATGAACGTTGCTTCTATCTCT TGGTGGTGTGCTATCTTCAACATCAA GTTGGTTTGGCACTTGATCTCTAACA GAGGTATCTTGCCATCTTACAAGACT TTCACTCCAATGGAAGTTTTGATCAT GACTAACGGTATCTTGATGATCATCC CAGTTATCTTCGCTTCTTTGGAATGG GCTCACTTCGTTAACTTCGAATCTGC TTCTTTGACTTTGACTTCTGTTGCTG TTATCTTGCCATTGGGTACTTTGGCT GCTCAAAGAATCGCTTCTTCTGCTCC ATCTTCTGCTAACTCTACTGGTGCTT CTTCTGGTATCAGATACGGTGTTTCT GGTCCATCTTCTTTCACTGGTTTCAA GGCTCCATCTTTCTCTACTGGTACTA CTGACAGACCACACGTTTCTATCTAC GCTAGATGTGAAGCTGGTACTTCTTC TAGAGAACACATCAACCCACAAGGTG TTGAATTGGCTAAGTTGGACCCAGAA ACTGACCACCACGTTAGAGTTGACAG AGCTTTCTTGCAAAGAGAAGAAAGAA TCAGAGCTCCATTGTAG |
| Magnaporthe oryzea | QWCPRR GQPCW | MDQTLSATGTATS PPGPALTVDPRFQ TITMLTPALMGQG FEEVQTTPAEIND VYFLAFNTAIGYS TQIGACFIMLLVL LTMTAKARFARIP TIINTAALVVSII RCTLLVIFFTSTM MEFYTIFSDDFSF VHPNDIRRSVAAT VFAPLQLALVEAA LMVQAWAMVELWP RAWKVSGIAFSLI LATVTVAFKCASA AVTVKSALEPLDP RPYLWIRQTDLAF TTAMVTWFCFLFN VRLIMHMWQNRSI LPTVKGLSPMEVL VMANGLLMVFPVL FAGLYYGNFGQFE SASLTITSVVLVL PLGTLVAQRLAVN NTVAGSSANTDMD DKLAFLGNATTVT SSAAGFAGSSASA TRSRLASPRQNSQ LSTSVSAGKPRAD PIDLELQRIDDED DDFSRSGSAGGVR VERSIERREERL | (codon optimized) ATGGACAAACTTTGTCTGCTACTGG TACTGCTACTTCTCCACCAGGTCCAG CTTTGACTGTTGACCCAAGATTCCAA ACTATCACTATGTTGACTCCAGCTTT GATGGGTCAAGGTTTCGAAGAAGTTC AAACTACTCCAGCTGAAATCAACGAC GTTTACTTCTTGGCTTTCAACACTGC TATCGGTTACTCTACTCAAATCGGTG CTTGTTTCATCATGTTGTTGGTTTTG TTGACTATGACTGCTAAGGCTAGATT CGCTAGAATCCCAACTATCATCAACA CTGCTGCTTTGGTTGTTTCTATCATC AGATGTACTTTGTTGGTTATCTTCTT CACTTCTACTATGATGGAATTCTACA CTATCTTCTCTGACGACTTCTCTTTC GTTCACCCAAACGACATCAGAAGATC TGTTGCTGCTACTGTTTTCGCTCCAT TGCAATTGGCTTTGGTTGAAGCTGCT TTGATGGTTCAAGCTTGGGCTATGGT TGAATTGTGGCCAAGAGCTTGGAAGG TTTCTGGTATCGCTTTCTCTTTGATC TTGGCTACTGTTACTGTTGCTTTCAA GTGTGCTTCTGCTGCTGTTACTGTTA AGTCTGCTTTGGAACCATTGGACCCA AGACCATACTTGTGGATCAGACAAAC TGACTTGGCTTTCACTACTGCTATGG TTACTTGGTTCTGTTTCTTGTTCAAC GTTAGATTGATCATGCACATGTGGCA AAACAGATCTATCTTGCCAACTGTTA AGGGTTTGTCTCCAATGGAAGTTTTG GTTATGGCTAACGGTTTGTTGATGGT TTTCCCAGTTTTGTTCGCTGGTTTGT ACTACGGTAACTTCGGTCAATTCGAA TCTGCTTCTTTGACTATCACTTCTGT TGTTTTGGTTTTGCCATTGGGTACTT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | | TGGTTGCTCAAAGATTGGCTGTTAAC AACACTGTTGCTGGTTCTTCTGCTAA CACTGACATGGACGACAAGTTGGCTT TCTTGGGTAACGCTACTACTGTTACT TCTTCTGCTGCTGGTTTCGCTGGTTC TTCTGCTTCTGCTACTAGATCTAGAT TGGCTTCTCCAAGACAAAACTCTCAA TTGTCTACTTCTGTTTCTGCTGGTAA GCCAAGAGCTGACCCAATCGACTTGG AATTGCAAAGAATCGACGACGAAGAC GACGACTTCTCTAGATCTGGTTCTGC TGGTGGTGTTAGAGTTGAAAGATCTA TCGAAAGAAGAGAAGAAAGATTGTAG |
| Botrytis cinerea | WCGRPG QPC | MASNSSNFDPLTQ SITILMADGITTV SFTPLDIDFFYYY NVACCINYGAQAG ACLLMFFVVVVLT KAVKRKTLLFVLN VLSLIFGFLRAML YAIYFLQGFNDFY AAFTFDFSRVPRS SYASSVAGSVIPL CMTITVNMSLYLQ AYTVCKNLDDIKR IILTTLSAIVALL AIGFRFAATVVNS VAILATSASSVPM QWLVKGTLVTETI SIWFFSLIFTGKL VWTLYNRRRNGWR QWSAVRILAAMGG CTMVIPSIFAILE YVTPVSFPEAGSI ALTSVALLLPISS LWAGMVTDEETSA IDVSNLTGSRTML GSQSGNFSRKTHA SDITAQSSHLDFS SRKGSNATMMRKG SNAMDQVTTIDCV VEDNQANRGLRDS TEMDLEAMGVRVN KSYGVQKA | (codon optimized) ATGGCTTCTAACTCTTCTAACTTCGA CCCATTGACTCAATCTATCACTATCT TGATGGCTGACGGTATCACTACTGTT TCTTTCACTCCATTGGACATCGACTT CTTCTACTACTACAACGTTGCTTGTT GTATCAACTACGGTGCTCAAGCTGGT GCTTGTTTGTTGATGTTCTTCGTTGT TGTTGTTTTGACTAAGGCTGTTAAGA GAAAGACTTTGTTGTTCGTTTTGAAC GTTTTGTCTTTGATCTTCGGTTTCTT GAGAGCTATGTTGTACGCTATCTACT TCTTGCAAGGTTTCAACGACTTCTAC GCTGCTTTCACTTTCGACTTCTCTAG AGTTCCAAGATCTTCTTACGCTTCTT CTGTTGCTGGTTCTGTTATCCCATTG TGTATGACTATCACTGTTAACATGTC TTTGTACTTGCAAGCTTACACTGTTT GTAAGAACTTGGACGACATCAAGAGA ATCATCTTGACTACTTTGTCTGCTAT CGTTGCTTTGTTGGCTATCGGTTTCA GATTCGCTGCTACTGTTGTTAACTCT GTTGCTATCTTGGCTACTTCTGCTTC TTCTGTTCCAATGCAATGGTTGGTTA AGGGTACTTTGGTTACTGAAACTATC TCTATCTGGTTCTTCTCTTTGATCTT CACTGGTAAGTTGGTTTGGACTTTGT ACAACAGAAGAAGAAACGGTTGGAGA CAATGGTCTGCTGTTAGAATCTTGGC TGCTATGGGTGGTTGTACTATGGTTA TCCCATCTATCTTCGCTATCTTGGAA TACGTTACTCCAGTTTCTTTCCCAGA AGCTGGTTCTATCGCTTTGACTTCTG TTGCTTTGTTGTTGCCAATCTCTTCT TTGTGGGCTGGTATGGTTACTGACGA AGAAACTTCTGCTATCGACGTTTCTA ACTTGACTGGTTCTAGAACTATGTTG GGTTCTCAATCTGGTAACTTCTCTAG AAAGACTCACGCTTCTGACATCACTG CTCAATCTTCTCACTTGGACTTCTCT TCTAGAAAGGGTTCTAACGCTACTAT GATGAGAAAGGGTTCTAACGCTATGG ACCAAGTTACTACTATCGACTGTGTT GTTGAAGACAACCAAGCTAACAGAGG TTTGAGAGACTCTACTGAAATGGACT TGGAAGCTATGGGTGTTAGAGTTAAC AAGTCTTACGGTGTTCAAAAGGCTTA G |
| Lodderomyces elongisporous | WMWTRY GRFSPV | MDEAINANLVSGD IIVSFNIPGLPEP VQVPFSEFDSFHK DQLIGVIILGVTI GACSLLILLLGM LYKSREKYWKSLL FMLNVCILAATIL RSGCFLDYYLSDL ASISYTFTGVYNG | (wild type) ATGGACGAAGCAATCAATGCAAACCT TGTTTCTGGAGATATTATAGTCTCTT TTAACATTCCTGGTTTGCCAGAACCG GTACAAGTGCCATTCAGCGAATTTGA TTCGTTTCATAAAGACCAGCTCATTG GAGTCATCATTCTTGGAGTCACTATT GGAGCATGCTCGCTTTTGTTGATATT GCTACTTGGAATGTTATACAAGAGCC |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | TSFASSDAANVFK<br>TIMFALIETSLTF<br>QVYVMFQGTTWKN<br>WGHAVTALSGLLS<br>VASVAFQIYTTIL<br>SHNNFNATISGTG<br>TLTSGVWMDLPTL<br>LFAASINFMTILL<br>LFKLGMAIRQRRY<br>LGLKQFDGFHILF<br>IMFTQTLFTPSIL<br>LVIHYFYQAMSGP<br>FIINMALFLVVAF<br>LPLSSLWAQTANT<br>TKKIESSPSMSFI<br>TRRKSEDESPLAA<br>NDEDRLRKFTTTL<br>DLSGNKNNTTNNN<br>NNSNNINNNMSNI<br>NYPSTGLGEDDKS<br>FIFEMEPSRERAA<br>IEEIDLGARIDTG<br>LPRDLEKFLVDGF<br>DDSDDGEGMIARE<br>VTMLKK<br>(SEQ ID NO: 52) | GTGAAAAGTATTGGAAATCACTATTA<br>TTTATGCTCAATGTATGCATCTTGGC<br>TGCCACAATCTTAAGGAGCGGTTGCT<br>TCTTAGACTATTATCTAAGTGATTTG<br>GCCAGTATCAGTTATACATTTACTGG<br>AGTATACAATGGTACCAGCTTTGCTA<br>GCTCTGACGCGGCAAATGTGTTCAAG<br>ACTATTATGTTTGCCTTGATTGAAAC<br>TTCGTTAACCTTTCAAGTGTATGTCA<br>TGTTTCAAGGGACCACTTGGAAAAAT<br>TGGGGCCATGCTGTCACTGCATTATC<br>GGGTCTCTTGTCTGTTGCCTCAGTGG<br>CGTTCCAGATCTACACCACGATTTTA<br>TCCCACAATAATTTCAATGCTACAAT<br>CTCGGGAACCGGTACATTAACTTCAG<br>GTGTTTGGATGGACTTACCAACACTC<br>TTGTTTGCCGCAAGTATCAATTTTAT<br>GACCATTTTGTTGTTATTTAAGTTGG<br>GAATGGCCATTAGACAAAGAAGGTAT<br>TTAGGTTTAAAACAGTTTGATGGGTT<br>CCATATCTTATTCATCATGTTTACCC<br>AAACATTGTTCATACCCTCGATTTTG<br>CTTGTGATCCACTACTTTTACCAGGC<br>AATGTCTGGACCATTCATCATCAACA<br>TGGCGTTGTTCTTGGTGGTGGCATTC<br>TTGCCATTGAGTTCATTATGGGCACA<br>AACTGCAAACACTACTAAAAAGATTG<br>AATCTTCGCCAAGTATGAGCTTTATT<br>ACTAGACGAAAATCAGAGGATGAGTC<br>ACCACTGGCTGCTAACGACGAGGATA<br>GGTTACGAAAATTCACCACAACTTTG<br>GATTTGTCGGGCAACAAGAACAATAC<br>AACAAACAATAATAACAATAGCAACA<br>ACATTAACAACAATATGAGCAACATC<br>AACTACCCTTCTACAGGACTGGGAGA<br>AGACGATAAATCCTTTATATTTGAGA<br>TGGAACCCAGTCGGGAAAGAGCTGCA<br>ATAGAAGAGATTGATCTTGGAGCAAG<br>GATCGATACCGGTTTGCCCAGAGATT<br>TAGAGAAATTTCTAGTTGATGGGTTT<br>GACGATAGTGATGACGGAGAAGGAAT<br>GATAGCCAGAGAAGTGACTATGTTGA<br>AAAAATAG (SEQ ID NO: 53) |
| Penicillium rubens | WCGHIG QGC | MATSSPIQPFDPF<br>TQNVTFRLQDGTE<br>FPVSVKALDVFVM<br>YNVRVCINYGCQF<br>GASFVLLVILVLL<br>TQSDKRRSAVFIL<br>NGLALFLNSSRLL<br>FQVIHFSTAFEQV<br>YPYVSGDYSSVPW<br>SAYAISIVAVVLT<br>TLVVVCIEASLVI<br>QVHVVCSTLRRRY<br>RHPLLAISILVAL<br>VPIGFRCAWMVAN<br>CKAIIKLTYTNDV<br>WWIESATNICVTI<br>SICFFCVIFVTKL<br>GFAIKQRRRLGVR<br>EFGPMKVIFVMGC<br>QTMVVPAIFSITQ<br>YYVVVPEFSSNVV<br>TLVVISLPLSSIW<br>AGAVLENARRTGS<br>QDRQRRRNLWRAL<br>VGGAESLLSPTKD<br>SPTSLSAMTAAQT<br>LCYSDHTMSKGSP<br>TSRDTDAFYGISV | (codon optimized)<br>ATGGCTACCTCTTCCCCAATCCAACC<br>ATTTGACCCATTCACCCAAAACGTTA<br>CCTTCCGTTTGCAAGACGGTACCGAA<br>TTCCCAGTTTCTGTCAAGGCTTTGGA<br>CGTCTTCGTCATGTACAACGTTAGAG<br>TCTGTATTAACTACGGTTGTCAATTC<br>GGTGCCTCCTTCGTCTTGTTAGTCAT<br>TTTAGTCTTGTTAACTCAATCCGACA<br>AGAGAAGATCTGCTGTCTTCATTTTG<br>AACGGTTTGGCTTTGTTCTTGAACTC<br>TTCTAGATTGTTGTTTCAAGTTATTC<br>ACTTCTCCACTGCCTTCGAACAAGTC<br>TACCCATACGTCTCTGGTGACTACTC<br>CTCTGTCCCATGGTCCGCTTACGCTA<br>TCTCCATTGTCGCTGTTGTTTTGACT<br>ACCTTGGTCGTTGTTTGTATCGAAGC<br>TTCTTTGGTTATTCAAGTTCACGTTG<br>TCTGTTCCACCTTGAGACGTAGATAC<br>AGACACCCATTATTAGCTATTTCTAT<br>TTTGGTCGCTTTGGTTCCAATCGGTT<br>TCAGATGTGCTTGGATGGTCGCTAAC<br>TGTAAGGCTATTATTAAATTGACCTA<br>CACCAACGACGTTTGGTGGATCGAAT<br>CTGCTACTAACATCTGTGTCACTATC<br>TCCATCTGTTTCTTCTGTGTTATCTT<br>CGTTACCAAGTTGGGTTTCGCCATCA<br>AGCAAAGAAGAAGATTGGGTGTTAGA |

TABLE 6-continued

Sequences of Fungal
GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | EHDISINRVQRNN SIV (SEQ ID NO: 54) | GAATTCGGTCCAATGAAGGTTATTTT CGTCATGGGTTGTCAAACTATGGTTG TTCCAGCTATTTTCTCCATCACCCAA TACTACGTCGTCGTCCCAGAATTCTC CTCTAACGTCGTTACTTTGGTTGTCA TTTCTTTACCATTATCTTCCATTTGG GCCGGTGCTGTCTTGGAAAACGCTAG AAGAACCGGTTCCCAAGATAGACAAA GAAGACGTAACTTGTGGAGAGCTTTG GTTGGTGGTGCTGAATCCTTGTTATC CCCAACTAAGGACTCTCCAACCTCTT TGTCTGCTATGACTGCTGCTCAAACC TTATGTTACTCTGATCACACCATGTC CAAGGGTTCTCCAACTTCCAGAGACA CCGATGCTTTCTACGGTATCTCCGTT GAACACGACATCTCCATTAACAGAGT TCAACGTAACAACTCCATCGTCTAG (SEQ ID NO: 55) |
| Candida guilliermondii | KKNSRFL TYWFFQP IM | MKSCSIGFGIPFI NEPNFETVSILTM DVSFIDADVNPDN ILLNFTIPGYQNG FSVPMVVINELQK SQMKYAIVYGCGV GASLILLFVVWIL CSRKTPLFIMNNI PLVLYVISSSLNL AYITGPLSSVSVF LTGILTSHDAINV VYASNALQMLLIF SIQSTMAYHVYVM FKSPQIKYLRYML VGFLGCLQIVTTC LYINYNVLYSRRM HKLYETGQTYQDG TVMTFVPFILFQC SVNFSSIFLVLKL IMAIRTRRYLGLR QFGGFHILMIVSL QTMLVPSILVLVN YAAHKAVPSNLLS SVSMMIIVLSLPA SSMWAAAANASSA PSSAASSLFRYTT SDSDRTLETKSDH FIMKHESHNSSPN SSPLTLVQKRISD ATLELPKELEDLI DSTSI (SEQ ID NO: 56) | (codon optimized) ATGAAGTCCTGCTCCATCGGTTTCGG TATCCCATTCATTAATGAACCAAACT TCGAAACTGTTTCTATTTTGACCATG GACGTTTCTTTCATTGACGCTGACGT CAATCCTGACAATATCTTGTTGAACT TCACCATTCCTGGTTACCAAAACGGT TTCTCTGTTCCAATGGTTGTTATTAA CGAATTGCAAAAGTCTCAAATGAAAT ACGCTATTGTTTACGGTTGTGGTGTC GGTGCCTCCTTGATTTTGTTGTTTGT CGTCTGGATTTTGTGTTCTAGAAAGA CTCCATTGTTTATCATGAACAACATT CCATTAGTTTTGTACGTCATCTCCTC TTCTTTGAACTTGGCTTACATTACCG GTCCATTGTCTTCTGTTTCCGTCTTC TTGACCGGTATCTTGACTTCTCACGA TGCCATTAACGTCGTTTACGCTTCCA ACGCTTTGCAAATGTTGTTGATCTTT TCTATCCAATCTACCATGGCCTACCA CGTTTACGTTATGTTCAAATCTCCAC AAATTAAATACTTGAGATACATGTTA GTCGGTTTCTTGGGTTGTTTACAAAT TGTCACCACCTGTTTATACATCAACT ACAATGTTTTGTACTCTCGTAGAATG CACAAATTGTACGAAACTGGTCAAAC CTACCAAGATGGTACCGTTATGACTT TCGTTCCATTCATCTTGTTCCAATGT TCTGTCAACTTCTCTTCTATTTTCTT GGTTTTGAAGTTGATTATGGCCATTA GAACCAGACGTTACTTGGGTTTGCGT CAATTCGGTGGTTTTCATATTTTGAT GATCGTTTCTTTACAAACTATGTTGG TCCCATCTATTTTGGTTTTGGTTAAC TACGCCGCTCATAAGGCTGTTCCTTC CAACTTGTTATCTTCCGTTTCTATGA TGATCATTGTTTTGTCTTTACCAGCT TCTTCTATGTGGGCCGCTGCTGCTAA CGCCTCTTCTGCCCCTTCCTCCGCTG CTTCCTCCTTGTTCAGATACACCACT TCTGATTCCGATAGAACTTTGGAAAC TAAATCTGACCACTTCATCATGAAGC ATGAGTCCCACAACTCTTCTCCAAAT TCCTCCCCATTGACTTTGGTTCAAAA GAGAATTTCTGATGCCACCTTAGAAT TACCAAAAGAGTTAGAAGACTTGATC GACTCCACCTCCATCTAG (SEQ ID NO: 57) |
| Candida tropicalis | KFKFRLT RYGWFSP N | MDINNTIQSSGDI IITYTIPGIEEPF ELPFEVLNHFQSE QSKNCLVMGVMIG | (codon optimized) ATGGACATCAACAACACCATCCAATC TTCCGGTGACATCATCATTACCTACA CCATCCCAGGTATCGAAGAACCATTC |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | SCSVLLIFLVGIL FKTNKFSTIGKSK NLSKNFLFYLNCL ITFIGIIRAACFS NYLLGPLNSASFA FTGWYNGESYASS EAANGFRVILFAL IETSMVFQVFVMF RGAGMKKLAYSVT ILCTALALVVVGF QINSAVLSHRRFV NTVNEIGDTGLSS IWLDLPTILFSVS VNLMSVLLIGKLI MAIKTRRYLGLKQ FDSFHVLLICSTQ TLLVPSLILFVHY FLFFRNANVMLIN ISILLIVLMLPFS SLWAQTANTTQYI NSSPSFSFISREP SANSTLHSSSGHY SEKSYGINKLNTQ GSSPATLKDDHNS VILEATNPMSGFD AQLPPDIARFLQD DIRIEPSSTQDFV STEVTYKKV (SEQ ID NO: 58) | GAATTGCCATTCGAAGTTTTGAACCA CTTCCAATCTGAACAATCCAAGAACT GTTTGGTCATGGGTGTTATGATCGGT TCTTGTTCCGTTTTGTTGATCTTCTT GGTCGGTATTTTGTTCAAAACCAACA AATTCTCTACTATTGGTAAGTCTAAG AACTTGTCTAAGAACTTCTTGTTCTA CTTGAACTGTTTGATCACCTTCATCG GTATCATTCGTGCTGCCTGTTTTTCT AACTACTTGTTGGGTCCATTGAACTC TGCTTCTTTCGCTTTCACTGGTTGGT ACAACGGTGAATCTTACGCTTCTTCC GAAGCTGCTAACGGTTTCAGAGTCAT CTTGTTCGCTTTGATTGAAACTTCTA TGGTCTTCCAAGTTTTCGTTATGTTC AGAGGTGCTGGTATGAAAAAGTTGGC TTACTCCGTTACCATTTTGTGTACCG CTTTGGCTTTGGTCGTTGTTGGTTTC CAAATTAACTCCGCTGTCTTATCTCA CAGAAGATTCGTCAACACCGTTAACG AAATTGGTGATACTGGTTTGTCCTCC ATTTGGTTGGACTTGCCAACCATCTT GTTCTCCGTCTCTGTCAACTTAATGT CTGTTTTGTTGATCGGTAAATTGATC ATGGCTATTAAGACTAGAAGATACTT GGGTTTGAAACAATTCGATTCCTTCC ACGTTTTGTTAATTTGTTCCACTCAA ACTTTGTTGGTCCCATCTTTAATCTT GTTCGTTCACTACTTCTTGTTCTTTA GAAACGCCAACGTTATGTTGATTAAC ATTTCCATCTTGTTGATCGTCTTGAT GTTGCCATTCTCTTCCTTGTGGGCTC AAACCGCCAACACCACCCAATACATC AACTCTTCCCCATCCTTCTCTTTCAT CTCTAGAGAACCATCTGCTAACTCTA CTTTGCACTCCTCTTCCGGTCACTAC TCTGAAAAGTCCTACGGTATTAACAA ATTGAACACCCAAGGTTCTTCCCCAG CCACCTTAAAGGATGATCACAACTCC GTCATCTTGGAAGCTACCAACCCAAT GTCTGGTTTCGACGCCCAATTGCCAC CAGACATTGCTAGATTCTTGCAAGAT GACATCAGAATTGAACCATCTTCTAC CCAAGATTTCGTTTCCACTGAAGTCA CCTACAAGAAGGTCTAG (SEQ ID NO: 59) |
| Candida parapsilosis | KPHWTT YGYYEPQ | MNKIVSKLSSSDV IVTVTIPNEEDGT YEVPFYAIDNYHY SRMENAVVLGATI GACSMLLIMLIGI LFKNFQRLRKSLL FNINFAILLMLIL RSACYINYLMNNL SSISFFFTGIFDD ESFMSSDAANAFK VILVALIEVSLTY QIYVMFKTPMLKS WGIFASVLAGVLG LATLATQIYTTVM SHVNFVNGTTGSP SQVTSAWMDMPTI LFSVSINVLSMFL VCKLGLAIRTRRY LGLKQFDAFHILF IMSTQTMIIPSII LFVHYFDQNDSQT TLVNISLLLVVIS LPLSSLWAQTANN VRRIDTSPSMSFI SREASNRSGNETL | (codon optimized) ATGAACAAGATTGTCTCCAAGTTGTC TTCTTCTGACGTCATCGTTACCGTCA CCATCCCAAACGAAGAAGATGGTACT TACGAAGTCCCATTCTACGCTATTGA CAACTACCACTACTCCCGTATGGAAA ACGCTGTTGTTTTAGGTGCTACCATT GGTGCTTGTTCTATGTTGTTGATCAT GTTGATTGGTATTTTGTTCAAGAACT TCCAAAGATTGAGAAAGTCTTTGTTG TTCAACATCAACTTCGCTATCTTATT GATGTTGATTTTGAGATCCGCTTGTT ACATCAACTACTTGATGAACAACTTG TCTTCCATTTCTTTCTTCTTCACCGG TATTTTCGATGATGAATCTTTCATGT CTTCCGACGCTGCCAACGCCTTCAAG GTTATCTTGGTTGCCTTGATTGAAGT TTCCTTGACCTACCAAATTTACGTTA TGTTCAAGACCCCAATGTTGAAGTCC TGGGGTATTTTCGCCTCTGTCTTGGC CGGTGTTTTGGGTTTGGCTACTTTGG CTACCCAAATCTACACTACCGTTATG TCTCACGTTAACTTCGTCAACGGTAC CACCGGTTCTCCATCTCAAGTTACTT CCGCTTGGATGGACATGCCAACTATC |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | HSGATISKYNTSN TVNTTPGTSKDDS LFILDRSIPEQRI VDTGLPKDLEKFI NNDFYEDDGGMIA REVTMLKTAHNNQ (SEQ ID NO: 60) | TTATTCTCCGTTTCTATTAACGTTTT GTCTATGTTCTTGGTTTGTAAGTTGG GTTTGGCCATCAGAACCAGACGTTAC TTGGGTTTAAAGCAATTCGACGCTTT CCACATTTTATTCATTATGTCCACTC AAACCATGATCATTCCATCCATCATC TTGTTCGTTCACTACTTCGATCAAAA CGACTCTCAAACCACCTTGGTCAACA TCTCTTTGTTATTGGTCGTCATTTCC TTGCCATTGTCTTCTTTGTGGGCTCA AACTGCTAACAACGTTAGAAGAATTG ACACTTCTCCATCCATGTCCTTCATC TCTAGAGAAGCTTCCAACAGATCTGG TAACGAAACCTTGCACTCTGGTGCTA CTATCTCTAAGTACAACACCTCCAAC ACCGTTAACACTACCCCAGGTACTTC TAAGGATGACTCTTTGTTCATCTTGG ACAGATCCATTCCAGAACAAAGAATT GTCGACACTGGTTTGCCAAAGGACTT GGAAAAGTTCATTAACAACGATTTTT ACGAAGACGATGGTGGTATGATTGCC AGAGAAGTCACCATGTTGAAGACCGC TCACAACAACCAATAG (SEQ ID NO: 61) |
| Geotrichum candidum | GDWGWF WYVPRP GDPAM | MAEDSIFPNNSTS PLTNPIVVETIKG TAYIPLHYLDDLQ YEKMLLASLFSVR IATSFVVIIWYFV AVNKAKRSKFLYI VNQVSLLIVFIQS ILSLIYVFSNFSK MSTILTGDYTGIT KRDINVSCVASVF QFLFIACIELALF IQATVVFQKSVRW LKFSVSLIQGSVA LTTTALYMAIIVQ SIYATLNPYAGNL IKGRFGYLLASLG KIFFSISVTSCMC IFVGKLVFAIHQR RTLGIKQFDGLQI LVIMSTQSMIIPT IIVLMSFLRRNAG SVYTMATLLVALS LPLSSLWAEAKTT RDSASYTAYRPSG SPNNRSLFAIFSD RLACGSGRNNRHD DDSRGNGSVNARK ADVESTIEMSSCY TDSPTYSKFEAGL DARGIVFYNEHGL PVVSGEVGGSSSN GTKLGSGHKYEVN TTVVLSDVDSPSP TDVTRK (SEQ ID NO: 62) | (codon optimized) ATGGCCGAAGACTCCATCTTCCCAAA CAACTCCACCTCTCCATTGACCAACC CAATTGTTGTTGAAACCATTAAGGGT ACCGCTTACATTCCATTACACTACTT GGATGATTTGCAATACGAAAAGATGT TGTTGGCTTCCTTGTTCTCCGTTAGA ATTGCTACTTCCTTCGTTGTTATTAT TTGGTACTTCGTCGCTGTCAACAAGG CTAAGAGATCTAAGTTTTTGTACATT GTCAACCAAGTTTCTTTGTTGATCGT TTTTATCCAATCCATTTTGTCTTTGA TTTACGTCTTCTCCAACTTCTCCAAG ATGTCTACCATTTTGACCGGTGATTA CACCGGTATCACTAAGAGAGACATTA ACGTCTCTTGTGTTGCCTCCGTTTTC CAATTCTTGTTCATCGCTTGTATCGA ATTGGCTTTGTTCATCCAAGCTACTG TCGTTTTCCAAAAATCTGTTAGATGG TTGAAGTTTTCCGTTTCTTTGATCCA AGGTTCCGTCGCTTTGACTACTACCG CCTTGTACATGGCCATTATTGTCCAA TCCATCTACGCTACTTTGAACCCATA CGCTGGTAACTTGATTAAAGGTCGTT TCGGTTACTTATTAGCTTCTTTGGGT AAGATTTTCTTCTCTATTTCTGTTAC TTCTTGTATGTGTATCTTCGTTGGTA AGTTGGTCTTTGCTATTCACCAAAGA AGAACTTTGGGTATTAAGCAATTCGA CGGTTTGCAAATTTTGGTCATTATGT CTACTCAATCCATGATCATCCCAACT ATTATCGTCTTGATGTCTTTTTTGAG ACGTAACGCTGGTTCTGTTTACACCA TGGCTACCTTGTTGGTCGCTTTGTCC TTGCCATTGTCCTCCTTGTGGGCTGA AGCCAAGACTACCAGAGACTCTGCTT CTTACACCGCTTACAGACCATCTGGT TCTCCAAACAACCGTTCTTTGTTCGC CATCTTCTCTGATAGATTGGCTTGTG GTTCTGGTAGAAACAACAGACACGAT GATGATTCTAGAGGTAACGGTTCTGT TAACGCCAGAAAGGCTGACGTCGAAT CTACTATCGAAATGTCCTCTTGTTAC ACTGATTCCCCAACCTACTCCAAGTT CGAAGCTGGTTTGGACGCTAGAGGTA TCGTCTTCTACAACGAACACGGTTTG CCAGTTGTCTCCGGTGAAGTTGGTGG |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | | TTCTTCCTCCAACGGTACTAAGTTGG<br>GTTCTGGTCATAAGTACGAAGTCAAC<br>ACTACTGTTGTTTTGTCTGATGTTGA<br>CTCTCCATCTCCAACCGACGTCACCC<br>GTAAGTAG (SEQ ID NO: 63) |
| *Zygosaccharomyces bailii* | HLVRLSP GAAMF | MSGLANNTSYNPL ESFIIFTSVYGGD TMVKFEDLQLVFT KRITEGILFGVKV GAASLTMIVMWMI SRRRTSPIFIMNQ LSLVFTILHASFY FKYLLDGFGSIVY TLTLFPQLITSSD LHVFATANVVEVL LVSSIEASLVFQV NVMFAGSNHRKFA WLLVGFSLGLALA TVALYFVTAVKMI ASAYASQPPTNPI YFNVSLFLLAASV FLMTLMLTVKLIL AIRSRRFLGLKQF DSFPHILLIMSCQT LIAPSVLYILGFI LDHRKGNDYLITV AQLLVVLSLPLSS MWATTANDASSGT SMSSKESVYGSDS LYSKSKCSQFTRT FMNRFSTKPTKND EISDSAFVAVDSL EKNAPQGISEHVC EFPQSDLSDQATS ISSRKKEAVVYAS TVDEDKGSFSSDI NGYTVTNMPLASA ASANCENSPCHVP RPYEENEGVVETR KIILKKNVKW (SEQ ID NO: 64) | (codon optimized)<br>ATGTCTGGTTTGGCTAACAACACCTC TTACAACCCATTGGAATCTTTCATTA TTTTCACTTCTGTTTACGGTGGTGAT ACCATGGTAAGTTCGAAGACTTGCA ATTAGTCTTCACCAAGCGTATTACTG AAGGTATTTTGTTCGGTGTCAAGGTT GGTGCCGCTTCTTTGACTATGATTGT TATGTGGATGATTTCCAGAAGAAGAA CCTCCCCAATCTTCATCATGAACCAA TTGTCTTTGGTTTTCACCATCTTGCA CGCTTCTTTTTACTTTAAGTACTTAT TGGACGGTTTCGGTTCTATTGTCTAC ACTTTGACCTTGTTCCCACAATTAAT TACTTCCTCTGACTTGCACGTTTTCG CTGGTTCTAACCACAGAAAGTTCGCT TGGTTGTTGGTCGGTTTCTCTTTGGG TTTGGCTTTGGCCACTGTCGCTTTGT ACTTCGTTACTGCTGTCAAGATGATC GCTTCCGCTTACGCTTCTCAACCACC AACTAACCCAATCTACTTCAACGTTT CCTTGTTCTTGTTGGCTGCCTCCGTT TTCTTGATGACTTTAATGTTGACCGT CAAGTTGATCTTGGCTATCAGATCCA GAAGATTCTTGGGTTTGAAGCAATTC GACTCTTTCCACATTTTGTTGATTAT GTCTTGTCAAACTTTGATCGCTCCAT CTGTTTTGTACATCTTGGGTTTTATT TTGGATCACAGAAAGGGTAACGACTA CTTGATTACCGTCGCTCAATTGTTGG TCGTTTTGTCTTTGCCATTGTCCTCC ATGTGGGCCACTACTGCTAACGATGC TTCCTCCGGTACTTCTATGTCTTCCA AGGAATCCGTCTACGGTTCTGATTCC TTATACTCTAAGTCTAAGTGTTCCCA ATTCACCAGAACCTTCATGAACAGAT TCTCTACTAAGCCAACTAAGAACGAC GAAATTTCTGATTCCGCTTTCGTCGC TGTTGATTCCTTGGAAAAGAACGCTC CACAAGGTATCTCTGAACACGTTTGT GAATTCCCACAATCTGACTTATCTGA TCAAGCTACTTCCATCTCCTCCAGAA AAAAGGAAGCTGTTGTTTACGCTTCC ACTGTTGATGAAGATAAGGGTTCTTT CTCCTCTGACATCAACGGTTACACTG TTACCAACATGCCATTGGCTTCCGCT GCTTCTGCTAACTGTGAAAACTCCCC ATGTCACGTTCCAAGACCATACGAAG AAAACGAAGGTGTCGTCGAAACCAGA AAAATTATTTTGAAGAAGAACGTCAA ATGGTAG (SEQ ID NO: 65) |
| *Zygosaccharomyces rouxii* | HFIELDP GQPMF | MSEINNSTYNPMN AYVTFTSIYGDDT MVRFKDVELVVNK RVTEAIMFGVKVG AASLTLIIMWMIS KKRTTPIFIINQS SLVFTIIHASLYF GYLLSGFGSIVYN MTSFPQLISSNDV RVYAATNIFEVLL VASIEISLVFQVK | (wild type)<br>ATGAGTGAGATTAACAATTCTACCTA CAATCCAATGAATGCATATGTAACGT TTACATCAATATATGGTGATGATACT ATGGTACGTTTCAAAGATGTGGAATT GGTAGTTAACAAAAGGGTTACAGAAG CCATTATGTTCGGCGTCAAAGTTGGT GCAGCTTCGTTGACACTCATCATCAT GTGGATGATCTCTAAGAAAAGAACAA CACCGATATTTATCATAAATCAGTCT TCGCTTGTATTTACCATAATACATGC |

TABLE 6-continued

Sequences of Fungal
GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | VMFANNNGRRWTW CLMVVSIGMALAT VGLYFATAVELIR AAYSNDTVSRHVF YNVSLILLASSVN LMTLMLVVKLVLA IRSRRFLGLKQFD SFHILLIMSCQTL IAPSILFILGWTL DPHTGNEVLITVG QLLIVLSLPLSSM WATTANNTSSSSS SVSCNDSSFGNDN LCSKSSQFRRTFM NRFRPKSVNGDGN SENTFVTIDDLEK SVFQELSTPVSGE SKIDHDHASSISC QKTCNHVHASTVN SDKGSWSSDGSCG SSPLRKTSTVNSE DLPPHILSAYDDD RGIVESKKIILKK L (SEQ ID NO: 66) | TTCGCTTTATTTTGGGTACCTTTTGT CAGGATTTGGTAGTATAGTTTACAAT ATGACATCGTTCCCGCAGTTAATAAG CTCCAATGACGTTCGTGTGTACGCAG CTACAAATATTTTTGAGGTCCTGTTG GTAGCATCTATCGAAATCTCTCTGGT TTTTCAGGTCAAAGTTATGTTTGCCA ACAATAATGGTCGAAGATGGACTTGG TGTTTGATGGTAGTTTCCATAGGGAT GGCACTAGCTACTGTAGGACTTTATT TTGCCACTGCCGTTGAGTTGATCAGA GCTGCTTACAGCAATGATACTGTTAG CCGCCATGTTTTTTACAATGTTTCTC TGATCTTACTAGCGTCATCTGTCAAT CTAATGACACTAATGCTAGTGGTAAA ATTAGTATTAGCGATCAGATCAAGAA GATTTTTGGGGTTAAAACAGTTTGAC AGTTTCCACATATTACTTATAATGTC TTGCCAGACTCTAATAGCACCTTCCA TTCTATTCATTTTGGGTTGGACCTTA GACCCTCATACTGGTAATGAGGTTTT AATTACAGTTGGTCAATTGCTAATAG TACTGTCATTACCGCTGTCATCTATG TGGGCTACAACCGCTAACAATACCAG TTCATCTAGTAGTTCGGTGTCCTGTA ATGACAGCTCTTTTGGTAATGACAAT CTCTGTTCCAAGAGTTCGCAATTTAG AAGAACTTTTATGAATAGATTCCGTC CCAAGTCGGTTAATGGTGACGGTAAT TCTGAAAATACCTTTGTTACAATTGA TGATTTGGAAAAAAGCGTTTTTCAAG AATTATCAACACCTGTTAGCGGAGAA TCAAAGATAGATCATGATCATGCAAG TAGTATTTCATGTCAAAAGACATGTA ATCATGTTCATGCTTCGACAGTGAAT TCAGATAAGGGATCTTGGTCCTCTGA TGGTAGTTGTGGCAGTTCTCCGTTAA GAAAGACTTCCACCGTTAATTCTGAA GATTTACCTCCACATATATTGAGCGC CTACGATGACGATCGAGGTATAGTAG AAAGTAAAAAAATTATCCTAAAGAAA TTATAG (SEQ ID NO: 67) |
| Kluyveromyces lactis | WSWITLR PGQPIF | MSEEIPSLNPLFY NETYNPLQSVLTY SSIYGDGTEITFQ QLQNLVHENITQA IIFGTRIGAAGLA LIIMWMVSKNRKT PIFIINQSSLVLT IVQSALYLSYLLS NFGGVPFALTLFP QMIGDRDKHLYGA VTLIQCLLVACIE VSLVFQVRVIFKA DRYRKIGIILTGV SASFGAATVAMWM ITAIKSIIVVYDS PLNKVDTYYYNIA VILLACSINFITL LLSVKLFLAFRAR RHLGLKQFDSFHI LLIMSTQTLIGPS VLYILAYALNNKG VKSLTSIATLLVV LSLPLTSIWAAAA NDAPSASTFYRQF NPYSAQNRDDSSS YSYGKAFSDKYSF SNSPQTSDGCSSK ELELSTQLEMDLE SGESFMDRAKRSD | (wild type) ATGTCAGAAGAGATACCCAGTTTGAA CCCATTGTTCTACAATGAGACATATA ATCCATTGCAGTCCGTCCTAACATAC AGTTCAATTTACGGAGATGGGACTGA AATAACATTTCAACAGCTACAAATC TTGTCCATGAAAACATCACCCAAGCA ATTATTTTTGGAACAAGGATCGGCGC TGCTGGATTAGCGTTGATTATAATGT GGATGGTCTCTAAGAATAGAAAGACG CCGATATTCATAATAAATCAGAGTTC TTTGGTTCTTACAATTGTTCAATCTG CTTTATATCTATCATATTTGTTGAGC AATTTTGGAGGAGTTCCCTTTGCTCT AACTTTGTTCCCACAGATGATAGGCG ACCGTGACAAACATCTTTACGGTGCC GTGACTCTAATTCAATGTCTATTGGT TGCCGTGTATTGAGGTCTCGTTAGTCT TTCAGGTAAGAGTCATTTTCAAAGCA GATAGATATAGGAAGATAGGAATCAT TTTGACTGGCGTCTCCGCTAGTTTTG GTGCTGCAACTGTAGCCATGTGGATG ATTACTGCAATAAAATCTATTATTGT AGTGATGATAGTCCATTGAACAAAG TTGACACATATTATTACAACATAGCA GTTATTTTACTTGCATGTTCAATAAA TTTCATCACTCTTCTTCTATCAGTGA AACTTTTCCTGGCTTTCAGAGCTAGG AGACATTTAGGTTTGAAACAATTTGA |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | FVSSPGSTDATVI KQLKASNIYTSET DADEEARAFWVNA IHENKDDGLMQSK TVFKELR (SEQ ID NO: 68) | CTCATTTCACATTCTACTCATCATGT CTACTCAGACATTAATAGGTCCATCG GTTTTGTATATTCTCGCCTACGCGCT GAACAATAAAGGAGTTAAGTCGTTGA CTTCTATTGCTACATTGCTTGTAGTT CTTTCCCTACCTTTGACATCTATCTG GGCTGCTGCTGCAAATGATGCACCAA GTGCCAGTACTTTCTATCGCCAATTC AACCCTTACTCTGCACAAAATCGTGA TGATTCATCATCCTACTCTTATGGTA AAGCCTTTAGTGACAAATACTCTTTC AGTAACTCACCACAAACTTCGGATGG TTGTAGTTCAAAGGAACTTGAACTAT CTACACAGTTGGAGATGGATTTAGAG TCTGGCGAATCTTTTATGGATAGAGC AAAAAGGTCCGATTTTGTTTCTTCTC CAGGATCAACAGATGCAACAGTGATT AAACAATTGAAAGCTTCCAACATCTA TACCTCAGAAACAGATGCTGATGAAG AGGCAAGGGCATTTTGGGTGAATGCA ATTCATGAAAACAAAGATGACGGTTT AATGCAATCGAAAACCGTATTCAAAG AATTAAGATAG (SEQ ID NO: 69) |
| Schizosaccharomyces pombe | TYADFLR AYQSWNT FVNPDRP NL | MRQPWWKDFTIPD ASAIIHQNITIVS IVGEIEVPVSTID AYERDRLLTGMTL SAQLALGVLTILM VCLLSSSEKRKHP VFVPNSASIVAMC LRAILNIVTICSN SYSILVNYGFILN MVHMYVHVFNILI LLLAPVIIFTAEM SMMIQVRIICAHD RKTQRIMTVISAC LTVLVLAFWITNM CQQIQYLLWLTPL SSKTIVGYSWPYF IAKILFAFSIIFH SGVFSYKLFRAIL IRKKIGQFPFGPM QCILVISCQCLIV PATFTIIDSFIHT YDGFSSMTQCLLI ISLPLSSLWASST ALKLQSMKTSSAQ GETTEVSIRVDRT FDIKHTPSDDYSI SDESETKKWT (SEQ ID NO: 70) | (wild type) ATGAGACAACCATGGTGGAAAGACTT TACTATTCCCGATGCATCCGCAATTA TTCACCAAAATATTACCATTGTCTCT ATTGTAGGAGAGATTGAAGTGCCAGT TTCAACAATTGATGCATATGAAAGAG ATAGACTTTTAACTGGAATGACTTTG TCTGCCCAACTTGCTTTAGGAGTCCT TACCATTTTGATGGTTTGTCTATTGT CATCATCCGAAAAACGAAAACACCCA GTTTTTGTTTTTAATTCGGCAAGTAT TGTTGCAATGTGTCTTCGGGCCATTT TGAATATAGTGACCATATGCAGCAAT AGCTACAGTATCCTGGTTAATTACGG GTTTATCTTAAACATGGTTCATATGT ATGTCCATGTGTTTAATATTTTAATT TTGTTGCTTGCACCGGTCATCATTTT TACTGCTGAGATGAGCATGATGATTC AAGTTCGTATAATTTGTGCACATGAT AGAAAGACACAAAGGATAATGACTGT TATTAGTGCCTGCTTAACTGTTTTGG TTCTCGCATTTTGGATTACTAACATG TGTCAACAGATTCAGTATCTGTTATG GTTAACTCCACTTAGCAGCAAGACCA TTGTTGGATACTCTTGGCCCTACTTT ATTGCTAAAATACTTTTTGCTTTTAG CATTATTTTTCACAGTGGTGTTTTTT CATACAAACTCTTTCGTGCCATATTA ATACGGAAAAAAATTGGGCAATTTCC ATTTGGTCCGATGCAGTGTATTTTAG TTATTAGCTGCCAATGTCTTATTGTT CCAGCTACCTTTACTATAATAGATAG TTTTTATCCATACGTATGATGGCTTTA GCTCTATGACTCAATGTCTGCTAATC ATTTCTCTTCCTCTTTCGAGTTTATG GGCGTCTAGTACAGCTCTGAAATTGC AAAGCATGAAAACTTCATCTGCGCAA GGAGAAACCACCGAGGTTTCGATTAG AGTTGATAGAACGTTTGATATCAAAC ATACTCCCAGTGACGATTATTCGATT TCTGATGAATCTGAAACTAAAAAGTG GACGTAG (SEQ ID NO: 71) |
| Vanderwaltozyma polyspora (receptor 1) | WHWLELD NGQPIY | MSSQSHPPLIDLF YDSSYDPGESLIY YTSIYGNNTYITF DELQTIVNKKVTQ | (wild type) ATGAGTTCCCAATCACACCCACCGCT AATCGATTTATTTACGATTCCAGTT ATGACCCTGGTGAAAGTTTAATTTAT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | GILFGVRCGAAFL<br>MLVAMWLISKNKR<br>SRIFITNQCCLVF<br>MIMHSGLYFRYLL<br>SRYGSVTFILTGF<br>QQLLTRNDIHIYG<br>ATDFIQVALVACI<br>ELSLIFQIKVIFA<br>GTNYGKLANYFIT<br>LGSLLGLATFGMY<br>MLTAINGTIKLYN<br>NEYDPNQRKYFNI<br>STILLASSINMLT<br>LILILKLVAAIRT<br>RRYLGLKQFDSFH<br>ILLIMSTQTLIIP<br>SILFILSYSLRED<br>MHTDQLIIIGNLI<br>VVLSLPLSSMWAS<br>SLNNSSKPTSLNT<br>DFSGPKSSEEGTA<br>ISLLSQNMEPSIV<br>TKYTRRSPGLYPV<br>SVGTPIEKEASYT<br>LFEATDIDFESSS<br>NDITRTS<br>(SEQ ID NO: 72) | TACACATCCATCTATGGTAATAATAC<br>ATACATAACTTTTGATGAACTCCAGA<br>CGATAGTGAACAAGAAGGTCACACAA<br>GGTATCTTATTTGGTGTCAGATGTGG<br>TGCTGCTTTCCTGATGTTGGTAGCAA<br>TGTGGTTGATTTCCAAAAATAAAAGA<br>TCTAGAATTTTCATTACCAACCAATG<br>TTGTCTGGTCTTCATGATAATGCATT<br>CTGGTCTTTATTTTAGGTACCTGCTT<br>TCAAGGTACGGTTCAGTTACTTTCAT<br>TCTAACAGGGTTCCAACAACTGCTTA<br>CAAGAAATGACATTCATATTTATGGA<br>GCTACTGATTTTATCCAAGTAGCTTT<br>GGTAGCTTGCATAGAATTATCTCTTA<br>TTTTCCAAATAAAAGTGATATTCGCT<br>GGTACAAACTATGGTAAGTTGGCTAA<br>TTATTTCATCACTCTAGGTTCATTAT<br>TGGGTTTAGCCACCTTTGGTATGTAC<br>ATGCTTACTGCTATTAACGGTACAAT<br>AAAATTATACAATAACGAATATGACC<br>CAAACCAAAGGAAATACTTTAACATT<br>TCTACAATATTGCTTGCATCATCAAT<br>TAATATGCTAACGCTGATACTTATAT<br>TGAAGCTGGTGGCAGCAATTAGAACA<br>AGACGTTACTTAGGTTTGAAGCAATT<br>CGATAGTTTTCACATCCTATTAATCA<br>TGTCGACTCAAACATTAATAATTCCT<br>TCTATCTTATTTATTCTATCATACAG<br>TTTGAGAGAGGATATGCATACTGATC<br>AATTAATAATCATCGGAAATCTGATC<br>GTGGTATTGTCATTACCATTGTCCTC<br>AATGTGGGCTTCGTCTCTAAACAATT<br>CAAGTAAACCTACATCTTTGAATACT<br>GATTTCTCAGGGCCAAAATCAAGTGA<br>AGAAGGGACAGCAATAAGTTTGCTAT<br>CACAAAACATGGAACCATCAATAGTC<br>ACTAAATATACAAGAAGATCACCTGG<br>GTTATACCCAGTAAGCGTGGGTACAC<br>CAATTGAAAAAGAAGCATCATACACT<br>CTTTTTGAAGCTACTGACATTGATTT<br>TGAAAGCAGTAGTAACGATATCACAA<br>GGACTTCATAG<br>(SEQ ID NO: 73) |
| Vanderwaltozyma polyspora (receptor 2) | WHWLRL RYGEPIY | MSGIDDMGDKPDI<br>LGLFYDANYDPGQ<br>GILTFISMYGNTT<br>ITFDELQLEVNSL<br>ITSGIMFGVRCGA<br>ACLTLLIMWMISK<br>NKKTPIFIINQCS<br>LILIIMHSGLYFK<br>NILSNLNSLSYIL<br>TGFTQNITKNNIH<br>VFGAANIIQVLLV<br>ATIELSLVFQIRV<br>MFKGDSFRKAGYG<br>LLSIASGLGIATV<br>VMYFYSAITNMIA<br>VYNQTYNSTAKLF<br>NVANILLSTSINF<br>MTVVLIVKLFLAV<br>RSRRYLGLKQFDS<br>FHILLIMSCQTLI<br>VPSILFILSYALS<br>TKLYTDHLVVIAT<br>LLVVLSLPLSSMW<br>ASAANNSPKPSSF<br>TTDYSNKNPSDTP<br>SFYSQSISSSMKS<br>KFPSKFIPNFKS<br>KDNSSDTRSENTY | (wild type)<br>ATGTCAGGAATTGATGATATGGGTGA<br>TAAACCAGATATTTTAGGTTTATTTT<br>ATGATGCTAACTATGATCCAGGTCAA<br>GGTATACTCACATTTATTTCAATGTA<br>CGGGAATACTACTATAACTTTTGATG<br>AGTTACAGTTAGAGGTCAATAGTTTA<br>ATTACAAGTGGTATTATGTTCGGCGT<br>CAGATGTGGTGCTGCTTGTTTGACAT<br>TGTTAATAATGTGGATGATTTCTAAG<br>AATAAGAAGACTCCAATTTTTATTAT<br>TAATCAATGCTCGCTAATCCTTATTA<br>TTATGCATTCAGGTTTATATTTTAAG<br>AATATTCTATCAAATTTGAATTCTTT<br>ATCATATATCTTAACTGGGTTTACTC<br>AAAATATCACTAAAAATAATATACAT<br>GTCTTTGGTGCCGCTAATATTATTCA<br>AGTTTTATTAGTAGCAACCATTGAAC<br>TGTCGTTAGTGTTTCAAATTCGAGTC<br>ATGTTTAAAGGTGACAGTTTTAGAAA<br>AGCTGGTTACGGTTTGTTGTCAATTG<br>CGTCTGGTTTGGGTATAGCTACTGTC<br>GTCATGTATTTTTACTCTGCCATTAC<br>AAATATGATTGCTGTTTATAATCAAA<br>CTTACAACTCCACTGCTAAATTATTT<br>AACGTTGCAAACATTCTTCTGTCTAC<br>ATCGATAAATTTTATGACGGTAGTAT<br>TAATTGTTAAATTATTTTTGGCTGTT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | IGNYDMEKNGSPN HSYSSKDQSEVYT IGVSSMHTDIKSQ KNISGQHLYTPST EIDEEARDFWAGR AVNNSVPNDYQPS ELPASILEELNSL DENNEGFLETKRI TFRKQ (SEQ ID NO: 74) | AGATCAAGAAGATATTTGGGTTTAAA GCAGTTCGATAGTTTCCATATTTTAT TGATTATGTCATGTCAAACATTGATT GTACCATCAATTCTTTTTATCTTATC ATACGCTTTAAGTACTAAGCTGTACA CTGATCATTTAGTTGTCATTGCAACT TTATTAGTCGTTCTATCTTTACCATT ATCTTCGATGTGGGCAAGCGCTGCAA ATAATTCTCCTAAACCAAGCTCGTTT ACAACCGATTATTCAAACAAGAATCC TAGTGACACACCAAGCTTCTACAGTC AAAGTATTAGTTCCTCGATGAAAAGC AAATTCCCAAGCAAATTCATACCCTT CAATTTCAAGTCTAAAGACAATTCTT CTGACACTAGATCAGAAAATACATAT ATTGGCAATTATGACATGGAAAAGAA TGGATCACCAAATCACTCTTATTCTT CCAAAGATCAAAGTGAAGTTTACACT ATAGGTGTAAGCTCTATGCACACAGA TATAAAGTCACAAAAGAATATCAGTG GACAGCATTTATATACCCCAAGTACA GAGATTGATGAAGAAGCTAGAGACTT CTGGGCGGGCAGAGCTGTTAATAATT CAGTTCCAAATGACTATCAACCATCT GAGTTACCAGCATCGATTCTTGAAGA ATTGAATTCACTGGATGAAAATAATG AAGGTTTCTTGGAGACAAAAAGAATA ACATTTAGAAAACAATAG (SEQ ID NO: 75) |
| Scheffersomyces stipitis | WHWTSY GVFEPG | MDTSINTLNPANI IVNYTLPNDPRVI SVPFGAFDEYVNQ SMQKAIIHGVSIG SCTIMLLIILIFN VKRKKSPAFYLNS VTLTAMIIRSALN LAYLLGPLAGLSF TFSGLVTPETNFS VSEATNAFQVIVV ALIEASMTFQVFV VFQSPEVKKLGIA LTSISAFTGAAAV GFTINSTIQQSRI YHSVVNGTPTPTV ATWSWVRDVPTIL FSTSVNIMSFILI LKLGFAIKTRRYL GLRQFGSLHILLM MATQTLLAPSILI LVHYGYGTSLNSQ LILISYLLVVLSL PVSSIWAATANNS PQLPSSATLSFMN KTTSHFSES (SEQ ID NO: 76) | (wild type) ATGGATACTAGTATCAATACTCTCAA CCCTGCGAATATCATTGTCAACTACA CCTTGCCAAATGATCCTAGAGTAATT AGTGTCCCATTTGGAGCTTTTGACGA ATATGTTAACCAATCTATGCAAAAGG CCATTATCCATGGAGTTTCCATTGGT TCATGCACCATAATGCTTTTAATTAT TTTGATCTTCAATGTCAAACGCAAGA AGTCGCCAGCTTTCTATCTTAATTCG GTTACGTTGACTGCAATGATTATTCG GTCTGCTCTTAATTTGGCATATTTGT TAGGTCCTTTGGCTGGATTAAGTTTT ACGTTCTCCGGCTTGGTAACTCCAGA AACCAATTTCTCTGTCTCTGAAGCCA CCAATGCTTTCCAGGTTATTGTTGTT GCTCTTATCGAGGCGTCCATGACATT TCAGGTGTTCGTCGTCTTCCAATCAC CAGAAGTGAAGAAGTTGGGTATAGCT CTTACCTCCATATCTGCATTCACGGG TGCTGCTGCTGTAGGATTTACTATCA ATAGTACAATCCAACAATCGAGAATT TATCATTCAGTTGTCAATGGAACTCC TACGCCAACGGTCGCTACCTGGTCTT GGGTTAGAGATGTGCCTACGATACTT TTTTCTACTTCGGTTAACATAATGTC TTTCATCTTGATTCTCAAGTTAGGGT TTGCCATAAAGACAAGAAGATACCTT GGCCTTCGGCAATTTGGCAGTTTGCA CATCTTATTGATGATGGCTACTCAAA CATTATTGGCCCCATCTATTCTCATT CTTGTACATTACGGATATGGCACATC TCTGAATAGCCAGCTCATTCTTATAA GTTACTTGCTTGTTGTTTTGTCTTTA CCAGTATCCTCTATCTGGGCAGCAAC AGCCAACAATTCTCCTCAACTTCCAT CTTCCGCAACTCTTTCATTCATGAAC AAAACGACCTCTCACTTTTCTGAAAG CTAG (SEQ ID NO: 77) |
| Schizosaccharomyces japonicus | VSDRVK QMLSHW | MYSWDEFRSPKQA EVLNQTVTLETIV | (codon optimized) ATGTACTCCTGGGACGAATTCAGATC |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | WNFRNP DTANL | STIQLPISEIDSM ERNRLLTGMTVAV QVGLGSFILVLMC IFSSSEKRKKPVF IFNFAGNLVMTLR TGTTGACCGGTATGACTGTCGCTGTT AIFEVIVLASNNY SIAVQYGFAFAAV RQYVHAFNIIILL LGPFILFIAEMSL MLQVRIICSQHRP TMITTTVISCIFT VVTLAFWITDMSQ EIAYQLFLKNYNM KQIVGYSWLYFIA KITFAASIIFHSS VFSFKLMRAIYIR RKIGQFPFGPMQC IFIVSCQCLIVPA IFTLIDSFTHTYD GFSSMTQCLLIIS LPLSSLWATHTAQ KLQTMKDNTNPPS GTQLTIRVDRTFD MKFVSDSSDGSFT EKTEETLP (SEQ ID NO: 78) | CCCAAAGCAAGCTGAAGTTTTGAACC AAACCGTTACCTTGGAAACTATTGTT TCCACCATTCAATTGCCAATCTCTGA AATTGACTCCATGGAAAGAAACAGAT TGTTGACCGGTATGACTGTCGCTGTT CAAGTTGGTTTAGGTTCCTTCATTTT AGTTTTGATGTGTATTTTCTCTTCCT CTGAAAAGAGAAAGAAGCCAGTCTTC ATCTTCAACTTCGCTGGTAACTTGGT TATGACTTTGAGAGCTATTTTCGAAG TTATCGTTTTGGCTTCTAACAACTAC TCTATCGCTGTTCAATACGGTTTCGC TTTTGCTGCCGTCAGACAATACGTTC ACGCCTTCAACATTATCATCTTGTTG TTGGGTCCATTCATCTTGTTCATCGC TGAAATGTCTTTGATGTTGCAAGTTA GAATCATTTGTTCCCAACACAGACCA ACTATGATTACCACCACTGTTATCTC TTGTATTTTCACTGTTGTTACCTTGG CCTTCTGGATCACCGACATGTCTCAA GAAATTGCTTACCAATTGTTCTTGAA AAACTACAACATGAAGCAAATTGTTG GTTACTCCTGGTTGTACTTTATCGCT AAGATCACCTTCGCTGCTTCCATTAT CTTCCATTCCTCCGTCTTCTCCTTCA AATTGATGCGTGCTATTTACATTCGT AGAAAGATCGGTCAATTCCCATTCGG TCCAATGCAATGTATCTTCATTGTTT CCTGTCAATGTTTGATCGTTCCAGCT ATTTTCACTTTGATCGATTCTTTCAC CCACACTTACGATGGTTTCTCCTCCA TGACTCAATGTTTGTTGATCATCTCC TTACCATTGTCTTCCTTGTGGGCCAC CCACACCGCTCAAAAGTTGCAAACCA TGAAGGATAACACTAACCCACCATCT GGTACCCAATTAACCATCAGAGTTGA TCGTACTTTCGACATGAAGTTCGTTT CCGACTCCTCTGACGGTTCTTTCACT GAAAAGACCGAAGAAACTTTGCCA (SEQ ID NO: 79) |
| Saccharomyces castellii | NWHWLRL DPGQPLY | MSDAPPPLSELFY NSSYNPGLSIISY TSIYGNGTEVTFN ELQSIVNKKITEA IMFGVRCGAAILT IIVMWMISKKKKT PIFIINQVSLFLI LLHSAFNFRYLLS NYSSVTFALTGFP QFIHRNDVHVYAA ASIFQVLLVASIE ISLMFQIRVIFKG DNFKRIGTILTAL SSSLGLATVAMYF VTAIKGIIATYKD VNDTQQKYFNVAT ILLASSINFMTLI LVIKLILAIRSRR FLGLKQFDSFHIL LIMSFQSLLAPSI LFILAYSLDPNQG TDVLVTVATLLVV LSLPLSSMWATAA NNASRPSSVGSDW TPSNSDYYSNGPS SVKIESVKSDEKV SLRSRIYNLYPKS KSEFEQSSEHTYV DKVDLENNFYELS TPIIERSPSSIIK KGKQGISTRETVK | (codon optimized) ATGTCTGACGCTCCACCACCATTGTC CGAATTGTTCTACAACTCCTCCTACA ACCCAGGTTTGTCTATCATTTCTTAC ACTTCCATTTACGGTAACGGTACTGA AGTTACCTTTAACGAATTACAATCTA TCGTCAACAAGAAGATTACTGAAGCT ATCATGTTCGGTGTCAGATGTGGTGC CGCTATTTTGACTATCATTGTCATGT GGATGATTTCTAAGAAGAAAAAGACC CCAATTTTCATCATCAACCAAGTTTC TTTATTCTTGATTTTGTTGCACTCCG CTTTCAACTTCAGATACTTGTTGTCT AACTACTCTTCCGTCACTTTCGCCTT GACCGGTTTCCCACAATTCATCCACA GAAACGACGTCCACGTCTACGCTGCT GCTTCTATCTTCCAAGTCTTGTTGGT CGCTTCTATTGAAATTTCCTTAATGT TCCAAATCAGAGTCATTTTCAAGGGT GATAACTTCAAGAGAATTGGTACTAT CTTGACCGCTTTGTCCTCTTCTTTGG GTTTAGCTACTGTTGCTATGTACTTT GTCACCGCTATTAAGGGTATTATTGC TACCTACAAGGATGTTAACGATACTC AACAAAAGTACTTCAACGTTGCTACT ATCTTGTTGGCTTCCTCTATCAACTT TATGACCTTGATCTTGGTTATCAAGT TGATCTTGGCTATCAGATCCAGAAGA TTCTTGGGTTTGAAACAATTCGACTC TTTCCATATCTTGTTGATCATGTCTT TTCAATCTTTGTTGGCCCCATCCATT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | KLDSLDDIYTPNT AADEEARKFWSED VSNELDSLQKIET ETSDELSPEMLQL MIGQEEEDDNLLA TKKITVKKQ (SEQ ID NO: 80) | TTGTTCATTTTGGCTTACTCTTTGGA CCCAAACCAAGGTACCGACGTCTTGG TTACTGTCGCTACTTTGTTGGTCGTC TTATCTTTGCCATTGTCCTCCATGTG GGCTACTGCTGCTAACAACGCCTCCA GACCATCCTCTGTTGGTTCCGACTGG ACTCCATCTAACTCCGACTACTACTC TAACGGTCCATCTTCTGTCAAGACCG AATCTGTCAAATCTGATGAAAAGGTC TCCTTGAGATCCAGAATTTACAACTT GTACCCAAAGTCTAAGTCTGAATTCG AACAATCCTCCGAACACACTTACGTT GACAAGGTCGACTTGGAAAACAACTT CTACGAATTGTCCACCCCAATCACCG AAAGATCTCCATCTTCTATCATTAAG AAGGGTAAGCAAGGTATTTCTACTAG AGAAACCGTCAAAAAGTTGGACTCCT TGGATGACATTTACACTCCAAACACT GCTGCTGATGAAGAAGCCAGAAAGTT CTGGTCTGAAGATGTTTCTAACGAAT TGGATTCCTTACAAAAAATCGAAACT GAAACTTCCGATGAATTATCCCCAGA AATGTTACAATTGATGATTGGTCAAG AAGAAGAAGACGATAACTTATTGGCT ACCAAGAAGATCACCGTCAAGAAGCA A (SEQ ID NO: 81) |
| Schizosaccharomyces octosporus | TYEDFLR VYKNWWS FQNPDRP DL | MREPWWKNYYTMN GTQVQNQSIPILS TQGYIQVPLSTID KAERNRILTGMTV SAQLALGVLIMVM SILLSSPEKRKTP VFIVNSASIISMC IRAILMIVNLCSE SYSLAVMYGFVFE LVGQYVHVFDILV MIIGTIIIITAEV SMLLQVRIICAHD RKTQRIVTCISSG LSLIVVAFWFTDM CQEIKYLLWLTPY NNHQISGYYWVYF VGKILFAVSIMFH SAVFSYKLFHAIQ IRKKIGQFPFGPM QCILIISCQCLFV PAIFTIIDSFIHT YDGFSSMTQCLLI VSLPLSSLWASST ALKLQSLKSTTSP GDTTQVSIRVDRT YDIKRIPTEELSS VDETEIKKWP (SEQ ID NO: 82) | (codon optimized) ATGCGTGAACCATGGTGGAAGAACTA CTACACCATGAACGGTACCCAAGTCC AAAACCAATCCATCCCAATTTTGTCC ACCCAAGGTTACATTCAAGTTCCATT GTCCACCATCGATAAGGCTGAAAGAA ACAGAATTTTGACTGGTATGACCGTT TCTGCTCAATTGGCCTTGGGTGTCTT GATCATGGTCATGTCTATTTTGTTGT CCTCCCCAGAAAAGAGAAAGACCCCA GTTTTCATCGTCAACTCTGCCTCTAT CATTTCCATGTGTATTAGAGCTATCT TGATGATTGTCAACTTGTGTTCTGAA TCCTACTCTTTGGCTGTTATGTACGG TTTCGTCTTCGAATTGGTTGGTCAAT ACGTTCACGTTTTTGACATTTTGGTT ATGATTATTGGTACCATCATCATTAT TACCGCTGAAGTTTCCATGTTGTTGC AAGTCAGAATTATTTGTGCTCACGAC AGAAAGACTCAAAGAATTGTTACCTG TATCTCTTCTGGTTTATCCTTGATCG TCGTTGCCTTCTGGTTCACTGATATG TGTCAAGAAATTAAGTACTTGTTGTG GTTGACCCCATACAACAACCACCAAA TCTCTGGTTACTACTGGGTTTACTTC GTCGGTAAGATCTTGTTCGCCGTTTC CATTATGTTCCACTCTGCCGTCTTCT CCTACAAGTTGTTCCACGCTATCCAA ATTAGAAAGAAGATTGGTCAATTCCC ATTCGGTCCAATGCAATGTATTTTAA TTATTTCCTGTCAATGTTTGTTCGTT CCAGCTATTTTCACTATCATCGACTC TTTCATCCACACTTACGACGGTTTTT CCTCCATGACCCAATGTTTGTTGATC GTCTCTTTGCCATTGTCCTCCTTGTG GGCCTCTTCCACTGCTTTAAAGTTGC AATCTTTGAAGTCTACCACCTCTCCA GGTGACACTACTCAAGTTTCCATTAG AGTCGACAGAACCTACGACATCAAGA GAATCCCAACTGAAGAATTGTCTTCT GTTGACGAAACCGAAATCAAGAAGTG GCCA (SEQ ID NO: 83) |
| Aspergillus nidulans | WCRFRG QVCG | MATHNQISDQCQW SYPEVFTTQAVEE | (codon optimized) ATGGCTACCCACAACCAAATCTCTGA |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | PTAEPASYHLHST<br>LTIMASNFDPWNQ<br>TITFRLEDGTPFD<br>ISVDYLDGILQYS<br>IRACVNYAAQLGA<br>SVILFVILVLLTR<br>AEKRASCLFWLNS<br>LALLLNFARLLCD<br>VLFFTGNFVRIYT<br>LISADESRVTASD<br>LATSIVGAIMTAL<br>LLTTIEISLVLQV<br>QVVCSNLRRIYRR<br>ALLCVSAVVATAT<br>IAIRYSLLAVNIR<br>AILEFSDPTTYNW<br>LESLATVALTISI<br>CYFCVIFVTKLGF<br>AIRLRRKLGLSEL<br>GPMKVVFIMGCQT<br>LVIPGKRTLSSLI<br>PPVIVSITHYVSD<br>VPELQTNVLTIVA<br>LSLPLSSIWAGTT<br>IDKPVTHSNVRNL<br>WQILSFSGYRPKQ<br>STYIATTTTATTN<br>AKQCTHCYSESRL<br>LTEKESGRNNDTS<br>SKSSSQYGIAVEH<br>DISVRSARRESFD<br>V<br>(SEQ ID NO: 84) | TCAATGTCAATGGTCTTACCCAGAAG<br>TCTTCACCACTCAAGCTGTCGAAGAA<br>CCAACCGCCGAACCAGCTTCTTACCA<br>CTTGCACTCTACCTTGACTATTATGG<br>CTTCTAACTTCGACCCATGGAACCAA<br>ACCATTACCTTCAGATTGGAAGACGG<br>TACTCCATTCGACATTTCTGTCGACT<br>ACTTGGACGGTATCTTGCAATACTCT<br>ATCAGAGCTTGTGTCAACTACGCTGC<br>TCAATTGGGTGCTTCTGTCATTTTGT<br>TTGTTATCTTGGTCTTGTTGACTAGA<br>GCCGAAAAAGAGCTTCTTGTTTGTT<br>CTGGTTAAACTCCTTAGCTTTGTTGT<br>TGAACTTCGCCAGATTGTTGTGTGAC<br>GTCTTGTTCTTCACCGGTAACTTCGT<br>CAGAATTTACACTTTGATCTCCGCTG<br>ACGAATCTAGAGTTACTGCTTCCGAC<br>TTGGCTACTTCCATCGTCGGTGCTAT<br>CATGACCGCTTTGTTGTTGACCACTA<br>TTGAAATTTCTTTGGTTTTGCAAGTC<br>CAAGTCGTTTGTTCTAACTTGAGAAG<br>AATCTACAGAAGAGCCTTGTTGTGTG<br>TTTCCGCCGTCGTTGCCACTGCTACC<br>ATTGCTATTAGATACTCCTTGTTGGC<br>TGTCAACATTAGAGCTATTTTGGAAT<br>TCTCCGACCCAACTACTTACAACTGG<br>TTGGAATCTTTAGCTACCGTCGCCTT<br>GACCATCTCCATCTGTTACTTCTGTG<br>TCATCTTCGTCACCAAGTTAGGTTTC<br>GCTATTAGATTGAGAAGAAAGTTGGG<br>TTTATCTGAATTGGGTCCAATGAAGG<br>TCGTCTTCATCATGGGTTGTCAAACC<br>TTGGTCATCCCAGGTAAAAGAACCTT<br>GTCTTCTTTGATTCCACCAGTCATTG<br>TTTCTATTACTCACTACGTCTCCGAC<br>GTCCCAGAATTGCAAACTAACGTTTT<br>GACTATCGTCGCCTTGTCCTTGCCAT<br>TGTCCTCTATTTGGGCTGGTACCACC<br>ATTGACAAGCCAGTCACTCACTCTAA<br>CGTTAGAAACTTGTGGCAAATCTTGT<br>CCTTCTCTGGTTACAGACCAAAGCAA<br>TCTACCTACATTGCTACCACTACTAC<br>CGCTACTACCAACGCTAAGCAATGTA<br>CCCACTGTTACTCTGAATCTAGATTG<br>TTGACTGAAAAGGAATCTGGTCGTAA<br>CAACGACACTTCTTCTAAGTCTTCCT<br>CCCAATACGGTATCGCTGTCGAACAC<br>GATATTTCCGTTAGATCTGCTCGTCG<br>TGAATCTTTTGACGTCTAG<br>(SEQ ID NO: 85) |
| Aspergillus oryzae | WCALPG QGC | MDSKFDPYSQNLT<br>FHAADGTPFQVPV<br>MTLNDFYQYCIQI<br>CINYGAQFGASVI<br>IFIILLLLTRPDK<br>RASSVFFLNGGAL<br>LLNMGRLLCHMIY<br>FTTDFVKAYQYFS<br>SDYSRAPTSAYAN<br>SILGVVLTTLLLV<br>CIETSLVLQVQVV<br>CANLRRRYRTVLL<br>CVSILVALIPVGL<br>RLGYMVENCKTIV<br>QTDTPLSLVWLES<br>ATNIVITISICFF<br>CSIFIIKLGFAIH<br>QRRRLGVRDFGPM<br>KVIFVMGCQTLTV<br>PALLSILQYAVSV<br>PELNSNIMTLVTI | (codon optimized)<br>ATGGACTCAAGTTCGACCCATACTC<br>TCAAAACTTGACTTTCCACGCTGCTG<br>ACGGTACCCCATTTCAAGTTCCAGTC<br>ATGACCTTGAACGACTTTTACCAATA<br>CTGTATTCAAATTTGTATCAACTACG<br>GTGCTCAATTCGGTGCTTCCGTCATC<br>ATTTTCATTATCTTGTTGTTATTGAC<br>TAGACCAGACAAAAGAGCTTCTTCTG<br>TTTTCTTCTTAAACGGTGGTGCCTTG<br>TTGTTGAACATGGGTAGATTGTTGTG<br>TCACATGATTTACTTCACTACTGACT<br>TCGTCAAGGCTTACCAATACTTCTCT<br>TCTGATTACTCTAGAGCCCCAACCTC<br>TGCCTACGCTAACTCCATTTTGGGTG<br>TCGTCTTGACCACCTTGTTGTTGGTT<br>TGTATCGAAACCTCCTTGGTTTTACA<br>AGTCCAAGTCGTCTGTGCTAACTTGA<br>GACGTAGATACAGAACCGTCTTATTG<br>TGTGTTTCTATCTTGGTCGCCTTGAT<br>CCCAGTCGGTTTGAGATTGGGTTACA |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | SLPLSSIWAGVSL<br>TRSSSTENSPSRG<br>ALWNRLTDSTGTR<br>SNQTSSTDTAVAM<br>TYPSNKSSTVCYA<br>DQSSVKRQYDPEQ<br>GHGISVEHDVSVH<br>SCQRL<br>(SEQ ID NO: 86) | TGGTTGAAAACTGTAAGACTATTGTT<br>CAAACTGATACCCCATTGTCTTTGGT<br>TTGGTTGGAATCTGCTACTAACATCG<br>TCATTACCATCTCCATCTGTTTCTTC<br>TGTTCTATCTTCATCATCAAGTTGGG<br>TTTCGCCATTCACCAAAGAAGAAGAT<br>TGGGTGTCAGAGATTTCGGTCCAATG<br>AAGGTCATTTTCGTCATGGGTTGTCA<br>AACTTTGACTGTTCCAGCTTTGTTGT<br>CTATTTTGCAATACGCTGTCTCTGTC<br>CCAGAATTGAACTCTAACATTATGAC<br>TTTGGTTACTATCTCTTTGCCATTGT<br>CCTCCATTTGGGCTGGTGTTTCTTTG<br>ACCCGTTCTTCCTCCACCGAAAACTC<br>TCCATCCAGAGGTGCTTTGTGGAACC<br>GTTTGACCGACTCTACCGGTACCAGA<br>TCTAACCAAACCTCTTCCACCGACAC<br>CGCCGTCGCTATGACCTACCCATCTA<br>ACAAGTCTTCTACTGTCTGTTACGCC<br>GATCAATCTTCTGTCAAGAGACAATA<br>CGATCCAGAACAAGGTCACGGTATCT<br>CTGTTGAACACGATGTTTCTGTCCAC<br>TCCTGTCAAAGATTGTAG<br>(SEQ ID NO: 87) |
| Beauvaria bassiana | WCMRPG QPCW | MDGSSAPSSPTPD<br>PTFDRFAGNVTFF<br>LADHITTTSVPMP<br>VLNAYYDESLCTT<br>MNYGAQLGACLVM<br>LVVVVALTPAAKL<br>ARRPASALHLVGL<br>LLCAVRSGLLFAY<br>FVSPISHFYQVWA<br>GDFSAVSRRYWDA<br>SLAANTLAFPLVV<br>VVEAALINQAWTM<br>VAFWPRAAKAAAC<br>ACSAVIVLLTIGT<br>RLAYTIVQNHAIV<br>TAVPPEHFLWAIQ<br>WSAVMGAVSIFWF<br>CAVFNVKLVCHLV<br>ANRGILPSISVVN<br>PMEVLVMTNGTLM<br>IIPSIFAGLEWAK<br>FTNFESGSLTLTS<br>VIIILPLGTLAAQ<br>RISGQGSQGYQAG<br>HLFHEQQQQQART<br>RSGAFGSASQQSH<br>PTNKVPSSITLST<br>SGTPITPQISAGS<br>RPELPLVDRSERL<br>DPIDLELGRIDAF<br>RGSSDFSPSTARP<br>KRMQRDNFA<br>(SEQ ID NO: 88) | (codon optimized)<br>ATGGATGGTTCTTCTGCTCCATCTTC<br>TCCAACTCCAGATCCAACCTTCGACA<br>GATTCGCCGGTAACGTCACTTTCTTC<br>TTGGCTGACCACATCACCACTACCTC<br>CGTTCCAATGCCAGTCTTGAACGCCT<br>ACTACGACGAATCCTTGTGTACTACC<br>ATGAACTACGGTGCTCAATTAGGTGC<br>TTGTTTAGTTATGTTGGTTGTCGTTG<br>TTGCTTTGACCCCAGCTGCTAAGTTG<br>GCTAGAAGACCAGCTTCTGCTTTGCA<br>TTTGGTTGGTTTGTTGTTGTGTGCTG<br>TTAGATCCGGTTTGTTGTTTGCTTAC<br>TTCGTCTCCCCAATCTCTCACTTTTA<br>CCAAGTTTGGGCTGGTGACTTCTCTG<br>CCGTTTCCAGAAGATACTGGGACGCT<br>TCTTTGGCTGCCAACACTTTAGCTTT<br>CCCATTGGTTGTCGTCGTTGAAGCTG<br>CTTTGATCAACCAAGCTTGGACCATG<br>GTTGCTTTCTGGCCAAGAGCCGCTAA<br>GGCCGCTGCCTGTGCTTGTTCTGCTG<br>TCATTGTCTTGTTGACTATTGGTACT<br>AGATTGGCCTACACTATCGTCCAAAA<br>CCACGCTATTGTTACTGCCGTCCCAC<br>CAGAACACTTCTTGTGGGCTATTCAA<br>TGGTCCGCTGTTATGGGTGCTGTTTC<br>CATCTTCTGGTTTTGTGCCGTTTTCA<br>ACGTCAAGTTGGTCTGTCACTTAGTC<br>GCTAACAGAGGTATCTTGCCATCTAT<br>CTCTGTTGTTAACCCAATGGAAGTCT<br>TGGTTATGACTAACGGTACCTTGATG<br>ATTATCCCATCTATCTTCGCTGGTTT<br>GGAATGGGCTAAGTTCACCAACTTCG<br>AATCCGGTTCTTTGACTTTGACTTCC<br>GTTATTATTATCTTGCCATTGGGTAC<br>TTTGGCTGCCCAACGTATTTCTGGTC<br>AAGGTTCCCAAGGTTACCAAGCTGGT<br>CACTTATTCCACGAACAACAACAACA<br>ACAAGCTCGTACCCGTTCCGGTGCCT<br>TCGGTTCCGCTTCTCAACAATCCCAT<br>CCAACTAACAAGGTTCCATCCTCTAT<br>TACCTTGTCTACCTCTGGTACTCCAA<br>TTACTCCACAAATCTCTGCCGGTTCC<br>CGTCCAGAATTACCATTGGTTGATAG<br>ATCCGAACGTTTGGACCCAATTGACT<br>TGGAATTGGGTAGAATCGATGCTTTC<br>AGAGGTTCTTCCGACTTCTCTCCATC |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | | CACCGCTAGACCAAAGCGTATGCAAC GTGATAACTTCGCCTAG (SEQ ID NO: 89) |
| Candida lustianiae | KWKWIKF RNTDVIG | MNPADINIEYTLG DTAFSSTFADFEA WKTRNTQFAIVNG VALACGIILMVVS WIIIVNKRAPIFA MNQTMLVIMVIKS AMYLKHIMGPLNS LTFRFTGLMEESW APYNVYVTINVLH VLLVAAVESSLVF QIHVVFKSSRARV AGRAIVSAMSTLA LLIVSLYLYSTVR HAQTLRAELSHGD TTTVEPWVDNVPL ILFSASLNVLCLL LALKLVFAVRTRR HLGLRQFDSFHIL IIMATQTFVIPSS LVIANYRYASSPL LSSISIIVAVCNL PLCSLWACSNNNS SYPTSSQNTILSR YETETSQATDASS TTCAGIAEKGFDK SPDSPTFGDQDSV SISHILDSLEKDV EGVTTHRLT (SEQ ID NO: 90) | (codon optimized) ATGAACCCAGCTGACATCAACATCGA ATACACCTTGGGTGATACTGCTTTCT CTTCCACTTTCGCTGATTTCGAAGCT TGGAAAACTAGAAACACTCAATTCGC TATTGTCAACGGTGTCGCTTTGGCTT GTGGTATTATCTTGATGGTCGTTTCT TGGATTATTATTGTTAACAAGAGAGC TCCAATCTTCGCTATGAACCAAACTA TGTTGGTTATCATGGTTATTAAGTCC GCTATGTACTTGAAGCATATCATGGG TCCATTGAACTCCTTGACCTTCCGTT TCACCGGTTTAATGGAAGAATCCTGG GCTCCATACAACGTTTACGTCACTAT TAACGTCTTGCATGTTTTGTTGGTCG CTGCTGTCGAATCCTCTTTGGTCTTC CAAATCCATGTTGTTTTCAAGTCTTC TAGAGCCAGAGTTGCTGGTAGAGCCA TTGTTTCTGCTATGTCCACTTTGGCC TTGTTGATCGTTTCTTTGTACTTGTA CTCTACTGTTAGACATGCTCAAACTT TGCGTGCTGAATTATCTCATGGTGAC ACTACCACTGTTGAACCATGGGTCGA TAACGTTCCATTGATTTTGTTTTCCG CTTCTTTGAACGTTTTGTGTTTGTTG TTGGCCTTGAAATTGGTTTTCGCTGT CAGAACCAGAAGACATTTAGGTTTAA GACAATTCGACTCTTTCCACATCTTG ATTATTATGGCCACTCAAACTTTCGT TATCCCATCCTCTTTGGTCATCGCTA ACTACAGATACGCTTCTTCCCCATTG TTGTCTTCCATTTCCATCATCGTCGC CGTCTGTAACTTGCCATTGTGTTCCT TGTGGGCTTGTTCTAACAACAACTCT TCCTACCCAACTTCTTCTCAAAACAC TATTTTGTCCAGATACGAAACTGAAA CCTCTCAAGCTACTGACGCTTCCTCT ACCACCTGTGCCGGTATTGCTGAAAA GGGTTTCGACAAGTCTCCAGACTCTC CAACTTTCGGTGACCAAGACTCCGTC TCTATCTCCCATATCTTGGACTCTTT GGAAAAGGATGTTGAAGGTGTCACCA CCCATAGATTGACTTAG (SEQ ID NO: 91) |
| Candida tenuis | FSWNYRL KWQPIS | MDSYLLNHPGDIS LNFALPLSDEVYT ITFNDLDSQSSFS IQYLVIHSCAITV CLTLLVLLNLFIR NKKTPVFVLNQVI LFFAIVRSSLFIG FMKSPLSTITASF TGIISDDQKHFYK VSVAANAALIILV MLIQVSFTYQIYI IFRSPEVRKFGVF MTSALGVLMAVTF GFYVNSAVASTKQ YQHIFYSTDPYIM DSWVTGLPPILYS ASVIAMSLVLVLK LVAAVRTRRYLGL KQFSSYHILLIMF TQTLFVPTILTIL AYAFYGYNDILIH ISTTITVVLLPFT SIWASIANNSRSL | (codon optimized) ATGGACTCCTACTTGTTGAACCATCC AGGTGACATCTCTTTGAACTTCGCCT TGCCATTGTCCGATGAAGTCTACACT ATTACCTTCAACGACTTAGACTCTCA ATCTTCTTTTTCCATTCAATACTTGG TCATCCACTCTTGTGCCATTACCGTC TGTTTGACCTTGTTGGTTTTGTTGAA CTTGTTCATCAGAAACAAGAAGACTC CAGTCTTCGTTTTGAACCAAGTCATC TTGTTCTTCGCTATCGTCAGATCTTC TTTGTTCATCGGTTTTATGAAGTCTC CATTGTCCACCATCACCGCCTCTTTC ACCGGTATCATTTCTGATGACCAAAA ACACTTCTACAAGGTCTCCGTCGCTG CTAACGCCGCTTTGATCATTTTGGTC ATGTTGATTCAAGTTTCTTTCACTTA CCAAATCTACATTATTTTCAGATCCC CAGAAGTTAGAAAGTTCGGTGTCTTC ATGACCTCCGCCTTGGGTGTCTTGAT GGCTGTTACCTTCGGTTTTTACGTTA ACTCCGCTGTCGCTTCTACCAAGCAA TACCAACACATCTTCTACTCTACCGA |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | MSAASLYFSGSNS SLSELSSPSPSDN DTLNENVFAFFPD KLQKMNSSEAVSA VDKVVVHDHFDTI SQKSIPHDILEIL QGNEGGQMKEHIS VYSDDSFSKTTPP IVGGNLLITNTDI GMK (SEQ ID NO: 92) | CCCATACATCATGGACTCTTGGGTCA CTGGTTTGCCACCAATCTTGTACTCT GCTTCCGTCATCGCTATGTCTTTGGT CTTGGTTTTGAAGTTGGTCGCTGCTG TCAGAACCAGAAGATACTTGGGTTTG AAGCAATTCTCCTCCTACCACATCTT GTTGATTATGTTCACCCAAACCTTGT TCGTTCCAACCATCTTGACCATCTTA GCTTACGCTTTCTACGGTTACAACGA TATCTTGATCCATATTTCTACCACCA TCACCGTTGTCTTGTTGCCATTCACC TCCATTTGGGCTTCTATCGCCAACAA CTCTAGATCCTTGATGTCTGCCGCTT CCTTGTACTTCTCCGGTTCCAACTCC TCTTTGTCTGAATTGTCTTCTCCATC TCCATCTGATAACGACACTTTGAACG AAAACGTCTTCGCCTTTTTTCCAGAC AAGTTGCAAAAGATGAACTCTTCTGA AGCCGTTTCTGCTGTCGACAAGGTCG TTGTTCACGACCACTTTGATACCATC TCCCAAAAGTCTATCCCACACGACAT CTTGGAAATTTTGCAAGGTAACGAAG GTGGTCAAATGAAGGAACACATCTCT GTCTACTCTGATGACTCTTTCTCCAA GACTACTCCACCAATTGTCGGTGGTA ACTTGTTGATCACCAACACCGACATC GGTATGAAG (SEQ ID NO: 93) |
| Neosartorya fischeri | WCHLPG QGC | MNSTFDPWTQNIT LTQSDGTTVISSL ALADDYLHYMIRL GINYGAQLGACAV LLLVLLLLTRPEK RVSSVFVLNVAAL LANIIRLGCQLSY FSTGFARMYALLA GDFSRVSRGAYAG QVMASVFFTIVFI CVEASLVLQVQVV CSNLRRQYRILLL GASTLAALVPIGV RLTYSVLNCMVIM HAGTMDHLDWLES ATNIVTTVSICFF CAVFVVKLGLAIK MRKRLGVKQFGPM RVIFIMGCQTMTI PAIFAICQYFSRI PEFSHNVLTLVII SLPLSSIWAGFAL VQANSTARSTESR HHLWNILSSDGAT RDKPSQCVSSPMT SPTTTCYSEQSTS KPQQDPENGFGIS VAHDISIHSFRKD AHGDI (SEQ ID NO: 94) | (codon optimized) ATGAACTCCACCTTCGACCCATGGAC CCAAAACATTACTTTGACTCAATCCG ACGGTACCACTGTCATCTCCTCTTTG GCTTTGGCCGATGACTACTTGCACTA CATGATTAGATTGGGTATCAACTACG GTGCCCAATTGGGTGCTTGTGCTGTT TTGTTGTTGGTTTTGTTATTGTTGAC TAGACCAGAAAAGAGAGTTTCTTCTG TCTTCGTTTTGAACGTCGCTGCTTTG TTGGCTAACATCATCAGATTGGGTTG TCAATTGTCCTACTTCTCTACCGGTT TCGCTAGAATGTACGCCTTGTTGGCC GGTGACTTCTCCAGAGTCTCTCGTGG TGCTTACGCCGGTCAAGTTATGGCCT CCGTCTTCTTCACCATTGTCTTCATT TGTGTTGAAGCTTCTTTGGTTTTGCA AGTTCAAGTCGTCTGTTCTAACTTGA GAAGACAATACAGAATCTTGTTATTG GGTGCTTCCACTTTGGCTGCCTTGGT TCCAATTGGTGTTCGTTTGACTTACT CCGTTTTAAACTGTATGGTTATTATG CACGCTGGTACTATGGACCACTTGGA TTGGTTGGAATCTGCTACCAACATCG TTACTACCGTTTCTATTTGTTTCTTC TGTGCTGTTTTCGTTGTCAAATTAGG TTTGGCTATCAAGATGAGAAAGCGTT TGGGTGTCAAACAATTCGGTCCAATG AGAGTTATCTTCATCATGGGTTGTCA AACCATGACCATCCCAGCTATTTTCG CTATTTGTCAATACTTCTCTAGAATT CCAGAATTTTCTCATAACGTTTTGAC TTTGGTTATCATCTCTTTGCCATTGT CTTCTATCTGGGCCGGTTTTGCTTTG GTCCAAGCCAACTCTACCGCCAGATC TACCGAATCTAGACATCATTTGTGGA ACATTTTGTCTTCCGATGGTGCTACC AGAGACAAGCCATCCCAATGTGTTTC TTCTCCAATGACCTCTCCAACCACTA CCTGTTACTCCGAACAATCCACCTCT AAGCCACAACAAGACCCAGAAAACGG TTTTGGTATTTCTGTTGCCCACGATA TTTCCATCCACTCTTTCAGAAAGGAC GCCCACGGTGATATTTAG |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | | (SEQ ID NO: 95) |
| Neurospora crassa | QWCRIHG QSCW | MASSSSPPADIFS GITQSLNSTHATL TLPIPPADRDHLE NQVLFLFDNHGQL LNVTTTYIDAFNN MLVSTTINYATQI GATFIMLAIMLLM TPRRRFKRLPTII SLLALCINLIRVV LLALFFPSHWTDF YVLYSGDWQFVPP GDMQISVAATVLS IPVTALLLSALMV QAWSMMQLWTPLW RALVVLVSGLLSL VTVAMSFANCIFQ AKNILYADPLPSY WVRKLYLALTTGS ISWFTFLFMIRLV MHMWTNRSILPSM KGLKAMDVLIITN SILMLIPVLFAGL EFLDSASGFESGS LTQTSVVIVLPLG TLVAQRIATRGYM PDSLEASSGPNGS LPLSNLSFAGGGG GGSGGHKDKENGG GIIPPTTNNTAAT NFSSSIACSGISC LPKVKRMTASSAS SSQRPLLTMTNST IASNDSSGFPSPG IHNTTTTTTQYQY SMGMNMPNFPPVP FPGYQSRTTGVTS HIVSDGRHHQGMN RHPSVDHFDRELA RIDDEDDDGYPFA SSEKAVMHGDDDD DVERGRRRALPPS LGGVRVERTIETR SEERMPSPDPLGV TKPRSFE (SEQ ID NO: 96) | (codon optimized) ATGGCGTCCTCTTCCTCACCACCTGC AGACATTTTCTCAGGGATCACGCAAT CACTAAATAGTACACACGCGACGCTT ACACTACCGATTCCGCCAGCGGACAG GGATCATCTGGAAAATCAAGTATTAT TTTTGTTTGACAATCACGGTCAGTTA CTTAATGTAACTACAACTTACATTGA CGCTTTTAACAATATGCTGGTCTCTA CTACTATAAACTATGCAACGCAAATT GGAGCTACTTTTATAATGCTAGCCAT TATGTTATTAATGACTCCCAGAAGGA GGTTCAAACGTTTACCAACAATTATT AGCTTGTTAGCCTTATGTATTAATTT GATCAGGGTGGTTTTGCTGGCCCTGT TTTTTCCTTCTCACTGGACAGACTTC TACGTGTTGTATTCCGGTGACTGGCA GTTTGTACCTCCAGGGGATATGCAAA TATCTGTTGCTGCTACGGTTTTGTCT ATCCCAGTGACGGCATTATTATTGAG CGCATTGATGGTTCAAGCCTGGTCAA TGATGCAATTATGGACACCACTGTGG AGGGCACTAGTGGTACTAGTGTCCGG GCTATTGTCACTGGTAACTGTGGCAA TGAGTTTCGCGAATTGCATTTTCCAA GCGAAAAATATTTTGTATGCCGACCC TTTACCCTCCTACTGGGTCAGAAAAT TGTACTTAGCATTAACGACTGGGTCT ATAAGTTGGTTCACATTCCTTTTTAT GATAAGATTGGTTATGCATATGTGGA CAAACAGATCTATATTACCAAGCATG AAGGGTTTGAAGGCTATGGATGTATT GATTATTACGAATTCTATATTGATGT TAATCCCAGTGTTGTTGCAGGCTTG GAATTTCTGGATAGTGCCTCTGGATT TGAGTCCGGGTCTTTGACTCAAACCT CTGTAGTGATTGTCCTGCCTTTGGGT ACTTTAGTAGCACAAAGAATAGCTAC GAGGGGTTACATGCCCGATAGTCTGG AGGCTTCTAGCGGACCAAATGGTTCA TTGCCGTTATCTAATTTAAGTTTCGC TGGAGGGGGCGGTGGTGGTTCTGGGG GACATAAAGATAAAGAAAACGGTGGC GGTATTATACCGCCTACTACGAACAA TACTGCTGCTACTAATTTTTCTTCAT CAATCGCGTGTTCTGGTATATCTTGT TTACCAAAAGTCAAAAGAATGACCGC GAGTTCAGCCTCAAGTAGCCAGAGAC CGTTGTTGACAATGACTAACTCAACC ATAGCGAGTAATGACAGTTCAGGTTT CCCTTCTCCTGGCATACATAATACCA CTACTACGACAACACAATACCAATAT TCCATGGGAATGAACATGCCGAACTT TCCTCCAGTCCCGTTCCCAGGTTACC AGTCACGTACTACCGGTGTTACTTCC CATATTGTGTCCGACGGTAGACATCA CCAGGGTATGAACAGGCACCCATCTG TTGACCATTTTGATAGGGAACTTGCT AGGATTGATGATGAAGATGACGATGG TTACCCTTTCGCATCAAGTGAAAAGG CCGTTATGCACGGAGACGATGACGAC GATGTGGAAGGGGACGTCGTAGAGC TCTACCACCATCCTTAGGTGGAGTTA GAGTTGAAAGGACGATCGAGACCAGG AGCGAGGAACGTATGCCATCTCCGGA CCCATTGGGTGTTACGAAGCCTAGAT CATTCGAGTAG (SEQ ID NO: 97) |
| Pseudogymnoascus | FCWRPG | MSTANVHLPADFD | (codon optimized) |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| destructans | QPCG | PTRQNITIYTPDG TPVVATLPMINLF NRQNNEICVVYGC QLGASLIMFLVVL LTTRVSKRKSPIF VLNVLSLIISCLR SLLQILYYIGPWT EIYRYLSFDYSTV PASAYANSVAATL LTLFLLITIEASL VLQTNVVCKSMSS HIRWPVTALSMVV SLLAISFRFGLTI RNIEGILGATVKS DSLMFSGASLISE TASIWFFCTIFVI KLGWTLYQRKKMG LKQWGPMQIITIM AGCTMLIPSLFTV LEFFPEETFYEAG TLAICLVAILLPL SSVWAAAAIDGDE PVRPHGSTPKFAS FNMGSDYKSSSAH LPRSIRKASVPAE HLSRTSEEELGDD GTLNRGGAYGMDR MSGSISPRGVRIE RTYEVHTAGRGGS IEREDIF (SEQ ID NO: 98) | ATGTCCACTGCCAACGTTCATTTACC AGCTGATTTCGATCCAACTAGACAAA ACATCACTATCTATACCCCAGACGGT ACCCCAGTTGTTGCTACCTTGCCAAT GATCAATTTGTTTAACAGACAAAACA ACGAAATCTGTGTTGTTTACGGTTGT CAATTGGGTGCCTCTTTAATTATGTT CTTGGTTGTTTTGTTGACCACCAGAG TTTCCAAGAGAAAATCTCCAATCTTC GTCTTGAACGTTTTGTCTTTGATTAT TTCTTGTTTAAGATCCTTGTTGCAAA TTTTATACTATATTGGTCCATGGACC GAGATCTACAGATACTTGTCTTTCGA TTACTCTACTGTCCCAGCTTCCGCTT ACGCTAATTCTGTTGCTGCCACTTTA TTAACCTTATTCTTATTGATTACCAT TGAAGCTTCTTTAGTTTTACAAACTA ACGTTGTCTGCAAGTCTATGTCTTCT CACATTCGTTGGCCAGTTACTGCTTT GTCCATGGTTGTCTCTTTATTGGCTA TTTCTTTTAGATTCGGTTTGACCATC CGTAACATCGAAGGTATCTTAGGTGC TACTGTCAAATCCGACTCCTAATGT TCTCTGGTGCCTCTTTGATCTCTGAA ACTGCTTCTATCTGGTTCTTCTGCAC TATTTTCGTTATTAAATTGGGTTGGA CCTTGTACCAAAGAAAGAAGATGGGT TTGAAGCAATGGGGTCCAATGCAAAT TATCACTATCATGGCTGGTTGCACCA TGTTGATCCCATCCTTGTTCACTGTT TTGGAATTCTTCCCTGAAGAAACTTT CTACGAGGCCGGTACTTTGGCTATCT GTTTGGTTGCTATTTTGTTGCCATTA TCTTCCGTCTGGGCTGCCGCTGCTAT TGATGGTGATGAACCAGTCCGTCCAC ATGGTTCTACCCCAAAATTCGCTTCT TTCAACATGGGTTCCGACTACAAATC TTCTTCTGCTCACTTGCCAAGATCTA TTAGAAAGGCCTCCGTCCCAGCTGAA CATTTATCTAGAACTTCTGAAGAAGA GTTAGGTGACGACGGTACTTTGAACA GAGGTGGTGCCTACGGTATGGACAGA ATGTCCGGTTCTATCTCCCCTAGAGG TGTCAGAATTGAAAGAACTTACGAAG TTCATACCGCTGGTAGAGGTGGTTCT ATCGAGAGAGAGGACATCTTCTAG (SEQ ID NO: 99) |
| Hypocrea jecorina | WCYRIGE PCW | MSSFDPYTQNITI LVSPSSPPISIPI PVIDAFNDETASI ITNYAAQLGAALA MLLVLLAATPTAR LLRADGPSLLHAL ALLVCVVRTVLLI YFFLTPFSHFYQV WTGDFSQVPAWNY RASIAGTVLSTLL TVVTDAALVNQAW TMVSLFAPRTKRA VCVLSLLITLLAI SFRVAYTVIQCEG IAELAAPRQYAWL IRATLIFNICSIA WFCALFNSKLVAH LVTNRGVLPSRRA MSPMEVLIMANGI LMIVPVVFAILEW HHFINFEAGSLTP TSIAIILPLSSLA AQRIANTSSS (SEQ ID NO: 100) | (codon optimized) ATGTCTTCCTTCGACCCATACACTCA AAACATTACTATTTTGGTTTCTCCAT CCTCTCCACCAATTTCCATTCCAATC CCAGTTATCGACGCTTTCAACGACGA AACCGCTTCTATCATTACTAACTACG CCGCTCAATTAGGTGCTGCTTTGGCC ATGTTATTAGTTTTGTTGGCCGCTAC TCCAACCGCTAGATTGTTAAGAGCTG ATGGTCCATCCTTGTTGCACGCTTTG GCCTTGTTAGTCTGTGTCGTCAGAAC TGTCTTATTGATCTACTTCTTCTTGA CCCCATTCTCTCACTTCTACCAAGTC TGGACCGGTGACTTCTCTCAAGTTCC AGCTTGGAACTACAGAGCTTCTATTG CTGGTACCGTTTTGTCTACTTTGTTG ACCGTTGTTACCGACGCTGCTTTGGT TAACCAAGCTTGGACTATGGTTTCTT TATTCGCTCCAAGAACTAAGAGAGCC GTTTGTGTTTTGTCCTTGTTAATCAC CTTGTTGGCCATTTCTTTCAGAGTCG CTTACACCGTCATTCAATGTGAAGGT ATCGCTGAATTGGCTGCTCCAAGACA ATACGCTTGGTTGATCAGAGCCACTT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | | TGATCTTTAACATCTGTTCCATTGCC<br>TGGTTCTGTGCTTTGTTCAACTCTAA<br>GTTGGTTGCTCACTTGGTTACCAACA<br>GAGGTGTCTTGCCATCCCGTAGAGCC<br>ATGTCCCCAATGGAAGTTTTGATTAT<br>GGCCAACGGTATCTTGATGATTGTTC<br>CAGTTGTTTTCGCTATCTTGGAATGG<br>CACCACTTCATTAACTTCGAAGCTGG<br>TTCTTTAACCCCAACCTCCATCGCCA<br>TTATCTTGCCATTGTCCTCTTTGGCC<br>GCCCAAAGAATCGCCAACACTTCTTC<br>CTCTTAG (SEQ ID NO: 101) |
| Tuber melanosporum | WTPRPGR GAY | MEQIPVYERPGFN PHKQNITLFKHDG STVTVGLHELDAM FTHSIRVAVVFAS QIGACALLSVIVA MVTKREKRRALFF LHIISLLLVVVRS VLQILYFVGPWAE TYNYVAYYYEDIP LSDKLISIWAGII QLILNICILLSLI LQVRVVYATSPKL NTIMTLVSCVIAS ISVGFFFTVIVQI SEAILNGVGYDGW VYKVHRGVFAGAI AFFSFIFIFKLAF AIRRRKALGLQRF GPLQVIFIMGCQT MIVPAIFATLENG VGFEGMSSLTATL AVISLPLSSMWAA AQTDGPSPQSTPR DGYRRFSTRRSAL NRSDPSGGRSVDM NTLDSTGNDSLAL HVDKTFTVESSPS SQSQAGPHKERGF EFA (SEQ ID NO: 102) | (codon optimized)<br>ATGGAGCAAATCCCAGTCTACGAGCG TCCAGGTTTCAACCCACACAAGCAAA ACATTACCTTGTTCAAGCATGATGGT TCTACTGTTACTGTCGGTTTGCATGA GTTGGACGCCATGTTCACTCATTCCA TCAGAGTTGCTGTCGTCTTCGCCTCT CAAATTGGTGCTTGTGCTTTGTTGTC TGTTATCGTTGCTATGGTCACCAAGA GAGAAAAGAGACGTGCTTTGTTCTTC TTGCACATTATTTCCTTGTTGTTGGT CGTTGTTCGTTCCGTCTTGCAAATCT TGTACTTCGTCGGTCCATGGGCTGAA ACTTATAATTACGTCGCCTACTACTA TGAAGACATTCCTTTGTCTGACAAAT TGATTTCCATTTGGGCTGGTATTATC CAATTGATTTTGAATATCTGTATTTT GTTATCTTTGATCTTGCAAGTTCGTG TCGTTTACGCCACCTCTCCAAAATTG AACACTATTATGACTTTAGTCTCTTG TGTTATCGCTTCTATTTCTGTCGGTT TCTTCTTTACTGTCATCGTTCAAATT TCTGAGGCTATTTTAAACGGTGTTGG TTACGACGGTTGGGTTTACAAAGTCC ATAGAGGTGTCTTCGCTGGTGCTATC GCCTTCTTCTCTTTCATCTTCATCTT TAAGTTGGCCTTCGCTATCAGAAGAA GAAAGGCTTTGGGTTTGCAAAGATTC GGTCCATTGCAAGTTATCTTCATCAT GGGTTGTCAAACTATGATTGTTCCAG CTATCTTTGCTACTTTGGAAAACGGT GTTGGTTTCGAAGGTATGTCCTCTTT GACTGCTACCTTGGCTGTCATTTCCT TACCATTGTCTTCTATGTGGGCCGCC GCTCAAACCGACGGTCCATCTCCACA ATCCACTCCAAGAGACGGTTATAGAA GATTCTCTACTCGTAGATCTGCCTTG AACAGATCTGACCCATCTGGTGGTAG ATCTGTTGACATGAACACCTTGGACT CTACCGGTAACGATTCCTTAGCTTTG CACGTTGATAAGACTTTTACTGTTGA ATCTTCCCCATCCTCCCAATCTCAAG CTGGTCCACACAAGGAAAGAGGTTTC GAATTCGCCTAG (SEQ ID NO: 103) |
| Dactylellina haptotyla | WCVYNS CP | MDHNTQHFNRPEY IEIPVPPSKGFNP HTNPAFFIYPDGS NMTFWFGQIDDFR RDQLFTNTIFSIQ IGAALVILCVMFC VTHADKRKTIVYL LNVSNLFVVIIRG VFFVHYFMGGLAR TYTTFTWDTSDVQ QSEKATSIVSSIC SLILMIGTQISLL LQVRICYALNPRS | (codon optimized)<br>ATGGACCACAACACCCAACACTTCAA CAGACCTGAATACATTGAAATCCCAG TTCCACCATCTAAGGGTTTCAACCCA CACACCAACCCTGCTTTCTTCATCTA CCCAGACGGTTCTAATATGACCTTTT GGTTCGGTCAAATCGACGATTTCAGA CGTGACCAATTATTCACTAACACCAT CTTTTCCATTCAAATTGGTGCCGCTT TGGTCATCTTATGTGTCATGTTTTGT GTTACCCACGCTGATAAGCGTAAAAC CATTGTCTACTTGTTAAACGTTTCCA ACTTGTTCGTTGTTATCATTAGAGGT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | KTAILVTCGSISG<br>IATTAYLLLGAYT<br>IQLREKPPDMKFM<br>KWAKPVVNALVAL<br>SIVSFSGIFSWRM<br>FQSVRNRRRMGFT<br>GIGSLESLLASGF<br>QCLVFPGLVTTAL<br>TVAGSTWYIAVNL<br>TTPSDLTAIYNCS<br>AFFAYAFSIPLLK<br>ERAQVEKTISVVI<br>AIAGVLVVAYGDG<br>ADDGSTSNGEKAR<br>LGGNVLIGIGSVL<br>YGLYEVLYKKLLC<br>PPSGASPGRSVVF<br>SNTVCACIGAFTL<br>LFLWIPLPLLHWS<br>GWEIFELPTGKTA<br>KLLGISIAANATF<br>SGSFLILISLTGP<br>VLSSVAALLTIFL<br>VAITDRILFGREL<br>TSAAILGGLLIIA<br>AFALLSWATWKEM<br>IEENEKDTIDSIS<br>DVGDHDD<br>(SEQ ID NO: 104) | GTTTTCTTTGTTCATTACTTCATGGG<br>TGGTTTGGCCAGAACCTATACCACTT<br>TCACCTGGGATACTTCTGATGTTCAA<br>CAATCTGAGAAGGCTACTTCCATTGT<br>CTCCTCTATTTGTTCTTTGATTTTGA<br>TGATCGGTACTCAAATCTCCTTATTG<br>TTGCAAGTCAGAATCTGTTACGCTTT<br>GAACCCAAGATCCAAGACCGCTATCT<br>TGGTTACTTGTGGTTCTATTTCCGGT<br>ATTGCTACCACTGCTTATTTATTGTT<br>GGGTGCTTACACTATTCAATTGAGAG<br>AAAAGCCACCAGACATGAAGTTCATG<br>AAGTGGGCTAAGCCAGTTGTTAACGC<br>TTTGGTTGCCTTGTCCATTGTCTCCT<br>TTTCTGGTATTTTCTCTTGGAGAATG<br>TTCCAATCTGTCAGAAACAGAAGAAG<br>AATGGGTTTCACTGGTATCGGTTCCT<br>TGGAATCTTTGTTGGCTTCTGGTTTC<br>CAATGTTTAGTCTTCCCTGGTTTGGT<br>TACTACCGCTTTGACCGTCGCCGGTT<br>CCACTTGGTATATCGCTGTTAACTTA<br>ACTACTCCATCTGACTTGACCGCTAT<br>TTACAACTGTTCCGCTTTTTTCGCTT<br>ATGCTTTCTCCATTCCATTGTTAAAG<br>GAAAGAGCTCAAGTTGAAAAGACCAT<br>TTCTGTTGTCATTGCTATCGCTGGTG<br>TCTTAGTCGTTGCTTACGGTGACGGT<br>GCTGACGACGGTTCCACCTCTAACGG<br>TGAAAAGGCTAGATTGGGTGGTAACG<br>TCTTGATCGGTATCGGTTCTGTCTTG<br>TATGGTTTATACGAAGTCTTGTATAA<br>GAAGTTATTATGTCCACCATCTGGTG<br>CTTCCCCAGGTAGATCTGTTGTTTTC<br>TCTAATACCGTTTGTGCTTGCATCGG<br>TGCTTTCACTTTGTTATTCTTGTGGA<br>TCCCATTGCCATTGTTGCACTGGTCC<br>GGTTGGGAAATTTTTGAATTGCCAAC<br>CGGTAAGACTGCTAAGTTATTGGGTA<br>TTTCCATTGCCGCTAACGCCACCTTC<br>TCTGGTTCTTTCTTGATCTTAATTTC<br>TTTGACTGGTCCAGTTTTGTCCTCTG<br>TTGCCGCCTTGTTGACCATTTTCTTG<br>GTTGCTATTACTGACAGAATTTTATT<br>CGGTAGAGAATTGACTTCTGCTGCCA<br>TTTTGGGTGGTTTGTTGATCATCGCT<br>GCCTTCGCTTTGTTATCTTGGGCTAC<br>TTGGAAGGAAATGATTGAAGAGAACG<br>AGAAGGATACTATCGATTCCATCTCT<br>GACGTTGGTGACCACGATGACTAG<br>(SEQ ID NO: 105) |
| *Sporothrix scheckii* | YCPLKGQ<br>SCW | MKPAAGPASSPFD<br>PFNQTFYLTGPDN<br>TTVPVSVPQVDYI<br>WHYIIGTSINYGS<br>QIGACLLMLLVML<br>TLTSKSRFSRAAT<br>LINVASLLIGVIR<br>CVLLAVYFTSSLT<br>ELYALFVGDYSQV<br>RRSDLCVSAVATF<br>FSLPQLVLIEAAL<br>FLQAYSMIKMWPS<br>LWRAVVLAMSVVV<br>AVCAIGFKFASVV<br>MRMRSTLTLDDSL<br>DFWLVEVDLAFTA<br>TTIFWFCFIYIIR<br>LVIHMWEYRSILP<br>PMGSVSAMEVLVM<br>TNGALMLVPVIFA<br>AIEINGLSSFESG | (codon optimized)<br>ATGAAACCCGCCGCTGGACCTGCATC<br>TAGTCCATTCGACCCATTTAACCAAA<br>CGTTTTACCTGACCGGTCCAGATAAT<br>ACCACTGTACCAGTCTCAGTCCCACA<br>AGTTGACTATATCTGGCATTATATTA<br>TTGGAACATCCATCAACTATGGTTCT<br>CAGATCGGAGCCTGTTTACTTATGCT<br>TCTTGTGATGTTGACATTGACTTCAA<br>AGTCAAGATTTTCTCGTGCGGCCACT<br>CTGATTAACGTAGCAAGCTTATTGAT<br>TGGAGTAATTCGTTGTGTTCTTTTAG<br>CTGTCTACTTTACTTCTTCTCTAACT<br>GAATTGTATGCTCTGTTCGTTGGCGA<br>TTACAGCCAGGTCCGTAGGTCTGATC<br>TTTGTGTCTCTGCTGTGGCAACCTTC<br>TTTAGTCTACCACAATTAGTTCTAAT<br>AGAAGCTGCTTTGTTTCTACAGGCTT<br>ATAGTATGATCAAAATGTGGCCATCC<br>CTGTGGAGAGCAGTGGTTTTAGCTAT<br>GTCAGTGGTGGTGGCTGTGTGTGCAA |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | SLVHTSVIVLLPL GSLIAQAMTRPDG YVQRTNTSGASGA SGAHPGRNGSGHG GHGGAYSRAMTNT LNTLDTLDTVDSK TSIMHHHHHHHRN HSNGMSKTKANSG TWSHASDANSTNA MISGGIATQVRIQ ANQSTLGNTGMSG GSGAPNSHTRNNS LAAMEPVEKQLHD IDATPLSASDCRV WVDREVEVRRDMV (SEQ ID NO: 106) | TCGGTTTTAAGTTCGCGTCCGTTGTT ATGCGTATGAGGTCAACATTAACATT GGACGATTCTTTGGATTTCTGGCTAG TGGAAGTCGATCTGGCTTTTACAGCA ACTACTATTTTTTGGTTTTGTTTCAT CTACATTATAAGGTTGGTTATTCATA TGTGGGAATATAGAAGCATTTTACCA CCAATGGGGTCTGTTTCTGCTATGGA GGTTCTTGTTATGACCAATGGAGCGT TGATGTTAGTTCCAGTGATTTTCGCC GCAATAGAAATCAATGGTTTATCAAG CTTTGAATCAGGGTCACTGGTTCATA CATCAGTGATTGTATTATTACCTTTA GGTAGCTTGATAGCGCAAGCAATGAC ACGTCCAGATGGGTATGTCCAAAGAA CGAATACATCTGGAGCATCAGGCGCA AGTGGTGCACATCCTGGTAGAAATGG ATCCGGACACGGTGGTCATGGTGGTG CGTACTCAAGAGCCATGACTAATACC CTAAATACATTGGATACATTGGATAC CGTAGACAGTAAGACATCCATAATGC ATCATCATCATCACCATCATAGAAAC CACTCAAATGGCATGAGTAAGACGAA GGCAAATAGTGGAACATGGAGCCATG CGTCAGATGCTAACTCCACCAATGCT ATGATCAGCGGTGGTATCGCAACTCA AGTTAGGATTCAAGCTAATCAGTCAA CCTTAGGAAATACGGGGATGTCCGGG GGCTCTGGAGCCCCTAATTCTCATAC TCGTAATAACTCATTGGCTGCTATGG AACCAGTGGAGAAGCAACTGCATGAT ATCGATGCCACACCTTTAAGCGCATC TGATTGCAGGGTCTGGGTTGATCGTG AGGTCGAGGTCAGAAGGGACATGGTC TAG (SEQ ID NO: 107) |
| Yarrowia lipolytica | WRWFWL PGYGEP NW | MQLPPRPDFDIAT LVASITVPETELV LGQMPLGALEQLY QNRLRLAILFGVR VGAAVLTLIAMHL ISKKNRTKILFLA NQMSLIMLIIHAA LYFRFLLGPFASM LMMVAYIVDPRSN VSNDISVSVATNV FMMLMIMSVQLSL AVQTRSVFHAWLK SRIYVTVGLILLS LVVFVFWTTHTIV SCIVLTHPTRDLP SMGWTRLASDVSF ACSISFASLVLLA KLVTAIRVRKTLG KKPLGYTKVLVIM STQSLVVPSILII VNYALPEKNSWIL SGVAYLMVVLSLP LSSIWATAVHDDE MQSNYLLSALKDG HVQPSESKLKTVF LNRLRPFSTTTNR DDESSVDSPAMPS TGFECDEKMPESD VTFLN (SEQ ID NO: 108) | (codon optimized) ATGCAATTGCCACCACGTCCAGACTT CGACATTGCCACTTTGGTTGCCTCTA TCACTGTTCCAGAAACTGAATTGGTC TTGGGTCAAATGCCATTGGGTGCTTT AGAACAATTGTACCAAAACAGATTGC GTTTGGCTATTTTGTTCGGTGTCAGA GTCGGTGCTGCTGTTTTGACCTTGAT TGCTATGCACTTAATCTCCAAGAAGA ACAGAACCAAGATCTTGTTCTTGGCT AACCAAATGTCTTTGATCATGTTGAT CATCCATGCTGCTTTGTACTTCAGAT TCTTGTTGGGTCCATTCGCCTCCATG TTGATGATGGTTGCTTACATCGTTGA TCCAAGATCTAACGTCTCTAACGATA TCTCTGTTTCTGTTGCCACCAACGTT TTCATGATGTTGATGATTATGTCCGT CCAATTGTCTTTGGCTGTTCAAACCC GTTCTGTTTTCCACGCTTGGTTGAAG TCTCGTATTTACGTTACCGTTGGTTT AATCTTGTTGTCCTTGGTCGTCTTCG TCTTCTGGACCACCCACACTATCGTT TCTTGTATCGTTTTAACCCATCCAAC TAGAGACTTGCCATCTATGGGTTGGA CTAGATTAGCTTCTGACGTTTCCTTC GCTTGTTCTATCTCTTTCGCTTCTTT GGTCTTGTTGGCTAAGTTGGTCACCG CCATCAGAGTTAGAAAGACCTTGGGT AAGAAGCCATTGGGTTACACCAAGGT TTTGGTCATCATGTCCACTCAATCTT TAGTCGTTCCATCTATCTTGATTATC GTTAACTACGCTTTGCCAGAAAAAAA CTCTTGGATCTTGTCTGGTGTCGCTT ACTTGATGGTTGTTTTGTCCTTACCA TTGTCCTCCATTTGGGCTACCGCCGT CCATGACGACGAAATGCAATCCAACT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | | ACTTGTTGTCTGCCTTGAAAGATGGT<br>CACGTTCAACCATCCGAATCTAAGTT<br>GAAGACTGTTTTCTTGAACAGATTGA<br>GACCATTCTCTACTACCACTAACAGA<br>GACGATGAATCCTCTGTTGATTCCCC<br>AGCCATGCCATCTCCAGAATCTGATG<br>TTACCTTCTTGAACACTGGTTTCGAA<br>TGTGACGAAAAGATGTAG<br>(SEQ ID NO: 109) |
| Torulaspora delbrueckii | GWMRLR LGQPL | MSDSAQNLSDLAF NSSYNPLDSFITF TSIYGDNTAVKFS VLQDMVDVNTNEA IVYGTRCGASVLT QIIMWMISKNRRT PVFIINQVSLTLI LIHSALYFKYLLS GFGSVVYGLTAFP QLIKPGDLRAFAA ANIVMVLLVASIE ASLIFQVKVIFTG DNMKRVGLILTII CTCMGLATVTMYF ITAVKSIVSLYRD MSGSSTVLYNVSL IMLASSIHPMALI LVVKLFLAVRSRR FLGLKQFDSFHIL LIISCQTLLVPSL LFIIAYSFPSSKN IESLKAIAVLTVV LSLPLSSMWATAA NNFTNSSSSGSDS APTNGGFYGRGSS NLYPEKTDNRSPK GARNALYELRSKN NAEGQADIYTVTD IENDIFNDLSKPV EQNIFSDVQIIDS HSLHKACSKEDPV MTLYTPNTAIEGE ERKLWTSDCSCST NGSTPVKKKSTGE YANLPPHLLRYDE NYDEEAGGRRKAS LKW (SEQ ID NO: 110) | (codon optimized)<br>ATGTCTGACTCCGCCCAAAACTTGTC<br>CGATTTGGCCTTCAACTCTTCTTATA<br>ACCCATTGGACTCCTTTATTACCTTT<br>ACCTCTATCTACGGTGATAACACTGC<br>TGTTAAGTTCTCCGTTTTACAAGACA<br>TGGTTGACGTTAATACTAATGAAGCC<br>ATCGTTTACGGTACCCGTTGTGGTGC<br>TTCTGTCTTGACCCAAATTATCATGT<br>GGATGATTTCTAAAAACAGAAGAACC<br>CCAGTCTTTATTATTAACCAAGTTTC<br>TTTGACTTTGATTTTAATTCACTCTG<br>CCTTGTACTTCAAGTACTTGTTGTCT<br>GGTTTCGGTTCCGTTGTCTACGGTTT<br>GACTGCTTTCCCACAATTGATTAAGC<br>CAGGTGATTTGAGAGCTTTCGCTGCT<br>GCTAACATCGTTATGGTCTTGTTGGT<br>CGCTTCTATTGAAGCTTCCTTAATCT<br>TCCAAGTCAAAGTTATCTTCACCGGT<br>GATAACATGAAGAGAGTCGGTTTAAT<br>CTTGACTATTATTTGTACTTGTATGG<br>GTTTAGCTACTGTTACCATGTACTTT<br>ATTACTGCCGTCAAGTCTATTGTCTC<br>TTTGTACCGTGACATGTCTGGTTCCT<br>CCACCGTTTTATATAACGTTTCTTTA<br>ATTATGTTGGCTTCCTCCATCCACTT<br>TATGGCTTTGATCTTGGTTGTCAAAT<br>TGTTCTTGGCTGTTAGATCTAGAAGA<br>TTCTTGGGTTTGAAACAATTCGATTC<br>TTTCCACATTTTGTTGATCATCTCTT<br>GTCAAACTTTGTTGGTTCCATCTTTA<br>TTATTCATTATTGCTTACTCTTTTCC<br>ATCTTCTAAGAACATTGAATCTTTGA<br>AGGCTATCGCTGTTTTGACCGTCGTT<br>TTGTCTTTGCCATTGTCTTCTATGTG<br>GGCTACTGCTGCTAATAACTTCACTA<br>ACTCTTCCTCCTCCGGTTCCGACTCC<br>GCTCCAACCAATGGTGGTTTCTACGG<br>TAGAGGTTCTTCCAACTTGTATCCTG<br>AAAAGACTGATAACAGATCCCCAAAG<br>GGTGCCAGAAACGCTTTATACGAATT<br>AAGATCTAAGAACAATGCTGAGGGTC<br>AAGCTGATATTTACACCGTTACCGAT<br>ATTGAAAACGATATTTTCAACGATTT<br>GTCCAAGCCAGTTGAGCAAAACATTT<br>TCTCTGATGTTCAAATTATTGATTCT<br>CATTCTTTGCATAAGGCTTGTTCTAA<br>AGAAGACCCAGTCATGACTTTGTACA<br>CTCCAAACACTGCTATTGAAGGTGAG<br>GAGAGAAAATTGTGGACTTCTGACTG<br>TTCCTGTTCCACTAACGGTTCCACCC<br>CAGTTAAGAAGAAGTCCACCGGTGAA<br>TACGCCAATTTACCACCACACTTATT<br>AAGATATGATGAAAACTACGATGAAG<br>AAGCTGGTGGTAGACGTAAGGCCTCC<br>TTGAAATGGTAG<br>(SEQ ID NO: 111) |
| Komagataella pastoris | FRWRNN EKNQPFG | MEEYSDSFDPSQQ LLNFTSLYGETDA TFAELDDYHFYVV KYAIVYGARIGVG | (codon optimized)<br>ATGGAAGAATACTCCGACTCCTTCGA<br>CCCATCCCAACAATTGTTGAACTTCA<br>CTTCCTTATACGGTGAAACCGATGCT |

TABLE 6-continued

Sequences of Fungal GPCRs and Peptide Ligands

| Fungi | sequence of peptide analyte used | sequence of GPCRs used (all sequences are wild type) | DNA coding sequence of corresponding GPCRs that senses peptide analyte (WT or codon-optimized noted) |
|---|---|---|---|
| | | MFCTLMLFVVSKS<br>WKTPIFVLNQSSL<br>ILLIIHSGFYIHY<br>LTNQFSSLTYMFT<br>RIPNETHAGVDLR<br>INVVTNTLYALLI<br>LSIEISLIYQVFV<br>IFKGVYENSLRWI<br>VTIFTALFAAAVV<br>AINFYVTTLQSVS<br>MYNSNVDFPRWAS<br>NVPLILFASSVNW<br>ACLLLSLKLFFAI<br>KVRRSLGLRQFDT<br>FHILAIMFSQTLI<br>IPSILIVLGYTGT<br>RDRDSLASLGFLL<br>IVVSLPFSSMWAA<br>TANNSNIPTSTGS<br>FAWKNRYSPSTYS<br>DDTTAVSKSFTIM<br>TAKDECFTTDTEG<br>SPRFIKGDRTSED<br>LHF<br>(SEQ ID NO: 112) | ACTTTCGCTGAATTGGACGACTACCA<br>CTTCTACGTCGTTAAGTACGCCATCG<br>TTTACGGTGCCAGAATTGGTGTCGGT<br>ATGTTTTGTACTTTGATGTTGTTCGT<br>TGTTTCCAAGTCTTGGAAGACTCCAA<br>TCTTCGTCTTGAACCAATCTTCTTTG<br>ATTTTGTTGATTATTCACTCCGGTTT<br>CTACATCCACTACTTGACCAACCAAT<br>TCTCTTCCTTGACCTACATGTTCACT<br>AGAATCCCAAACGAAACCCATGCTGG<br>TGTCGATTTGCGTATTAACGTCGTTA<br>CCAACACCTTGTACGCTTTGTTGATC<br>TTATCTATTGAAATTTCCTTAATTTA<br>CCAAGTCTTCGTTATCTTCAAAGGTG<br>TCTACGAAAACTCTTTAAGATGGATT<br>GTTACTATTTTCACCGCTTTATTCGC<br>CGCCGCCGTCGTTGCTATTAACTTCT<br>ACGTCACTACTTTGCAATCTGTCTCT<br>ATGTACAACTCTAACGTTGACTTTCC<br>AAGATGGGCTTCTAACGTCCCATTGA<br>TCTTGTTCGCTTCTTCTGTCAACTGG<br>GCTTGTTTGTTGTTGTCCTTGAAGTT<br>GTTCTTCGCTATCAAGGTTAGAAGAT<br>CTTTGGGTTTGAGACAATTCGACACT<br>TTTCACATCTTGGCCATCATGTTCTC<br>TCAAACTTTGATTATCCCATCCATTT<br>TGATTGTCTTGGGTTACACTGGTACC<br>AGAGACAGAGACTCCTTGGCTTCTTT<br>GGGTTTCTTGTTGATCGTTGTTTCTT<br>TGCCATTTTCCTCTATGTGGGCTGCC<br>ACTGCTAACAACTCCAACATCCCAAC<br>CTCTACCGGTTCTTTCGCCTGGAAGA<br>ACAGATACTCCCCATCTACTTACTCC<br>GACGATACCACTGCTGTTTCCAAGTC<br>CTTCACTATTATGACCGCTAAGGATG<br>AATGTTTCACCACTGATACCGAAGGT<br>TCTCCAAGATTCATCAAGGGTGACAG<br>AACCTCCGAAGATTTGCACTTCTAG<br>(SEQ ID NO: 113) |

6.8.4. Key Characteristics of Peptide Ligands

Twenty three natural fungal peptides were synthesized and tested for activation of their corresponding receptor in the biosensor strain. Physico-chemical properties, e.g., peptide length, overall charge, charge distribution and hydrophobicity/hydrophilicity were determined for all 23 functionally verified peptide ligands using the program ProtParam on the Expasy server [Walker (2005) ISBN 978-1-59259-890-8]. Sequence variability and conserved sequence motifs within the set of peptide ligands were determined using an alignment and clustering method described in [Andreatta et al. (2013)].

A. Physicochemical Characteristics of Peptide Ligands

Natural mating peptide ligands featured diversity in length (9-23 residues), overall charge and number of charged residues as well as hydrophobicity (GRAVY, Grand average of hydropathy [Kyte and Doolittle (1982)] ranging from hydrophobic to mildly hydrophilic (see Table 9).

B. Sequence-Function Relationship and Sequence Diversity

Functional domains within alpha-factor: previously reported Alanine scanning mutagenesis revealed defined functional domains within the S. cerevisiae mating pheromone alpha-factor [Naider et al. (2004)]. Residues at the C-terminus were found to be mainly involved in binding to the receptor, while residues at the N-terminus were shown to contribute to signaling due to receptor activation. NMR studies also showed that alpha factor adopts a bended secondary structure due to the tendency of the internal residue stretch to form a loop [Higashijima et al. (1983)].

Sequence motifs of peptide ligands: A motif search for the peptides listed below was performed using a 13-residue motif length as an input parameter, because this is the length of the well characterized alpha factor. The peptides were clustered into 3 groups by conservation of residues (see FIG. 12B): all three clusters showed conservation of internal prolines and Cluster 1 and cluster 3 sequence motif featured the conservation of the aromatic N-terminal "activation domain" also found in S. cerevisiae alpha factor.

Correlation between sequence motifs and physicochemical properties: The peptide alignments within the clusters showed that sequences within the same cluster varied in length, overall charge, distribution of charged residues and hydrophobicity/hydrophilicity (see FIG. 12). Cluster 1 featured high variability in overall charge (from negative to positive) and charge distribution across the sequence as well as hydrophobic and hydrophilic members. Cluster 1 and 2 featured variability in the length of group members showing a variation of up to 3 additional residues.

6.9. Example 9: Identification of Biomarkers Specific for a Disease Sample

The design of *S. cerevisiae* biosensor allowed for simple plug-and-play engineering of new receptor-ligand pairs into the existing biosensor strain. The first step in developing yeast biosensors for additional targets using this platform was the identification of specific peptide biomarkers, for which specific receptors can be adapted via receptor engineering and directed evolution. As shown in FIG. 15, a pipeline for identification of viable peptide biomarkers was developed.

First, mass spectrometric analysis is used to identify the peptidome of a given sample. A sample can be anything from a blood sample to a nasal swab or water sample. The peptidome of a sample includes peptides a priori present in the sample or otherwise released after proteolytic treatment (e.g. treatment with trypsin or chemotrypsin).

The resulting peptides are then compared against our existing fungal ligand library to identify the highest homology match. The inventors' fungal ligand library is a list of fungal peptide pheromones—unmodified peptides between 9-15 residues in length—which are predicted or have been validated to activate their cognate fungal mating GPCR. The GPCR corresponding to homologous library peptide is then used as parent for biosensor engineering and provides an advantageous starting point for directed evolution experiments towards the peptide target.

6.10. Example 10: Trypsination of Cholera Toxin to Release Target Ligands

Cholera toxin (CTx) is a heteromeric protein complex secreted by the *bacterium Vibrio cholerae*. It is responsible for the massive, watery diarrhea characteristic of cholera infection and it was shown to be an abundant protein in stool samples of cholera-infected patients. [LaRocque et al. (2008)]. CTx is composed of 2 subunits, CtxA (27 kDa) and CtxB (11.6 kDa), where CtxB assembles in a pentameric ring around a single CtxA subunit.

Trypsin digestion of un-denatured, completely folded Ctx (the protein form expected in an untreated stool sample) was performed and the resulting peptidome was determined by mass spectrometry (see peptide list in Table 7). Then, a similarity search of the resulting Ctx peptidome was performed with the inventors' existing library of functional peptides tested in their sensor strain. A peptide HFGVLD-EQLHR (SEQ ID NO: 132) with 36% identity to a functional member of the inventors' fungal peptide library, the fungi *Zygosaccharomyces rouxii* (see FIG. 16) was detected.

The conservation of N-termini of these peptides is encouraging since the N-terminal end of mating pheromones was shown to be significant for receptor activation. [Naider et al. (2004)]. In addition, while tryptic release of some peptides may be less efficient than others because several predicted trypsin cleavage sites might not be solvent exposed and accessible, the high peptide count of the identified peptide (Table 7) indicates its high abundance in the analyzed sample. Importantly, the same peptide identified in this work was previously reported in tryptic digests of clinical stool samples from cholera infected patients. [LaRocque et al. (2008)]. Directed evolution experiments towards GPCR binding of the identified Ctx peptide is performed.

TABLE 7

Peptidome of Cholera Toxin after trypsin treatment

| Peptide released by trypsin digest | Peptide count |
|---|---|
| Cholera toxin subunit A | |
| ADGYGLAGFPPEHR (SEQ ID NO: 114) | 7 |
| ADSRPPDE (SEQ ID NO: 115) | 2 |
| ADSRPPDEIK (SEQ ID NO: 116) | 4 |
| ADSRPPDEIKQS (SEQ ID NO: 117) | 1 |
| ADSRPPDEIKQSGGLMPR (SEQ ID NO: 118) | 9 |
| AGFPPEHR (SEQ ID NO: 119) | 2 |
| ALGGIPYSQIYGWYR (SEQ ID NO: 120) | 1 |
| APAADGYGLAGFPPEHR (SEQ ID NO: 121) | 5 |
| ATAPNMFNVNDVLGAYSPHPDEQEVSALGGIPYSQIYGWYR (SEQ ID NO: 122) | 4 |
| AYSPHPDEQEVSALGGIPYSQIYGWYR (SEQ ID NO: 123) | 1 |
| DIAPAADGYGLAGFPPEHR (SEQ ID NO: 124) | 1 |
| DRYYSNLDIAPAADGYGLAGFPPEHR (SEQ ID NO: 125) | 34 |
| DSRPPDEIK (SEQ ID NO: 126) | 3 |
| DVLGAYSPHPDEQEVSALGGIPYSQIYGWYR (SEQ ID NO: 127) | 1 |
| FGVLDEQLHR (SEQ ID NO: 128) | 8 |
| FLDEYQSKVKRQIFSGYQSDIDTHNR (SEQ ID NO: 129) | 2 |
| FLDEYQSKVKRQIFSGYQSDIDTHNRIKDEL (SEQ ID NO: 130) | 5 |
| FNVNDVLGAYSPHPDEQEVSALGGIPYSQIYGWYR (SEQ ID NO: 131) | 1 |
| GAYSPHPDEQEVSALGGIPYSQIYGWYR (SEQ ID NO: 132) | 2 |
| GGIPYSQIYGWYR (SEQ ID NO: 133) | 2 |
| GQSEYFDR (SEQ ID NO: 134) | 4 |
| GQSEYFDRGTQMNINLYDHAR (SEQ ID NO: 135) | 6 |
| GTQMNINLYDHAR (SEQ ID NO: 136) | 45 |
| GTQTGFVR (SEQ ID NO: 137) | 15 |
| GTQTGFVRHDDGYVSTSISLR (SEQ ID NO: 138) | 3 |
| GYQSDIDTHNR (SEQ ID NO: 139) | 1 |
| GYRDRYYSNLDIAPAADGYGLAGFPPEHR (SEQ ID NO: 140) | 3 |
| HDDGYVSTS (SEQ ID NO: 141) | 1 |
| HDDGYVSTSISLR (SEQ ID NO: 142) | 38 |
| HFGVLDEQLHR (SEQ ID NO: 143) | 76 |
| KQSGGLMPR (SEQ ID NO: 144) | 5 |
| LDIAPAADGYGLAGFPPEHR (SEQ ID NO: 145) | 2 |

TABLE 7-continued

Peptidome of Cholera Toxin after trypsin treatment

| Peptide released by trypsin digest | Peptide count |
|---|---|
| NVNDVLGAYSPHPDEQEVSALGGIPYSQIYGWYR (SEQ ID NO: 146) | 11 |
| QEVSALGGIPYSQIYGWYR (SEQ ID NO: 147) | 1 |
| QIFSGYQSDIDTH (SEQ ID NO: 148) | 1 |
| QIFSGYQSDIDTHN (SEQ ID NO: 149) | 1 |
| QIFSGYQSDIDTHNR (SEQ ID NO: 150) | 41 |
| QSDIDTHNR (SEQ ID NO: 151) | 2 |
| QSGGLMPR (SEQ ID NO: 152) | 6 |
| RHDDGYVSTSISLR (SEQ ID NO: 153) | 21 |
| RQIFSGYQSDIDTHNR (SEQ ID NO: 154) | 7 |
| SAHLVGQTILSGH (SEQ ID NO: 155) | 1 |
| SAHLVGQTILSGHSTY (SEQ ID NO: 156) | 1 |
| SAHLVGQTILSGHSTYY (SEQ ID NO: 157) | 5 |
| SAHLVGQTILSGHSTYYIYVIATAPNMF (SEQ ID NO: 158) | 5 |
| SDIDTHNR (SEQ ID NO: 159) | 98 |
| SGYQSDIDTHNR (SEQ ID NO: 160) | 6 |
| SNLDIAPAADGYGLAGFPPEHR (SEQ ID NO: 161) | 14 |
| SQIYGWYR (SEQ ID NO: 162) | 4 |
| SRPPDEIKQSGGLMPR (SEQ ID NO: 163) | 1 |
| TAPNMFNVNDVLGAYSPHPDEQEVSALGGIPYSQIYGWYR (SEQ ID NO: 164) | 2 |
| VIATAPNMFNVNDVLGAYSPHPDEQEVSALGGIPYSQIYGWYR (SEQ ID NO: 165) | 1 |
| VKRQIFSGYQSDIDTHNRIKDEL (SEQ ID NO: 166) | 2 |
| VLDEQLHR (SEQ ID NO: 167) | 1 |
| YQSDIDTHNR (SEQ ID NO: 168) | 2 |
| YSNLDIAPAADGYGLAGFPPEHR (SEQ ID NO: 169) | 17 |
| YSPHPDEQEVSALGGIPYSQIYGWYR (SEQ ID NO: 170) | 1 |
| YSQIYGWYR (SEQ ID NO: 171) | 1 |
| YYSNLDIAPAADGYGLA (SEQ ID NO: 172) | 1 |
| YYSNLDIAPAADGYGLAGFPPEHR (SEQ ID NO: 173) | 29 |
| Cholera subunit B | |
| AIAAISMAN (SEQ ID NO: 174) | 1 |
| EMAIITFK (SEQ ID NO: 175) | 1 |
| FSYTESLAGK (SEQ ID NO: 176) | 1 |
| IFSYTESLAGK (SEQ ID NO: 177) | 2 |
| NDKIFSYTESLAGK (SEQ ID NO: 178) | 2 |
| NGATFQVEVPGSQH (SEQ ID NO: 179) | 1 |
| NGATFQVEVPGSQHIDSQK (SEQ ID NO: 180) | 10 |
| NGATFQVEVPGSQHIDSQKK (SEQ ID NO: 181) | 18 |
| SYTESLAGKR (SEQ ID NO: 182) | 5 |
| TPHAIAAISMAN (SEQ ID NO: 183) | 2 |
| YTESLAGK (SEQ ID NO: 184) | 1 |

6.11 Example 11: Dipstick Test

Materials and Methods. To assemble the dipstick, the biosensor strains were pre-cultured in 50 mL of yeast extract peptone dextrose media (YPD) at 30° C. at 300 RPM for 72 hours. The culture was diluted with water to an $OD_{600}$ of 2.5 and vacuum filtered onto a glass fiber filter paper (Thermo Scientific, DS0281-7500) using a plastic stencil to generate spots with a diameter of 5 mm. An appropriate culture volume was used to give about $5 \times 10^7$ cells per spot. The filter paper with biosensor spots was cut into small squares (8×8 mm, 1 biosensor spot) and placed onto a strip of wicking paper made of a standard brown paper towel (fig. S8B, C). Each paper-based dipstick assay contained two different spots—an indicator (biosensor) spot and a control spot composed of S. cerevisiae carrying off-target receptor as a negative control.

To characterize its functionality, the dipstick was dipped into 1 mL of liquid sample and incubated at 30° C. The lycopene readout was inspected visually and quantitatively measured using time-lapse photography analyzed with ImageJ. A 24-well plate was used to easily array several dipsticks in the field of view of the camera. For all assays, a 10× stock of media was used and diluted to reach the appropriate 1× concentration. All measurements were performed in three or more replicates. For YPD assays (FIG. 17B-D), the dipstick was dipped into 1×YPD media supplemented with 1 µM of the indicated fungal pathogen peptide. For soil assays (FIG. 17D), 0.5 g of soil was pre-conditioned with 2 nmol (in 200 µL of water) of the indicated fungal pathogen peptide and allowed to air dry for 1 hour. The dipstick was inserted into the soil and 2 mL of 1×YPD media was added to give a concentration of 1 µM of fungal peptide. For urine and serum assays (FIG. 17D), the samples were vortexed briefly to resuspend particles, supplemented with 1×YPD media to give a concentration of 50% of urine or serum. For blood assays (FIG. 17D), the sample was supplemented with 1×YPD media to give a final concentration of 2% blood.

Additionally, we designed a small plastic holder to facilitate the ease of use of this dipstick assay. This plastic holder was 3D printed out of acrylonitrile butadiene styrene (ABS). We validated the holder it did not negatively impact the assay functionality.

To assay the long-term stability of the paper-dipstick, the biosensor spots were prepared on filter paper as described above and allowed to air-dry for 20 minutes at room temperature. The filter papers were then placed in plastic pouches, flushed with argon, sealed and stored in the dark at room temperature. After 38 weeks of storage the filter papers were removed from the storage pouches, and assembled with the paper towel wicking paper as described above. To characterize the functionality, the assembled paper dipsticks were rehydrated by dipping directly into 1 mL of liquid sample made of 1×YPD media supplemented either with 1 µM of the indicated fungal pathogen peptide or water as a control and incubated at 30° C. The lycopene readout was inspected visually and quantitatively measured using time-lapse photography. All measurements were performed in three or more replicates.

We also determined a visibility threshold for paper-based dipstick assay when measured by time-lapse photography and pixel color analysis. This was done by visually inspecting time-lapse clips. The visible threshold for the dipstick assay was determined to be 4 Δ Red Color units and is shown by a grey line in FIG. 17B, D).

To enable quantitative characterization of the paper-based dipstick assay we developed a method to measure lycopene production based on time-lapse photography and pixel color value analysis. Specifically, dipsticks dipped in samples and a tripod-mounted digital single-lens reflex camera (DSLR, Nikon D7000) were placed in a dark box kept at 30° C. Flash photographs were taken automatically every 5 minutes. The resulting sequence of photographs was analyzed using ImageJ[139]. For each time point, the average pixel color values were measured for each of the two dipstick spots using constant measurement areas. The apparent level of red color of each spot was first calculated by the following:

$$R_{apparent} = \frac{R - \left(\frac{G+B}{2}\right)}{R} \quad (E1)$$

where R, G, B are the measured red, green and blue color values, respectively. Since the color of the biosensor spots ranges from off-white to red-orange the color values are such that R>G>B is always true. Therefore, $R_{apparent}$ is a value that scores the level of red from 0 to 1. We then calculated the total level of positive lycopene readout produced by the dipstick by the following:

$$\Delta \text{Red Color} = R_{app,\ indicator} - R_{app,\ negative} \quad (E2)$$

where $R_{app,\ indicator}$ and $R_{app,\ negative}$ are the apparent red color values of the indicator biosensor spot and the negative control yeast spot, respectively given by Eq. E1. Importantly, since the two yeast spots of the dipstick assay are always in close proximity to each other, the Δ Red Color value is not sensitive to variations in light levels and can be used to compare dipsticks placed anywhere in the field of view of the camera. Using these sequences of photographs we also generated time-lapse clips showing that the lycopene color change can be visualized by the naked eye. These clips are motion and exposure equalized to remove flicker between frames.

Results and Discussion. Biosensor and control cells were spotted onto filter paper, and detection was performed by simply dipping the paper into liquid samples containing synthetic mating peptides (FIG. 17A). In addition to visual inspection, we quantified lycopene accumulation on paper using pixel color analysis.

Using a P. brasiliensis dipstick assay, we observed a robust and highly reproducible signal that surpassed the visible lycopene threshold to give a clear Yes/No readout (FIG. 17B). Similar results were achieved using a C. albicans dipstick assay (FIG. 17C). As expected, no cross-reactivity was observed between these two pathogens. Lastly, to ensure the signal remains visible in complex samples, we performed dipstick tests in soil, urine, serum and blood supplemented with synthetic mating peptides. In all sample types, micromolar levels of peptide were successfully detected (FIG. 17D). Importantly, the dipstick assay retained its functionality after being stored for 38 weeks at room temperature. Further, see FIG. 18A-E.

6.12 Example 12: Detection of Yeast Strains

Materials and Methods.

Preparation of Culture Supernatant from Clinically Isolated Fungal Pathogens

*H. capsulatum*—Strains Hc01 and Hc06 are clinical isolates representing North America class 2 (NAm2) and North America class 1 (NAm1), respectively.[127] *H. capsulatum* strains were added to liquid SDA medium (40 g/L glucose, 10 g/L peptone) at $10^5$ cells/mL and incubated for 10 days at 26° C. without agitation to induce conversion to mycelia. Conversion to mycelia was confirmed by phase-contrast microscopy. Mycelia were then transferred to HMM media.[128] and the cultures incubated at 26° C. After 3 weeks of growth, mycelia were separated from the supernatant by filtration through a cellulose filter (Whatman qualitative filter paper #2, 8 µm-diameter pores) and the filtrate subsequently filtered through a polyethersulfone membrane (0.45 µm diameter pores) to obtain the final culture filtrate. The supernatants were lyophilized, resuspended in 0.1 volume of $H_2O$ (10× concentration) and kept at −20° C.

*Paracoccidioides*—Strains *P. brasiliensis* Pb18 and *P. lutzii* Pb01 are clinical isolates containing mating loci MAT1-2 and MAT1-1, respectively.[129] The mycelium form was grown at 24° C. at 150 rpm in synthetic McVeigh Morton (MMvM) liquid medium.[130] Supernatants were collected by filtration 10 days after the yeast-mycelium transition. The supernatants were lyophilized, resuspended in 0.1 volume of $H_2O$ (10× concentration) and kept at −20° C.

*C. albicans*—Human isolates GC75 with MTLα/MTLα[131] and ySB36[132] were utilized, the latter being found to be heterozygous for its mating loci, MTLa/MTLα. Homozygous MTLα/MTLα derivatives of ySB36 were obtained by selection on sorbose as previously described.[133] In brief: ySB36 was cultured for 16 hours in YPD liquid media at 30° C., washed once with water and ~$10^5$ cells were plated on 2% sorbose media (0.67% yeast nitrogen base without amino acids, 2% sorbose). Colonies were visible after 4 days incubation at 30° C. Several colonies were re-streaked on 2% sorbose media, followed by re-streaking on YPD media and genotyping by colony PCR (see primers Listed in Table 8 below). One homozygous MTLα/MTLα isolate (ySB45) was used for supernatant preparation. Phenotypically switched opaque colonies of GC75 and ySB45 were isolated by Phloxine B staining as previously described.[134] In brief: A single colony of GC75 or ySB45 was incubated for 24 h at 25° C. in liquid YPD media without agitation. In total ~$2 \times 10^3$ cells were plated on YPD agar supplemented with 5 µg/ml Phloxine B (Sigma Aldrich) and incubated at 25° C. for 4 days. Opaque colonies stained pink on Phloxine B containing media. For supernatant preparation, a single opaque colony of *C. albicans* GC75 or ySB45 was cultured overnight in YPD media at 25° C., and used to inoculate 50 ml of YPD liquid media. Cells were cultured for ~24 h at 25° C. to a final $OD_{600}$ of 9.5 (~$2.8 \times 10^8$ cells/ml) and 7.9 (~2.3×10⁸ cells/ml), respectively. Cells were pelleted by centrifugation, the supernatant was reduced to dryness by vacuum concentration and resuspended in 0.1 volume H$_2$O (10× concentration) and kept at −20° C.

TABLE 8

Primers for cloning of fungal receptors and for genotyping of *C. albicans* isolates. Gibson assembly was used for receptor cloning except where restriction sites are indicated.

Primers used for cloning fungal receptors from genomic DNA and pLPreB:
Sc.Ste2:
MJ492:
(SEQ ID NO: 185)
ACCAAGAACTTAGTTTCGACGGATACTAGTAAAATGTCTGATGCGGCTCC
TTC MJ493:
(SEQ ID NO: 186)
ACGAAATTACTTTTTCAAAGCCGTCTCGAGCTATAAATTATTATTATCTT
CAGTCCAGAA Ca.Ste2:
MJ440:
SEQ ID NO: 187)
acgtcaaggagaaaaaaccccggaaactagtaAAATGAATATCAATTCAA
CTTTCATACC MJ362:
(SEQ ID NO: 188)
gcaagtctcgagCTACACTCTTTTGATGGTGATTTG Cg.Ste2:
MJ498:
(SEQ ID NO: 189)
ACCAAGAACTTAGTTTCGACGGATACTAGTAAAATGGAGATGGGCTACGA
TCC

MJ499:
(SEQ ID NO: 190)
ACGAAATTACTTTTTCAAAGCCGTCTCGAGCTATTTGTCACACTGACTTT
GTTG

Le.Ste2:
MJ504:
(SEQ ID NO: 191)
ACCAAGAACTTAGTTTCGACGGATACTAGTAAAATGGACGAAGCAATCAA
TGCAAAC

MJ505:
(SEQ ID NO: 192)
ACGAAATTACTTTTTCAAAGCCGTCTCGAGCTATTTTTTCAACATAGTCA
CTTC

Pb.Ste2:
MJ508:
(SEQ ID NO: 193)
ACCAAGAACTTAGTTTCGACGGATACTAGTAAAATGGCACCCTCATTCGA
CC

MJ509:
(SEQ ID NO: 194)
ACGAAATTACTTTTTCAAAGCCGTCTCGAGCTAGGCCTTTGTGCCAGCTT
C

Zr.Ste2:
MJ518:
(SEQ ID NO: 195)
ACCAAGAACTTAGTTTCGACGGATACTAGTAAAATGAGTGAGATTAACAA
TTCTACCTAC

MJ519:
(SEQ ID NO: 196)
ACGAAATTACTTTTTCAAAGCCGTCTCGAGCTATAATTTCTTTAGGATAA
TTTTTTACT

Primers used for genotyping MTL loci of *C. albicans*

TABLE 8-continued

Primers for cloning of fungal receptors and for genotyping of *C. albicans* isolates. Gibson assembly was used for receptor cloning except where restriction sites are indicated.

MTLa:
SB469:
(SEQ ID NO: 197)
TGTAAACATCCTCAATTGTACCCGA

SB470:
(SEQ ID NO: 198)
TTCGAGTACATTCTGGTCGCG

MTLa1:
SB471:
(SEQ ID NO: 199)
TTCGAGTACATTCTGGTCGCG

SB472:
(SEQ ID NO: 200)
ATCAATTCCCTTTCTCTTCGATTAGG

*S. cerevisiae*—samples were obtained from *S. cerevisiae* strain FY250 with MTLα[135] and W303-1B with MTLα (ATCC 201238). Cells were cultured in 50 ml YPD media for 20 h at 30° C. to a final OD$_{600}$ of 9.8 (~2.9×10⁸ cells/ml) and 8.5 (~2.5×10⁸ cells/ml), respectively. Cells were pelleted by centrifugation, the supernatant of FY250 was reduced to dryness by vacuum concentration and resuspended in 0.1 volume H$_2$O (10× concentration) and kept at −20° C. The supernatant of W303-1B was kept at 1× concentration at −20° C.

Detection of mating peptides in supernatants of clinically isolated fungal strains. *P. brasiliensis* or *C. albicans* biosensor strains (yMJ258 and yMJ260, respectively) and a control *S. cerevisiae* strain (yMJ251) were used to test for the presence of the respective mating peptides in supernatants derived from clinically isolated pathogenic fungi or *S. cerevisiae* (supernatants preparation described above). Cells were seeded at an OD$_{600}$ of 2 in the indicated supernatant mixed with standard complete synthetic media (2% dextrose) supplemented with 5% YPD in 96-well microtiter plates, cultured at 30° C. and 800 RPM, and lycopene production was measured by absorbance as described above. A 2× stock of media and a 10× stock of the supernatant were used and diluted to reach the appropriate 1× concentration. The control supernatant for W303-1B was diluted to 50% in the final assay. Statistical significance of signal (i.e. biosensor strain treated with its cognate-supernatant) over noise (same biosensor strain treated with non-cognate supernatants) was determined by performing a paired parametric t-test in Prism (GraphPad). The highest P-value resulting from sample comparisons is given as P≤0.01, *P≤0.001 (FIG. 22E). All measurements were performed in triplicates.

Determination of lycopene content in microtiter plate format.

To determine the relative lycopene content directly in a cell suspension, we adapted the method proposed by Myers et al.[140] to characterize pigmented cells through optical density measurements at multiple wavelengths. This method greatly reduces the noise due to variations in cell growth phase, cell density and other sample irregularities. This enabled the precise evaluation of lycopene content in a high throughput microtiter plate format.

As described by Myers et al.[140], the optical density of the cell suspension measured at a sensitive wavelength (i.e. corresponding to an absorption maxima of the pigment) is approximately composed of two additive components: scatter due to cells and absorbance due to the pigment. Therefore the pigment content in a cell suspension is proportional to the measured optical density corrected for the scattering component as follows:

$$[pigment] \propto Abs_{S,P} = OD_S - OD_{S,scat} \quad (E3)$$

where $Abs_{S,P}$ is the absorbance due to the pigment at the sensitive wavelength S, $OD_S$ is the measured optical density at the sensitive wavelength S, and $OD_{S,scat}$ is a calculated scattering component at the sensitive wavelength S. Since there was noticeable Raleigh-like wavelength dependence in the scatter of lycopene null strains we chose the following functional form to approximate scatter at a particular wavelength $\lambda$:

$$OD_{\lambda,scat} = B - \log_{10}\left(1 - \frac{A}{\lambda}\right) \quad (E4)$$

where A and B are constants that reflect changes in cell density and other sample irregularities. At each time point and for each sample, we can calculate the corresponding values of A and B by using the optical density values measured at two robust wavelengths (i.e. corresponding to wavelengths where scatter is the only or dominant component). Substituting these additional scatter-only optical density measurements into Eq. E4 and solving for A and B we get:

$$A = R1\left(\frac{1-T}{\frac{R1}{R2} - T}\right), \text{ where } T = 10^{OD_{R1} - OD_{R2}} \quad (E5)$$

$$B = OD_{R1} + \log_{10}\left(1 - \frac{A}{R2}\right) \quad (E6)$$

where $OD_{R1}$ and $OD_{R2}$ are the measured optical densities at the robust wavelengths R1 and R2. Therefore, by setting $\lambda$=S and substituting Eq. E4 into Eq. E3, the relative content of lycopene in a cell suspension is given by:

$$[pigment] \propto Abs_{S,P} = OD_S + \log_{10}(1 - A/S) - B \quad (E7)$$

To apply this method to lycopene in yeast, we determined the appropriate sensitive and robust wavelengths by obtaining the absorbance spectrum of lycopene directly in yeast cells. The spectrum was determined by subtracting the optical density spectrum of a lycopene null strain yMJ105 from that of a constitutive lycopene producing strain LW2671 (FIG. 19B). This spectrum showed the characteristic profile of lycopene absorbance and had two major absorbance maxima at 485 nm and 520 nm (FIG. 19C). Based on this spectrum, 520 nm was chosen as the sensitive wavelength (S=520) since it is furthest away from other natural chromophores in yeast that absorb below 500 nm (e.g. flavins). 395 nm and 600 nm were chosen as the two robust wavelengths (R1=600 and R2=395) with low absorbance from lycopene and other natural chromophores.

Three additional considerations were crucial to yield reproducible lycopene measurements in a microtiter plate format. First, all three optical density measurements (at 395 nm, 520 nm and 600 nm) were taken at the same time for each well to reduce errors due to the settling of cells during the measurement of a whole microtiter plate. Second, assay wells were blanked using a reference well on the same microtiter plate containing identical media conditions as the assay wells but with no cells. This was particularly important when colored media was used. Finally, high cell densities ($OD_{600} \geq 2$) were used to yield larger bulk lycopene signals even with the short path length of micro titer plates (~3 mm). Since these high optical density values were outside the linear range of the photodetector, all optical density values were first corrected using the following formula to give true optical density values:

$$OD_{true} = \frac{k \cdot OD_{meas}}{OD_{sat} - OD_{meas}} \quad (E8)$$

where $OD_{meas}$ is the measured optical density, $OD_{sat}$ is the saturation value of the photodetector and k is the true optical density at which the detector reaches half saturation of the measured optical density. Appropriate values for $OD_{sat}$ and k were determined by plotting direct optical density measurements of a range of cultures of several strains, against the true optical densities determined by dilution to the linear range. Optical densities were taken at 395 nm, 520 nm and 600 nm. All points were fit once with Eq. E8 using Prism (GraphPad) to give $OD_{sat}$=3.57 and k=3.16. These values were used to correct all optical density measurements in this study.

Results and Discussion. Next, we challenged our biosensor for detection of naturally secreted mating peptides using clinically-isolated *Paracoccidioides* strains. Paracoccidioidomycosis (PCM), an invasive fungal infection endemic to Latin America, is one of many neglected tropical diseases that primarily affect poor populations and lack systematic surveillance.[141] PCM is caused by inhalation of airborne conidia produced by mycelium of the soil ascomycete *P. brasiliensis*.[136] Recent identification of the genetic components underlying its mating system[137] enabled us to pursue specific yeast-based detection of *P. brasiliensis*, which could facilitate detection of its environmental reservoir.

Specifically, we challenged our yeast biosensor to detect cultured mycelial *P. brasiliensis* isolated from human patients. Biosensor cells expressing *P. brasiliensis* mating receptor, which exhibited specific and sensitive detection of its synthetic mating peptide (FIGS. 20A-B and 21A-D), were mixed with spent supernatants from two clinically isolated Paracoccidioides strains (Table 10). In response, we observed lycopene production well above the visible threshold (FIG. 22E). Secreted mating peptides were similarly detected from clinical isolates of *C. albicans* and *H. capsulatum* (FIG. 22E). Interestingly, the peptide produced by *H. capsulatum*[137], the causative agent of Histoplasmosis,[138] is identical to that of *P. brasiliensis* and could be detected using both biosensor strains (FIG. 22A-D).

TABLE 9

| Species | Association | Pathogenic Target | Synthetic Peptide Sequence | Receptor UniProt ID | Receptor Source |
|---|---|---|---|---|---|
| *Saccharomyces cerevisiae* | Baker's yeast | — | WHWLQLKPGQPMY | D6VTK4 | ATCC 200895 |
| *Candida glabrata* | Candidiasis | Human | WHWVRLRKGQGIF | Q6FLY8 | ATCC 2001 |
| *Candida albicans* | Candidiasis | Human | GFRLTNFGYFEPG | Q59Q04 | ATCC MYA-2876 |
| *Lodderomyces elongisporus* | Candidiasis | Human | WMWTRYGRFSPV | A5E1D9 | ATCC 11503 |
| *Paracoccidioides brasiliensis* (*lutzii*) | Paracoccidioido-mycosis | Human | WCTRPGQGC | C1GFU7 | Plasmid pLPreB(30) |
| *Botrytis cinerea* (*Botryotinia fuckeliana*) | Gray mold | Plants | WCGRPGQPC | G2YE05 | codon-optimized synthetic DNA |
| *Fusarium graminearum* (*Gibberella zeae*) | Wheat head blight | Plants | WCWWKGQPCW | I1RG07 | codon-optimized synthetic DNA |
| *Magnaporthe oryzae* | Rice blast | Plants | QWCPRRGQPCW | G4MR89 | codon-optimized synthetic DNA |
| *Zygosaccharomyces bailii* | Spoilage | Food spoilage | HLVRLSPGAAMF | S6EXB4 | codon-optimized synthetic DNA |
| *Zygosaccharomyces rouxii* | Spoilage | Food spoilage | HFIELDPGQPMF | C5DX97 | ATCC 2623 |
| *Histoplasma capsulatum* | Histoplasmosis | Human | WCTRPGQGC | C0NQ16 | codon-optimized synthetic DNA |

TABLE 10

| Strain | Genotype | Comments |
|---|---|---|
| FY251 | MATa his3-Δ200, leu2-Δ1 trp1-Δ63, ura3-52 | ATCC 96098 |
| BY4733 | MATα his3Δ200 leu2Δ0 met15Δ0 trp1Δ63 ura3Δ0 | ATCC 200895 |
| LW2591 | BY4733 MATα-inc HOΔ::ReRec | Reiterative Recombination acceptor strain (32) |
| LW2671 | BY4733 derivative overexpressing CrtEBI | Constitutive lycopene producing strain (40) |
| yMJ105 | LW2591 sst2-Δ far1-Δ | Parental biosensor strain |
| Fluorescence Readout Strains | | |
| yMJ183 | yMJ105 ste2-Δ fus1Δ::pFUS1-HIS3-tHIS3 ReRec[1]::pFUS1-yCherry-tACT1 | Receptor-less fluorescence biosensor strain |
| yMJ281 | yMJ183 + pMJ093 | S. cerevisiae biosensor |
| yMJ282 | yMJ183 + pMJ090 | C. albicans biosensor |
| yMJ284 | yMJ183 + pMJ095 | B. cinerea biosensor |
| yMJ285 | yMJ183 + pMJ096 | C. glabrata biosensor |
| yMJ286 | yMJ183 + pMJ097 | F. graminearum biosensor |
| yMJ288 | yMJ183 + pMJ099 | L. elongisporous biosensor |
| yMJ289 | yMJ183 + pMJ100 | M. oryzea biosensor |
| yMJ290 | yMJ183 + pMJ101 | P. brasiliensis biosensor |
| yMJ294 | yMJ183 + pMJ105 | Z. bailii biosensor |
| yMJ295 | yMJ183 + pMJ106 | Z. rouxii biosensor |
| yMJ312 | yMJ183 + pMJ117 | H. capsulatum biosensor |
| yJM06 | yMJ183 + pJM13 | Codon-optimized C. glabrata biosensor |
| Lycopene Biosensor Strains | | |
| yMJ116 | yMJ105 ReRec[1]::pTEF1-CrtE-tADH1-(CrtB-pPGK1, rev) | Lycopene null strain |
| yMJ118 | yMJ105 ReRec[1]::pTEF1-CrtE-tADH1-(CrtB-pPGK1, rev) ReRec[2]::pFUS1-CrtI-tACT1 | Unoptimized lycopene biosensor Lyco-1 |
| yMJ151 | yMJ118 + pMJ006 | "+2X CrtI" intermediate |
| yMJ152 | yMJ118 + pMJ009 | "+tHMG1" intermediate |
| yMJ165 | yMJ118 + pMJ012 | "+FAD1" intermediate |
| yMJ251 | yMJ105 met15Δ::pFUS1-CrtI-tACT1-MET15 ReRec[1]::pTEF1-CrtE-tADH1-(CrtB-pPGK1, rev) ReRec[2]::pFUS1-CrtI-tACT1 ReRec[3]::pTDH3-FAD1-tPGK1 | Optimized lycopene biosensor Lyco-2 (Sc biosensor) |
| yMJ258 | yMJ251 ste2Δ::pTDH3-Pb.Ste2-tSTE2 | Pb biosensor |
| yMJ260 | yMJ251 ste2Δ::pTDH3-Ca.Ste2-tSTE2 | Ca biosensor |
| Strains Used to Generate Pathogen and Control Supernatants | | |
| W303-1B | MATα leu2-3, 112 trp1-1 can1-100 ura3-1 ade2-1 his3-11, 15 | ATCC 201238 |
| FY250 | MATα his3-Δ200, leu2-Δ1 trp1-Δ63, ura3-52 | (50) |
| GC75 | Candida albicans, MTLα/MTLα | Genebank assembly number GCA_000773735.1 (46) |
| ySB36 | Candida albicans, MTLα/MTLα | Clinical isolate obtained from A-C. Uhlemann, mating loci (MTL) were genotyped by PCR |
| ySB45 | Candida albicans, MTLα/MTLα | sorbose selected isolate, derivative of isolate ySB36, MTL were genotyped by PCR |
| Pb01 | Paracoccidioides lutzii, MAT1-1 | Supernatant prepared by Prof. Fernando Rodrigues (44) |
| Pb18 | Paracoccidioides brasiliensis, MAT1-2 | Supernatant prepared by Prof. Fernando Rodrigues (44) |
| Hc01 | Histoplasma capsulatum, NAm2 | Supernatant prepared by Prof. Chad Rappleye (42) |
| Hc06 | Histoplasma capsulatum, NAm1 | Supernatant prepared by Prof. Chad Rappleye (42) |

7. REFERENCE LIST

1 Gu, M. B., Choi, S. H. & Kim, S. W. Some observations in freeze-drying of recombinant bioluminescent *Escherichia coli* for toxicity monitoring. *J Biotechnol* 88, 95-105 (2001).

2 Yagi, K. Applications of whole-cell bacterial sensors in biotechnology and environmental science. *Appl Microbiol Biotechnol* 73, 1251-1258 (2007).

3 Ptitsyn, L. R. et al. A biosensor for environmental genotoxin screening based on an SOS lux assay in recombinant *Escherichia coli* cells. *Appl Environ Microbiol* 63, 4377-4384 (1997).

4 Van Dyk, T. K. et al. Rapid and sensitive pollutant detection by induction of heat shock gene-bioluminescence gene fusions. *Appl Environ Microbiol* 60, 1414-1420 (1994).

5 Belkin, S., Smulski, D. R., Vollmer, A. C., Van Dyk, T. K. & LaRossa, R. A. Oxidative stress detection with Escherichia coli harboring a katG'::lux fusion. *Appl Environ Microbiol* 62, 2252-2256 (1996).

6 Werlen, C., Jaspers, M. C. & van der Meer, J. R. Measurement of biologically available naphthalene in gas and aqueous phases by use of a Pseudomonas putida biosensor. *Appl Environ Microbiol* 70, 43-51 (2004).

7 Stocker, J. et al. Development of a set of simple bacterial biosensors for quantitative and rapid measurements of arsenite and arsenate in potable water. *Environ Sci Technol* 37, 4743-4750 (2003).

8 Hansen, L. H. & Sorensen, S. J. Versatile biosensor vectors for detection and quantification of mercury. *FEMS Microbiol Lett* 193, 123-127 (2000).

9 Olivo, P. D., Collins, P. L., Peeples, M. E. & Schlesinger, S. Detection and quantitation of human respiratory syncytial virus (RSV) using minigenome cDNA and a Sindbis virus replicon: a prototype assay for negative-strand RNA viruses. *Virology* 251, 198-205 (1998).

10 Levskaya, A. et al. Synthetic biology: engineering *Escherichia coli* to see light. *Nature* 438, 441-442 (2005).

11 Sauer, S. & Kliem, M. Mass spectrometry tools for the classification and identification of bacteria. *Nat Rev Microbiol* 8, 74-82, (2010).

12 Mischak, H. et al. Capillary electrophoresis-mass spectrometry as a powerful tool in biomarker discovery and clinical diagnosis: an update of recent developments. *Mass Spectrom Rev* 28, 703-724 (2009).

13 Conklin, B. R. et al. Engineering GPCR signaling pathways with RASSLs. *Nat Methods* 5, 673-678 (2008).

14 Dong, S., Rogan, S. C. & Roth, B. L. Directed molecular evolution of DREADDs: a generic approach to creating next-generation RASSLs. *Nat Protoc* 5, 561-573 (2010).

15 Wendland, J., Dunkler, A. & Walther, A. Characterization of alpha-factor pheromone and pheromone receptor genes of *Ashbya gossypii*. *FEMS Yeast Res* 11, 418-429 (2011).

16 Gomes-Rezende, J. A. et al. Functionality of the Paracoccidioides Mating α-Pheromone-Receptor System. *PLoS ONE* 7, e47033, (2012).

17 Janiak, A. M. et al. Functional expression of the Candida albicans α-factor receptor in Saccharomyces cerevisiae. *Fungal Genetics and Biology* 42, 328-338 (2005).

18 Mayrhofer, S. & Poggeler, S. Functional characterization of an alpha-factor-like Sordaria macrospora peptide pheromone and analysis of its interaction with its cognate receptor in *Saccharomyces cerevisiae*. *Eukaryot Cell* 4, 661-672 (2005).

19 Pierce, K. L., Premont, R. T. & Lefkowitz, R. J. Seven-transmembrane receptors. *Nat Rev Mol Cell Biol* 3, 639-650 (2002).

20 Wang, Y. & Dohlman, H. G. Pheromone signaling mechanisms in yeast: a prototypical sex machine. *Science* 306, 1508-1509 (2004).

21 King, K., Dohlman, H. G., Thorner, J., Caron, M. G. & Lefkowitz, R. J. Control of yeast mating signal transduction by a mammalian beta 2-adrenergic receptor and Gs alpha subunit. *Science* 250, 121-123 (1990).

22 Sander, P. et al. Heterologous expression of the human D2S dopamine receptor in protease-deficient *Saccharomyces cerevisiae* strains. *Eur J Biochem* 226, 697-705 (1994).

23 Harris, J. R. et al. Field evaluation of crystal VC Rapid Dipstick test for cholera during a cholera outbreak in Guinea-Bissau. *Trop Med Int Health* 14, 1117-1121 (2009).

24 Miret, J. J., Rakhilina, L., Silverman, L. & Oehlen, B. Functional expression of heteromeric calcitonin gene-related peptide and adrenomedullin receptors in yeast. *J Blot Chem* 277, 6881-6887 (2002).

25 Ignatovica, V., Megnis, K., Lapins, M., Schioth, H. B. & Klovins, J. Identification and analysis of functionally important amino acids in human purinergic 12 receptor using a *Saccharomyces cerevisiae* expression system. *FEBS J* 279, 180-191 (2012).

26 Erickson, J. R. et al. Edg-2/Vzg-1 couples to the yeast pheromone response pathway selectively in response to lysophosphatidic acid. *J Biol Chem* 273, 1506-1510 (1998).

27 Price, L. A., Kajkowski, E. M., Hadcock, J. R., Ozenberger, B. A. & Pausch, M. H. Functional coupling of a mammalian somatostatin receptor to the yeast pheromone response pathway. *Mol Cell Biol* 15, 6188-6195 (1995).

28 Price, L. A., Strnad, J., Pausch, M. H. & Hadcock, J. R. Pharmacological characterization of the rat A2a adenosine receptor functionally coupled to the yeast pheromone response pathway. *Mol Pharmacol* 50, 829-837 (1996).

29 Erlenbach, I. et al. Functional expression of M(1), M(3) and M(5) muscarinic acetylcholine receptors in yeast. *J Neurochem* 77, 1327-1337 (2001).

30 Armbruster, B. N., Li, X., Pausch, M. H., Herlitze, S. & Roth, B. L. Evolving the lock to fit the key to create a family of G protein-coupled receptors potently activated by an inert ligand. *Proc Natl Acad Sci USA* 104, 5163-5168 (2007).

31 Pei, Y., Rogan, S. C., Yan, F. & Roth, B. L. Engineered GPCRs as tools to modulate signal transduction. *Physiology (Bethesda)* 23, 313-321, (2008).

32 Ault, A. D. & Broach, J. R. Creation of GPCR-based chemical sensors by directed evolution in yeast. *Protein Eng Des Sel* 19, 1-8 (2006).

33 Martin, S. H., Wingfield, B. D., Wingfield, M. J. & Steenkamp, E. T. Causes and Consequences of Variability in Peptide Mating Pheromones of Ascomycete Fungi. *Molecular Biology and Evolution* 28, 1987-2003 (2011).

34 Martin, S. H., Steenkamp, E. T., Wingfield, M. J., Wingfield, B. D. Mate-recognition and species boundaries in the ascomycetes. *Fungal Diversity* 58, 1-12 (2013).

35 Leavitt, L. M., Macaluso, C. R., Kim, K. S., Martin, N. P. & Dumont, M. E. Dominant negative mutations in the alpha-factor receptor, a G protein-coupled receptor encoded by the STE2 gene of the yeast *Saccharomyces cerevisiae*. *Mol Gen Genet* 261, 917-932 (1999).

36 Martin, N. P., Celic, A. & Dumont, M. E. Mutagenic mapping of helical structures in the transmembrane segments of the yeast alpha-factor receptor. *J Mol Biol* 317, 765-788 (2002).

37 Naider, F. & Becker, J. M. The alpha-factor mating pheromone of *Saccharomyces cerevisiae*: a model for studying the interaction of peptide hormones and G protein-coupled receptors. *Peptides* 25, 1441-1463 (2004).

38 Mathew, E. et al. Differential interactions of fluorescent agonists and antagonists with the yeast G protein coupled receptor Ste2p. *J Mol Biol* 409, 513-528 (2011).

39 Hauser, M., Kauffman, S., Lee, B. K., Naider, F. & Becker, J. M. The first extracellular loop of the *Saccharomyces cerevisiae* G protein-coupled receptor Ste2p undergoes a conformational change upon ligand binding. *J Biol Chem* 282, 10387-10397 (2007).

40 Lin, J. C., Parrish, W., Eilers, M., Smith, S. O. & Konopka, J. B. Aromatic residues at the extracellular ends of transmembrane domains 5 and 6 promote ligand activation of the G protein-coupled alpha-factor receptor. *Biochemistry* 42, 293-301 (2003).

41 Umanah, G. K., Huang, L. Y., Maccarone, J. M., Naider, F. & Becker, J. M. Changes in conformation at the cytoplasmic ends of the fifth and sixth transmembrane helices of a yeast G protein-coupled receptor in response to ligand binding. *Biochemistry* 50, 6841-6854 (2011).

42 Umanah, G. K. et al. Identification of residue-to-residue contact between a peptide ligand and its G protein-coupled receptor using periodate-mediated dihydroxyphenylalanine cross-linking and mass spectrometry. *J Biol Chem* 285, 39425-39436 (2010).

43 Son, C. D., Sargsyan, H., Naider, F. & Becker, J. M. Identification of ligand binding regions of the *Saccharomyces cerevisiae* alpha-factor pheromone receptor by photoaffinity cross-linking. *Biochemistry* 43, 13193-13203 (2004).

44 Minic, J. et al. Functional expression of olfactory receptors in yeast and development of a bioassay for odorant screening. *FEBS J* 272, 524-537 (2005).

45 Alper, H., Jin, Y. S., Moxley, J. F. & Stephanopoulos, G. Identifying gene targets for the metabolic engineering of lycopene biosynthesis in *Escherichia coli*. *Metab Eng* 7, 155-164 (2005).

46 Armstrong, G. A. Genetics of eubacterial carotenoid biosynthesis: a colorful tale. *Annu Rev Microbiol* 51, 629-659 (1997).

47 Chemler, J. A., Yan, Y. & Koffas, M. A. Biosynthesis of isoprenoids, polyunsaturated fatty acids and flavonoids in *Saccharomyces cerevisiae*. *Microb Cell Fact* 5, 20 (2006).

48 van der Meer, J. R. & Belkin, S. Where microbiology meets microengineering: design and applications of reporter bacteria. *Nat Rev Microbiol* 8, 511-522 (2010).

49 Radhika, V. et al. Chemical sensing of DNT by engineered olfactory yeast strain. *Nat Chem Biol* 3, 325-330 (2007).

50 Xu, Y., Ault, A. D., Broach, J. R. Yeast That Smell. *J. Biochem. Technol.* 1 (2008).

51 Struss, A. K., Pasini, P., Daunert S. in *Recognition Receptors in Biosensors* (ed M. Zourob) 565-598 (Springer New York, 2010).

52 MacKay, V. L. et al. Gene expression analyzed by high-resolution state array analysis and quantitative proteomics: response of yeast to mating pheromone. *Mol Cell Proteomics* 3, 478-489 (2004).

53 Hagen, D. C., McCaffrey, G. & Sprague, G. F., Jr. Pheromone response elements are necessary and sufficient for basal and pheromone-induced transcription of the FUS1 gene of *Saccharomyces cerevisiae*. *Mol Cell Biol* 11, 2952-2961 (1991).

54 Wang, Y. & Dohlman, H. G. Pheromone-regulated sumoylation of transcription factors that mediate the invasive to mating developmental switch in yeast. *J Biol Chem* 281, 1964-1969 (2006).

55 Fukuda, N., Ishii, J., Kaishima, M. & Kondo, A. Amplification of agonist stimulation of human G-protein-coupled receptor signaling in yeast. *Anal Biochem* 417, 182-187 (2011).

56 Takahashi, S. & Pryciak, P. M. Membrane localization of scaffold proteins promotes graded signaling in the yeast MAP kinase cascade. *Curr Biol* 18, 1184-1191 (2008).

57 Cairns, B. R., Ramer, S. W. & Kornberg, R. D. Order of action of components in the yeast pheromone response pathway revealed with a dominant allele of the STE11 kinase and the multiple phosphorylation of the STET kinase. *Genes Dev* 6, 1305-1318 (1992).

58 Bashor, C. J., Helman, N. C., Yan, S. & Lim, W. A. Using engineered scaffold interactions to reshape MAP kinase pathway signaling dynamics. *Science* 319, 1539-1543 (2008).

59 Verwaal, R. et al. High-level production of beta-carotene in *Saccharomyces cerevisiae* by successive transformation with carotenogenic genes from *Xanthophyllomyces dendrorhous*. *Appl Environ Microbiol* 73, 4342-4350 (2007).

60 Ebert, M. P. et al. Identification of gastric cancer patients by serum protein profiling. *J Proteome Res* 3, 1261-1266 (2004).

61 Hingorani, S. R. et al. Preinvasive and invasive ductal pancreatic cancer and its early detection in the mouse. *Cancer Cell* 4, 437-450 (2003).

62 Villanueva, J. et al. Serum peptide profiling by magnetic particle-assisted, automated sample processing and MALDI-TOF mass spectrometry. *Anal Chem* 76, 1560-1570 (2004).

63 Villanueva, J. et al. Differential exoprotease activities confer tumor-specific serum peptidome patterns. *J Clin Invest* 116, 271-284 (2006).

64 Yang, H. et al. Prognostic polypeptide blood plasma biomarkers of Alzheimer's disease progression. *J Alzheimers Dis* 40, 659-666 (2014).

65 Lin, X. et al. DJ-1 isoforms in whole blood as potential biomarkers of Parkinson disease. *Sci Rep* 2, 954 (2012).

66 Niwa, T. Biomarker discovery for kidney diseases by mass spectrometry. *J Chromatogr B Analyt Technol Biomed Life Sci* 870, 148-153 (2008).

67 Gujraty, K. et al. Functional characterization of peptide-based anthrax toxin inhibitors. *Mol Pharm* 2, 367-372 (2005).

68 Ma, H., Zhou, B., Kim, Y. & Janda, K. D. A cyclic peptide-polymer probe for the detection of *Clostridium botulinum* neurotoxin serotype A. *Toxicon* 47, 901-908 (2006).

69 Higgins, D. A. et al. The major Vibrio cholerae autoinducer and its role in virulence factor production. *Nature* 450, 883-886 (2007).

70 Cloak, O. M., Solow, B. T., Briggs, C. E., Chen, C. Y. & Fratamico, P. M. Quorum sensing and production of autoinducer-2 in *Campylobacter* spp., *Escherichia coli* 0157:H7, and *Salmonella enterica* serovar Typhimurium in foods. *Appl Environ Microbiol* 68, 4666-4671 (2002).

71 Pausch, M. H. G-protein-coupled receptors in *Saccharomyces cerevisiae*: high-throughput screening assays for drug discovery. *Trends Biotechnol* 15, 487-494 (1997).

72 Tracewell, C. A. & Arnold, F. H. Directed enzyme evolution: climbing fitness peaks one amino acid at a time. *Curr Opin Chem Biol* 13, 3-9 (2009).

73 Shin, H. J., Park, H. H. & Lim, W. K. Freeze-dried recombinant bacteria for on-site detection of phenolic compounds by color change. *J Biotechnol* 119, 36-43 (2005).

74 Su, L., Jia, W., Hou, C. & Lei, Y. Microbial biosensors: A review. *Biosens. Bioelectron.* 26, 1788-1799 (2011).

75. Eilam, Y. & Grossowicz, N. Nystatin Effects on Cellular Calcium in *Saccharomyces-Cerevisiae. Biochim. Biophys. Acta* 692, 238-243 (1982).

76. Garjonyte, R., Melvydas, V. & Malinauskas, A. Amperometric biosensors for lactic acid based on baker's and wine yeast. *Microchim. Acta* 164, 177-183 (2009).

77. Mavrodi, D. V. et al. Functional Analysis of Genes for Biosynthesis of Pyocyanin and Phenazine-1-Carboxamide from *Pseudomonas aeruginosa* PAO1. *J. Bacteriol.* 183, 6454-6465 (2001).

78. Bellin, D. L. et al. Integrated circuit-based electrochemical sensor for spatially resolved detection of redox-active metabolites in biofilms. *Nat. Commun.* 5, 3256 (2014).
79. Spira, M. E. & Hai, A. Multi-electrode array technologies for neuroscience and cardiology. *Nat. Nanotechnol.* 8, 83-94 (2013).
80. Ali, R., Zielinski, R. E. & Berkowitz, G. A. Expression of plant cyclic nucleotide-gated cation channels in yeast. *J Exp Bot* 57, 125-138 (2006).
81. Bourbonnais, Y., Bolin, D. & Shields, D. Secretion of somatostatin by *Saccharomyces cerevisiae*. Correct proteolytic processing of pro-alpha-factor-somatostatin hybrids requires the products of the KEX2 and STE13 genes. *J. Biol. Chem.* 263, 15342-15347 (1988).
82. Miyajima, A., Bond, M. W., Otsu, K., Arai, K. & Arai, N. Secretion of mature mouse interleukin-2 by *Saccharomyces cerevisiae*: use of a general secretion vector containing promoter and leader sequences of the mating pheromone α-factor. *Gene* 37, 155-161 (1985).
83. Ro, D. K. et al. Production of the antimalarial drug precursor artemisinic acid in engineered yeast. *Nature* 440, 940-943 (2006)
84. Huat, L. B. et al. Entamoeba histolytica acetyl-CoA synthetase: biomarker of acute amoebic liver abscess. *Asian Pac J Trop Biomed* 4, 446-450, (2014)
85. Rafati, S. et al. Amastin peptide-binding antibodies as biomarkers of active human visceral leishmaniasis. *Clin Vaccine Immunol* 13, 1104-1110 (2006).
86. Huzarewich, R. L., Siemens, C. G. & Booth, S. A. Application of "omics" to prion biomarker discovery. *J Biomed Biotechnol* 2010, 613504.
87. van Holten, T. C. et al. Circulating biomarkers for predicting cardiovascular disease risk; a systematic review and comprehensive overview of meta-analyses. *PLoS ONE* 8, e62080 (2013)
88. Van Everbroeck, B., Boons, J. & Cras, P. Cerebrospinal fluid biomarkers in Creutzfeldt-Jakob disease. *Clin Neurol Neurosurg* 107, 355-360 (2005)
89. Pisa, D., Alonso, R., Rabano, A., Rodal, I. & Carrasco, L. Different Brain Regions are Infected with Fungi in Alzheimer's Disease. *Sci Rep* 5, 15015 (2015)
90. Lee M E, Aswani A, Han A S, Tomlin C J, Dueber J E. Expression-level optimization of a multi-enzyme pathway in the absence of a high-throughput assay. Nucleic Acids Research 2013; 41(22):10668-10678
91. Hwan Han et al. Optimization of bio-indigo production by recombinant *E. coli* harboring fmo gene. Enzyme and Microbial Technology (2008).
92. Santos, C. N., and G. Stephanopoulos. 2008. Melanin-based high-throughput screen for L-tyrosine production in *Escherichia coli*. Appl. Environ. Microbiol. 74:1190-1197
93. Bourbonnais, Y., Bolin, D. & Shields, D. Secretion of somatostatin by *Saccharomyces cerevisiae*. Correct proteolytic processing of pro-alpha-factor-somatostatin hybrids requires the products of the KEX2 and STE13 genes. *J. Biol. Chem.* 263, 15342-15347 (1988)
94. Miyajima, A., Bond, M. W., Otsu, K., Arai, K. & Arai, N. Secretion of mature mouse interleukin-2 by *Saccharomyces cerevisiae*: use of a general secretion vector containing promoter and leader sequences of the mating pheromone α-factor. *Gene* 37, 155-161 (1985)
95. Ro, D. K. et al. Production of the antimalarial drug precursor artemisinic acid in engineered yeast. *Nature* 440, 940-943 (2006)
96. Su, L., Jia, W., Hou, C. & Lei, Y. Microbial biosensors: A review. *Biosens. Bioelectron.* 26, 1788-1799 (2011);

Eilam, Y. & Grossowicz, N. Nystatin Effects on Cellular Calcium in *Saccharomyces-Cerevisiae*. *Biochim. Biophys. Acta* 692, 238-243 (1982)
97. Garjonyte, R., Melvydas, V. & Malinauskas, A. Amperometric biosensors for lactic acid based on baker's and wine yeast. *Microchim. Acta* 164, 177-183 (2009)
98. Mavrodi, D. V. et al. Functional Analysis of Genes for Biosynthesis of Pyocyanin and Phenazine-1-Carboxamide from *Pseudomonas aeruginosa* PAO1. *J. Bacteriol.* 183, 6454-6465 (2001)
99. Bellin, D. L. et al. Integrated circuit-based electrochemical sensor for spatially resolved detection of redox-active metabolites in biofilms. *Nat. Commun.* 5, 3256 (2014)
100. Spira, M. E. & Hai, A. Multi-electrode array technologies for neuroscience and cardiology. *Nat. Nanotechnol.* 8, 83-94 (2013)
101. Ali, R., Zielinski, R. E. & Berkowitz, G. A. Expression of plant cyclic nucleotide-gated cation channels in yeast. *J Exp Bot* 57, 125-138 (2006)
102. De Nobel J G and Barnett J A (1991), "Passage of molecules through yeast cell walls: A brief essay-review". Yeast 7(4):313-23
102. De Nobel J G, Klis F M, Munnik T, Priem J, van den Ende H (1990), "An assay of relative cell wall porosity in *Saccharomyces cerevisiae, Kluyveromyces lactis* and *Schizosaccharomyces pombe*". Yeast 6(6):483-90.
103. Hollis, R. P., Killham, K. & Glover, L. A. Design and Application of a Biosensor for Monitoring Toxicity of Compounds to Eukaryotes. Appl. Environ. Microbiol. 66, 1676-1679 (2000)
104. Radhika, V., Proikas-Cezanne, T., Jayaraman, M., Onesime, D., Ha, J. H. & Dhanasekaran, D. N. Chemical sensing of DNT by engineered olfactory yeast strain. Nat. Chem. Biol. 3, 325-330 (2007).
105. Rider, T. H., Petrovick, M. S., Nargi, F. E., Harper, J. D., Schwoebel, E. D., Mathews, R. H., Blanchard, D. J., Bortolin, L. T., Young, A. M., Chen, J. & Hollis, M. A. A B Cell-Based Sensor for Rapid Identification of Pathogens. Science 301, 213-215 (2003)
106. Andreatta M, Lund O, Nielsen M (2013), Simultaneous alignment and clustering of peptide data using a Gibbs sampling approach. Bioinformatics 29(1):8-14.
107. Huat et al. Asian Pac J Trop Biomed 4(6):446-50 (2014)
108. Rafati et al. Clin Vaccine Immunol 13(10) (2006).
109. Pi H, Chien C T, Fields S (1997) Transcriptional activation upon pheromone stimulation mediated by a small domain of *Saccharomyces cervisiae* Ste12. Molecular and Cellular Biology 17(11):6410-18
110. Sievers, F. et al. Fast, scalable generation of high-quality protein multiple sequence alignments using Clustal Omega. Molecular Systems Biology 7, 539-539 (2014)
111. Krogh, A., Larsson, B., von Heijne, G. & Sonnhammer, E. L. L. Predicting transmembrane protein topology with a hidden markov model: application to complete genomes1. Journal of Molecular Biology 305, 567-580 (2001).
112. Ćelić, A. et al. Sequences in the Intracellular Loops of the Yeast Pheromone Receptor Ste2p Required for G Protein Activation†. Biochemistry 42, 3004-3017 (2003)
113. Sánchez, C., Braña, A. F., Méndez, C. & Salas, J. A. Reevaluation of the Violacein Biosynthetic Pathway and its Relationship to Indolocarbazole Biosynthesis. ChemBioChem 7, 1231-1240 (2006).
114. Pfaller, M. A. & Diekema, D. J. Epidemiology of Invasive Candidiasis: a 115. Ramírez-Zavaleta, C. Y., Salas-Delgado, G. E., Peñas, A. D. L. & Castaño, I. Subtelomeric Silencing of the MTL3 Locus of Candida glabrata Requires yKu70, yKu80, and Rif1 Proteins. Eukaryotic Cell 9, 1602-1611 (2010).

116. Berman, J. & Sudbery, P. E. *Candida albicans*: A molecular revolution built on lessons from budding yeast. Nat Rev Genet 3, 918-932 (2002).

117. Brown, G. D. et al. Hidden Killers: Human Fungal Infections. Sci Transl Med 4, 165rv13-165rv13 (2012)

118. Ramírez-Zavala, B., Reuβ, O., Park, Y.-N., Ohlsen, K. & Morschhäuser, J. Environmental Induction of White-Opaque Switching in *Candida albicans*. PLoS Pathog 4, e1000089 (2008)

119. Huang, G. et al. N-Acetylglucosamine Induces White to Opaque Switching, a Mating Prerequisite in *Candida albicans*. PLoS Pathog 6, e1000806 (2010)

120. Hull, C. M., Raisner, R. M. & Johnson, A. D. Evidence for Mating of the 'Asexual' Yeast *Candida albicans* in a Mammalian Host. Science 289, 307-310 (2000).

121. Lachke, S. A., Lockhart, S. R., Daniels, K. J. & Soll, D. R. Skin Facilitates *Candida albicans* Mating. Infect. Immun. 71, 4970-4976 (2003).

122. Dumitru, R. et al. In Vivo and In Vitro Anaerobic Mating in *Candida albicans*. Eukaryotic Cell 6, 465-472 (2007).

123. Lequin, R. M. Enzyme Immunoassay (EIA)/Enzyme-Linked Immunosorbent Assay (ELISA). Clinical Chemistry 51, 2415-2418 (2005).

124. Kyte, J. & Doolittle, R. F. A simple method for displaying the hydropathic character of a protein. Journal of Molecular Biology 157, 105-132 (1982).

125. Higashijima, T., Fujimura, K., Masui, Y., Sakakibara, S. & Miyazawa, T. Physiological activities of peptides are correlated with the conformations of membrane-bound molecules: α-Mating factor from *Saccharomyces cerevisiae* and analog peptides. FEBS Letters 159, 229-232 (1983).

126. LaRocque, R. C. et al. Proteomic Analysis of *Vibrio cholerae* in Human Stool. Infect. Immun. 76, 4145-4151 (2008).

127. K. D. Goughenour, J.-M. Balada-Llasat, C. A. Rappleye, Quantitative Microplate-Based Growth Assay for Determination of Antifungal Susceptibility of *Histoplasma capsulatum* Yeasts. J. Clin. Microbiol. 53, 3286-3295 (2015).

128. P. L. Worsham, W. E. Goldman, Quantitative plating of *Histoplasma capsulatum* without addition of conditioned medium or siderophores. J. Med. Vet. Mycol. 26, 137-143 (1988).

129. I. Torres, A. M. García, O. Hernández, A. González, J. G. McEwen, A. Restrepo, M. Arango, Presence and expression of the mating type locus in *Paracoccidioides brasiliensis* isolates. Fungal Genet. Biol. 47, 373-380 (2010).

130. A. Restrepo, B. E. Jiménez, Growth of *Paracoccidioides brasiliensis* yeast phase in a chemically defined culture medium. J. Clin. Microbiol. 12, 279-281 (1980).

131. E. Blignaut, C. Pujol, S. Lockhart, S. Joly, D. R. Soll, Ca3 fingerprinting of *Candida albicans* isolates from human immunodeficiency virus-positive and healthy individuals reveals a new clade in South Africa. J. Clin. Microbiol. 40, 826-836 (2002).

132. B. B. Magee, P. T. Magee, Induction of mating in *Candida albicans* by construction of MTLa and MTLalpha strains. Science. 289, 310-313 (2000).

133. G. Janbon, F. Sherman, E. Rustchenko, Monosomy of a specific chromosome determines L-sorbose utilization: a novel regulatory mechanism in *Candida albicans*. Proc. Natl. Acad. Sci. U.S.A. 95, 5150-5155 (1998).

134. J. M. Anderson, D. R. Soll, Unique phenotype of opaque cells in the white-opaque transition of *Candida albicans*. J. Bacteriol. 169, 5579-5588 (1987).

135. P. W. Sherwood, M. Carlson, Mutations in GSF1 and GSF2 alter glucose signaling in *Saccharomyces cerevisiae*. Genetics. 147, 557-566 (1997).

136. M. S. S. Felipe, F. A. G. Torres, A. Q. Maranhão, I. Silva-Pereira, M. J. Poças-Fonseca, E. G. Campos, L. M. P. Moraes, F. B. M. Arraes, M. J. A. Carvalho, R. V. Andrade, A. M. Nicola, M. M. Teixeira, R. S. A. Jesuíno, M. Pereira, C. M. A. Soares, M. M. Brígido, Functional genome of the human pathogenic fungus *Paracoccidioides brasiliensis*. FEMS Immunol. Med. Microbiol. 45, 369-381 (2005).

137. J. A. Gomes-Rezende, A. G. Gomes-Alves, J. F. Menino, M. A. Coelho, P. Ludovico, P. Gonçalves, M. H. J. Sturme, F. Rodrigues, Functionality of the Paracoccidioides mating α-pheromone-receptor system. PLoS One. 7, e47033 (2012).

138. G. D. Brown, D. W. Denning, N. A. R. Gow, S. M. Levitz, M. G. Netea, T. C. White, Hidden killers: human fungal infections. Sci. Transl. Med. 4, 165rv13 (2012).

139. M. D. Abràmoff, P. J. Magalhães, S. J. Ram, Image processing with ImageJ. Biophotonics international. 11, 36-42 (2004).

140. J. A. Myers, B. S. Curtis, W. R. Curtis, Improving accuracy of cell and chromophore concentration measurements using optical density. BMC Biophys. 6, 4 (2013).

141. P. J. Hotez, M. E. Bottazzi, C. Franco-Paredes, S. K. Ault, M. R. Periago, The neglected tropical diseases of Latin America and the Caribbean: a review of disease burden and distribution and a roadmap for control and elimination. PLoS Negl. Trop. Dis. 2, e300 (2008).

Various references are cited herein, the contents of which are hereby incorporated by reference in their entireties.

---

What is claimed is:

1. A method of detecting the presence of an agent of interest in a sample, comprising:
   a) contacting the sample with a sensor fungal cell comprising a fungal non-native G-protein coupled receptor (GPCR) that binds to a peptide analyte derived from the agent, wherein the peptide analyte is a ligand for the fungal non-native GPCR,
   b) binding of the peptide analyte present in the sample to the fungal non-native GPCR, wherein binding of the peptide analyte to the fungal non-native GPCR triggers an appearance of a reporter, wherein the reporter is a biosynthesized; and
   c) detecting the appearance of the reporter by the naked eye, wherein the appearance of the reporter indicates the presence of the agent in the sample.

2. The method of claim 1, wherein the agent is selected from the group consisting of human pathogenic agents, agricultural agents, industrial/model organism agents, and bioterrorism agents.

3. The method of claim 1, wherein the non-native fungal GPCR receptor is engineered to bind to the peptide analyte.

4. The method of claim 3, wherein the non-native fungal GPCR receptor is engineered by directed evolution.

5. The method of claim 1, wherein the non-native fungal GPCR receptor is a fungal pheromone GPCR.

6. The method of claim 1, wherein the non-native fungal GPCR receptor is a GPCR comprising an amino acid sequence selected from the group consisting of SEQ ID NOs: 6, 9, 12, 15, 18, 21, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110 and 112.

7. The method of claim 1, wherein the agent is an infectious disease agent.

8. The method of claim 7, wherein the sensor fungal cell is a yeast cell.

9. The method of claim 8, wherein the sensor fungal cell is *S. cerevisiae*.

10. The method of claim 1, wherein the sensor fungal cell is engineered to express the non-native fungal GPCR receptor.

11. The method of claim 1, wherein the peptide analyte is a cognate ligand for the non-native GPCR receptor.

12. The method of claim 1, wherein the peptide analyte is a non-cognate ligand for the non-native GPCR receptor.

13. The method of claim 1, wherein the peptide analyte is a fungal mating pheromone.

14. The method of claim 13, wherein the fungal mating pheromone is selected from the group consisting of human fungal mating pheromones, non-human animal fungal mating pheromones, plant fungal mating pheromones, food fungal mating pheromones, and industrial/model fungal mating pheromones.

15. The method of claim 14, wherein the human fungal mating pheromone is selected from the group consisting of the mating pheromones of *C. albicans, C. glabrata, P. brasiliensis, L. elongisporous, P. rubens, C. guillermondi, C. tropicalis, C. parapsilosis, C. lusitaniae, S. scheckii,* and *Candida krusei*.

16. The method of claim 14, wherein the non-human animal fungal mating pheromone is the mating pheromone of *P. destructans*.

17. The method of claim 14, wherein the plant fungal mating pheromone is selected from the group consisting of the mating pheromones of *F. graminearum, M. oryzea, B. cinerea*, and *G. candidum*, and *C. purpurea*.

18. The method of claim 14, wherein the food fungal mating pheromone is selected from the group consisting of the mating pheromones of *Zygosaccharomyces bailii, Zygosaccharomyces rouxii*, and *N. fischeri*.

19. The method of claim 14, wherein the industrial/model fungal mating pheromone is selected from the group consisting of the mating pheromones of *S. cerevisiae, K. lactis, S. pombe, V. polyspora* (receptor 1), *V. polyspora* (receptor 2), *S. stipitis, S. japonicas, S. castellii, S. octosporus, A. oryzae, T melanosporum, D. haptotyla, C. tenuis, Y. lipolytica, T delbrueckii, B. bassiana, K. pastoris, A. nidulans, N. crassa*, and *H. jecorina*.

20. The method of claim 1, wherein the peptide analyte is a peptide comprising an amino acid sequence selected from the group consisting of SEQ ID NOs: 5, 8, 11, 14, 17, 20 and 34-49.

21. The method of any one of claims 1-6, 11-12 and 13, wherein the peptide analyte has a length of about 3-30 residues.

22. The method of claim 21, wherein the peptide analyte has a length of about 9-23 residues.

23. The method of claim 1, wherein the peptide analyte is associated with a bacterial infection.

24. The method of claim 23, wherein the peptide analyte is derived from *Vibrio cholera*.

25. The method of claim 24, wherein the peptide analyte derived from *Vibrio cholerae* is selected from the group consisting of a peptide having an amino acid sequence set forth in VEVPGSQHIDSQKKA (SEQ ID NO: 26), a peptide having an amino acid sequence that is at least about 80%, at least about 90%, or at least about 95% homologous to SEQ ID NO: 26, a peptide having an amino acid sequence set forth in VPGSQHIDS (SEQ ID NO: 27), and a peptide having an amino acid sequence that is at least about 80%, at least about 90%, or at least about 95% homologous to SEQ ID NO: 27.

26. The method of any one of claims 23-25, wherein the peptide analyte is derived from cholera toxin.

27. The method of claim 26, wherein the peptide analyte derived from cholera toxin is a peptide comprising an amino acid sequence selected from the group consisting of SEQ ID NOs: 114-184.

28. The method of claim 1, wherein the reporter is lycopene.

29. The method of claim 1, wherein the sample is selected from the group consisting of water samples and body fluid samples.

30. The method of claim 29, wherein the water sample is selected from the group consisting of fresh water, sea water, and sewage samples.

31. The method of claim 29, wherein the body fluid sample is selected from the group consisting of intestinal fluids, diarrhea, mucus, blood, cerebrospinal fluid, lymph, pus, saliva, vomit, urine, bile, and sweat.

32. The method of claim 1, wherein the peptide analyte is derived from *Aspergillus, Candida, Cryptococcus, Histoplasma, Pneumocystis, Stachybotrys* and *Paracoccidioides*.

\* \* \* \* \*

SEQUENCE LISTING

```
<160> NUMBER OF SEQ ID NOS: 221

<210> SEQ ID NO 1
<211> LENGTH: 1479
<212> TYPE: DNA
<213> ORGANISM: Erwinia herbicola

<400> SEQUENCE: 1
atgaagaaaa ccgtagtgat tggtgcaggt tttggtggtt tagctttggc tatacgtcta      60
```

```
caagctgcag gtattcctac agtgctattg gagcaaagag acaaaccagg aggaagagct    120
tatgtttggc acgatcaagg ctttacctttt gatgctggtc ctacagtcat cactgatcct    180
actgcattgg aagctttgtt caccttagct ggtagaagaa tggaagatta tgtccgtcta    240
ttgcctgtca agccgtttta cagattgtgt tgggaatctg gtaaaaccct agattacgcc    300
aatgacagtg ctgaactaga agctcagatt acgcagttta atcccagaga tgtcgaaggt    360
tacaggagat tccttgccta ttcccaagct gttttccaag agggttatct tcgtttgggt    420
tcagttccat tcctgtcctt tagggatatg cttagagcag gtcctcagtt gttgaagcta    480
caagcatggc aaagtgtgta tcagtctgtt tcgagattta tcgaggatga acatctgaga    540
caagcattct cattccacag tcttctagtt ggaggtaatc cctttaccac atcgagcata    600
tatacgttga ttcacgcttt ggaaagagaa tggggagttt ggtttcctga aggtggaaca    660
ggtgctttgg ttaatggtat ggtgaagcta ttcacggatt tgggtggaga aatagagctg    720
aatgcaagag tggaagaact tgttgtagca gacaacagag tctcacaagt tagacttgct    780
gatggtagga tcttcgatac agatgctgta gcttcaaacg cagatgtagt gaacacttat    840
aaaaagttgt tgggacatca tcctgttgga caaaagagag cagctgcttt ggagaggaaa    900
tctatgagca actcgttgtt tgtcctttac tttgggctga atcaaccaca ctcacaacta    960
gctcatcaca caatctgctt tggtcctaga tacagagagc tgatagatga aatttttcact   1020 ggatctgctt tagcagacga ttttttccctg tacttgcatt caccatgtgt tactgatccc   1080
tctttagcac cacctggttg tgctagcttc tatgtactag cacctgtacc acatttgggt   1140
aatgctccat tagattgggc acaagaagga ccgaaattga gggataggat cttcgactat   1200
ttggaagaac gttacatgcc aggtttgaga tctcagttgg ttacacagag gatattcaca   1260
ccagctgatt ttcatgatac tctagatgcg catttaggta gcgcttttttc cattgagcca   1320 cttttgacgc aaagtgcttg gtttagacca cacaacagag attctgacat tgccaatctg   1380
tacctagtag gtgcaggaac tcatccagga gctggtattc ctggagttgt agcttctgct   1440
aaagctactg ctagtctgat gatcgaggat ttgcagtaa                           1479

<210> SEQ ID NO 2
<211> LENGTH: 924
<212> TYPE: DNA
<213> ORGANISM: Erwinia herbicola

<400> SEQUENCE: 2
atggtttctg gttcgaaagc aggagtatca cctcataggg aaatcgaagt catgagacag     60
tccattgatg accacttagc aggattgttg ccagaaacag attcccagga tatcgttagc    120
cttgctatga gagaaggtgt tatggcacct ggtaaacgta tcagaccttt gctgatgtta    180
cttgctgcaa gagacctgag atatcagggt tctatgccta cactactgga tctagcttgt    240
gctgttgaac tgacacatac tgcttccttg atgctggatg acatgccttg tatggacaat    300
gcggaactta agagaggtca accaacaacc cacaagaaat tcggagaatc tgttgccatt    360
ttggcttctg taggtctgtt gtcgaaagct tttggcttga ttgctgcaac tggtgatctt    420
ccaggtgaaa ggagagcaca agctgtaaac gagctatcta ctgcagttgg tgttcaaggt    480
ctagtcttag acagttcag agatttgaat gacgcagctt ggacagaac tcctgatgct    540 atcctgtcta cgaaccatct gaagactggc atcttgttct cagctatgtt gcaaatcgta    600
gccattgctt ctgcttcttc accatctact agggaaacgt tacacgcatt cgcattggac    660
```

| | |
|---|---:|
| tttggtcaag cctttcaact gctagacgat ttgagggatg atcatccaga gacaggtaaa | 720 |
| gaccgtaaca aagacgctgg taaaagcact ctagtcaaca gattgggtgc tgatgcagct | 780 |
| agacagaaac tgagagagca cattgactct gctgacaaac acctgacatt tgcatgtcca | 840 |
| caaggaggtg ctataaggca gtttatgcac ctatggtttg gacaccatct tgctgattgg | 900 |
| tctccagtga tgaagatcgc ctaa | 924 |

<210> SEQ ID NO 3
<211> LENGTH: 930
<212> TYPE: DNA
<213> ORGANISM: Erwinia herbicola

<400> SEQUENCE: 3

| | |
|---|---:|
| atgagtcaac cacctttgtt ggatcatgct actcaaacga tggctaatgg ttccaagtcc | 60 |
| tttgctacag cagctaaact gtttgaccca gctactagaa gatcagtgct tatgctgtac | 120 |
| acttggtgta gacactgtga tgacgttata gatgaccaga cacatggttt cgcatctgaa | 180 |
| gctgctgcag aagaagaggc tactcagaga ttggctagat tgagaacgct tacacttgca | 240 |
| gcttttgaag gtgctgagat gcaagatcct gcttttgctg cattccaaga agttgcacta | 300 |
| acacacggta ttacgccaag aatggcactt gatcacttgg atggtttcgc aatggatgtt | 360 |
| gctcaaactc gttacgtgac ctttgaagac accttgagat actgctacca tgttgctgga | 420 |
| gtagttggtt tgatgatggc aagagtaatg ggtgtaagac acgaaagggt tttggacaga | 480 |
| gcttgtgatc taggtttggc ttttcagctg acaaacatcg cgagagatat tatcgacgat | 540 |
| gcagctattg acagatgcta tctacctgct gaatggttgc aagatgctgg tctaactcct | 600 |
| gagaattacg ctgcaagaga gaacagagct gcattagcaa gagttgctga aggctgata | 660 |
| gacgctgctg aaccctatta catctcaagt caagctggat tgcatgatct accacctaga | 720 |
| tgtgcttggg ctatagctac tgcaagatct gtctacagag agattggcat caaggtaaaa | 780 |
| gctgcaggtg ttctgcttg ggatagacgt caacacacta gcaaaggaga gaagattgcg | 840 |
| atgcttatgg ctgcaccagg acaagtcatt cgtgccaaaa caaccagagt tacaccaaga | 900 |
| cctgctggtt tatggcaaag acctgtctaa | 930 |

<210> SEQ ID NO 4
<211> LENGTH: 921
<212> TYPE: DNA
<213> ORGANISM: Saccharomyces cerevisiae

<400> SEQUENCE: 4

| | |
|---|---:|
| atgcagttga gcaaggctgc tgagatgtgt tatgagataa caaactctta cttacacata | 60 |
| gaccagaaat ctcagataat agcaagtaca caagaagcga tacggttgac aagaaaatac | 120 |
| ttactaagtg aaattttgt acgttggagt ccactgaatg gggaaatatc attctcgtac | 180 |
| aacggaggaa aagattgcca ggtattacta ctgttatatc tgagttgctt atgggaatat | 240 |
| ttcttcatta aggctcaaaa ttcccaattc gatttcgagt ttcaaagctt ccccatgcaa | 300 |
| agacttccaa ctgttttcat tgatcaagaa gaaactttcc ctacattaga gaattttgta | 360 |
| ctggaaaacct cagagcgata ttgcctttcc ttatacgaat cacaaaggca atctggtgca | 420 |
| tcggtcaata tggcagacgc atttagagat tttataaaga tatacctga gaccgaagct | 480 |
| atagtgatag gtattagaca cacagaccca tttggtgaag cattaaagcc tattcaaaga | 540 |
| acagattcta actggcctga ttttatgagg ttgcaacctc tcttacactg ggacttaacc | 600 |
| aatatatgga gtttcttact gtattctaat gagccaattt gtggactata tggtaaaggt | 660 |

```
ttcacatcaa tcggcggaat taacaactca ttgcctaacc cacacttgag aaaggactcc    720
aataatccag ccttgcattt tgaatgggaa atcattcatg catttggcaa ggacgcagaa    780
ggcgaacgta gttccgctat aaacacgtca cctatttccg tggtggataa ggaaagattc    840
agcaaatacc atgacaatta ctatcctggc tggtatttgg ttgatgacac tttagagaga    900
gcaggcagga tcaagaatta a                                              921
```

<210> SEQ ID NO 5
<211> LENGTH: 13
<212> TYPE: PRT
<213> ORGANISM: Candida albicans

<400> SEQUENCE: 5

```
Gly Phe Arg Leu Thr Asn Phe Gly Tyr Phe Glu Pro Gly
1               5                   10
```

<210> SEQ ID NO 6
<211> LENGTH: 469
<212> TYPE: PRT
<213> ORGANISM: Candida albicans

<400> SEQUENCE: 6

```
Met Asn Ile Asn Ser Thr Phe Ile Pro Asp Lys Pro Gly Asp Ile Ile
1               5                   10                  15

Ile Ser Tyr Ser Ile Pro Gly Leu Asp Gln Pro Ile Gln Ile Pro Phe
            20                  25                  30

His Ser Leu Asp Ser Phe Gln Thr Asp Gln Ala Lys Ile Ala Leu Val
        35                  40                  45

Met Gly Ile Thr Ile Gly Ser Cys Ser Met Thr Leu Ile Phe Leu Ile
    50                  55                  60

Ser Ile Met Tyr Lys Thr Asn Lys Leu Thr Asn Leu Lys Leu Lys Leu
65                  70                  75                  80

Lys Leu Lys Tyr Ile Leu Gln Trp Ile Asn Gln Lys Ile Phe Thr Lys
                85                  90                  95

Lys Arg Asn Asp Asn Lys Gln Gln Gln Gln Gln Gln Gln Gln Gln Ile
            100                 105                 110

Glu Ser Ser Ser Tyr Asn Asn Thr Thr Thr Leu Gly Gly Tyr Lys
        115                 120                 125

Leu Phe Leu Phe Tyr Leu Asn Ser Leu Ile Leu Leu Ile Gly Ile Ile
    130                 135                 140

Arg Ser Gly Cys Tyr Leu Asn Tyr Asn Leu Gly Pro Leu Asn Ser Leu
145                 150                 155                 160

Ser Phe Val Phe Thr Gly Trp Tyr Asp Gly Ser Ser Phe Ile Ser Ser
                165                 170                 175

Asp Val Thr Asn Gly Phe Lys Cys Ile Leu Tyr Ala Leu Val Glu Ile
            180                 185                 190

Ser Leu Gly Phe Gln Val Tyr Val Met Phe Lys Thr Ser Asn Leu Lys
        195                 200                 205

Ile Trp Gly Ile Met Ala Ser Leu Leu Ser Ile Gly Leu Gly Leu Ile
    210                 215                 220

Val Val Ala Phe Gln Ile Asn Leu Thr Ile Leu Ser His Ile Arg Phe
225                 230                 235                 240

Ser Arg Ala Ile Ser Thr Asn Arg Ser Glu Glu Glu Ser Ser Ser Ser
                245                 250                 255

Leu Ser Ser Asp Ser Val Gly Tyr Val Ile Asn Ser Ile Trp Met Asp
```

```
                  260                 265                 270
Leu Pro Thr Ile Leu Phe Ser Ile Ser Ile Asn Ile Met Thr Ile Leu
                275                 280                 285

Leu Ile Gly Lys Leu Ile Ile Ala Ile Arg Thr Arg Arg Tyr Leu Gly
            290                 295                 300

Leu Lys Gln Phe Asp Ser Phe His Ile Leu Leu Ile Gly Phe Ser Gln
305                 310                 315                 320

Thr Leu Ile Ile Pro Ser Ile Ile Leu Val Val His Tyr Phe Tyr Leu
                325                 330                 335

Ser Gln Asn Lys Asp Ser Leu Leu Gln Gln Ile Ser Leu Leu Leu Ile
            340                 345                 350

Ile Leu Met Leu Pro Leu Ser Ser Leu Trp Ala Gln Thr Ala Asn Asn
        355                 360                 365

Thr His Asn Ile Asn Ser Ser Pro Ser Leu Ser Phe Ile Ser Arg His
        370                 375                 380

His Leu Ser Asp Ser Ser Arg Ser Gly Gly Ser Asn Thr Ile Val Ser
385                 390                 395                 400

Asn Gly Gly Ser Asn Gly Gly Gly Gly Gly Gly Asn Phe Pro Val
            405                 410                 415

Ser Gly Ile Asp Ala Gln Leu Pro Pro Asp Ile Glu Lys Ile Leu His
                420                 425                 430

Glu Asp Asn Asn Tyr Lys Leu Leu Asn Ser Asn Glu Ser Val Asn
        435                 440                 445

Asp Gly Asp Ile Ile Ile Asn Asp Glu Gly Met Ile Thr Lys Gln Ile
    450                 455                 460

Thr Ile Lys Arg Val
465

<210> SEQ ID NO 7
<211> LENGTH: 1410
<212> TYPE: DNA
<213> ORGANISM: Candida albicans

<400> SEQUENCE: 7
atgaatatca attcaacttt catacctgat aaaccaggcg atataattat tagttattca      60
attccaggat tagatcaacc aattcaaatt cctttccatt cattagattc atttcaaacc     120
gatcaagcta aaatagcttt agtcatgggg ataactattg ggagttgttc aatgacatta     180 attttttga  tttctataat gtataaaact aataaattaa caaatttaaa attaaaatta     240
aaattaaaat atatcttgca atggataaat caaaaaatct tcaccaaaaa aaggaatgac     300
aacaaacaac aacaacaaca acaacaacaa caaattgaat catcatcata taacaatact     360
actactacgc tgggggggtta taaattattt ttattttatc ttaattcatt gattttatta    420
attggtatta ttcgatcagg ttgttattta aattataatt taggtccatt aaattcactt     480
agttttgtat ttactggttg gtatgatgga tcatcattta tcatccga tgtaactaat       540 ggatttaaat gtatttata tgctttagtg gaaatttcat taggtttcca agtttatgtg     600
atgttcaaaa cttcaaattt aaaaatttgg gggataatgg catcattatt atcaattggt     660
ttaggattga ttgttgttgc ctttcaaatc aatttaacaa tttatctca tattcgattt     720 tcccgggcta tatcaactaa cagaagtgaa gaagaatcat catcatcatt atcatctgat    780
tcggttgggt atgtgattaa ttcaatatgg atggatttac caacaatatt attttccatt    840
agtattaata taatgacaat attattgatt ggtaaactta taattgctat tagaacaaga    900
```

```
cgttatttag gattgaaaca atttgatagt ttccatattt tattaattgg tttcagtcaa    960
acattaatta ttccttcaat tatttggtg gttcattatt tttatttatc acaaaataaa    1020
gattctttat tacaacaaat tagtctttta ttgattattt taatgttacc attaagttct   1080
ttatgggctc aaactgctaa taatactcat aatattaatt catctccaag tttatcattc    1140
atatctcgtc atcatctgtc tgatagtagt cgtagtggtg gttccaatac aattgttagt    1200
aatggtggta gtaatggtgg tggtggtggt ggtgggaatt tccctgtttc aggtattgat    1260
gcacaattac cacctgatat tgaaaaaatc ttacatgaag ataataatta taaattactt    1320
aatagtaata atgaaagtgt aaatgatgga gatattatca ttaatgatga aggtatgatt    1380
actaaacaaa tcaccatcaa aagagtgtag                                    1410
```

<210> SEQ ID NO 8
<211> LENGTH: 13
<212> TYPE: PRT
<213> ORGANISM: Candida glabrata

<400> SEQUENCE: 8

```
Trp His Trp Val Arg Leu Arg Lys Gly Gln Gly Leu Phe
1               5                   10
```

<210> SEQ ID NO 9
<211> LENGTH: 417
<212> TYPE: PRT
<213> ORGANISM: Candida glabrata

<400> SEQUENCE: 9

```
Met Glu Met Gly Tyr Asp Pro Arg Met Tyr Asn Pro Arg Asn Glu Tyr
1               5                   10                  15

Leu Asn Phe Thr Ser Val Tyr Asp Val Asn Asp Thr Ile Arg Phe Ser
            20                  25                  30

Thr Leu Asp Ala Ile Val Lys Gly Leu Leu Arg Ile Ala Ile Val His
        35                  40                  45

Gly Val Arg Leu Gly Ala Ile Phe Met Thr Leu Ile Ile Met Phe Ile
    50                  55                  60

Ser Ser Asn Thr Trp Lys Lys Pro Ile Phe Ile Asn Met Val Ser
65                  70                  75                  80

Leu Met Leu Val Met Ile His Ser Ala Leu Ser Phe His Tyr Leu Leu
                85                  90                  95

Ser Asn Tyr Ser Ser Ile Ser Tyr Ile Leu Thr Gly Phe Pro Gln Leu
            100                 105                 110

Ile Thr Ser Asn Asn Lys Arg Ile Gln Asp Ala Ala Ser Ile Val Gln
        115                 120                 125

Val Leu Leu Val Ala Ala Ile Glu Ala Ser Leu Val Phe Gln Ile His
    130                 135                 140

Val Met Phe Thr Ile Glu Asn Ile Lys Leu Ile Arg Glu Ile Val Leu
145                 150                 155                 160

Ser Ile Ser Ile Ala Met Gly Leu Ala Thr Val Ala Thr Tyr Leu Ala
                165                 170                 175

Ala Ala Ile Lys Leu Ile Arg Gly Leu His Asp Glu Val Met Pro Gln
            180                 185                 190

Thr His Leu Ile Phe Asn Leu Ser Ile Ile Leu Leu Ala Ser Ser Ile
        195                 200                 205

Asn Phe Met Thr Phe Ile Leu Val Ile Lys Leu Phe Phe Ala Ile Arg
    210                 215                 220
```

```
Ser Arg Arg Tyr Leu Gly Leu Arg Gln Phe Asp Ala Phe His Ile Leu
225                 230                 235                 240

Leu Ile Met Phe Cys Gln Ser Leu Leu Ile Pro Ser Val Leu Tyr Ile
            245                 250                 255

Ile Val Tyr Ala Val Asp Ser Arg Ser Asn Gln Asp Tyr Leu Ile Pro
        260                 265                 270

Ile Ala Asn Leu Phe Val Val Leu Ser Leu Pro Leu Ser Ser Ile Trp
    275                 280                 285

Ala Asn Thr Ser Asn Asn Ser Ser Arg Ser Pro Lys Tyr Trp Lys Asn
290                 295                 300

Ser Gln Thr Asn Lys Ser Asn Gly Ser Phe Val Ser Ser Ile Ser Val
305                 310                 315                 320

Asn Ser Asp Ser Gln Asn Pro Leu Tyr Lys Lys Ile Val Arg Phe Thr
                325                 330                 335

Ser Lys Gly Asp Thr Thr Arg Ser Ile Val Ser Asp Ser Thr Leu Ala
            340                 345                 350

Glu Val Gly Lys Tyr Ser Met Gln Asp Val Ser Asn Ser Asn Phe Glu
        355                 360                 365

Cys Arg Asp Leu Asp Phe Glu Lys Val Lys His Thr Cys Glu Asn Phe
    370                 375                 380

Gly Arg Ile Ser Glu Thr Tyr Ser Glu Leu Ser Thr Leu Asp Thr Thr
385                 390                 395                 400

Ala Leu Asn Glu Thr Arg Leu Phe Trp Lys Gln Gln Ser Gln Cys Asp
                405                 410                 415

Lys

<210> SEQ ID NO 10
<211> LENGTH: 1254
<212> TYPE: DNA
<213> ORGANISM: Candida glabrata

<400> SEQUENCE: 10
atggagatgg gctacgatcc aagaatgtat aatccaagaa atgaatactt gaatttcacg      60
tcggtatatg atgtaaatga cacaatcaga ttttcgactc tggacgccat tgtaaaagga     120
ttgcttagaa ttgccattgt tcatggagtt agattgggag caatattcat gacgttaata     180
ataatgttta tctcatcaaa tacatggaaa aaacccatat ttataattaa catggtgtcg     240
ttgatgttag ttatgattca ttccgcactt agcttccatt acctttatc gaattattct      300 tcaatttctt atatactgac agggtttcct cagttgatta caagcaataa taaacgaatt     360
caagatgcag cgagtatagt ccaagttta ttggttgctg cgatagaagc atcattggta     420
tttcagattc atgttatgtt tacgattgaa acattaagc ttattagaga atagtactc       480 tctatatcga tagcaatggg attggcaaca gtggctacat atcttgctgc agcaataaag     540
ctgataagag gactgcatga tgaggtaatg ccacaaacac atcttatttt caatttatct     600
ataatattgc ttgcatcctc cataaatttt atgacattta tattggtcat taaacttttc     660
ttcgctatta gatctagaag atatctcggt cttcgtcaat tcgatgcttt tcatatttta     720
ttaatcatgt tctgccagtc attattgata ccctcagtat tatatattat agtttacgcg     780
gttgatagca gatctaatca ggattatctg attccaattg ccaatttatt tgttgttta     840 tctttgccat tatcctctat ctgggctaac acatcaaata actcatccag atctccaaaa     900
tattggaaaa actctcaaac gaataagagc aatgggtctt tgtctcttc aatatctgtc      960 aatagtgact cacaaaaccc tttgtacaaa aagattgtac gttttacatc aaaaggcgac    1020
```

```
actacccgta gtattgtaag tgattcaaca ttagcagagg tgggaaaata ctctatgcaa    1080
gacgttagca attcaaactt tgaatgtcga gaccttgatt ttgagaaggt aaaacatact    1140
tgcgaaaatt ttggcagaat atctgaaaca tatagtgagt taagtacttt agataccact    1200
gccctcaatg agactcggtt gttttggaaa caacaaagtc agtgtgacaa atag          1254
```

<210> SEQ ID NO 11
<211> LENGTH: 9
<212> TYPE: PRT
<213> ORGANISM: Paracoccidioides brasiliensis

<400> SEQUENCE: 11

Trp Cys Thr Arg Pro Gly Gln Gly Cys
1               5

<210> SEQ ID NO 12
<211> LENGTH: 356
<212> TYPE: PRT
<213> ORGANISM: Paracoccidioides brasiliensis

<400> SEQUENCE: 12

Met Ala Pro Ser Phe Asp Pro Phe Asn Gln Ser Val Val Phe His Lys
1               5                   10                  15

Ala Asp Gly Thr Pro Phe Asn Val Ser Ile His Glu Leu Asp Asp Phe
            20                  25                  30

Val Gln Tyr Asn Thr Lys Val Cys Ile Asn Tyr Ser Ser Gln Leu Gly
        35                  40                  45

Ala Ser Val Ile Ala Gly Leu Met Leu Ala Met Thr His Ser Glu
    50                  55                  60

Lys Arg Arg Leu Pro Val Phe Phe Leu Asn Thr Phe Ala Leu Ala Met
65                  70                  75                  80

Asn Phe Ala Arg Leu Leu Cys Met Thr Ile Tyr Phe Thr Thr Gly Phe
                85                  90                  95

Asn Lys Ser Tyr Ala Tyr Phe Gly Gln Asp Tyr Ser Gln Val Pro Gly
            100                 105                 110

Ser Ala Tyr Ala Ala Ser Val Leu Gly Val Val Phe Thr Thr Leu Leu
        115                 120                 125

Val Ile Ser Met Glu Met Ser Leu Leu Ile Gln Thr Arg Val Val Cys
    130                 135                 140

Thr Thr Leu Pro Asp Ile Gln Arg Tyr Leu Leu Met Ala Val Ser Ser
145                 150                 155                 160

Ala Ile Ser Leu Met Ala Ile Gly Phe Arg Leu Gly Leu Met Val Glu
                165                 170                 175

Asn Cys Ile Ala Ile Val Gln Ala Ser Asn Phe Ala Pro Phe Ile Trp
            180                 185                 190

Leu Gln Ser Ala Ser Asn Ile Thr Ile Thr Ile Ser Thr Cys Phe Phe
        195                 200                 205

Ser Ala Val Phe Val Thr Lys Leu Ala Tyr Ala Leu Val Thr Arg Ile
    210                 215                 220

Arg Leu Gly Leu Thr Arg Phe Gly Ala Met Gln Val Met Phe Ile Met
225                 230                 235                 240

Ser Cys Gln Thr Met Val Ile Pro Ala Ile Phe Ser Ile Leu Gln Tyr
                245                 250                 255

Pro Leu Pro Lys Tyr Glu Met Asn Ser Asn Leu Phe Thr Leu Val Ala
            260                 265                 270

```
Ile Phe Leu Pro Leu Ser Ser Leu Trp Ala Ser Val Ala Thr Arg Ser
        275                 280                 285

Ser Phe Glu Thr Ser Ser Ser Gly Arg His Gln Tyr Leu Trp Pro Ser
290                 295                 300

Glu Gln Ser Asn Asn Val Thr Asn Ser Glu Ile Lys Tyr Gln Val Ser
305                 310                 315                 320

Phe Ser Gln Asn His Thr Thr Leu Arg Ser Gly Ser Val Ala Thr
            325                 330                 335

Thr Leu Ser Pro Asp Arg Leu Asp Pro Val Tyr Cys Glu Val Glu Ala
        340                 345                 350

Gly Thr Lys Ala
        355

<210> SEQ ID NO 13
<211> LENGTH: 1071
<212> TYPE: DNA
<213> ORGANISM: Paracoccidioides brasiliensis

<400> SEQUENCE: 13
atggcaccct cattcgaccc cttcaaccaa agcgtggtct tccacaaggc cgacggaact      60
ccattcaacg tctcaatcca tgaactagac gacttcgtgc agtacaacac caaagtctgc     120
atcaactact cttcccagct cggagcatct gtcattgcag gactcatgct tgccatgctg     180
acacactcag aaaagcgtcg tctgccagtt ttcttcctaa cacattcgc actggccatg     240
aactttgccc gcctgctctg catgaccatc tacttcacca cgggcttcaa caagtcctat     300
gcctactttg gtcaggatta ctcccaggtg cctgggagcg cctacgcagc ctctgtcttg     360
ggcgttgtct tcaccactct cctggtaatc agcatggaaa tgtccctcct gatccaaaca     420
agggttgtct gcacgaccct tccggatatc caacgttatc tactcatggc agtttcctcc     480
gcgatttccc tgatggccat cgggttccgc cttggcttaa tggttgagaa ctgcattgcc     540
attgtgcagg cgtcgaattt cgccccttt atctggcttc aaagcgcctc gaacatcacc     600
attacgatca gcacatgttt cttcagtgcc gtctttgtta cgaaattggc atatgcactc     660
gtcactcgta tacgactagg cttgacgagg tttggtgcta tgcaggttat gttcatcatg     720
tcctgccaga ctatggtgat ccagccatc ttctcaattc ccaataccc actccccaag     780
tacgaaatga actccaacct ctttacgctg gtggccattt cctcccctct ttcctcgcta     840
tgggcttcag ttgctacgag atccagtttc gagacgtctt cttccggccg ccatcagtat     900
ctttggccaa gcgaacagag caataacgtc accaattcgg aaattaagta tcaggtcagc     960
ttctctcaga accacactac gttgcggtct ggagggtctg tggccacgac actctccccg    1020
gaccggctcg acccggttta ttgtgaagtt gaagctggca caaaggccta g             1071

<210> SEQ ID NO 14
<211> LENGTH: 10
<212> TYPE: PRT
<213> ORGANISM: Fusarium graminearum

<400> SEQUENCE: 14

Trp Cys Trp Trp Lys Gly Gln Pro Cys Trp
1               5                   10

<210> SEQ ID NO 15
<211> LENGTH: 386
<212> TYPE: PRT
<213> ORGANISM: Fusarium graminearum
```

<400> SEQUENCE: 15

```
Met Ser Lys Glu Val Phe Asp Pro Phe Thr Gln Asn Val Thr Phe Phe
1               5                   10                  15

Ala Pro Asp Gly Lys Thr Glu Ile Ser Ile Pro Val Ala Ala Ile Asp
            20                  25                  30

Gln Val Arg Arg Met Met Val Asn Thr Thr Ile Asn Tyr Ala Thr Gln
        35                  40                  45

Leu Gly Ala Cys Leu Ile Met Leu Val Val Leu Leu Val Met Val Pro
    50                  55                  60

Lys Glu Lys Phe Arg Arg Pro Phe Met Ile Leu Gln Ile Thr Ser Leu
65                  70                  75                  80

Val Ile Ser Cys Cys Arg Met Leu Leu Leu Ser Ile Phe His Ser Ser
                85                  90                  95

Gln Phe Leu Asp Phe Tyr Val Phe Trp Gly Asp His Ser Arg Ile
            100                 105                 110

Pro Arg Ser Ala Tyr Ala Pro Ser Val Ala Gly Asn Thr Met Ser Leu
        115                 120                 125

Cys Leu Val Ile Ser Val Glu Thr Met Leu Met Ser Gln Ala Trp Thr
    130                 135                 140

Met Val Arg Leu Trp Pro Asn Val Trp Lys Tyr Ile Ile Ala Gly Val
145                 150                 155                 160

Ser Leu Ile Val Ser Ile Met Ala Ile Ser Val Arg Leu Ala Tyr Thr
                165                 170                 175

Ile Ile Gln Asn Asn Ala Val Leu Lys Leu Glu Pro Ala Phe His Met
            180                 185                 190

Phe Trp Leu Ile Lys Trp Thr Val Ile Met Asn Val Ala Ser Ile Ser
        195                 200                 205

Trp Trp Cys Ala Ile Phe Asn Ile Lys Leu Val Trp His Leu Ile Ser
    210                 215                 220

Asn Arg Gly Ile Leu Pro Ser Tyr Lys Thr Phe Thr Pro Met Glu Val
225                 230                 235                 240

Leu Ile Met Thr Asn Gly Ile Leu Met Ile Ile Pro Val Ile Phe Ala
                245                 250                 255

Ser Leu Glu Trp Ala His Phe Val Asn Phe Glu Ser Ala Ser Leu Thr
            260                 265                 270

Leu Thr Ser Val Ala Val Ile Leu Pro Leu Gly Thr Leu Ala Ala Gln
        275                 280                 285

Arg Ile Ala Ser Ser Ala Pro Ser Ser Ala Asn Ser Thr Gly Ala Ser
    290                 295                 300

Ser Gly Ile Arg Tyr Gly Val Ser Gly Pro Ser Ser Phe Thr Gly Phe
305                 310                 315                 320

Lys Ala Pro Ser Phe Ser Thr Gly Thr Thr Asp Arg Pro His Val Ser
                325                 330                 335

Ile Tyr Ala Arg Cys Glu Ala Gly Thr Ser Ser Arg Glu His Ile Asn
            340                 345                 350

Pro Gln Gly Val Glu Leu Ala Lys Leu Asp Pro Glu Thr Asp His His
        355                 360                 365

Val Arg Val Asp Arg Ala Phe Leu Gln Arg Glu Arg Ile Arg Ala
    370                 375                 380

Pro Leu
385
```

<210> SEQ ID NO 16

<211> LENGTH: 1161
<212> TYPE: DNA
<213> ORGANISM: Fusarium graminearum

<400> SEQUENCE: 16

```
atgtctaagg aagttttcga cccattcact caaaacgtta ctttcttcgc tccagacggt     60
aagactgaaa tctctatccc agttgctgct atcgaccaag ttagaagaat gatggttaac    120
actactatca actacgctac tcaattgggt gcttgtttga tcatgttggt tgttttgttg    180
gttatggttc caaaggaaaa gttcagaaga ccattcatga tcttgcaaat cacttctttg    240
gttatctctt gttgtagaat gttgttgttg tctatcttcc actcttctca attcttggac    300
ttctacgttt tctggggtga cgaccactct agaatcccaa gatctgctta cgctccatct    360
gttgctggta acactatgtc tttgtgtttg gttatctctg ttgaaactat gttgatgtct    420
caagcttgga ctatggttag attgtggcca aacgtttgga agtacatcat cgctggtgtt    480
tctttgatcg tttctatcat ggctatctct gttagattgg cttacactat catccaaaac    540
aacgctgttt tgaagttgga accagctttc cacatgttct ggttgatcaa gtggactgtt    600
atcatgaacg ttgcttctat ctcttggtgg tgtgctatct tcaacatcaa gttggtttgg    660
cacttgatct ctaacagagg tatcttgcca tcttacaaga ctttcactcc aatggaagtt    720
ttgatcatga ctaacggtat cttgatgatc atcccagtta tcttcgcttc tttggaatgg    780
gctcacttcg ttaacttcga atctgcttct ttgactttga cttctgttgc tgttatcttg    840
ccattgggta ctttggctgc tcaaagaatc gcttcttctg ctccatcttc tgctaactct    900
actggtgctt cttctggtat cagatacggt gtttctggtc catcttcttt cactggtttc    960
aaggctccat ctttctctac tggtactact gacagaccac acgtttctat ctacgctaga   1020
tgtgaagctg gtacttcttc tagagaacac atcaacccac aaggtgttga attggctaag   1080
ttggacccag aaactgacca ccacgttaga gttgacagag ctttcttgca aagagaagaa   1140
agaatcagag ctccattgta g                                             1161
```

<210> SEQ ID NO 17
<211> LENGTH: 11
<212> TYPE: PRT
<213> ORGANISM: Magnaporthe oryzea

<400> SEQUENCE: 17

```
Gln Trp Cys Pro Arg Arg Gly Gln Pro Cys Trp
1               5                   10
```

<210> SEQ ID NO 18
<211> LENGTH: 415
<212> TYPE: PRT
<213> ORGANISM: Magnaporthe oryzea

<400> SEQUENCE: 18

```
Met Asp Gln Thr Leu Ser Ala Thr Gly Thr Ala Thr Ser Pro Pro Gly
1               5                   10                  15

Pro Ala Leu Thr Val Asp Pro Arg Phe Gln Thr Ile Thr Met Leu Thr
            20                  25                  30

Pro Ala Leu Met Gly Gln Gly Phe Glu Glu Val Gln Thr Thr Pro Ala
        35                  40                  45

Glu Ile Asn Asp Val Tyr Phe Leu Ala Phe Asn Thr Ala Ile Gly Tyr
    50                  55                  60

Ser Thr Gln Ile Gly Ala Cys Phe Ile Met Leu Leu Val Leu Leu Thr
65                  70                  75                  80
```

```
Met Thr Ala Lys Ala Arg Phe Ala Arg Ile Pro Thr Ile Ile Asn Thr
                85                  90                  95
Ala Ala Leu Val Val Ser Ile Ile Arg Cys Thr Leu Leu Val Ile Phe
            100                 105                 110
Phe Thr Ser Thr Met Met Glu Phe Tyr Thr Ile Phe Ser Asp Asp Phe
        115                 120                 125
Ser Phe Val His Pro Asn Asp Ile Arg Arg Ser Val Ala Ala Thr Val
    130                 135                 140
Phe Ala Pro Leu Gln Leu Ala Leu Val Glu Ala Ala Leu Met Val Gln
145                 150                 155                 160
Ala Trp Ala Met Val Glu Leu Trp Pro Arg Ala Trp Lys Val Ser Gly
                165                 170                 175
Ile Ala Phe Ser Leu Ile Leu Ala Thr Val Thr Val Ala Phe Lys Cys
            180                 185                 190
Ala Ser Ala Ala Val Thr Val Lys Ser Ala Leu Glu Pro Leu Asp Pro
        195                 200                 205
Arg Pro Tyr Leu Trp Ile Arg Gln Thr Asp Leu Ala Phe Thr Thr Ala
    210                 215                 220
Met Val Thr Trp Phe Cys Phe Leu Phe Asn Val Arg Leu Ile Met His
225                 230                 235                 240
Met Trp Gln Asn Arg Ser Ile Leu Pro Thr Val Lys Gly Leu Ser Pro
                245                 250                 255
Met Glu Val Leu Val Met Ala Asn Gly Leu Leu Met Val Phe Pro Val
            260                 265                 270
Leu Phe Ala Gly Leu Tyr Tyr Gly Asn Phe Gly Gln Phe Glu Ser Ala
        275                 280                 285
Ser Leu Thr Ile Thr Ser Val Val Leu Val Leu Pro Leu Gly Thr Leu
    290                 295                 300
Val Ala Gln Arg Leu Ala Val Asn Asn Thr Val Ala Gly Ser Ser Ala
305                 310                 315                 320
Asn Thr Asp Met Asp Asp Lys Leu Ala Phe Leu Gly Asn Ala Thr Thr
                325                 330                 335
Val Thr Ser Ser Ala Ala Gly Phe Ala Gly Ser Ser Ala Ser Ala Thr
            340                 345                 350
Arg Ser Arg Leu Ala Ser Pro Arg Gln Asn Ser Gln Leu Ser Thr Ser
        355                 360                 365
Val Ser Ala Gly Lys Pro Arg Ala Asp Pro Ile Asp Leu Glu Leu Gln
    370                 375                 380
Arg Ile Asp Asp Glu Asp Asp Phe Ser Arg Ser Gly Ser Ala Gly
385                 390                 395                 400
Gly Val Arg Val Glu Arg Ser Ile Glu Arg Arg Glu Glu Arg Leu
                405                 410                 415

<210> SEQ ID NO 19
<211> LENGTH: 1248
<212> TYPE: DNA
<213> ORGANISM: Magnaporthe oryzea

<400> SEQUENCE: 19
atggaccaaa ctttgtctgc tactggtact gctacttctc caccaggtcc agctttgact      60
gttgacccaa gattccaaac tatcactatg ttgactccag ctttgatggg tcaaggtttc     120
gaagaagttc aaactactcc agctgaaatc aacgacgttt acttcttggc tttcaacact     180
gctatcggtt actctactca aatcggtgct tgtttcatca tgttgttggt tttgttgact     240
```

```
atgactgcta aggctagatt cgctagaatc ccaactatca tcaacactgc tgctttggtt    300
gtttctatca tcagatgtac tttgttggtt atcttcttca cttctactat gatggaattc    360
tacactatct tctctgacga cttctctttc gttcacccaa acgacatcag aagatctgtt    420
gctgctactg ttttcgctcc attgcaattg gctttggttg aagctgcttt gatggttcaa    480
gcttgggcta tggttgaatt gtggccaaga gcttggaagg tttctggtat cgctttctct    540
ttgatcttgg ctactgttac tgttgctttc aagtgtgctt ctgctgctgt tactgttaag    600
tctgctttgg aaccattgga cccaagacca tacttgtgga tcagacaaac tgacttggct    660
ttcactactg ctatggttac ttggttctgt ttcttgttca cgttagatt gatcatgcac     720 atgtggcaaa acagatctat cttgccaact gttaagggtt tgtctccaat ggaagttttg    780
gttatggcta acgtttgtt gatggttttc ccagttttgt tcgctggttt gtactacggt     840
aacttcggtc aattcgaatc tgcttctttg actatcactt ctgttgtttt ggttttgcca    900
ttgggtactt tggttgctca aagattggct gttaacaaca ctgttgctgg ttcttctgct    960
aacactgaca tggacgacaa gttggctttc ttgggtaacg ctactactgt tacttcttct   1020
gctgctggtt tcgctggttc ttctgcttct gctactagat ctagattggc ttctccaaga   1080
caaaactctc aattgtctac ttctgtttct gctggtaagc caagagctga cccaatcgac   1140
ttggaattgc aaagaatcga cgacgaagac gacgacttct ctagatctgg ttctgctggt   1200
ggtgttagag ttgaaagatc tatcgaaaga agagaagaaa gattgtag               1248
```

<210> SEQ ID NO 20
<211> LENGTH: 9
<212> TYPE: PRT
<213> ORGANISM: Botrytis cinerea

<400> SEQUENCE: 20

Trp Cys Gly Arg Pro Gly Gln Pro Cys
1               5

<210> SEQ ID NO 21
<211> LENGTH: 398
<212> TYPE: PRT
<213> ORGANISM: Botrytis cinerea

<400> SEQUENCE: 21

Met Ala Ser Asn Ser Ser Asn Phe Asp Pro Leu Thr Gln Ser Ile Thr
1               5                   10                  15

Ile Leu Met Ala Asp Gly Ile Thr Thr Val Ser Phe Thr Pro Leu Asp
            20                  25                  30

Ile Asp Phe Phe Tyr Tyr Tyr Asn Val Ala Cys Cys Ile Asn Tyr Gly
        35                  40                  45

Ala Gln Ala Gly Ala Cys Leu Leu Met Phe Phe Val Val Val Val Leu
    50                  55                  60

Thr Lys Ala Val Lys Arg Lys Thr Leu Leu Phe Val Leu Asn Val Leu
65                  70                  75                  80

Ser Leu Ile Phe Gly Phe Leu Arg Ala Met Leu Tyr Ala Ile Tyr Phe
                85                  90                  95

Leu Gln Gly Phe Asn Asp Phe Tyr Ala Ala Phe Thr Phe Asp Phe Ser
            100                 105                 110

Arg Val Pro Arg Ser Ser Tyr Ala Ser Ser Val Ala Gly Ser Val Ile
        115                 120                 125

Pro Leu Cys Met Thr Ile Thr Val Asn Met Ser Leu Tyr Leu Gln Ala

Tyr Thr Val Cys Lys Asn Leu Asp Asp Ile Lys Arg Ile Ile Leu Thr
145                 150                 155                 160

Thr Leu Ser Ala Ile Val Ala Leu Leu Ala Ile Gly Phe Arg Phe Ala
            165                 170                 175

Ala Thr Val Val Asn Ser Val Ala Ile Leu Ala Thr Ser Ala Ser Ser
                180                 185                 190

Val Pro Met Gln Trp Leu Val Lys Gly Thr Leu Val Thr Glu Thr Ile
            195                 200                 205

Ser Ile Trp Phe Phe Ser Leu Ile Phe Thr Gly Lys Leu Val Trp Thr
    210                 215                 220

Leu Tyr Asn Arg Arg Arg Asn Gly Trp Arg Gln Trp Ser Ala Val Arg
225                 230                 235                 240

Ile Leu Ala Ala Met Gly Gly Cys Thr Met Val Ile Pro Ser Ile Phe
                245                 250                 255

Ala Ile Leu Glu Tyr Val Thr Pro Val Ser Phe Pro Glu Ala Gly Ser
                260                 265                 270

Ile Ala Leu Thr Ser Val Ala Leu Leu Leu Pro Ile Ser Ser Leu Trp
            275                 280                 285

Ala Gly Met Val Thr Asp Glu Glu Thr Ser Ala Ile Asp Val Ser Asn
    290                 295                 300

Leu Thr Gly Ser Arg Thr Met Leu Gly Ser Gln Ser Gly Asn Phe Ser
305                 310                 315                 320

Arg Lys Thr His Ala Ser Asp Ile Thr Ala Gln Ser Ser His Leu Asp
                325                 330                 335

Phe Ser Ser Arg Lys Gly Ser Asn Ala Thr Met Met Arg Lys Gly Ser
                340                 345                 350

Asn Ala Met Asp Gln Val Thr Thr Ile Asp Cys Val Val Glu Asp Asn
            355                 360                 365

Gln Ala Asn Arg Gly Leu Arg Asp Ser Thr Glu Met Asp Leu Glu Ala
    370                 375                 380

Met Gly Val Arg Val Asn Lys Ser Tyr Gly Val Gln Lys Ala
385                 390                 395

<210> SEQ ID NO 22
<211> LENGTH: 1197
<212> TYPE: DNA
<213> ORGANISM: Botrytis cinerea

<400> SEQUENCE: 22

```
atggcttcta actcttctaa cttcgaccca ttgactcaat ctatcactat cttgatggct     60
gacggtatca ctactgtttc tttcactcca ttggacatcg acttcttcta ctactacaac    120
gttgcttgtt gtatcaacta cggtgctcaa gctggtgctt gtttgttgat gttcttcgtt    180
gttgttgttt tgactaaggc tgttaagaga aagactttgt tgttcgtttt gaacgttttg    240
tctttgatct tcggtttctt gagagctatg ttgtacgcta tctacttctt gcaaggtttc    300
aacgacttct acgctgcttt cactttcgac ttctctagag ttccaagatc ttcttacgct    360
tcttctgttg ctggttctgt tatcccattg tgtatgacta tcactgttaa catgtctttg    420
tacttgcaag cttacactgt ttgtaagaac ttggacgaca tcaagagaat catcttgact    480
actttgtctg ctatcgttgc tttgttggct atcggtttca gattcgctgc tactgttgtt    540
aactctgttg ctatcttggc tacttctgct tcttctgttc caatgcaatg gttggttaag    600
ggtactttgg ttactgaaac tatctctatc tggttcttct ctttgatctt cactggtaag    660
```

```
ttggtttgga ctttgtacaa cagaagaaga aacggttgga gacaatggtc tgctgttaga    720
atcttggctg ctatgggtgg ttgtactatg gttatcccat ctatcttcgc tatcttggaa    780
tacgttactc cagtttcttt cccagaagct ggttctatcg ctttgacttc tgttgctttg    840
ttgttgccaa tctcttcttt gtgggctggt atggttactg acgaagaaac ttctgctatc    900
gacgtttcta acttgactgg ttctagaact atgttgggtt ctcaatctgg taacttctct    960
agaaagactc acgcttctga catcactgct caatcttctc acttggactt ctcttctaga   1020
aagggttcta acgctactat gatgagaaag ggttctaacg ctatggacca agttactact   1080
atcgactgtg ttgttgaaga caaccaagct aacagaggtt tgagagactc tactgaaatg   1140
gacttggaag ctatgggtgt tagagttaac aagtcttacg gtgttcaaaa ggcttag      1197
```

<210> SEQ ID NO 23
<211> LENGTH: 14
<212> TYPE: PRT
<213> ORGANISM: Vibrio cholerae

<400> SEQUENCE: 23

Trp His Trp Leu Glu Leu Pro Gly Ser Gln His Ile Asp Ser
1               5                   10

<210> SEQ ID NO 24
<211> LENGTH: 13
<212> TYPE: PRT
<213> ORGANISM: Saccharomyces cerevisiae

<400> SEQUENCE: 24

Trp His Trp Leu Gln Leu Lys Pro Gly Gln Pro Met Tyr
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Trp His Trp Leu Glu Val Pro Gly Ser Gln Pro Met Tyr
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp His Trp Leu Glu Val Pro Gly Ser Gln His Ile Asp Ser
1               5                   10

<210> SEQ ID NO 27
<211> LENGTH: 15
<212> TYPE: PRT
<213> ORGANISM: Vibrio cholerae

<400> SEQUENCE: 27

Val Glu Val Pro Gly Ser Gln His Ile Asp Ser Gln Lys Lys Ala
1               5                   10                  15

<210> SEQ ID NO 28
<211> LENGTH: 9
<212> TYPE: PRT
<213> ORGANISM: Vibrio cholerae

<400> SEQUENCE: 28

Val Pro Gly Ser Gln His Ile Asp Ser
1               5

<210> SEQ ID NO 29
<211> LENGTH: 431
<212> TYPE: PRT
<213> ORGANISM: Saccharomyces cerevisiae

<400> SEQUENCE: 29

Met Ser Asp Ala Ala Pro Ser Leu Ser Asn Leu Phe Tyr Asp Pro Thr
1               5                   10                  15

Tyr Asn Pro Gly Gln Ser Thr Ile Asn Tyr Thr Ser Ile Tyr Gly Asn
            20                  25                  30

Gly Ser Thr Ile Thr Phe Asp Glu Leu Gln Gly Leu Val Asn Ser Thr
        35                  40                  45

Val Thr Gln Ala Ile Met Phe Gly Val Arg Cys Gly Ala Ala Ala Leu
    50                  55                  60

Thr Leu Ile Val Met Trp Met Thr Ser Arg Ser Arg Lys Thr Pro Ile
65                  70                  75                  80

Phe Ile Ile Asn Gln Val Ser Leu Phe Leu Ile Leu His Ser Ala
                85                  90                  95

Leu Tyr Phe Lys Tyr Leu Leu Ser Asn Tyr Ser Ser Val Thr Tyr Ala
            100                 105                 110

Leu Thr Gly Phe Pro Gln Phe Ile Ser Arg Gly Asp Val His Val Tyr
        115                 120                 125

Gly Ala Thr Asn Ile Ile Gln Val Leu Leu Val Ala Ser Ile Glu Thr
    130                 135                 140

Ser Leu Val Phe Gln Ile Lys Val Ile Phe Thr Gly Asp Asn Phe Lys
145                 150                 155                 160

Arg Ile Gly Leu Met Leu Thr Ser Ile Ser Phe Thr Leu Gly Ile Ala
                165                 170                 175

Thr Val Thr Met Tyr Phe Val Ser Ala Val Lys Gly Met Ile Val Thr
            180                 185                 190

Tyr Asn Asp Val Ser Ala Thr Gln Asp Lys Tyr Phe Asn Ala Ser Thr
        195                 200                 205

Ile Leu Leu Ala Ser Ser Ile Asn Phe Met Ser Phe Val Leu Val Val
    210                 215                 220

Lys Leu Ile Leu Ala Ile Arg Ser Arg Arg Phe Leu Gly Leu Lys Gln
225                 230                 235                 240

Phe Asp Ser Phe His Ile Leu Leu Ile Met Ser Cys Gln Ser Leu Leu
                245                 250                 255

Val Pro Ser Ile Ile Phe Ile Leu Ala Tyr Ser Leu Lys Pro Asn Gln
            260                 265                 270

Gly Thr Asp Val Leu Thr Thr Val Ala Thr Leu Leu Ala Val Leu Ser
        275                 280                 285

Leu Pro Leu Ser Ser Met Trp Ala Thr Ala Ala Asn Asn Ala Ser Lys
    290                 295                 300

Thr Asn Thr Ile Thr Ser Asp Phe Thr Thr Ser Thr Asp Arg Phe Tyr
305                 310                 315                 320

```
Pro Gly Thr Leu Ser Ser Phe Gln Thr Asp Ser Ile Asn Asn Asp Ala
                325                 330                 335

Lys Ser Ser Leu Arg Ser Arg Leu Tyr Asp Leu Tyr Pro Arg Arg Lys
            340                 345                 350

Glu Thr Thr Ser Asp Lys His Ser Glu Arg Thr Phe Val Ser Glu Thr
            355                 360                 365

Ala Asp Asp Ile Glu Lys Asn Gln Phe Tyr Gln Leu Pro Thr Pro Thr
        370                 375                 380

Ser Ser Lys Asn Thr Arg Ile Gly Pro Phe Ala Asp Ala Ser Tyr Lys
385                 390                 395                 400

Glu Gly Glu Val Glu Pro Val Asp Met Tyr Thr Pro Asp Thr Ala Ala
                405                 410                 415

Asp Glu Glu Ala Arg Lys Phe Trp Thr Glu Asp Asn Asn Asn Leu
            420                 425                 430

<210> SEQ ID NO 30
<211> LENGTH: 1293
<212> TYPE: DNA
<213> ORGANISM: Saccharomyces cerevisiae

<400> SEQUENCE: 30
atgtctgatg cggctccttc attgagcaat ctattttatg atccaacgta taatcctggt      60
caaagcacca ttaactacac ttccatatat gggaatggat ctaccatcac tttcgatgag     120
ttgcaaggtt tagttaacag tactgttact caggccatta tgtttggtgt cagatgtggt     180
gcagctgctt tgactttgat tgtcatgtgg atgacatcga gaagcagaaa acgccgatt      240 ttcattatca accaagtttc attgttttta atcattttgc attctgcact ctattttaaa     300
tatttactgt ctaattactc ttcagtgact tacgctctca ccggatttcc tcagttcatc     360
agtagaggtg acgttcatgt ttatggtgct acaaatataa ttcaagtcct tcttgtggct     420
tctattgaga cttcactggt gtttcagata aaagttattt tcacaggcga caacttcaaa     480
aggataggtt tgatgctgac gtcgatatct ttcactttag ggattgctac agttaccatg     540
tattttgtaa gcgctgttaa aggtatgatt gtgacttata atgatgttag tgccacccaa     600
gataaatact tcaatgcatc cacaatttta cttgcatcct caataaactt tatgtcattt     660
gtcctggtag ttaaattgat tttagctatt agatcaagaa gattccttgg tctcaagcag     720
ttcgatagtt tccatatttt actcataatg tcatgtcaat cttttgttggt tccatcgata     780 atattcatcc tcgcatacag tttgaaacca aaccagggaa cagatgtctt gactactgtt     840
gcaacattac ttgctgtatt gtctttacca ttatcatcaa tgtgggccac ggctgctaat     900
aatgcatcca aaacaaacac aattacttca gactttacaa catccacaga taggttttat     960
ccaggcacgc tgtctagctt tcaaactgat agtatcaaca cgatgctaa aagcagtctc    1020 agaagtagat tatatgacct atatcctaga aggaaggaaa caacatcgga taaacattcg    1080
gaaagaactt ttgtttctga gactgcagat gatatagaga aaaatcagtt ttatcagttg    1140
cccacaccta cgagttcaaa aaatactagg ataggaccgt ttgctgatgc aagttacaaa    1200
gagggagaag ttgaacccgt cgacatgtac actcccgata cggcagctga tgaggaagcc    1260
agaaagttct ggactgaaga taataataat tta                                 1293

<210> SEQ ID NO 31
<211> LENGTH: 1293
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 31

```
atgtctgatg cggctccttc attgagcaat ctattttatg atccaacgta taatcctggt    60
caaagcacca ttaactacac ttccatatat gggaatggat ctaccatcac tttcgatgag   120
ttgcaaggtt tagttaacag tactgttact caggccatta tgtttggtgt cagatgtggt   180
gcagctgctt tgactttgat tgtcatgtgg atgacatcga gaagcagaaa acgccgatt    240
ttcattatca accaagtttc attgttttta atcattttgc attctgcact ctattttaaa   300
tatttactgt ctaattactc ttcagtgact tacgctctca ccggatttcc tcagttcatc   360
agtagaggtg acgttcatgt ttatggtgct acaaatataa ttcaagtcct tcttgtggct   420
tctattgaga cttcactggt gtttcagata aagttatttt tcacaggcga caacttcaaa   480
aggataggtt tgatgctgac gtcgatatct ttcactttag ggattgctac agttaccatg   540
tatttttgtaa gcgctgttaa aggtatgatt gtgacttata atgatgttag tgccacccaa   600
gataaatact tcaatgcatc cacaatttta cttgcatcct caataaactt tatgtcattt   660
gtcctggtag ttaaattgat tttagctatt agatcaagaa gattccttgg tctcaagcag   720
ttcgatagtt tccatatttt actcataatg tcatgtcaat ctttgttggt tccatcgata   780
atattcatcc tcgcatacag tttgaaacca aaccagggaa cagatgcctt gactactgtt   840
gcaacattac ttgctgtatt gtctttacca ttatcatcaa tgtgggccac ggctgctaat   900
aatgcatcca aaacaaacac aattacttca gactttacaa catccacaga taggttttat   960
ccaggcacgc tgtctagctt tcaaactgat agtatcaaca acgatgctaa aagcagtctc  1020
agaagtagat tatatgacct atatcctaga aggaaggaaa caacatcgga taaacattcg  1080
gaaagaactt ttgtttctga gactgcagat gatatagaga aaaatcagtt ttatcagttg  1140
cccacaccta cgagttcaaa aaatactagg ataggaccgt ttgctgatgc aagttacaaa  1200
gagggagaag ttgaacccgt cgacatgtac actcccgata cggcagctga tgaggaagcc  1260
agaaagttct ggactgaaga taataataat tta                              1293
```

<210> SEQ ID NO 32
<211> LENGTH: 1293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
atgtctgatg cggctccttc attgagcaat ctattttatg atccaacgta taatcctggt    60
caaagcacca ttaactacac ttccatatat gggaatggat ctaccatcac tttcgatgag   120
ttgcaaggtt tagttaacag tactgttact caggccatta tgtttggtgt cagatgtggt   180
gcagctgctt tgactttgat tgtcatgtgg atgacatcga gaagcagaaa acgccgatt    240
ttcattatca accaagtttc attgttttta atcattttgc attctgcact ctattttaaa   300
tatttactgt ctaattactc ttcagtgact tacgctctca ccggatttcc tcagttcatc   360
agtagaggtg acgttcatgt ttatggtgct acaaatataa ttcaagtcct tcttgtggct   420
tctattgaga cttcactggt gtttcagata aagttatttt tcacaggcga caacttcaaa   480
aggataggtt tgatgctgac gtcgatatct ttcactttag ggattgctac agttaccatg   540
```

```
tattttgtaa gcgctgttaa aggtatgatt gtgacttata atgatgttag tgccacccaa    600
gataaatact tcaatgcatc cacaattcta cttgcatcct caataaactt tatgtcattt    660
gtcctggtag ttaaattgat tttagctatt agatcaagaa gattccttgg tctcaagcag    720
ttcgatagtt tccatatttt actcataatg tcatgtcaat ctttgttggt tccatcgata    780
atattcatcc tcgcatacag tttgaaacca aaccagggaa cagatgcctt gactactgtt    840
gcaacattac ttgctgtatt gtctttacca ttatcatcaa tgtgggccac ggctgctaat    900
aatgcatcca aacaaacac aattacttca gactttacaa catccacaga taggttttat     960
ccaggcacgc tgtctagctt tcaaactgat agtatcaaca acgatgctaa aagcagtctc    1020
agaagtagat tatatgacct atatcctaga aggaaggaaa caacatcgga taaacattcg    1080
gaaagaactt ttgtttctga gactgcagat gatatagaga aaaatcagtt ttatcagttg    1140
cccacaccta cgagttcaaa aaatactagg ataggaccgt ttgctgatgc aagttacaaa    1200
gagggagaag ttgaacccgt cgacatgtac actcccgata cggcagctga tgaggaagcc    1260
agaaagttct ggactgaaga taataataat tta                                 1293
```

```
<210> SEQ ID NO 33
<211> LENGTH: 9
<212> TYPE: PRT
<213> ORGANISM: Penicillium rubens

<400> SEQUENCE: 33

Trp Cys Gly His Ile Gly Gln Gly Cys
1               5

<210> SEQ ID NO 34
<211> LENGTH: 12
<212> TYPE: PRT
<213> ORGANISM: Lodderomyces elongisporous

<400> SEQUENCE: 34

Trp Met Trp Thr Arg Tyr Gly Arg Phe Ser Pro Val
1               5                   10

<210> SEQ ID NO 35
<211> LENGTH: 12
<212> TYPE: PRT
<213> ORGANISM: Zygosaccharomyces bailii

<400> SEQUENCE: 35

His Leu Val Arg Leu Ser Pro Gly Ala Ala Met Phe
1               5                   10

<210> SEQ ID NO 36
<211> LENGTH: 12
<212> TYPE: PRT
<213> ORGANISM: Zygosaccharomyces rouxii

<400> SEQUENCE: 36

His Phe Ile Glu Leu Asp Pro Gly Gln Pro Met Phe
1               5                   10

<210> SEQ ID NO 37
<211> LENGTH: 12
<212> TYPE: PRT
<213> ORGANISM: Scheffersomyces stipitis

<400> SEQUENCE: 37

Trp His Trp Thr Ser Tyr Gly Val Phe Glu Pro Gly
```

```
<210> SEQ ID NO 38
<211> LENGTH: 13
<212> TYPE: PRT
<213> ORGANISM: Vibrio cholerae

<400> SEQUENCE: 38

Trp His Trp Leu Gln Leu Lys Pro Gly Gln Pro Met Tyr
1               5                   10

<210> SEQ ID NO 39
<211> LENGTH: 13
<212> TYPE: PRT
<213> ORGANISM: Kluyveromyces lactis

<400> SEQUENCE: 39

Trp Ser Trp Ile Thr Leu Arg Pro Gly Gln Pro Ile Phe
1               5                   10

<210> SEQ ID NO 40
<211> LENGTH: 13
<212> TYPE: PRT
<213> ORGANISM: Vanderwaltozyma polyspora

<400> SEQUENCE: 40

Trp His Trp Leu Glu Leu Asp Asn Gly Gln Pro Ile Tyr
1               5                   10

<210> SEQ ID NO 41
<211> LENGTH: 13
<212> TYPE: PRT
<213> ORGANISM: Vanderwaltozyma polyspora

<400> SEQUENCE: 41

Trp His Trp Leu Arg Leu Arg Tyr Gly Glu Pro Ile Tyr
1               5                   10

<210> SEQ ID NO 42
<211> LENGTH: 13
<212> TYPE: PRT
<213> ORGANISM: Candida parapsilosis

<400> SEQUENCE: 42

Lys Pro His Trp Thr Thr Tyr Gly Tyr Tyr Glu Pro Gln
1               5                   10

<210> SEQ ID NO 43
<211> LENGTH: 14
<212> TYPE: PRT
<213> ORGANISM: Saccharomyces castellii

<400> SEQUENCE: 43

Asn Trp His Trp Leu Arg Leu Asp Pro Gly Gln Pro Leu Tyr
1               5                   10

<210> SEQ ID NO 44
<211> LENGTH: 15
<212> TYPE: PRT
<213> ORGANISM: Candida tropicalis

<400> SEQUENCE: 44

Lys Phe Lys Phe Arg Leu Thr Arg Tyr Gly Trp Phe Ser Pro Asn
1               5                   10                  15
```

<210> SEQ ID NO 45
<211> LENGTH: 16
<212> TYPE: PRT
<213> ORGANISM: Candida guilliermondii

<400> SEQUENCE: 45

Lys Lys Asn Ser Arg Phe Leu Thr Tyr Trp Phe Phe Gln Pro Ile Met
1               5                   10                  15

<210> SEQ ID NO 46
<211> LENGTH: 17
<212> TYPE: PRT
<213> ORGANISM: Geotrichum candidum

<400> SEQUENCE: 46

Gly Asp Trp Gly Trp Phe Trp Tyr Val Pro Arg Pro Gly Asp Pro Ala
1               5                   10                  15

Met

<210> SEQ ID NO 47
<211> LENGTH: 23
<212> TYPE: PRT
<213> ORGANISM: Schizosaccharomyces pombe

<400> SEQUENCE: 47

Thr Tyr Ala Asp Phe Leu Arg Ala Tyr Gln Ser Trp Asn Thr Phe Val
1               5                   10                  15

Asn Pro Asp Arg Pro Asn Leu
            20

<210> SEQ ID NO 48
<211> LENGTH: 23
<212> TYPE: PRT
<213> ORGANISM: Schizosaccharomyces japonicus

<400> SEQUENCE: 48

Val Ser Asp Arg Val Lys Gln Met Leu Ser His Trp Trp Asn Phe Arg
1               5                   10                  15

Asn Pro Asp Thr Ala Asn Leu
            20

<210> SEQ ID NO 49
<211> LENGTH: 23
<212> TYPE: PRT
<213> ORGANISM: Schizosaccharomyces octosporus

<400> SEQUENCE: 49

Thr Tyr Glu Asp Phe Leu Arg Val Tyr Lys Asn Trp Trp Ser Phe Gln
1               5                   10                  15

Asn Pro Asp Arg Pro Asp Leu
            20

<210> SEQ ID NO 50
<211> LENGTH: 431
<212> TYPE: PRT
<213> ORGANISM: Saccharomyces cerevisiae

<400> SEQUENCE: 50

Met Ser Asp Ala Ala Pro Ser Leu Ser Asn Leu Phe Tyr Asp Pro Thr
1               5                   10                  15

Tyr Asn Pro Gly Gln Ser Thr Ile Asn Tyr Thr Ser Ile Tyr Gly Asn
            20                  25                  30

Gly Ser Thr Ile Thr Phe Asp Glu Leu Gln Gly Leu Val Asn Ser Thr
          35                  40                  45

Val Thr Gln Ala Ile Met Phe Gly Val Arg Cys Gly Ala Ala Ala Leu
 50                  55                  60

Thr Leu Ile Val Met Trp Met Thr Ser Arg Ser Arg Lys Thr Pro Ile
 65                  70                  75                  80

Phe Ile Ile Asn Gln Val Ser Leu Phe Leu Ile Leu His Ser Ala
                  85                  90                  95

Leu Tyr Phe Lys Tyr Leu Leu Ser Asn Tyr Ser Ser Val Thr Tyr Ala
                 100                 105                 110

Leu Thr Gly Phe Pro Gln Phe Ile Ser Arg Gly Asp Val His Val Tyr
                 115                 120                 125

Gly Ala Thr Asn Ile Ile Gln Val Leu Leu Val Ala Ser Ile Glu Thr
         130                 135                 140

Ser Leu Val Phe Gln Ile Lys Val Ile Phe Thr Gly Asp Asn Phe Lys
145                 150                 155                 160

Arg Ile Gly Leu Met Leu Thr Ser Ile Ser Phe Thr Leu Gly Ile Ala
                 165                 170                 175

Thr Val Thr Met Tyr Phe Val Ser Ala Val Lys Gly Met Ile Val Thr
                 180                 185                 190

Tyr Asn Asp Val Ser Ala Thr Gln Asp Lys Tyr Phe Asn Ala Ser Thr
         195                 200                 205

Ile Leu Leu Ala Ser Ser Ile Asn Phe Met Ser Phe Val Leu Val Val
210                 215                 220

Lys Leu Ile Leu Ala Ile Arg Ser Arg Arg Phe Leu Gly Leu Lys Gln
225                 230                 235                 240

Phe Asp Ser Phe His Ile Leu Leu Ile Met Ser Cys Gln Ser Leu Leu
                 245                 250                 255

Val Pro Ser Ile Ile Phe Ile Leu Ala Tyr Ser Leu Lys Pro Asn Gln
                 260                 265                 270

Gly Thr Asp Val Leu Thr Thr Val Ala Thr Leu Leu Ala Val Leu Ser
         275                 280                 285

Leu Pro Leu Ser Ser Met Trp Ala Thr Ala Ala Asn Asn Ala Ser Lys
290                 295                 300

Thr Asn Thr Ile Thr Ser Asp Phe Thr Thr Ser Thr Asp Arg Phe Tyr
305                 310                 315                 320

Pro Gly Thr Leu Ser Ser Phe Gln Thr Asp Ser Ile Asn Asn Asp Ala
                 325                 330                 335

Lys Ser Ser Leu Arg Ser Arg Leu Tyr Asp Leu Tyr Pro Arg Arg Lys
                 340                 345                 350

Glu Thr Thr Ser Asp Lys His Ser Glu Arg Thr Phe Val Ser Glu Thr
         355                 360                 365

Ala Asp Asp Ile Glu Lys Asn Gln Phe Tyr Gln Leu Pro Thr Pro Thr
370                 375                 380

Ser Ser Lys Asn Thr Arg Ile Gly Pro Phe Ala Asp Ala Ser Tyr Lys
385                 390                 395                 400

Glu Gly Glu Val Glu Pro Val Asp Met Tyr Thr Pro Asp Thr Ala Ala
                 405                 410                 415

Asp Glu Glu Ala Arg Lys Phe Trp Thr Glu Asp Asn Asn Asn Leu
                 420                 425                 430

<210> SEQ ID NO 51
<211> LENGTH: 1296

<212> TYPE: DNA
<213> ORGANISM: Saccharomyces cerevisiae

<400> SEQUENCE: 51

```
atgtctgatg cggctccttc attgagcaat ctattttatg atccaacgta taatcctggt      60
caaagcacca ttaactacac ttccatatat gggaatggat ctaccatcac tttcgatgag     120
ttgcaaggtt tagttaacag tactgttact caggccatta tgtttggtgt cagatgtggt     180
gcagctgctt tgactttgat tgtcatgtgg atgacatcga aagcagaaaa acgccgatt      240
ttcattatca accaagtttc attgttttta atcattttgc attctgcact ctattttaaa     300
tatttactgt ctaattactc ttcagtgact tacgctctca ccggatttcc tcagttcatc     360
agtagaggtg acgttcatgt ttatggtgct acaaatataa ttcaagtcct tcttgtggct     420
tctattgaga cttcactggt gtttcagata aaagttattt tcacaggcga caacttcaaa     480
aggataggtt tgatgctgac gtcgatatct ttcactttag ggattgctac agttaccatg     540
tatttcgtaa gcgctgttaa aggtatgatt gtgacttata atgatgttag tgccacccaa     600
gataaatact tcaatgcatc cacaatttta cttgcatcct caataaactt tatgtcattt     660
gtcctggtag ttaaattgat tttagctatt agatcaagaa gattccttgg tctcaagcag     720
ttcgatagtt tccatatttt actcataatg tcatgtcaat ctttgttggt tccatcgata     780
atattcatcc tcgcatacag tttgaaacca aaccagggaa cagatgtctt gactactgtt     840
gcaacattac ttgctgtatt gtctttacca ttatcatcaa tgtgggccac ggctgctaat     900
aatgcatcca aaacaaacac aattacttca gactttacaa catccacaga taggttttat     960
ccaggcacgc tgtctagctt tcaaactgat agtatcaaca acgatgctaa aagcagtctc    1020
agaagtagat tatatgacct atatcctaga aggaaggaaa caacatcgga taaacattcg    1080
gaaagaactt ttgtttctga gactgcagat gatatagaga aaaatcagtt ttatcagttg    1140
cccacaccta cgagttcaaa aaatactagg ataggaccgt ttgctgatgc aagttacaaa    1200
gagggagaag ttgaacccgt cgacatgtac actcccgata cggcagctga tgaggaagcc    1260
agaaagttct ggactgaaga taataataat ttatag                              1296
```

<210> SEQ ID NO 52
<211> LENGTH: 435
<212> TYPE: PRT
<213> ORGANISM: Lodderomyces elongisporous

<400> SEQUENCE: 52

```
Met Asp Glu Ala Ile Asn Ala Asn Leu Val Ser Gly Asp Ile Ile Val
1               5                   10                  15

Ser Phe Asn Ile Pro Gly Leu Pro Glu Pro Val Gln Val Pro Phe Ser
                20                  25                  30

Glu Phe Asp Ser Phe His Lys Asp Gln Leu Ile Gly Val Ile Ile Leu
            35                  40                  45

Gly Val Thr Ile Gly Ala Cys Ser Leu Leu Ile Leu Leu Leu Gly
        50                  55                  60

Met Leu Tyr Lys Ser Arg Glu Lys Tyr Trp Lys Ser Leu Leu Phe Met
65                  70                  75                  80

Leu Asn Val Cys Ile Leu Ala Ala Thr Ile Leu Arg Ser Gly Cys Phe
                85                  90                  95

Leu Asp Tyr Tyr Leu Ser Asp Leu Ala Ser Ile Ser Tyr Thr Phe Thr
            100                 105                 110

Gly Val Tyr Asn Gly Thr Ser Phe Ala Ser Ser Asp Ala Ala Asn Val
```

```
                115                 120                 125
Phe Lys Thr Ile Met Phe Ala Leu Ile Glu Thr Ser Leu Thr Phe Gln
130                 135                 140

Val Tyr Val Met Phe Gln Gly Thr Thr Trp Lys Asn Trp Gly His Ala
145                 150                 155                 160

Val Thr Ala Leu Ser Gly Leu Leu Ser Val Ala Ser Val Ala Phe Gln
                165                 170                 175

Ile Tyr Thr Thr Ile Leu Ser His Asn Asn Phe Asn Ala Thr Ile Ser
                180                 185                 190

Gly Thr Gly Thr Leu Thr Ser Gly Val Trp Met Asp Leu Pro Thr Leu
                195                 200                 205

Leu Phe Ala Ala Ser Ile Asn Phe Met Thr Ile Leu Leu Leu Phe Lys
210                 215                 220

Leu Gly Met Ala Ile Arg Gln Arg Arg Tyr Leu Gly Leu Lys Gln Phe
225                 230                 235                 240

Asp Gly Phe His Ile Leu Phe Ile Met Phe Thr Gln Thr Leu Phe Ile
                245                 250                 255

Pro Ser Ile Leu Leu Val Ile His Tyr Phe Tyr Gln Ala Met Ser Gly
                260                 265                 270

Pro Phe Ile Ile Asn Met Ala Leu Phe Leu Val Val Ala Phe Leu Pro
                275                 280                 285

Leu Ser Ser Leu Trp Ala Gln Thr Ala Asn Thr Thr Lys Lys Ile Glu
290                 295                 300

Ser Ser Pro Ser Met Ser Phe Ile Thr Arg Arg Lys Ser Glu Asp Glu
305                 310                 315                 320

Ser Pro Leu Ala Ala Asn Asp Glu Asp Arg Leu Arg Lys Phe Thr Thr
                325                 330                 335

Thr Leu Asp Leu Ser Gly Asn Lys Asn Thr Thr Asn Asn Asn Asn Asn
                340                 345                 350

Asn Ser Asn Asn Ile Asn Asn Asn Met Ser Asn Ile Asn Tyr Pro Ser
                355                 360                 365

Thr Gly Leu Gly Glu Asp Asp Lys Ser Phe Ile Phe Glu Met Glu Pro
370                 375                 380

Ser Arg Glu Arg Ala Ala Ile Glu Glu Ile Asp Leu Gly Ala Arg Ile
385                 390                 395                 400

Asp Thr Gly Leu Pro Arg Asp Leu Glu Lys Phe Leu Val Asp Gly Phe
                405                 410                 415

Asp Asp Ser Asp Asp Gly Glu Gly Met Ile Ala Arg Glu Val Thr Met
                420                 425                 430

Leu Lys Lys
        435

<210> SEQ ID NO 53
<211> LENGTH: 1308
<212> TYPE: DNA
<213> ORGANISM: Lodderomyces elongisporous

<400> SEQUENCE: 53
atggacgaag caatcaatgc aaaccttgtt tctggagata ttatagtctc ttttaacatt      60
cctggtttgc cagaaccggt acaagtgcca ttcagcgaat tgattcgtt tcataaagac     120 cagctcattg gagtcatcat tcttggagtc actattggag catgctcgct tttgttgata    180
ttgctacttg gaatgttata caagagccgt gaaaagtatt ggaaatcact attatttatg    240
ctcaatgtat gcatcttggc tgccacaatc ttaaggagcg gttgcttctt agactattat    300
```

```
ctaagtgatt tggccagtat cagttataca tttactggag tatacaatgg taccagcttt    360
gctagctctg acgcggcaaa tgtgttcaag actattatgt ttgccttgat tgaaacttcg    420
ttaacctttc aagtgtatgt catgtttcaa gggaccactt ggaaaaattg gggccatgct    480
gtcactgcat tatcgggtct cttgtctgtt gcctcagtgg cgttccagat ctacaccacg    540
attttatccc acaataattt caatgctaca atctcgggaa ccggtacatt aacttcaggt    600
gtttggatgg acttaccaac actcttgttt gccgcaagta tcaattttat gaccattttg    660
ttgttattta agttgggaat ggccattaga caaagaaggt atttaggttt aaaacagttt    720
gatgggttcc atatcttatt catcatgttt acccaaacat tgttcatacc ctcgattttg    780
cttgtgatcc actacttta ccaggcaatg tctggaccat tcatcatcaa catggcgttg    840
ttcttggtgg tggcattctt gccattgagt tcattatggg cacaaactgc aaacactact    900
aaaaagattg aatcttcgcc aagtatgagc tttattacta gacgaaaatc agaggatgag    960
tcaccactgg ctgctaacga cgaggatagg ttacgaaaat tcaccacaac tttggatttg   1020
tcgggcaaca agaacaatac aacaaacaat aataacaata gcaacaacat taacaacaat   1080
atgagcaaca tcaactaccc ttctacagga ctgggagaag acgataaatc ctttatattt   1140
gagatggaac ccagtcggga aagagctgca atagaagaga ttgatcttgg agcaaggatc   1200
gataccggtt tgcccagaga tttagagaaa tttctagttg atgggtttga cgatagtgat   1260
gacggagaag gaatgatagc cagagaagtg actatgttga aaaaatag             1308

<210> SEQ ID NO 54
<211> LENGTH: 380
<212> TYPE: PRT
<213> ORGANISM: Penicillium rubens

<400> SEQUENCE: 54

Met Ala Thr Ser Ser Pro Ile Gln Pro Phe Asp Pro Phe Thr Gln Asn
1               5                   10                  15

Val Thr Phe Arg Leu Gln Asp Gly Thr Glu Phe Pro Val Ser Val Lys
                20                  25                  30

Ala Leu Asp Val Phe Val Met Tyr Asn Val Arg Val Cys Ile Asn Tyr
            35                  40                  45

Gly Cys Gln Phe Gly Ala Ser Phe Val Leu Leu Val Ile Leu Val Leu
        50                  55                  60

Leu Thr Gln Ser Asp Lys Arg Arg Ser Ala Val Phe Ile Leu Asn Gly
65                  70                  75                  80

Leu Ala Leu Phe Leu Asn Ser Ser Arg Leu Leu Phe Gln Val Ile His
                85                  90                  95

Phe Ser Thr Ala Phe Glu Gln Val Tyr Pro Tyr Val Ser Gly Asp Tyr
            100                 105                 110

Ser Ser Val Pro Trp Ser Ala Tyr Ala Ile Ser Ile Val Ala Val Val
        115                 120                 125

Leu Thr Thr Leu Val Val Cys Ile Glu Ala Ser Leu Val Ile Gln
    130                 135                 140

Val His Val Val Cys Ser Thr Leu Arg Arg Arg Tyr Arg His Pro Leu
145                 150                 155                 160

Leu Ala Ile Ser Ile Leu Val Ala Leu Val Pro Ile Gly Phe Arg Cys
                165                 170                 175

Ala Trp Met Val Ala Asn Cys Lys Ala Ile Ile Lys Leu Thr Tyr Thr
            180                 185                 190
```

```
Asn Asp Val Trp Trp Ile Glu Ser Ala Thr Asn Ile Cys Val Thr Ile
        195                 200                 205

Ser Ile Cys Phe Phe Cys Val Ile Phe Val Thr Lys Leu Gly Phe Ala
    210                 215                 220

Ile Lys Gln Arg Arg Arg Leu Gly Val Arg Glu Phe Gly Pro Met Lys
225                 230                 235                 240

Val Ile Phe Val Met Gly Cys Gln Thr Met Val Pro Ala Ile Phe
                245                 250                 255

Ser Ile Thr Gln Tyr Tyr Val Val Pro Glu Phe Ser Ser Asn Val
            260                 265                 270

Val Thr Leu Val Val Ile Ser Leu Pro Leu Ser Ser Ile Trp Ala Gly
        275                 280                 285

Ala Val Leu Glu Asn Ala Arg Arg Thr Gly Ser Gln Asp Arg Gln Arg
        290                 295                 300

Arg Arg Asn Leu Trp Arg Ala Leu Val Gly Gly Ala Glu Ser Leu Leu
305                 310                 315                 320

Ser Pro Thr Lys Asp Ser Pro Thr Ser Leu Ser Ala Met Thr Ala Ala
                325                 330                 335

Gln Thr Leu Cys Tyr Ser Asp His Thr Met Ser Lys Gly Ser Pro Thr
            340                 345                 350

Ser Arg Asp Thr Asp Ala Phe Tyr Gly Ile Ser Val Glu His Asp Ile
        355                 360                 365

Ser Ile Asn Arg Val Gln Arg Asn Asn Ser Ile Val
        370                 375                 380

<210> SEQ ID NO 55
<211> LENGTH: 1143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atggctacct cttccccaat ccaaccattt gacccattca cccaaaacgt taccttccgt      60
ttgcaagacg gtaccgaatt cccagttcct gtcaaggctt tggacgtctt cgtcatgtac    120
aacgttagag tctgtattaa ctacggttgt caattcggtg cctccttcgt cttgttagtc    180
attttagtct tgttaactca atccgacaag agaagatctg ctgtcttcat tttgaacggt    240
ttggctttgt tcttgaactc ttctagattg ttgtttcaag ttattcactt ctccactgcc    300
ttcgaacaag tctacccata cgtctctggt gactactcct ctgtcccatg gtccgcttac    360
gctatctcca ttgtcgctgt tgttttgact accttggtcg ttgtttgtat cgaagcttct    420
ttggttattc aagttcacgt tgtctgttcc accttgagac gtagatacag acacccatta    480
ttagctattt ctattttggt cgctttggtt ccaatcggtt tcagatgtgc ttggatggtc    540
gctaactgta aggctattat taaattgacc tacaccaacg acgtttggtg gatcgaatct    600
gctactaaca tctgtgtcac tatctccatc tgtttcttct gtgttatctt cgttaccaag    660
ttgggtttcg ccatcaagca agaagaagaa ttgggtgtta gagaattcgg tccaatgaag    720
gttattttcg tcatgggttg tcaaactatg gttgttccag ctattttctc catcacccaa    780
tactacgtcg tcgtcccaga attctcctct aacgtcgtta ctttggttgt catttcttta    840
ccattatctt ccatttgggc cggtgctgtc ttggaaaacg ctagaagaac cggttcccaa    900
gatagacaaa gaagacgtaa cttgtggaga gctttggttg gtggtgctga atccttgtta    960
```

```
tccccaacta aggactctcc aacctctttg tctgctatga ctgctgctca aaccttatgt    1020
tactctgatc acaccatgtc caagggttct ccaacttcca gagacaccga tgctttctac    1080
ggtatctccg ttgaacacga catctccatt aacagagttc aacgtaacaa ctccatcgtc    1140
tag                                                                  1143
```

<210> SEQ ID NO 56
<211> LENGTH: 395
<212> TYPE: PRT
<213> ORGANISM: Candida guilliermondii

<400> SEQUENCE: 56

```
Met Lys Ser Cys Ser Ile Gly Phe Gly Ile Pro Phe Ile Asn Glu Pro
1               5                   10                  15

Asn Phe Glu Thr Val Ser Ile Leu Thr Met Asp Val Ser Phe Ile Asp
            20                  25                  30

Ala Asp Val Asn Pro Asp Asn Ile Leu Leu Asn Phe Thr Ile Pro Gly
        35                  40                  45

Tyr Gln Asn Gly Phe Ser Val Pro Met Val Val Ile Asn Glu Leu Gln
    50                  55                  60

Lys Ser Gln Met Lys Tyr Ala Ile Val Tyr Gly Cys Gly Val Gly Ala
65                  70                  75                  80

Ser Leu Ile Leu Leu Phe Val Val Trp Ile Leu Cys Ser Arg Lys Thr
                85                  90                  95

Pro Leu Phe Ile Met Asn Asn Ile Pro Leu Val Leu Tyr Val Ile Ser
            100                 105                 110

Ser Ser Leu Asn Leu Ala Tyr Ile Thr Gly Pro Leu Ser Ser Val Ser
        115                 120                 125

Val Phe Leu Thr Gly Ile Leu Thr Ser His Asp Ala Ile Asn Val Val
    130                 135                 140

Tyr Ala Ser Asn Ala Leu Gln Met Leu Leu Ile Phe Ser Ile Gln Ser
145                 150                 155                 160

Thr Met Ala Tyr His Val Tyr Val Met Phe Lys Ser Pro Gln Ile Lys
                165                 170                 175

Tyr Leu Arg Tyr Met Leu Val Gly Phe Leu Gly Cys Leu Gln Ile Val
            180                 185                 190

Thr Thr Cys Leu Tyr Ile Asn Tyr Asn Val Leu Tyr Ser Arg Arg Met
        195                 200                 205

His Lys Leu Tyr Glu Thr Gly Gln Thr Tyr Gln Asp Gly Thr Val Met
    210                 215                 220

Thr Phe Val Pro Phe Ile Leu Phe Gln Cys Ser Val Asn Phe Ser Ser
225                 230                 235                 240

Ile Phe Leu Val Leu Lys Leu Ile Met Ala Ile Arg Thr Arg Arg Tyr
                245                 250                 255

Leu Gly Leu Arg Gln Phe Gly Gly Phe His Ile Leu Met Ile Val Ser
            260                 265                 270

Leu Gln Thr Met Leu Val Pro Ser Ile Leu Val Leu Val Asn Tyr Ala
        275                 280                 285

Ala His Lys Ala Val Pro Ser Asn Leu Leu Ser Ser Val Ser Met Met
    290                 295                 300

Ile Ile Val Leu Ser Leu Pro Ala Ser Ser Met Trp Ala Ala Ala
305                 310                 315                 320

Asn Ala Ser Ser Ala Pro Ser Ser Ala Ala Ser Leu Phe Arg Tyr
                325                 330                 335
```

```
Thr Thr Ser Asp Ser Asp Arg Thr Leu Glu Thr Lys Ser Asp His Phe
            340                 345                 350

Ile Met Lys His Glu Ser His Asn Ser Ser Pro Asn Ser Ser Pro Leu
        355                 360                 365

Thr Leu Val Gln Lys Arg Ile Ser Asp Ala Thr Leu Glu Leu Pro Lys
    370                 375                 380

Glu Leu Glu Asp Leu Ile Asp Ser Thr Ser Ile
385                 390                 395

<210> SEQ ID NO 57
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
atgaagtcct gctccatcgg tttcggtatc ccattcatta atgaaccaaa cttcgaaact      60
gtttctattt tgaccatgga cgtttctttc attgacgctg acgtcaatcc tgacaatatc     120
ttgttgaact tcaccattcc tggttaccaa acggtttct  ctgttccaat ggttgttatt     180
aacgaattgc aaaagtctca atgaaatac  gctattgttt acggttgtgg tgtcggtgcc     240
tccttgattt tgttgtttgt cgtctggatt ttgtgttcta gaaagactcc attgtttatc     300
atgaacaaca ttccattagt tttgtacgtc atctcctctt ctttgaactt ggcttacatt     360
accggtccat tgtcttctgt ttccgtcttc ttgaccggta tcttgacttc tcacgatgcc     420
attaacgtcg tttacgcttc caacgctttg caaatgttgt tgatcttttc tatccaatct     480
accatggcct accacgttta cgttatgttc aaatctccac aaattaaata cttgagatac     540
atgttagtcg gtttcttggg ttgttacaa attgtcacca cctgtttata catcaactac     600
aatgttttgt actctcgtag aatgcacaaa ttgtacgaaa ctggtcaaac ctaccaagat     660
ggtaccgtta tgactttcgt tccattcatc ttgttccaat gttctgtcaa cttctcttct     720
attttcttgg ttttgaagtt gattatggcc attagaacca gacgttactt gggttttgcgt    780 caattcggtg gttttcatat tttgatgatc gtttctttac aaactatgtt ggtcccatct     840
attttggttt tggttaacta cgccgctcat aaggctgttc cttccaactt gttatcttcc     900
gtttctatga tgatcattgt tttgtcttta ccagcttctt ctatgtgggc cgctgctgct     960
aacgcctctt ctgcccctc ctccgctgct tcctccttgt tcagatacac cacttctgat    1020
tccgatagaa ctttggaaac taaatctgac cacttcatca tgaagcatga gtcccacaac    1080
tcttctccaa attcctcccc attgactttg gttcaaaaga gaatttctga tgccaccta     1140 gaattaccaa aagagttaga agacttgatc gactccacct ccatctag                1188

<210> SEQ ID NO 58
<211> LENGTH: 412
<212> TYPE: PRT
<213> ORGANISM: Candida tropicalis

<400> SEQUENCE: 58

Met Asp Ile Asn Asn Thr Ile Gln Ser Ser Gly Asp Ile Ile Ile Thr
1               5                   10                  15

Tyr Thr Ile Pro Gly Ile Glu Glu Pro Phe Glu Leu Pro Phe Glu Val
            20                  25                  30

Leu Asn His Phe Gln Ser Glu Gln Ser Lys Asn Cys Leu Val Met Gly
        35                  40                  45
```

```
Val Met Ile Gly Ser Cys Ser Val Leu Leu Ile Phe Leu Val Gly Ile
 50              55                  60
Leu Phe Lys Thr Asn Lys Phe Ser Thr Ile Gly Lys Ser Lys Asn Leu
 65              70                  75                  80
Ser Lys Asn Phe Leu Phe Tyr Leu Asn Cys Leu Ile Thr Phe Ile Gly
                 85                  90                  95
Ile Ile Arg Ala Ala Cys Phe Ser Asn Tyr Leu Leu Gly Pro Leu Asn
                100                 105                 110
Ser Ala Ser Phe Ala Phe Thr Gly Trp Tyr Asn Gly Glu Ser Tyr Ala
                115                 120                 125
Ser Ser Glu Ala Ala Asn Gly Phe Arg Val Ile Leu Phe Ala Leu Ile
                130                 135                 140
Glu Thr Ser Met Val Phe Gln Val Phe Val Met Phe Arg Gly Ala Gly
145                 150                 155                 160
Met Lys Lys Leu Ala Tyr Ser Val Thr Ile Leu Cys Thr Ala Leu Ala
                165                 170                 175
Leu Val Val Val Gly Phe Gln Ile Asn Ser Ala Val Leu Ser His Arg
                180                 185                 190
Arg Phe Val Asn Thr Val Asn Glu Ile Gly Asp Thr Gly Leu Ser Ser
                195                 200                 205
Ile Trp Leu Asp Leu Pro Thr Ile Leu Phe Ser Val Ser Val Asn Leu
210                 215                 220
Met Ser Val Leu Leu Ile Gly Lys Leu Ile Met Ala Ile Lys Thr Arg
225                 230                 235                 240
Arg Tyr Leu Gly Leu Lys Gln Phe Asp Ser Phe His Val Leu Leu Ile
                245                 250                 255
Cys Ser Thr Gln Thr Leu Leu Val Pro Ser Leu Ile Leu Phe Val His
                260                 265                 270
Tyr Phe Leu Phe Phe Arg Asn Ala Asn Val Met Leu Ile Asn Ile Ser
                275                 280                 285
Ile Leu Leu Ile Val Leu Met Leu Pro Phe Ser Ser Leu Trp Ala Gln
                290                 295                 300
Thr Ala Asn Thr Thr Gln Tyr Ile Asn Ser Ser Pro Ser Phe Ser Phe
305                 310                 315                 320
Ile Ser Arg Glu Pro Ser Ala Asn Ser Thr Leu His Ser Ser Ser Gly
                325                 330                 335
His Tyr Ser Glu Lys Ser Tyr Gly Ile Asn Lys Leu Asn Thr Gln Gly
                340                 345                 350
Ser Ser Pro Ala Thr Leu Lys Asp Asp His Asn Ser Val Ile Leu Glu
                355                 360                 365
Ala Thr Asn Pro Met Ser Gly Phe Asp Ala Gln Leu Pro Pro Asp Ile
                370                 375                 380
Ala Arg Phe Leu Gln Asp Asp Ile Arg Ile Glu Pro Ser Ser Thr Gln
385                 390                 395                 400
Asp Phe Val Ser Thr Glu Val Thr Tyr Lys Lys Val
                405                 410
```

<210> SEQ ID NO 59
<211> LENGTH: 1239
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

```
atggacatca acaacaccat ccaatcttcc ggtgacatca tcattaccta caccatccca      60
ggtatcgaag aaccattcga attgccattc gaagttttga accacttcca atctgaacaa     120
tccaagaact gtttggtcat gggtgttatg atcggttctt gttccgtttt gttgatcttc     180
ttggtcggta ttttgttcaa aaccaacaaa ttctctacta ttggtaagtc taagaacttg     240
tctaagaact tcttgttcta cttgaactgt tgatcacct tcatcggtat cattcgtgct      300
gcctgttttt ctaactactt gttgggtcca ttgaactctg cttctttcgc tttcactggt    360
tggtacaacg tgaatctta cgcttcttcc gaagctgcta acggtttcag agtcatcttg     420
ttcgctttga ttgaaacttc tatggtcttc caagttttcg ttatgttcag aggtgctggt    480
atgaaaaagt tggcttactc cgttaccatt tgtgtaccg ctttggcttt ggtcgttgtt     540
ggtttccaaa ttaactccgc tgtcttatct cacagaagat cgtcaacac cgttaacgaa     600
attggtgata ctggtttgtc ctccatttgg ttggacttgc caaccatctt gttctccgtc    660
tctgtcaact aatgtctgt tttgttgatc ggtaaattga tcatggctat taagactaga    720
agatacttgg gtttgaaaca attcgattcc ttccacgttt tgttaatttg ttccactcaa    780
actttgttgg tcccatcttt aatcttgttc gttcactact tcttgttctt tagaaacgcc    840
aacgttatgt tgattaacat ttccatcttg ttgatcgtct tgatgttgcc attctcttcc    900
ttgtgggctc aaaccgccaa caccacccaa tacatcaact cttccccatc cttctctttc    960
atctctagag aaccatctgc taactctact ttgcactcct cttccggtca ctactctgaa   1020
aagtcctacg gtattaacaa attgaacacc caaggttctt ccccagccac cttaaaggat   1080
gatcacaact ccgtcatctt ggaagctacc aacccaatgt ctggtttcga cgcccaattg   1140
ccaccagaca ttgctagatt cttgcaagat gacatcagaa ttgaaccatc ttctacccaa   1200
gatttcgttt ccactgaagt cacctacaag aaggtctag                          1239
```

<210> SEQ ID NO 60
<211> LENGTH: 403
<212> TYPE: PRT
<213> ORGANISM: Candida parapsilosis

<400> SEQUENCE: 60

```
Met Asn Lys Ile Val Ser Lys Leu Ser Ser Asp Val Ile Val Thr
1               5                  10                  15

Val Thr Ile Pro Asn Glu Glu Asp Gly Thr Tyr Glu Val Pro Phe Tyr
            20                  25                  30

Ala Ile Asp Asn Tyr His Tyr Ser Arg Met Glu Asn Ala Val Val Leu
            35                  40                  45

Gly Ala Thr Ile Gly Ala Cys Ser Met Leu Leu Ile Met Leu Ile Gly
        50                  55                  60

Ile Leu Phe Lys Asn Phe Gln Arg Leu Arg Lys Ser Leu Leu Phe Asn
65                  70                  75                  80

Ile Asn Phe Ala Ile Leu Leu Met Leu Ile Leu Arg Ser Ala Cys Tyr
                85                  90                  95

Ile Asn Tyr Leu Met Asn Asn Leu Ser Ser Ile Ser Phe Phe Phe Thr
            100                 105                 110

Gly Ile Phe Asp Asp Glu Ser Phe Met Ser Ser Asp Ala Ala Asn Ala
        115                 120                 125

Phe Lys Val Ile Leu Val Ala Leu Ile Glu Val Ser Leu Thr Tyr Gln
    130                 135                 140
```

Ile Tyr Val Met Phe Lys Thr Pro Met Leu Lys Ser Trp Gly Ile Phe
145                 150                 155                 160

Ala Ser Val Leu Ala Gly Val Leu Gly Leu Ala Thr Leu Ala Thr Gln
            165                 170                 175

Ile Tyr Thr Thr Val Met Ser His Val Asn Phe Val Asn Gly Thr Thr
            180                 185                 190

Gly Ser Pro Ser Gln Val Thr Ser Ala Trp Met Asp Met Pro Thr Ile
            195                 200                 205

Leu Phe Ser Val Ser Ile Asn Val Leu Ser Met Phe Leu Val Cys Lys
210                 215                 220

Leu Gly Leu Ala Ile Arg Thr Arg Arg Tyr Leu Gly Leu Lys Gln Phe
225                 230                 235                 240

Asp Ala Phe His Ile Leu Phe Ile Met Ser Thr Gln Thr Met Ile Ile
            245                 250                 255

Pro Ser Ile Ile Leu Phe Val His Tyr Phe Asp Gln Asn Asp Ser Gln
            260                 265                 270

Thr Thr Leu Val Asn Ile Ser Leu Leu Leu Val Val Ile Ser Leu Pro
            275                 280                 285

Leu Ser Ser Leu Trp Ala Gln Thr Ala Asn Asn Val Arg Arg Ile Asp
290                 295                 300

Thr Ser Pro Ser Met Ser Phe Ile Ser Arg Glu Ala Ser Asn Arg Ser
305                 310                 315                 320

Gly Asn Glu Thr Leu His Ser Gly Ala Thr Ile Ser Lys Tyr Asn Thr
            325                 330                 335

Ser Asn Thr Val Asn Thr Thr Pro Gly Thr Ser Lys Asp Asp Ser Leu
            340                 345                 350

Phe Ile Leu Asp Arg Ser Ile Pro Glu Gln Arg Ile Val Asp Thr Gly
            355                 360                 365

Leu Pro Lys Asp Leu Glu Lys Phe Ile Asn Asn Asp Phe Tyr Glu Asp
            370                 375                 380

Asp Gly Gly Met Ile Ala Arg Glu Val Thr Met Leu Lys Thr Ala His
385                 390                 395                 400

Asn Asn Gln

<210> SEQ ID NO 61
<211> LENGTH: 1212
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atgaacaaga ttgtctccaa gttgtcttct tctgacgtca tcgttaccgt caccatccca      60
aacgaagaag atggtactta cgaagtccca ttctacgcta ttgacaacta ccactactcc     120
cgtatggaaa acgctgttgt tttaggtgct accattggtg cttgttctat gttgttgatc     180
atgttgattg gtattttgtt caagaacttc caaagattga gaagtctttt gttgttcaac     240
atcaacttcg ctatcttatt gatgttgatt ttgagatccg cttgttacat caactacttg     300
atgaacaact gtcttccatt tctttcttc ttcaccggta ttttcgatga tgaatctttc     360
atgtcttccg acgctgccaa cgccttcaag gttatcttgg ttgccttgat tgaagtttcc     420
ttgacctacc aaatttacgt tatgttcaag accccaatgt tgaagtcctg gggtattttc     480
gcctctgtct tggccggtgt ttttggtttg gctacttttgg ctacccaaat ctacactacc     540

-continued

```
gttatgtctc acgttaactt cgtcaacggt accaccggtt ctccatctca agttacttcc     600
gcttggatgg acatgccaac tatcttattc tccgtttcta ttaacgtttt gtctatgttc     660
ttggtttgta agttgggttt ggccatcaga accagacgtt acttgggttt aaagcaattc     720
gacgctttcc acattttatt cattatgtcc actcaaacca tgatcattcc atccatcatc     780
ttgttcgttc actacttcga tcaaaacgac tctcaaacca ccttggtcaa catctctttg     840
ttattggtcg tcatttcctt gccattgtct tctttgtggg ctcaaactgc taacaacgtt     900
agaagaattg acacttctcc atccatgtcc ttcatctcta gagaagcttc caacagatct     960
ggtaacgaaa ccttgcactc tggtgctact atctctaagt acaacacctc caacaccgtt    1020
aacactaccc caggtacttc taaggatgac tctttgttca tcttggacag atccattcca    1080
gaacaaagaa ttgtcgacac tggttttgcca aaggacttgg aaaagttcat taacaacgat    1140
ttttacgaag acgatggtgg tatgattgcc agagaagtca ccatgttgaa gaccgctcac    1200
aacaaccaat ag                                                         1212
```

<210> SEQ ID NO 62
<211> LENGTH: 435
<212> TYPE: PRT
<213> ORGANISM: Geotrichum candidum

<400> SEQUENCE: 62

```
Met Ala Glu Asp Ser Ile Phe Pro Asn Asn Ser Thr Ser Pro Leu Thr
1               5                   10                  15

Asn Pro Ile Val Val Glu Thr Ile Lys Gly Thr Ala Tyr Ile Pro Leu
            20                  25                  30

His Tyr Leu Asp Asp Leu Gln Tyr Glu Lys Met Leu Leu Ala Ser Leu
        35                  40                  45

Phe Ser Val Arg Ile Ala Thr Ser Phe Val Val Ile Trp Tyr Phe
    50                  55                  60

Val Ala Val Asn Lys Ala Lys Arg Ser Lys Phe Leu Tyr Ile Val Asn
65                  70                  75                  80

Gln Val Ser Leu Leu Ile Val Phe Ile Gln Ser Ile Leu Ser Leu Ile
                85                  90                  95

Tyr Val Phe Ser Asn Phe Ser Lys Met Ser Thr Ile Leu Thr Gly Asp
            100                 105                 110

Tyr Thr Gly Ile Thr Lys Arg Asp Ile Asn Val Ser Cys Val Ala Ser
        115                 120                 125

Val Phe Gln Phe Leu Phe Ile Ala Cys Ile Glu Leu Ala Leu Phe Ile
    130                 135                 140

Gln Ala Thr Val Val Phe Gln Lys Ser Val Arg Trp Leu Lys Phe Ser
145                 150                 155                 160

Val Ser Leu Ile Gln Gly Ser Val Ala Leu Thr Thr Ala Leu Tyr
                165                 170                 175

Met Ala Ile Ile Val Gln Ser Ile Tyr Ala Thr Leu Asn Pro Tyr Ala
            180                 185                 190

Gly Asn Leu Ile Lys Gly Arg Phe Gly Tyr Leu Leu Ala Ser Leu Gly
        195                 200                 205

Lys Ile Phe Phe Ser Ile Ser Val Thr Ser Cys Met Cys Ile Phe Val
    210                 215                 220

Gly Lys Leu Val Phe Ala Ile His Gln Arg Arg Thr Leu Gly Ile Lys
225                 230                 235                 240

Gln Phe Asp Gly Leu Gln Ile Leu Val Ile Met Ser Thr Gln Ser Met
                245                 250                 255
```

```
Ile Ile Pro Thr Ile Ile Val Leu Met Ser Phe Leu Arg Arg Asn Ala
            260                 265                 270
Gly Ser Val Tyr Thr Met Ala Thr Leu Leu Val Ala Leu Ser Leu Pro
        275                 280                 285
Leu Ser Ser Leu Trp Ala Glu Ala Lys Thr Thr Arg Asp Ser Ala Ser
290                 295                 300
Tyr Thr Ala Tyr Arg Pro Ser Gly Ser Pro Asn Asn Arg Ser Leu Phe
305                 310                 315                 320
Ala Ile Phe Ser Asp Arg Leu Ala Cys Gly Ser Gly Arg Asn Asn Arg
                325                 330                 335
His Asp Asp Ser Arg Gly Asn Gly Ser Val Asn Ala Arg Lys Ala
            340                 345                 350
Asp Val Glu Ser Thr Ile Glu Met Ser Ser Cys Tyr Thr Asp Ser Pro
            355                 360                 365
Thr Tyr Ser Lys Phe Glu Ala Gly Leu Asp Ala Arg Gly Ile Val Phe
    370                 375                 380
Tyr Asn Glu His Gly Leu Pro Val Val Ser Gly Glu Val Gly Gly Ser
385                 390                 395                 400
Ser Ser Asn Gly Thr Lys Leu Gly Ser Gly His Lys Tyr Glu Val Asn
                405                 410                 415
Thr Thr Val Val Leu Ser Asp Val Asp Ser Pro Ser Pro Thr Asp Val
            420                 425                 430
Thr Arg Lys
        435

<210> SEQ ID NO 63
<211> LENGTH: 1308
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
atggccgaag actccatctt cccaaacaac tccacctctc cattgaccaa cccaattgtt      60
gttgaaacca ttaagggtac cgcttacatt ccattacact acttggatga tttgcaatac     120
gaaaagatgt tgttggcttc cttgttctcc gttagaattg ctacttcctt cgttgttatt     180
atttggtact tcgtcgctgt caacaaggct aagagatcta agttttttgta cattgtcaac     240 caagtttctt tgttgatcgt tttatccaa tccattttgt ctttgattta cgtcttctcc      300
aacttctcca agatgtctac cattttgacc ggtgattaca ccggtatcac taagagagac     360
attaacgtct cttgtgttgc ctccgttttc caattcttgt tcatcgcttg tatcgaattg     420
gctttgttca tccaagctac tgtcgttttc caaaaatctg ttagatggtt gaagttttcc     480
gtttctttga tccaaggttc cgtcgctttg actactaccg ccttgtacat ggccattatt     540
gtccaatcca tctacgctac tttgaaccca tacgctggta acttgattaa aggtcgtttc     600
ggttacttat tagcttcttt gggtaagatt ttcttctcta tttctgttac ttcttgtatg     660
tgtatcttcg ttggtaagtt ggtctttgct attcaccaaa gaagaacttt gggtattaag     720
caattcgacg gtttgcaaat tttggtcatt atgtctactc aatccatgat catcccaact     780
attatcgtct tgatgtcttt tttgagacgt aacgctggtt ctgtttacac catggctacc     840
ttgttggtcg ctttgtcctt gccattgtcc tccttgtggg ctgaagccaa gactaccaga     900
gactctgctt cttacaccgc ttacagacca tctggttctc caaacaaccg ttctttgttc     960
```

-continued

```
gccatcttct ctgatagatt ggcttgtggt tctggtagaa acaacagaca cgatgatgat    1020
tctagaggta acggttctgt taacgccaga aaggctgacg tcgaatctac tatcgaaatg    1080
tcctcttgtt acactgattc cccaacctac tccaagttcg aagctggttt ggacgctaga    1140
ggtatcgtct ctacaacga acacggtttg ccagttgtct ccggtgaagt tggtggttct    1200
tcctccaacg gtactaagtt gggttctggt cataagtacg aagtcaacac tactgttgtt    1260
ttgtctgatg ttgactctcc atctccaacc gacgtcaccc gtaagtag                1308
```

<210> SEQ ID NO 64
<211> LENGTH: 452
<212> TYPE: PRT
<213> ORGANISM: Zygosaccharomyces bailii

<400> SEQUENCE: 64

```
Met Ser Gly Leu Ala Asn Asn Thr Ser Tyr Asn Pro Leu Glu Ser Phe
1               5                   10                  15

Ile Ile Phe Thr Ser Val Tyr Gly Gly Asp Thr Met Val Lys Phe Glu
            20                  25                  30

Asp Leu Gln Leu Val Phe Thr Lys Arg Ile Thr Glu Gly Ile Leu Phe
        35                  40                  45

Gly Val Lys Val Gly Ala Ala Ser Leu Thr Met Ile Val Met Trp Met
    50                  55                  60

Ile Ser Arg Arg Arg Thr Ser Pro Ile Phe Ile Met Asn Gln Leu Ser
65                  70                  75                  80

Leu Val Phe Thr Ile Leu His Ala Ser Phe Tyr Phe Lys Tyr Leu Leu
                85                  90                  95

Asp Gly Phe Gly Ser Ile Val Tyr Thr Leu Thr Leu Phe Pro Gln Leu
            100                 105                 110

Ile Thr Ser Ser Asp Leu His Val Phe Ala Thr Ala Asn Val Val Glu
        115                 120                 125

Val Leu Leu Val Ser Ser Ile Glu Ala Ser Leu Val Phe Gln Val Asn
    130                 135                 140

Val Met Phe Ala Gly Ser Asn His Arg Lys Phe Ala Trp Leu Leu Val
145                 150                 155                 160

Gly Phe Ser Leu Gly Leu Ala Leu Ala Thr Val Ala Leu Tyr Phe Val
                165                 170                 175

Thr Ala Val Lys Met Ile Ala Ser Ala Tyr Ala Ser Gln Pro Pro Thr
            180                 185                 190

Asn Pro Ile Tyr Phe Asn Val Ser Leu Phe Leu Leu Ala Ala Ser Val
        195                 200                 205

Phe Leu Met Thr Leu Met Leu Thr Val Lys Leu Ile Leu Ala Ile Arg
    210                 215                 220

Ser Arg Arg Phe Leu Gly Leu Lys Gln Phe Asp Ser Phe His Ile Leu
225                 230                 235                 240

Leu Ile Met Ser Cys Gln Thr Leu Ile Ala Pro Ser Val Leu Tyr Ile
                245                 250                 255

Leu Gly Phe Ile Leu Asp His Arg Lys Gly Asn Asp Tyr Leu Ile Thr
            260                 265                 270

Val Ala Gln Leu Leu Val Val Leu Ser Leu Pro Leu Ser Ser Met Trp
        275                 280                 285

Ala Thr Thr Ala Asn Asp Ala Ser Ser Gly Thr Ser Met Ser Ser Lys
    290                 295                 300

Glu Ser Val Tyr Gly Ser Asp Ser Leu Tyr Ser Lys Ser Lys Cys Ser
```

|  | | | 305 | | | | 310 | | | | 315 | | | | 320 | |

Gln Phe Thr Arg Thr Phe Met Asn Arg Phe Ser Thr Lys Pro Thr Lys
                325                         330                         335

Asn Asp Glu Ile Ser Asp Ser Ala Phe Val Ala Val Asp Ser Leu Glu
                340                         345                 350

Lys Asn Ala Pro Gln Gly Ile Ser Glu His Val Cys Glu Phe Pro Gln
                355                         360                 365

Ser Asp Leu Ser Asp Gln Ala Thr Ser Ile Ser Arg Lys Lys Glu
    370                         375                 380

Ala Val Val Tyr Ala Ser Thr Val Asp Glu Asp Lys Gly Ser Phe Ser
385                         390                         395                         400

Ser Asp Ile Asn Gly Tyr Thr Val Thr Asn Met Pro Leu Ala Ser Ala
                    405                         410                         415

Ala Ser Ala Asn Cys Glu Asn Ser Pro Cys His Val Pro Arg Pro Tyr
                    420                         425                         430

Glu Glu Asn Glu Gly Val Val Glu Thr Arg Lys Ile Ile Leu Lys Lys
                    435                         440                         445

Asn Val Lys Trp
    450

<210> SEQ ID NO 65
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
atgtctggtt tggctaacaa cacctcttac aacccattgg aatctttcat tattttcact      60
tctgtttacg gtggtgatac catggttaag ttcgaagact tgcaattagt cttcaccaag     120
cgtattactg aagtatttt gttcggtgtc aaggttggtg ccgcttcttt gactatgatt     180
gttatgtgga tgatttccag aagaagaacc tccccaatct tcatcatgaa ccaattgtct     240
ttggttttca ccatcttgca cgcttctttt tactttaagt acttattgga cggtttcggt     300
tctattgtct acactttgac cttgttccca caattaatta cttcctctga cttgcacgtt     360
ttcgctactg ctaacgttgt tgaagtctta ttggtttctt ccatcgaagc ctctttggtt     420
ttccaagtca acgtcatgtt cgctggttct aaccacagaa agttcgcttg ttgttggtc      480 ggtttctctt tgggtttggc tttggccact gtcgctttgt acttcgttac tgctgtcaag     540
atgatcgctt ccgcttacgc ttctcaacca ccaactaacc aatctactt caacgtttcc      600 ttgttcttgt tggctgcctc cgttttcttg atgacttaa tgttgaccgt caagttgatc      660
ttggctatca gatccagaag attcttgggt ttgaagcaat cgactctttt ccacattttg     720
ttgattatgt cttgtcaaac tttgatcgct ccatctgttt tgtacatctt gggttttatt     780
ttggatcaca gaaagggtaa cgactacttg attaccgtcg ctcaattgtt ggtcgttttg     840 tcttttgccat tgtcctccat gtgggccact actgctaacg atgcttcctc cggtacttct     900
atgtcttcca aggaatccgt ctacggttct gattccttat actctaagtc taagtgttcc     960
caattcacca gaaccttcat gaacagattc tctactaagc caactaagaa cgacgaaatt     1020
tctgattccg ctttcgtcgc tgttgattcc ttggaaaaga acgctccaca aggtatctct     1080
gaacacgttt gtgaattccc acaatctgac ttatctgatc aagctacttc catctcctcc     1140
agaaaaaagg aagctgttgt ttacgcttcc actgttgatg aagataaggg ttcttttctcc     1200

```
tctgacatca acggttacac tgttaccaac atgccattgg cttccgctgc ttctgctaac    1260
tgtgaaaact ccccatgtca cgttccaaga ccatacgaag aaaacgaagg tgtcgtcgaa    1320
accagaaaaa ttattttgaa gaagaacgtc aaatggtag                           1359
```

<210> SEQ ID NO 66
<211> LENGTH: 443
<212> TYPE: PRT
<213> ORGANISM: Zygosaccharomyces rouxii

<400> SEQUENCE: 66

```
Met Ser Glu Ile Asn Asn Ser Thr Tyr Asn Pro Met Asn Ala Tyr Val
1               5                   10                  15

Thr Phe Thr Ser Ile Tyr Gly Asp Asp Thr Met Val Arg Phe Lys Asp
            20                  25                  30

Val Glu Leu Val Val Asn Lys Arg Val Thr Glu Ala Ile Met Phe Gly
        35                  40                  45

Val Lys Val Gly Ala Ala Ser Leu Thr Leu Ile Ile Met Trp Met Ile
    50                  55                  60

Ser Lys Lys Arg Thr Thr Pro Ile Phe Ile Ile Asn Gln Ser Ser Leu
65                  70                  75                  80

Val Phe Thr Ile Ile His Ala Ser Leu Tyr Phe Gly Tyr Leu Leu Ser
                85                  90                  95

Gly Phe Gly Ser Ile Val Tyr Asn Met Thr Ser Phe Pro Gln Leu Ile
            100                 105                 110

Ser Ser Asn Asp Val Arg Val Tyr Ala Ala Thr Asn Ile Phe Glu Val
        115                 120                 125

Leu Leu Val Ala Ser Ile Glu Ile Ser Leu Val Phe Gln Val Lys Val
    130                 135                 140

Met Phe Ala Asn Asn Asn Gly Arg Arg Trp Thr Trp Cys Leu Met Val
145                 150                 155                 160

Val Ser Ile Gly Met Ala Leu Ala Thr Val Gly Leu Tyr Phe Ala Thr
                165                 170                 175

Ala Val Glu Leu Ile Arg Ala Ala Tyr Ser Asn Asp Thr Val Ser Arg
            180                 185                 190

His Val Phe Tyr Asn Val Ser Leu Ile Leu Leu Ala Ser Ser Val Asn
        195                 200                 205

Leu Met Thr Leu Met Leu Val Val Lys Leu Val Leu Ala Ile Arg Ser
    210                 215                 220

Arg Arg Phe Leu Gly Leu Lys Gln Phe Asp Ser Phe His Ile Leu Leu
225                 230                 235                 240

Ile Met Ser Cys Gln Thr Leu Ile Ala Pro Ser Ile Leu Phe Ile Leu
                245                 250                 255

Gly Trp Thr Leu Asp Pro His Thr Gly Asn Glu Val Leu Ile Thr Val
            260                 265                 270

Gly Gln Leu Leu Ile Val Leu Ser Leu Pro Leu Ser Ser Met Trp Ala
        275                 280                 285

Thr Thr Ala Asn Asn Thr Ser Ser Ser Ser Ser Val Ser Cys Asn
    290                 295                 300

Asp Ser Ser Phe Gly Asn Asp Asn Leu Cys Ser Lys Ser Ser Gln Phe
305                 310                 315                 320

Arg Arg Thr Phe Met Asn Arg Phe Arg Pro Lys Ser Val Asn Gly Asp
                325                 330                 335

Gly Asn Ser Glu Asn Thr Phe Val Thr Ile Asp Asp Leu Glu Lys Ser
```

Val Phe Gln Glu Leu Ser Thr Pro Val Ser Gly Glu Ser Lys Ile Asp
        340                 345                 350

His Asp His Ala Ser Ser Ile Ser Cys Gln Lys Thr Cys Asn His Val
355                 360                 365

His Ala Ser Thr Val Asn Ser Asp Lys Gly Ser Trp Ser Ser Asp Gly
370                 375                 380

Ser Cys Gly Ser Ser Pro Leu Arg Lys Thr Thr Val Asn Ser Glu
385                 390                 395                 400

Asp Leu Pro Pro His Ile Leu Ser Ala Tyr Asp Asp Arg Gly Ile
            405                 410                 415

Val Glu Ser Lys Lys Ile Ile Leu Lys Lys Leu
        420                 425                 430

435                 440

<210> SEQ ID NO 67
<211> LENGTH: 1332
<212> TYPE: DNA
<213> ORGANISM: Zygosaccharomyces rouxii

<400> SEQUENCE: 67

```
atgagtgaga ttaacaattc tacctacaat ccaatgaatg catatgtaac gtttacatca      60
atatatggtg atgatactat ggtacgtttc aaagatgtgg aattggtagt taacaaaagg     120
gttacagaag ccattatgtt cggcgtcaaa gttggtgcag cttcgttgac actcatcatc     180
atgtggatga tctctaagaa aagaacaaca ccgatattta tcataaatca gtcttcgctt     240
gtatttacca taatacatgc ttcgctttat tttgggtacc ttttgtcagg atttggtagt     300
atagtttaca atatgacatc gttcccgcag ttaataagct ccaatgacgt tcgtgtgtac     360
gcagctacaa atattttga ggtcctgttg gtagcatcta tcgaaatctc tctggttttt     420
caggtcaaag ttatgtttgc caacaataat ggtcgaagat ggacttggtg tttgatggta     480
gtttccatag ggatggcact agctactgta ggactttatt tgccactgc cgttgagttg     540
atcagagctg cttacagcaa tgatactgtt agccgccatg ttttttacaa tgtttctctg     600
atcttactag cgtcatctgt caatctaatg acactaatgc tagtggtaaa attagtatta     660
gcgatcagat caagaagatt tttggggtta aaacagtttg acagtttcca catattactt     720
ataatgtctt gccagactct aatagcacct tccattctat tcattttggg ttggaccta     780
gaccctcata ctggtaatga ggttttaatt acagttggtc aattgctaat agtactgtca     840
ttaccgctgt catctatgtg ggctacaacc gctaacaata ccagttcatc tagtagttcg     900
gtgtcctgta atgacagctc ttttggtaat gacaatctct gttccaagag ttcgcaattt     960
agaagaactt ttatgaatag attccgtccc aagtcggtta atggtgacgg taattctgaa    1020
aatacctttg ttacaattga tgatttggaa aaaagcgttt ttcaagaatt atcaacacct    1080
gttagcggag aatcaaagat agatcatgat catgcaagta gtatttcatg tcaaaagaca    1140
tgtaatcatg ttcatgcttc gacagtgaat tcagataagg gatcttggtc ctctgatggt    1200
agttgtggca gttctccgtt aagaaagact tccaccgtta attctgaaga tttacctcca    1260
catatattga gcgcctacga tgacgatcga ggtatagtag aaagtaaaaa aattatccta    1320
aagaaattat ag                                                         1332
```

<210> SEQ ID NO 68
<211> LENGTH: 436
<212> TYPE: PRT
<213> ORGANISM: Kluyveromyces lactis

<400> SEQUENCE: 68

Met Ser Glu Glu Ile Pro Ser Leu Asn Pro Leu Phe Tyr Asn Glu Thr
1               5                   10                  15

Tyr Asn Pro Leu Gln Ser Val Leu Thr Tyr Ser Ser Ile Tyr Gly Asp
            20                  25                  30

Gly Thr Glu Ile Thr Phe Gln Gln Leu Gln Asn Leu Val His Glu Asn
        35                  40                  45

Ile Thr Gln Ala Ile Ile Phe Gly Thr Arg Ile Gly Ala Ala Gly Leu
    50                  55                  60

Ala Leu Ile Ile Met Trp Met Val Ser Lys Asn Arg Lys Thr Pro Ile
65                  70                  75                  80

Phe Ile Ile Asn Gln Ser Ser Leu Val Leu Thr Ile Val Gln Ser Ala
                85                  90                  95

Leu Tyr Leu Ser Tyr Leu Leu Ser Asn Phe Gly Val Pro Phe Ala
            100                 105                 110

Leu Thr Leu Phe Pro Gln Met Ile Gly Asp Arg Asp Lys His Leu Tyr
            115                 120                 125

Gly Ala Val Thr Leu Ile Gln Cys Leu Leu Val Ala Cys Ile Glu Val
        130                 135                 140

Ser Leu Val Phe Gln Val Arg Val Ile Phe Lys Ala Asp Arg Tyr Arg
145                 150                 155                 160

Lys Ile Gly Ile Ile Leu Thr Gly Val Ser Ala Ser Phe Gly Ala Ala
                165                 170                 175

Thr Val Ala Met Trp Met Ile Thr Ala Ile Lys Ser Ile Ile Val Val
            180                 185                 190

Tyr Asp Ser Pro Leu Asn Lys Val Asp Thr Tyr Tyr Asn Ile Ala
            195                 200                 205

Val Ile Leu Leu Ala Cys Ser Ile Asn Phe Ile Thr Leu Leu Leu Ser
    210                 215                 220

Val Lys Leu Phe Leu Ala Phe Arg Ala Arg His Leu Gly Leu Lys
225                 230                 235                 240

Gln Phe Asp Ser Phe His Ile Leu Leu Ile Met Ser Thr Gln Thr Leu
                245                 250                 255

Ile Gly Pro Ser Val Leu Tyr Ile Leu Ala Tyr Ala Leu Asn Asn Lys
            260                 265                 270

Gly Val Lys Ser Leu Thr Ser Ile Ala Thr Leu Leu Val Val Leu Ser
        275                 280                 285

Leu Pro Leu Thr Ser Ile Trp Ala Ala Ala Asn Asp Ala Pro Ser
    290                 295                 300

Ala Ser Thr Phe Tyr Arg Gln Phe Asn Pro Tyr Ser Ala Gln Asn Arg
305                 310                 315                 320

Asp Asp Ser Ser Ser Tyr Ser Tyr Gly Lys Ala Phe Ser Asp Lys Tyr
                325                 330                 335

Ser Phe Ser Asn Ser Pro Gln Thr Ser Asp Gly Cys Ser Ser Lys Glu
            340                 345                 350

Leu Glu Leu Ser Thr Gln Leu Glu Met Asp Leu Glu Ser Gly Glu Ser
        355                 360                 365

Phe Met Asp Arg Ala Lys Arg Ser Asp Phe Val Ser Ser Pro Gly Ser
    370                 375                 380

Thr Asp Ala Thr Val Ile Lys Gln Leu Lys Ala Ser Asn Ile Tyr Thr
385                 390                 395                 400

Ser Glu Thr Asp Ala Asp Glu Glu Ala Arg Ala Phe Trp Val Asn Ala 405                 410                 415
Ile His Glu Asn Lys Asp Asp Gly Leu Met Gln Ser Lys Thr Val Phe
            420                 425                 430

Lys Glu Leu Arg
        435

<210> SEQ ID NO 69
<211> LENGTH: 1311
<212> TYPE: DNA
<213> ORGANISM: Kluyveromyces lactis

<400> SEQUENCE: 69
atgtcagaag agatacccag tttgaaccca ttgttctaca atgagacata taatccattg      60
cagtccgtcc taacatacag ttcaatttac ggagatggga ctgaaataac atttcaacag     120
ctacaaaatc ttgtccatga aacatcacc caagcaatta ttttggaac aaggatcggc      180 gctgctggat tagcgttgat tataatgtgg atggtctcta agaatagaaa gacgccgata     240
ttcataataa atcagagttc tttggttctt acaattgttc aatctgcttt atatctatca     300
tatttgttga gcaattttgg aggagttccc tttgctctaa ctttgttccc acagatgata     360
ggcgaccgtg acaaacatct ttacggtgcc gtgactctaa ttcaatgtct attggttgcg     420
tgtattgagg tctcgttagt ctttcaggta agagtcattt tcaaagcaga tagatatagg     480
aagataggaa tcattttgac tggcgtctcc gctagttttg gtgctgcaac tgtagccatg     540
tggatgatta ctgcaataaa atctattatt gtagtgtatg atagtccatt gaacaaagtt     600
gacacatatt attacaacat agcagttatt ttacttgcat gttcaataaa tttcatcact     660
cttcttctat cagtgaaact tttcctggct ttcagagcta ggagacattt aggtttgaaa     720
caatttgact catttcacat tctactcatc atgtctactc agacattaat aggtccatcg     780
gttttgtata ttctcgccta cgcgctgaac aataaaggag ttaagtcgtt gacttctatt     840
gctacattgc ttgtagttct ttccctacct ttgacatcta tctgggctgc tgctgcaaat     900
gatgcaccaa gtgccagtac tttctatcgc caattcaacc cttactctgc acaaaatcgt     960
gatgattcat catcctactc ttatggtaaa gcctttagtg acaaatactc tttcagtaac    1020
tcaccacaaa cttcggatgg ttgtagttca aaggaacttg aactatctac acagttggag    1080
atggatttag agtctggcga atcttttatg gatagagcaa aaaggtccga ttttgtttct    1140
tctccaggat caacagatgc aacagtgatt aaacaattga agcttccaa catctatacc     1200 tcagaaacag atgctgatga agaggcaagg gcattttggg tgaatgcaat tcatgaaaac    1260
aaagatgacg gtttaatgca atcgaaaacc gtattcaaag aattaagata g             1311

<210> SEQ ID NO 70
<211> LENGTH: 348
<212> TYPE: PRT
<213> ORGANISM: Schizosaccharomyces pombe

<400> SEQUENCE: 70

Met Arg Gln Pro Trp Trp Lys Asp Phe Thr Ile Pro Asp Ala Ser Ala
1               5                   10                  15

Ile Ile His Gln Asn Ile Thr Ile Val Ser Ile Val Gly Glu Ile Glu
            20                  25                  30

Val Pro Val Ser Thr Ile Asp Ala Tyr Glu Arg Asp Arg Leu Leu Thr
        35                  40                  45

Gly Met Thr Leu Ser Ala Gln Leu Ala Leu Gly Val Leu Thr Ile Leu
    50                  55                  60

```
Met Val Cys Leu Leu Ser Ser Glu Lys Arg Lys His Pro Val Phe
 65                  70                  75                  80

Val Phe Asn Ser Ala Ser Ile Val Ala Met Cys Leu Arg Ala Ile Leu
             85                  90                  95

Asn Ile Val Thr Ile Cys Ser Asn Ser Tyr Ser Ile Leu Val Asn Tyr
            100                 105                 110

Gly Phe Ile Leu Asn Met Val His Met Tyr Val His Val Phe Asn Ile
            115                 120                 125

Leu Ile Leu Leu Leu Ala Pro Val Ile Phe Thr Ala Glu Met Ser
130                 135                 140

Met Met Ile Gln Val Arg Ile Ile Cys Ala His Asp Arg Lys Thr Gln
145                 150                 155                 160

Arg Ile Met Thr Val Ile Ser Ala Cys Leu Thr Val Leu Val Leu Ala
                165                 170                 175

Phe Trp Ile Thr Asn Met Cys Gln Gln Ile Gln Tyr Leu Leu Trp Leu
            180                 185                 190

Thr Pro Leu Ser Ser Lys Thr Ile Val Gly Tyr Ser Trp Pro Tyr Phe
            195                 200                 205

Ile Ala Lys Ile Leu Phe Ala Phe Ser Ile Ile Phe His Ser Gly Val
210                 215                 220

Phe Ser Tyr Lys Leu Phe Arg Ala Ile Leu Ile Arg Lys Lys Ile Gly
225                 230                 235                 240

Gln Phe Pro Phe Gly Pro Met Gln Cys Ile Leu Val Ile Ser Cys Gln
                245                 250                 255

Cys Leu Ile Val Pro Ala Thr Phe Thr Ile Ile Asp Ser Phe Ile His
            260                 265                 270

Thr Tyr Asp Gly Phe Ser Ser Met Thr Gln Cys Leu Leu Ile Ile Ser
            275                 280                 285

Leu Pro Leu Ser Ser Leu Trp Ala Ser Ser Thr Ala Leu Lys Leu Gln
290                 295                 300

Ser Met Lys Thr Ser Ser Ala Gln Gly Glu Thr Thr Glu Val Ser Ile
305                 310                 315                 320

Arg Val Asp Arg Thr Phe Asp Ile Lys His Thr Pro Ser Asp Asp Tyr
                325                 330                 335

Ser Ile Ser Asp Glu Ser Glu Thr Lys Lys Trp Thr
            340                 345
```

<210> SEQ ID NO 71
<211> LENGTH: 1047
<212> TYPE: DNA
<213> ORGANISM: Schizosaccharomyces pombe

<400> SEQUENCE: 71

```
atgagacaac catggtggaa agactttact attcccgatg catccgcaat tattcaccaa    60
aatattacca ttgtctctat tgtaggagag attgaagtgc cagtttcaac aattgatgca   120
tatgaaagag atagacttttt aactggaatg actttgtctg cccaacttgc tttaggagtc   180
cttaccattt tgatggtttg tctattgtca tcatccgaaa aacgaaaaca cccagttttt   240
gtttttaatt cggcaagtat tgttgcaatg tgtcttcggg ccattttgaa tatagtgacc   300
atatgcagca atagctacag tatcctggtt aattacgggt ttatcttaaa catggttcat   360
atgtatgtcc atgtgtttaa tatttttaatt ttgttgcttg caccggtcat cattttttact   420 gctgagatga gcatgatgat tcaagttcgt ataatttgtg cacatgatag aaagacacaa   480
```

```
aggataatga ctgttattag tgcctgctta actgttttgg ttctcgcatt ttggattact    540
aacatgtgtc aacagattca gtatctgtta tggttaactc cacttagcag caagaccatt    600
gttggatact cttggcccta ctttattgct aaaatacttt ttgcttttag cattattttt    660
cacagtggtg ttttttcata caaactcttt cgtgccatat taatacggaa aaaaattggg    720
caatttccat ttggtccgat gcagtgtatt ttagttatta gctgccaatg tcttattgtt    780
ccagctacct ttactataat agatagtttt atccatacgt atgatggctt tagctctatg    840
actcaatgtc tgctaatcat ttctcttcct ctttcgagtt tatgggcgtc tagtacagct    900
ctgaaattgc aaagcatgaa aacttcatct gcgcaaggag aaaccaccga ggtttcgatt    960
agagttgata gaacgtttga tatcaaacat actcccagtg acgattattc gatttctgat   1020
gaatctgaaa ctaaaaagtg gacgtag                                        1047
```

<210> SEQ ID NO 72
<211> LENGTH: 384
<212> TYPE: PRT
<213> ORGANISM: Vanderwaltozyma polyspora

<400> SEQUENCE: 72

```
Met Ser Ser Gln Ser His Pro Pro Leu Ile Asp Leu Phe Tyr Asp Ser
1               5                   10                  15

Ser Tyr Asp Pro Gly Glu Ser Leu Ile Tyr Tyr Thr Ser Ile Tyr Gly
            20                  25                  30

Asn Asn Thr Tyr Ile Thr Phe Asp Glu Leu Gln Thr Ile Val Asn Lys
        35                  40                  45

Lys Val Thr Gln Gly Ile Leu Phe Gly Val Arg Cys Gly Ala Ala Phe
    50                  55                  60

Leu Met Leu Val Ala Met Trp Leu Ile Ser Lys Asn Lys Arg Ser Arg
65                  70                  75                  80

Ile Phe Ile Thr Asn Gln Cys Cys Leu Val Phe Met Ile Met His Ser
                85                  90                  95

Gly Leu Tyr Phe Arg Tyr Leu Leu Ser Arg Tyr Gly Ser Val Thr Phe
            100                 105                 110

Ile Leu Thr Gly Phe Gln Gln Leu Leu Thr Arg Asn Asp Ile His Ile
        115                 120                 125

Tyr Gly Ala Thr Asp Phe Ile Gln Val Ala Leu Val Ala Cys Ile Glu
    130                 135                 140

Leu Ser Leu Ile Phe Gln Ile Lys Val Ile Phe Ala Gly Thr Asn Tyr
145                 150                 155                 160

Gly Lys Leu Ala Asn Tyr Phe Ile Thr Leu Gly Ser Leu Leu Gly Leu
                165                 170                 175

Ala Thr Phe Gly Met Tyr Met Leu Thr Ala Ile Asn Gly Thr Ile Lys
            180                 185                 190

Leu Tyr Asn Asn Glu Tyr Asp Pro Asn Gln Arg Lys Tyr Phe Asn Ile
        195                 200                 205

Ser Thr Ile Leu Leu Ala Ser Ser Ile Asn Met Leu Thr Leu Ile Leu
    210                 215                 220

Ile Leu Lys Leu Val Ala Ala Ile Arg Thr Arg Arg Tyr Leu Gly Leu
225                 230                 235                 240

Lys Gln Phe Asp Ser Phe His Ile Leu Leu Ile Met Ser Thr Gln Thr
                245                 250                 255

Leu Ile Ile Pro Ser Ile Leu Phe Ile Leu Ser Tyr Ser Leu Arg Glu
            260                 265                 270
```

```
Asp Met His Thr Asp Gln Leu Ile Ile Gly Asn Leu Ile Val Val
            275                 280                 285

Leu Ser Leu Pro Leu Ser Ser Met Trp Ala Ser Ser Leu Asn Asn Ser
    290                 295                 300

Ser Lys Pro Thr Ser Leu Asn Thr Asp Phe Ser Gly Pro Lys Ser Ser
305                 310                 315                 320

Glu Glu Gly Thr Ala Ile Ser Leu Leu Ser Gln Asn Met Glu Pro Ser
                325                 330                 335

Ile Val Thr Lys Tyr Thr Arg Arg Ser Pro Gly Leu Tyr Pro Val Ser
            340                 345                 350

Val Gly Thr Pro Ile Glu Lys Glu Ala Ser Tyr Thr Leu Phe Glu Ala
        355                 360                 365

Thr Asp Ile Asp Phe Glu Ser Ser Ser Asn Asp Ile Thr Arg Thr Ser
    370                 375                 380
```

<210> SEQ ID NO 73
<211> LENGTH: 1155
<212> TYPE: DNA
<213> ORGANISM: Vanderwaltozyma polyspora

<400> SEQUENCE: 73

```
atgagttccc aatcacaccc accgctaatc gatttatttt acgattccag ttatgaccct     60
ggtgaaagtt taatttatta cacatccatc tatggtaata atacatacat aacttttgat    120
gaactccaga cgatagtgaa caagaaggtc acacaaggta tcttatttgg tgtcagatgt    180
ggtgctgctt tcctgatgtt ggtagcaatg tggttgattt ccaaaaataa agatctaga    240
attttcatta ccaaccaatg ttgtctggtc ttcatgataa tgcattctgg tctttatttt    300
aggtacctgc tttcaaggta cggttcagtt actttcattc taacagggtt ccaacaactg    360
cttacaagaa atgacattca tatttatgga gctactgatt ttatccaagt agctttggta    420
gcttgcatag aattatctct tattttccaa ataaaagtga tattcgctgg tacaaactat    480
ggtaagttgg ctaattattt catcactcta ggttcattat tgggtttagc cacctttggt    540
atgtacatgc ttactgctat taacggtaca ataaaattat acaataacga atatgaccca    600
aaccaaagga aatactttaa catttctaca atattgcttg catcatcaat taatatgcta    660
acgctgatac ttatattgaa gctggtggca gcaattagaa caagacgtta cttaggtttg    720
aagcaattcg atagttttca tcctatta atcatgtcga ctcaaacatt aataattcct    780
tctatcttat ttattctatc atacagtttg agagaggata tgcatactga tcaattaata    840
atcatcggaa atctgatcgt ggtattgtca ttaccattgt cctcaatgtg gcttcgtct    900
ctaaacaatt caagtaaacc tacatctttg aatactgatt tctcagggcc aaaatcaagt    960
gaagaaggga cagcaataag tttgctatca caaacatgg aaccatcaat agtcactaaa   1020
tatacaagaa gatcacctgg gttatacca gtaagcgtgg gtacaccaat tgaaaaagaa   1080
gcatcataca ctcttttga agctactgac attgattttg aaagcagtag taacgatatc   1140
acaaggactt catag                                                   1155
```

<210> SEQ ID NO 74
<211> LENGTH: 473
<212> TYPE: PRT
<213> ORGANISM: Vanderwaltozyma polyspora

<400> SEQUENCE: 74

```
Met Ser Gly Ile Asp Asp Met Gly Asp Lys Pro Asp Ile Leu Gly Leu
1               5                   10                  15
```

```
Phe Tyr Asp Ala Asn Tyr Asp Pro Gly Gln Gly Ile Leu Thr Phe Ile
                20                  25                  30

Ser Met Tyr Gly Asn Thr Thr Ile Thr Phe Asp Glu Leu Gln Leu Glu
            35                  40                  45

Val Asn Ser Leu Ile Thr Ser Gly Ile Met Phe Gly Val Arg Cys Gly
 50                  55                  60

Ala Ala Cys Leu Thr Leu Leu Ile Met Trp Met Ile Ser Lys Asn Lys
 65                  70                  75                  80

Lys Thr Pro Ile Phe Ile Ile Asn Gln Cys Ser Leu Ile Leu Ile Ile
                 85                  90                  95

Met His Ser Gly Leu Tyr Phe Lys Asn Ile Leu Ser Asn Leu Asn Ser
                100                 105                 110

Leu Ser Tyr Ile Leu Thr Gly Phe Thr Gln Asn Ile Thr Lys Asn Asn
                115                 120                 125

Ile His Val Phe Gly Ala Ala Asn Ile Ile Gln Val Leu Leu Val Ala
    130                 135                 140

Thr Ile Glu Leu Ser Leu Val Phe Gln Ile Arg Val Met Phe Lys Gly
145                 150                 155                 160

Asp Ser Phe Arg Lys Ala Gly Tyr Gly Leu Leu Ser Ile Ala Ser Gly
                165                 170                 175

Leu Gly Ile Ala Thr Val Val Met Tyr Phe Tyr Ser Ala Ile Thr Asn
                180                 185                 190

Met Ile Ala Val Tyr Asn Gln Thr Tyr Asn Ser Thr Ala Lys Leu Phe
            195                 200                 205

Asn Val Ala Asn Ile Leu Leu Ser Thr Ser Ile Asn Phe Met Thr Val
            210                 215                 220

Val Leu Ile Val Lys Leu Phe Leu Ala Val Arg Ser Arg Arg Tyr Leu
225                 230                 235                 240

Gly Leu Lys Gln Phe Asp Ser Phe His Ile Leu Leu Ile Met Ser Cys
                245                 250                 255

Gln Thr Leu Ile Val Pro Ser Ile Leu Phe Ile Leu Ser Tyr Ala Leu
                260                 265                 270

Ser Thr Lys Leu Tyr Thr Asp His Leu Val Val Ile Ala Thr Leu Leu
            275                 280                 285

Val Val Leu Ser Leu Pro Leu Ser Ser Met Trp Ala Ser Ala Ala Asn
290                 295                 300

Asn Ser Pro Lys Pro Ser Ser Phe Thr Thr Asp Tyr Ser Asn Lys Asn
305                 310                 315                 320

Pro Ser Asp Thr Pro Ser Phe Tyr Ser Gln Ser Ile Ser Ser Ser Met
                325                 330                 335

Lys Ser Lys Phe Pro Ser Lys Phe Ile Pro Phe Asn Phe Lys Ser Lys
                340                 345                 350

Asp Asn Ser Ser Asp Thr Arg Ser Glu Asn Thr Tyr Ile Gly Asn Tyr
            355                 360                 365

Asp Met Glu Lys Asn Gly Ser Pro Asn His Ser Tyr Ser Ser Lys Asp
            370                 375                 380

Gln Ser Glu Val Tyr Thr Ile Gly Val Ser Ser Met His Thr Asp Ile
385                 390                 395                 400

Lys Ser Gln Lys Asn Ile Ser Gly Gln His Leu Tyr Thr Pro Ser Thr
                405                 410                 415

Glu Ile Asp Glu Glu Ala Arg Asp Phe Trp Ala Gly Arg Ala Val Asn
                420                 425                 430
```

Asn Ser Val Pro Asn Asp Tyr Gln Pro Ser Glu Leu Pro Ala Ser Ile
        435                 440                 445

Leu Glu Glu Leu Asn Ser Leu Asp Glu Asn Asn Glu Gly Phe Leu Glu
    450                 455                 460

Thr Lys Arg Ile Thr Phe Arg Lys Gln
465                 470

<210> SEQ ID NO 75
<211> LENGTH: 1422
<212> TYPE: DNA
<213> ORGANISM: Vanderwaltozyma polyspora

<400> SEQUENCE: 75

| | |
|---|---:|
| atgtcaggaa ttgatgatat gggtgataaa ccagatattt taggtttatt ttatgatgct | 60 |
| aactatgatc caggtcaagg tatactcaca tttatttcaa tgtacgggaa tactactata | 120 |
| acttttgatg agttacagtt agaggtcaat agtttaatta caagtggtat tatgttcggc | 180 |
| gtcagatgtg gtgctgcttg tttgacattg ttaataatgt ggatgatttc taagaataag | 240 |
| aagactccaa ttttattat taatcaatgc tcgctaatcc ttattattat gcattcaggt | 300 |
| ttatatttta agaatattct atcaaatttg aattctttat catatatctt aactgggttt | 360 |
| actcaaaata tcactaaaaa taatatacat gtctttggtg ccgctaatat tattcaagtt | 420 |
| ttattagtag caaccattga actgtcgtta gtgtttcaaa ttcgagtcat gtttaaaggt | 480 |
| gacagtttta gaaaagctgg ttacggtttg ttgtcaattg cgtctggttt gggtatagct | 540 |
| actgtcgtca tgtatttta ctctgccatt acaaatatga ttgctgttta taatcaaact | 600 |
| tacaactcca ctgctaaatt atttaacgtt gcaaacattc ttctgtctac atcgataaat | 660 |
| tttatgacgg tagtattaat tgttaaatta ttttggctg ttagatcaag aagatatttg | 720 |
| ggtttaaagc agttcgatag tttccatatt ttattgatta tgtcatgtca acattgatt | 780 |
| gtaccatcaa ttcttttat cttatcatac gctttaagta ctaagctgta cactgatcat | 840 |
| ttagttgtca ttgcaacttt attagtcgtt ctatctttac cattatcttc gatgtgggca | 900 |
| agcgctgcaa ataattctcc taaaccaagc tcgtttacaa ccgattattc aaacaagaat | 960 |
| cctagtgaca caccaagctt ctacagtcaa agtattagtt cctcgatgaa aagcaaattc | 1020 |
| ccaagcaaat tcatacccctt caatttcaag tctaaagaca attcttctga cactagatca | 1080 |
| gaaaatacat atattggcaa ttatgacatg gaaaagaatg gatcaccaaa tcactcttat | 1140 |
| tcttccaaag atcaaagtga agtttacact ataggtgtaa gctctatgca cacagatata | 1200 |
| aagtcacaaa agaatatcag tggacagcat ttatataccc caagtacaga gattgatgaa | 1260 |
| gaagctagag acttctgggc gggcagagct gttaataatt cagttccaaa tgactatcaa | 1320 |
| ccatctgagt taccagcatc gattcttgaa gaattgaatt cactggatga aaataatgaa | 1380 |
| ggtttcttgg agacaaaaag aataacattt agaaaacaat ag | 1422 |

<210> SEQ ID NO 76
<211> LENGTH: 321
<212> TYPE: PRT
<213> ORGANISM: Scheffersomyces stipitis

<400> SEQUENCE: 76

Met Asp Thr Ser Ile Asn Thr Leu Asn Pro Ala Asn Ile Ile Val Asn
1               5                   10                  15

Tyr Thr Leu Pro Asn Asp Pro Arg Val Ile Ser Val Pro Phe Gly Ala
            20                  25                  30

```
Phe Asp Glu Tyr Val Asn Gln Ser Met Gln Lys Ala Ile Ile His Gly
             35                  40                  45

Val Ser Ile Gly Ser Cys Thr Ile Met Leu Leu Ile Ile Leu Ile Phe
 50                  55                  60

Asn Val Lys Arg Lys Lys Ser Pro Ala Phe Tyr Leu Asn Ser Val Thr
 65                  70                  75                  80

Leu Thr Ala Met Ile Ile Arg Ser Ala Leu Asn Leu Ala Tyr Leu Leu
                 85                  90                  95

Gly Pro Leu Ala Gly Leu Ser Phe Thr Phe Ser Gly Leu Val Thr Pro
            100                 105                 110

Glu Thr Asn Phe Ser Val Ser Glu Ala Thr Asn Ala Phe Gln Val Ile
            115                 120                 125

Val Val Ala Leu Ile Glu Ala Ser Met Thr Phe Gln Val Phe Val Val
130                 135                 140

Phe Gln Ser Pro Glu Val Lys Lys Leu Gly Ile Ala Leu Thr Ser Ile
145                 150                 155                 160

Ser Ala Phe Thr Gly Ala Ala Val Gly Phe Thr Ile Asn Ser Thr
                165                 170                 175

Ile Gln Gln Ser Arg Ile Tyr His Ser Val Val Asn Gly Thr Pro Thr
            180                 185                 190

Pro Thr Val Ala Thr Trp Ser Trp Val Arg Asp Val Pro Thr Ile Leu
            195                 200                 205

Phe Ser Thr Ser Val Asn Ile Met Ser Phe Ile Leu Ile Leu Lys Leu
210                 215                 220

Gly Phe Ala Ile Lys Thr Arg Arg Tyr Leu Gly Leu Arg Gln Phe Gly
225                 230                 235                 240

Ser Leu His Ile Leu Leu Met Met Ala Thr Gln Thr Leu Leu Ala Pro
                245                 250                 255

Ser Ile Leu Ile Leu Val His Tyr Gly Tyr Gly Thr Ser Leu Asn Ser
            260                 265                 270

Gln Leu Ile Leu Ile Ser Tyr Leu Leu Val Val Leu Ser Leu Pro Val
            275                 280                 285

Ser Ser Ile Trp Ala Ala Thr Ala Asn Asn Ser Pro Gln Leu Pro Ser
290                 295                 300

Ser Ala Thr Leu Ser Phe Met Asn Lys Thr Thr Ser His Phe Ser Glu
305                 310                 315                 320

Ser
```

<210> SEQ ID NO 77
<211> LENGTH: 966
<212> TYPE: DNA
<213> ORGANISM: Scheffersomyces stipitis

<400> SEQUENCE: 77

```
atggatacta gtatcaatac tctcaaccct gcgaatatca ttgtcaacta caccttgcca      60
aatgatccta gagtaattag tgtcccattt ggagcttttg acgaatatgt taaccaatct     120
atgcaaaagg ccattatcca tggagtttcc attggttcat gcaccataat gcttttaatt     180
attttgatct tcaatgtcaa acgcaagaag tcgccagctt tctatcttaa ttcggttacg     240
ttgactgcaa tgattattcg gtctgctctt aatttggcat atttgctagg tcctttggct     300
ggattaagtt ttacgttctc cggcttggta actccagaaa ccaatttctc tgtctctgaa     360
gccaccaatg ctttccaggt tattgttgtt gctcttatcg aggcgtccat gacatttcag     420
gtgttcgtcg tcttccaatc accagaagtg aagaagttgg gtatagctct tacctccata     480
```

```
tctgcattca cgggtgctgc tgctgtagga tttactatca atagtacaat ccaacaatcg    540
agaatttatc attcagttgt caatggaact cctacgccaa cggtcgctac ctggtcttgg    600
gttagagatg tgcctacgat actttttct acttcggtta acataatgtc tttcatcttg     660
attctcaagt tagggtttgc cataaagaca agaagatacc ttggccttcg gcaatttggc    720
agtttgcaca tcttattgat gatggctact caaacattat tggccccatc tattctcatt    780
cttgtacatt acggatatgg cacatctctg aatagccagc tcattcttat aagttacttg    840
cttgttgttt tgtctttacc agtatcctct atctgggcag caacagccaa caattctcct    900
caacttccat cttccgcaac tctttcattc atgaacaaaa cgacctctca cttttctgaa    960
agctag                                                               966
```

```
<210> SEQ ID NO 78
<211> LENGTH: 346
<212> TYPE: PRT
<213> ORGANISM: Schizosaccharomyces japonicus

<400> SEQUENCE: 78

Met Tyr Ser Trp Asp Glu Phe Arg Ser Pro Lys Gln Ala Glu Val Leu
1               5                   10                  15

Asn Gln Thr Val Thr Leu Glu Thr Ile Val Ser Thr Ile Gln Leu Pro
            20                  25                  30

Ile Ser Glu Ile Asp Ser Met Glu Arg Asn Arg Leu Leu Thr Gly Met
        35                  40                  45

Thr Val Ala Val Gln Val Gly Leu Gly Ser Phe Ile Leu Val Leu Met
    50                  55                  60

Cys Ile Phe Ser Ser Ser Glu Lys Arg Lys Lys Pro Val Phe Ile Phe
65                  70                  75                  80

Asn Phe Ala Gly Asn Leu Val Met Thr Leu Arg Ala Ile Phe Glu Val
                85                  90                  95

Ile Val Leu Ala Ser Asn Asn Tyr Ser Ile Ala Val Gln Tyr Gly Phe
            100                 105                 110

Ala Phe Ala Ala Val Arg Gln Tyr Val His Ala Phe Asn Ile Ile Ile
        115                 120                 125

Leu Leu Leu Gly Pro Phe Ile Leu Phe Ile Ala Glu Met Ser Leu Met
    130                 135                 140

Leu Gln Val Arg Ile Ile Cys Ser Gln His Arg Pro Thr Met Ile Thr
145                 150                 155                 160

Thr Thr Val Ile Ser Cys Ile Phe Thr Val Val Thr Leu Ala Phe Trp
                165                 170                 175

Ile Thr Asp Met Ser Gln Glu Ile Ala Tyr Gln Leu Phe Leu Lys Asn
            180                 185                 190

Tyr Asn Met Lys Gln Ile Val Gly Tyr Ser Trp Leu Tyr Phe Ile Ala
        195                 200                 205

Lys Ile Thr Phe Ala Ala Ser Ile Ile Phe His Ser Ser Val Phe Ser
    210                 215                 220

Phe Lys Leu Met Arg Ala Ile Tyr Ile Arg Arg Lys Ile Gly Gln Phe
225                 230                 235                 240

Pro Phe Gly Pro Met Gln Cys Ile Phe Ile Val Ser Cys Gln Cys Leu
                245                 250                 255

Ile Val Pro Ala Ile Phe Thr Leu Ile Asp Ser Phe Thr His Thr Tyr
            260                 265                 270

Asp Gly Phe Ser Ser Met Thr Gln Cys Leu Leu Ile Ile Ser Leu Pro
```

```
                275                 280                 285
Leu Ser Ser Leu Trp Ala Thr His Thr Ala Gln Lys Leu Gln Thr Met
            290                 295                 300
Lys Asp Asn Thr Asn Pro Pro Ser Gly Thr Gln Leu Thr Ile Arg Val
305                 310                 315                 320
Asp Arg Thr Phe Asp Met Lys Phe Val Ser Asp Ser Ser Asp Gly Ser
                325                 330                 335
Phe Thr Glu Lys Thr Glu Glu Thr Leu Pro
            340                 345

<210> SEQ ID NO 79
<211> LENGTH: 1038
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
atgtactcct gggacgaatt cagatcccca aagcaagctg aagttttgaa ccaaaccgtt      60
accttggaaa ctattgtttc caccattcaa ttgccaatct ctgaaattga ctccatggaa    120
agaaacagat tgttgaccgg tatgactgtc gctgttcaag ttggtttagg ttccttcatt    180
ttagttttga tgtgtatttt ctcttcctct gaaaagagaa agaagccagt cttcatcttc    240
aacttcgctg gtaacttggt tatgactttg agagctattt cgaagttat cgttttggct    300 tctaacaact actctatcgc tgttcaatac ggtttcgctt ttgctgccgt cagacaatac    360
gttcacgcct tcaacattat catcttgttg ttgggtccat tcatcttgtt catcgctgaa    420
atgtctttga tgttgcaagt tagaatcatt tgttcccaac acagaccaac tatgattacc    480
accactgtta tctcttgtat tttcactgtt gttaccttgg ccttctggat caccgacatg    540
tctcaagaaa ttgcttacca attgttcttg aaaaactaca acatgaagca aattgttggt    600
tactcctggt tgtactttat cgctaagatc accttcgctg cttccattat cttccattcc    660
tccgtcttct ccttcaaatt gatgcgtgct atttacattc gtagaaagat cggtcaattc    720
ccattcggtc aatgcaatg tatcttcatt gtttcctgtc aatgtttgat cgttccagct    780
attttcactt tgatcgattc tttcacccac acttacgatg gtttctcctc catgactcaa    840
tgtttgttga tcatctcctt accattgtct tccttgtggg ccacccacac cgctcaaaag    900
ttgcaaacca tgaaggataa cactaaccca ccatctggta cccaattaac catcagagtt    960
gatcgtactt cgacatgaa gttcgtttcc gactcctctg acggttcttt cactgaaaag   1020
accgaagaaa ctttgcca                                                  1038

<210> SEQ ID NO 80
<211> LENGTH: 477
<212> TYPE: PRT
<213> ORGANISM: Saccharomyces castellii

<400> SEQUENCE: 80

Met Ser Asp Ala Pro Pro Leu Ser Glu Leu Phe Tyr Asn Ser Ser
1               5                   10                  15

Tyr Asn Pro Gly Leu Ser Ile Ile Ser Tyr Thr Ser Ile Tyr Gly Asn
            20                  25                  30

Gly Thr Glu Val Thr Phe Asn Glu Leu Gln Ser Ile Val Asn Lys Lys
        35                  40                  45

Ile Thr Glu Ala Ile Met Phe Gly Val Arg Cys Gly Ala Ala Ile Leu
```

```
                50                  55                  60
Thr Ile Ile Val Met Trp Met Ile Ser Lys Lys Lys Thr Pro Ile
65                   70                  75                  80
Phe Ile Ile Asn Gln Val Ser Leu Phe Leu Ile Leu Leu His Ser Ala
                    85                  90                  95
Phe Asn Phe Arg Tyr Leu Leu Ser Asn Tyr Ser Ser Val Thr Phe Ala
                    100                 105                 110
Leu Thr Gly Phe Pro Gln Phe Ile His Arg Asn Asp Val His Val Tyr
                    115                 120                 125
Ala Ala Ala Ser Ile Phe Gln Val Leu Leu Val Ala Ser Ile Glu Ile
                    130                 135                 140
Ser Leu Met Phe Gln Ile Arg Val Ile Phe Lys Gly Asp Asn Phe Lys
145                 150                 155                 160
Arg Ile Gly Thr Ile Leu Thr Ala Leu Ser Ser Leu Gly Leu Ala
                    165                 170                 175
Thr Val Ala Met Tyr Phe Val Thr Ala Ile Lys Gly Ile Ile Ala Thr
                    180                 185                 190
Tyr Lys Asp Val Asn Asp Thr Gln Gln Lys Tyr Phe Asn Val Ala Thr
                    195                 200                 205
Ile Leu Leu Ala Ser Ser Ile Asn Phe Met Thr Leu Ile Leu Val Ile
                    210                 215                 220
Lys Leu Ile Leu Ala Ile Arg Ser Arg Arg Phe Leu Gly Leu Lys Gln
225                 230                 235                 240
Phe Asp Ser Phe His Ile Leu Leu Ile Met Ser Phe Gln Ser Leu Leu
                    245                 250                 255
Ala Pro Ser Ile Leu Phe Ile Leu Ala Tyr Ser Leu Asp Pro Asn Gln
                    260                 265                 270
Gly Thr Asp Val Leu Val Thr Val Ala Thr Leu Leu Val Val Leu Ser
                    275                 280                 285
Leu Pro Leu Ser Ser Met Trp Ala Thr Ala Ala Asn Asn Ala Ser Arg
                    290                 295                 300
Pro Ser Ser Val Gly Ser Asp Trp Thr Pro Ser Asn Ser Asp Tyr Tyr
305                 310                 315                 320
Ser Asn Gly Pro Ser Ser Val Lys Thr Glu Ser Val Lys Ser Asp Glu
                    325                 330                 335
Lys Val Ser Leu Arg Ser Arg Ile Tyr Asn Leu Tyr Pro Lys Ser Lys
                    340                 345                 350
Ser Glu Phe Glu Gln Ser Ser Glu His Thr Tyr Val Asp Lys Val Asp
                    355                 360                 365
Leu Glu Asn Asn Phe Tyr Glu Leu Ser Thr Pro Ile Thr Glu Arg Ser
                    370                 375                 380
Pro Ser Ser Ile Ile Lys Lys Gly Lys Gln Gly Ile Ser Thr Arg Glu
385                 390                 395                 400
Thr Val Lys Lys Leu Asp Ser Leu Asp Asp Ile Tyr Thr Pro Asn Thr
                    405                 410                 415
Ala Ala Asp Glu Glu Ala Arg Lys Phe Trp Ser Glu Asp Val Ser Asn
                    420                 425                 430
Glu Leu Asp Ser Leu Gln Lys Ile Glu Thr Glu Thr Ser Asp Glu Leu
                    435                 440                 445
Ser Pro Glu Met Leu Gln Leu Met Ile Gly Gln Glu Glu Glu Asp Asp
                    450                 455                 460
Asn Leu Leu Ala Thr Lys Lys Ile Thr Val Lys Lys Gln
465                 470                 475
```

<210> SEQ ID NO 81
<211> LENGTH: 1431
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81

| | | | | | |
|---|---|---|---|---|---|
| atgtctgacg | ctccaccacc | attgtccgaa | ttgttctaca | actcctccta | caacccaggt | 60 |
| ttgtctatca | tttcttacac | ttccatttac | ggtaacggta | ctgaagttac | ctttaacgaa | 120 |
| ttacaatcta | tcgtcaacaa | gaagattact | gaagctatca | tgttcggtgt | cagatgtggt | 180 |
| gccgctattt | tgactatcat | tgtcatgtgg | atgatttcta | agaagaaaaa | gaccccaatt | 240 |
| ttcatcatca | accaagtttc | tttattcttg | attttgttgc | actccgcttt | caacttcaga | 300 |
| tacttgttgt | ctaactactc | ttccgtcact | ttcgccttga | ccggtttccc | acaattcatc | 360 |
| cacagaaacg | acgtccacgt | ctacgctgct | gcttctatct | tccaagtctt | gttggtcgct | 420 |
| tctattgaaa | tttccttaat | gttccaaatc | agagtcattt | tcaagggtga | taacttcaag | 480 |
| agaattggta | ctatcttgac | cgctttgtcc | tcttctttgg | gtttagctac | tgttgctatg | 540 |
| tactttgtca | ccgctattaa | gggtattatt | gctacctaca | aggatgttaa | cgatactcaa | 600 |
| caaaagtact | tcaacgttgc | tactatcttg | ttggcttcct | ctatcaactt | tatgaccttg | 660 |
| atcttggtta | tcaagttgat | cttggctatc | agatccagaa | gattcttggg | tttgaaacaa | 720 |
| ttcgactctt | tccatatctt | gttgatcatg | tcttttcaat | ctttgttggc | cccatccatt | 780 |
| ttgttcattt | tggcttactc | tttggaccca | aaccaaggta | ccgacgtctt | ggttactgtc | 840 |
| gctactttgt | tggtcgtctt | atctttgcca | ttgtcctcca | tgtgggctac | tgctgctaac | 900 |
| aacgcctcca | gaccatcctc | tgttggttcc | gactggactc | catctaactc | cgactactac | 960 |
| tctaacggtc | catcttctgt | caagaccgaa | tctgtcaaat | ctgatgaaaa | ggtctccttg | 1020 |
| agatccagaa | tttacaactt | gtacccaaag | tctaagtctg | aattcgaaca | atcctccgaa | 1080 |
| cacacttacg | ttgacaaggt | cgacttggaa | aacaacttct | acgaattgtc | cacccccaatc | 1140 |
| accgaaagat | ctccatcttc | tatcattaag | aagggtaagc | aaggtatttc | tactagagaa | 1200 |
| accgtcaaaa | agttggactc | cttggatgac | atttacactc | caaacactgc | tgctgatgaa | 1260 |
| gaagccagaa | agttctggtc | tgaagatgtt | tctaacgaat | tggattcctt | acaaaaaatc | 1320 |
| gaaactgaaa | cttccgatga | attatcccca | gaaatgttac | aattgatgat | tggtcaagaa | 1380 |
| gaagaagacg | ataacttatt | ggctaccaag | aagatcaccg | tcaagaagca | a | 1431 |

<210> SEQ ID NO 82
<211> LENGTH: 348
<212> TYPE: PRT
<213> ORGANISM: Schizosaccharomyces octosporus

<400> SEQUENCE: 82

Met Arg Glu Pro Trp Trp Lys Asn Tyr Tyr Thr Met Asn Gly Thr Gln
1               5                   10                  15

Val Gln Asn Gln Ser Ile Pro Ile Leu Ser Thr Gln Gly Tyr Ile Gln
            20                  25                  30

Val Pro Leu Ser Thr Ile Asp Lys Ala Glu Arg Asn Arg Ile Leu Thr
        35                  40                  45

Gly Met Thr Val Ser Ala Gln Leu Ala Leu Gly Val Leu Ile Met Val
    50                  55                  60

Met Ser Ile Leu Leu Ser Ser Pro Glu Lys Arg Lys Thr Pro Val Phe
65                  70                  75                  80

Ile Val Asn Ser Ala Ser Ile Ile Ser Met Cys Ile Arg Ala Ile Leu
                85                  90                  95

Met Ile Val Asn Leu Cys Ser Glu Ser Tyr Ser Leu Ala Val Met Tyr
            100                 105                 110

Gly Phe Val Phe Glu Leu Val Gly Gln Tyr Val His Val Phe Asp Ile
        115                 120                 125

Leu Val Met Ile Ile Gly Thr Ile Ile Ile Thr Ala Glu Val Ser
    130                 135                 140

Met Leu Leu Gln Val Arg Ile Ile Cys Ala His Asp Arg Lys Thr Gln
145                 150                 155                 160

Arg Ile Val Thr Cys Ile Ser Ser Gly Leu Ser Leu Ile Val Val Ala
                165                 170                 175

Phe Trp Phe Thr Asp Met Cys Gln Glu Ile Lys Tyr Leu Leu Trp Leu
            180                 185                 190

Thr Pro Tyr Asn Asn His Gln Ile Ser Gly Tyr Tyr Trp Val Tyr Phe
        195                 200                 205

Val Gly Lys Ile Leu Phe Ala Val Ser Ile Met Phe His Ser Ala Val
    210                 215                 220

Phe Ser Tyr Lys Leu Phe His Ala Ile Gln Ile Arg Lys Lys Ile Gly
225                 230                 235                 240

Gln Phe Pro Phe Gly Pro Met Gln Cys Ile Leu Ile Ser Cys Gln
                245                 250                 255

Cys Leu Phe Val Pro Ala Ile Phe Thr Ile Ile Asp Ser Phe Ile His
            260                 265                 270

Thr Tyr Asp Gly Phe Ser Ser Met Thr Gln Cys Leu Leu Ile Val Ser
        275                 280                 285

Leu Pro Leu Ser Ser Leu Trp Ala Ser Ser Thr Ala Leu Lys Leu Gln
    290                 295                 300

Ser Leu Lys Ser Thr Thr Ser Pro Gly Asp Thr Thr Gln Val Ser Ile
305                 310                 315                 320

Arg Val Asp Arg Thr Tyr Asp Ile Lys Arg Ile Pro Thr Glu Glu Leu
                325                 330                 335

Ser Ser Val Asp Glu Thr Glu Ile Lys Lys Trp Pro
            340                 345

<210> SEQ ID NO 83
<211> LENGTH: 1044
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
atgcgtgaac catggtggaa gaactactac accatgaacg gtacccaagt ccaaaaccaa      60
tccatcccaa ttttgtccac ccaaggttac attcaagttc cattgtccac catcgataag     120
gctgaaagaa acagaatttt gactggtatg accgtttctg ctcaattggc cttgggtgtc     180
ttgatcatgg tcatgtctat tttgttgtcc tccccagaaa agagaaagac cccagttttc     240
atcgtcaact ctgcctctat catttccatg tgtattagag ctatcttgat gattgtcaac     300
ttgtgttctg aatcctactc tttggctgtt atgtacggtt tcgtcttcga attggttggt     360
caatacgttc acgttttga cattttggtt atgattattg gtaccatcat cattattacc     420

-continued

```
gctgaagttt ccatgttgtt gcaagtcaga attatttgtg ctcacgacag aaagactcaa      480
agaattgtta cctgtatctc ttctggttta tccttgatcg tcgttgcctt ctggttcact      540
gatatgtgtc aagaaattaa gtacttgttg tggttgaccc catacaacaa ccaccaaatc      600
tctggttact actgggttta cttcgtcggt aagatcttgt tcgccgtttc cattatgttc      660
cactctgccg tcttctccta caagttgttc cacgctatcc aaattagaaa gaagattggt      720
caattcccat tcggtccaat gcaatgtatt ttaattattt cctgtcaatg tttgttcgtt      780
ccagctattt tcactatcat cgactctttc atccacactt acgacggttt ttcctccatg      840
acccaatgtt tgttgatcgt ctctttgcca ttgtcctcct tgtgggcctc ttccactgct      900
ttaaagttgc aatctttgaa gtctaccacc tctccaggtg acactactca agtttccatt      960
agagtcgaca gaacctacga catcaagaga atcccaactg aagaattgtc ttctgttgac     1020
gaaaccgaaa tcaagaagtg gcca                                           1044
```

<210> SEQ ID NO 84
<211> LENGTH: 430
<212> TYPE: PRT
<213> ORGANISM: Aspergillus nidulans

<400> SEQUENCE: 84

Met Ala Thr His Asn Gln Ile Ser Asp Gln Cys Gln Trp Ser Tyr Pro
1               5                   10                  15

Glu Val Phe Thr Thr Gln Ala Val Glu Glu Pro Thr Ala Glu Pro Ala
            20                  25                  30

Ser Tyr His Leu His Ser Thr Leu Thr Ile Met Ala Ser Asn Phe Asp
        35                  40                  45

Pro Trp Asn Gln Thr Ile Thr Phe Arg Leu Glu Asp Gly Thr Pro Phe
    50                  55                  60

Asp Ile Ser Val Asp Tyr Leu Asp Gly Ile Leu Gln Tyr Ser Ile Arg
65                  70                  75                  80

Ala Cys Val Asn Tyr Ala Ala Gln Leu Gly Ala Ser Val Ile Leu Phe
                85                  90                  95

Val Ile Leu Val Leu Leu Thr Arg Ala Glu Lys Arg Ala Ser Cys Leu
            100                 105                 110

Phe Trp Leu Asn Ser Leu Ala Leu Leu Leu Asn Phe Ala Arg Leu Leu
        115                 120                 125

Cys Asp Val Leu Phe Phe Thr Gly Asn Phe Val Arg Ile Tyr Thr Leu
    130                 135                 140

Ile Ser Ala Asp Glu Ser Arg Val Thr Ala Ser Asp Leu Ala Thr Ser
145                 150                 155                 160

Ile Val Gly Ala Ile Met Thr Ala Leu Leu Thr Thr Ile Glu Ile
                165                 170                 175

Ser Leu Val Leu Gln Val Gln Val Val Cys Ser Asn Leu Arg Arg Ile
            180                 185                 190

Tyr Arg Arg Ala Leu Leu Cys Val Ser Ala Val Val Ala Thr Ala Thr
        195                 200                 205

Ile Ala Ile Arg Tyr Ser Leu Leu Ala Val Asn Ile Arg Ala Ile Leu
    210                 215                 220

Glu Phe Ser Asp Pro Thr Thr Tyr Asn Trp Leu Glu Ser Leu Ala Thr
225                 230                 235                 240

Val Ala Leu Thr Ile Ser Ile Cys Tyr Phe Cys Val Ile Phe Val Thr
                245                 250                 255

```
Lys Leu Gly Phe Ala Ile Arg Leu Arg Arg Lys Leu Gly Leu Ser Glu
                260                 265                 270

Leu Gly Pro Met Lys Val Val Phe Ile Met Gly Cys Gln Thr Leu Val
            275                 280                 285

Ile Pro Gly Lys Arg Thr Leu Ser Ser Leu Ile Pro Pro Val Ile Val
        290                 295                 300

Ser Ile Thr His Tyr Val Ser Asp Val Pro Glu Leu Gln Thr Asn Val
305                 310                 315                 320

Leu Thr Ile Val Ala Leu Ser Leu Pro Leu Ser Ile Trp Ala Gly
                325                 330                 335

Thr Thr Ile Asp Lys Pro Val Thr His Ser Asn Val Arg Asn Leu Trp
                340                 345                 350

Gln Ile Leu Ser Phe Ser Gly Tyr Arg Pro Lys Gln Ser Thr Tyr Ile
            355                 360                 365

Ala Thr Thr Thr Thr Ala Thr Thr Asn Ala Lys Gln Cys Thr His Cys
        370                 375                 380

Tyr Ser Glu Ser Arg Leu Leu Thr Glu Lys Ser Gly Arg Asn Asn
385                 390                 395                 400

Asp Thr Ser Ser Lys Ser Ser Ser Gln Tyr Gly Ile Ala Val Glu His
                405                 410                 415

Asp Ile Ser Val Arg Ser Ala Arg Arg Glu Ser Phe Asp Val
                420                 425                 430

<210> SEQ ID NO 85
<211> LENGTH: 1293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
atggctaccc acaaccaaat ctctgatcaa tgtcaatggt cttacccaga agtcttcacc      60
actcaagctg tcgaagaacc aaccgccgaa ccagcttctt accacttgca ctctaccttg     120
actattatgg cttctaactt cgacccatgg aaccaaacca ttccttcag attggaagac     180 ggtactccat cgacatttc tgtcgactac ttggacggta tcttgcaata tctctatcaga     240 gcttgtgtca actacgctgc tcaattgggt gcttctgtca ttttgtttgt tatcttggtc     300
ttgttgacta gagccgaaaa aagagcttct tgtttgttct ggttaaactc cttagctttg     360 tgttgaact cgccagatt gttgtgtgac gtcttgttct tcaccggtaa cttcgtcaga     420
atttacactt tgatctccgc tgacgaatct agagttactg cttccgactt ggctacttcc     480
atcgtcggtg ctatcatgac cgctttgttg ttgaccacta ttgaaatttc tttggttttg     540
caagtccaag tcgtttgttc taacttgaga agaatctaca aagagccctt gttgtgtgtt     600
tccgccgtcg ttgccactgc taccattgct attagatact ccttgttggc tgtcaacatt     660
agagctattt tggaattctc cgacccaact acttacaact ggttggaatc tttagctacc     720
gtcgccttga ccatctccat ctgttacttc tgtgtcatct tcgtcaccaa gttaggtttc     780
gctattagat tgagaagaaa gttgggttta tctgaattgg gtccaatgaa ggtcgtcttc     840
atcatgggtt gtcaaaacctt ggtcatccca ggtaaaagaa ccttgtcttc tttgattcca     900
ccagtcattg tttctattac tcactacgtc tccgacgtcc cagaattgca aactaacgtt     960
ttgactatcg tcgccttgtc cttgccattg tcctctattt gggctggtac caccattgac    1020
aagccagtca ctcactctaa cgttagaaac ttgtggcaaa tcttgtcctt ctctggttac    1080
```

```
agaccaaagc aatctaccta cattgctacc actactaccg ctactaccaa cgctaagcaa    1140
tgtacccact gttactctga atctagattg ttgactgaaa aggaatctgg tcgtaacaac    1200
gacacttctt ctaagtcttc ctcccaatac ggtatcgctg tcgaacacga tatttccgtt    1260
agatctgctc gtcgtgaatc ttttgacgtc tag                                 1293
```

<210> SEQ ID NO 86
<211> LENGTH: 369
<212> TYPE: PRT
<213> ORGANISM: Aspergillus oryzae

<400> SEQUENCE: 86

```
Met Asp Ser Lys Phe Asp Pro Tyr Ser Gln Asn Leu Thr Phe His Ala
1               5                   10                  15

Ala Asp Gly Thr Pro Phe Gln Val Pro Val Met Thr Leu Asn Asp Phe
            20                  25                  30

Tyr Gln Tyr Cys Ile Gln Ile Cys Ile Asn Tyr Gly Ala Gln Phe Gly
        35                  40                  45

Ala Ser Val Ile Ile Phe Ile Ile Leu Leu Leu Thr Arg Pro Asp
    50                  55                  60

Lys Arg Ala Ser Ser Val Phe Phe Leu Asn Gly Gly Ala Leu Leu Leu
65                  70                  75                  80

Asn Met Gly Arg Leu Leu Cys His Met Ile Tyr Phe Thr Thr Asp Phe
                85                  90                  95

Val Lys Ala Tyr Gln Tyr Phe Ser Ser Asp Tyr Ser Arg Ala Pro Thr
            100                 105                 110

Ser Ala Tyr Ala Asn Ser Ile Leu Gly Val Val Leu Thr Thr Leu Leu
        115                 120                 125

Leu Val Cys Ile Glu Thr Ser Leu Val Leu Gln Val Gln Val Val Cys
    130                 135                 140

Ala Asn Leu Arg Arg Arg Tyr Arg Thr Val Leu Leu Cys Val Ser Ile
145                 150                 155                 160

Leu Val Ala Leu Ile Pro Val Gly Leu Arg Leu Gly Tyr Met Val Glu
                165                 170                 175

Asn Cys Lys Thr Ile Val Gln Thr Asp Thr Pro Leu Ser Leu Val Trp
            180                 185                 190

Leu Glu Ser Ala Thr Asn Ile Val Ile Thr Ile Ser Ile Cys Phe Phe
        195                 200                 205

Cys Ser Ile Phe Ile Ile Lys Leu Gly Phe Ala Ile His Gln Arg Arg
    210                 215                 220

Arg Leu Gly Val Arg Asp Phe Gly Pro Met Lys Val Ile Phe Val Met
225                 230                 235                 240

Gly Cys Gln Thr Leu Thr Val Pro Ala Leu Leu Ser Ile Leu Gln Tyr
                245                 250                 255

Ala Val Ser Val Pro Glu Leu Asn Ser Asn Ile Met Thr Leu Val Thr
            260                 265                 270

Ile Ser Leu Pro Leu Ser Ser Ile Trp Ala Gly Val Ser Leu Thr Arg
        275                 280                 285

Ser Ser Thr Glu Asn Ser Pro Ser Arg Gly Ala Leu Trp Asn Arg
    290                 295                 300

Leu Thr Asp Ser Thr Gly Thr Arg Ser Asn Gln Thr Ser Ser Thr Asp
305                 310                 315                 320

Thr Ala Val Ala Met Thr Tyr Pro Ser Asn Lys Ser Ser Thr Val Cys
                325                 330                 335
```

```
Tyr Ala Asp Gln Ser Ser Val Lys Arg Gln Tyr Asp Pro Glu Gln Gly
            340                 345                 350

His Gly Ile Ser Val Glu His Asp Val Ser Val His Ser Cys Gln Arg
        355                 360                 365

Leu

<210> SEQ ID NO 87
<211> LENGTH: 1110
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 87
atggactcta agttcgaccc atactctcaa aacttgactt tccacgctgc tgacggtacc     60
ccatttcaag ttccagtcat gaccttgaac gacttttacc aatactgtat tcaaatttgt    120
atcaactacg gtgctcaatt cggtgcttcc gtcatcattt tcattatctt gttgttattg    180
actagaccag acaaaagagc ttcttctgtt ttcttcttaa acggtggtgc cttgttgttg    240
aacatgggta gattgttgtg tcacatgatt tacttcacta ctgacttcgt caaggcttac    300
caatacttct cttctgatta ctctagagcc ccaacctctg cctacgctaa ctccattttg    360
ggtgtcgtct tgaccacctt gttgttggtt tgtatcgaaa cctccttggt tttacaagtc    420
caagtcgtct gtgctaactt gagacgtaga tacagaaccg tcttattgtg tgtttctatc    480
ttggtcgcct tgatcccagt cggtttgaga ttgggttaca tggttgaaaa ctgtaagact    540
attgttcaaa ctgatacccc attgtctttg gtttggttgg aatctgctac taacatcgtc    600
attaccatct ccatctgttt cttctgttct atcttcatca tcaagttggg tttcgccatt    660
caccaaagaa gaagattggg tgtcagagat ttcggtccaa tgaaggtcat tttcgtcatg    720
ggttgtcaaa ctttgactgt tccagctttg ttgtctattt tgcaatacgc tgtctctgtc    780
ccagaattga actctaacat tatgactttg gttactatct ctttgccatt gtcctccatt    840
tgggctggtg tttctttgac ccgttcttcc tccaccgaaa actctccatc cagaggtgct    900
ttgtggaacc gtttgaccga ctctaccggt accagatcta accaaacctc ttccaccgac    960
accgccgtcg ctatgaccta cccatctaac aagtcttcta ctgtctgtta cgccgatcaa   1020
tcttctgtca agagacaata cgatccagaa caaggtcacg gtatctctgt tgaacacgat   1080
gtttctgtcc actcctgtca aagattgtag                                    1110

<210> SEQ ID NO 88
<211> LENGTH: 412
<212> TYPE: PRT
<213> ORGANISM: Beauvaria bassiana
<400> SEQUENCE: 88

Met Asp Gly Ser Ser Ala Pro Ser Ser Pro Thr Pro Asp Pro Thr Phe
1               5                   10                  15

Asp Arg Phe Ala Gly Asn Val Thr Phe Phe Leu Ala Asp His Ile Thr
            20                  25                  30

Thr Thr Ser Val Pro Met Pro Val Leu Asn Ala Tyr Tyr Asp Glu Ser
        35                  40                  45

Leu Cys Thr Thr Met Asn Tyr Gly Ala Gln Leu Gly Ala Cys Leu Val
    50                  55                  60

Met Leu Val Val Val Val Ala Leu Thr Pro Ala Ala Lys Leu Ala Arg
```

|     |     |     |     | 65  |     |     |     |     | 70  |     |     |     |     | 75  |     |     |     |     | 80  |
|-----|-----|-----|-----|-----|-----|-----|-----|-----|-----|-----|-----|-----|-----|-----|-----|-----|-----|-----|-----|

Arg Pro Ala Ser Ala Leu His Leu Val Gly Leu Leu Cys Ala Val
                85                      90                      95

Arg Ser Gly Leu Leu Phe Ala Tyr Phe Val Ser Pro Ile Ser His Phe
            100                     105                     110

Tyr Gln Val Trp Ala Gly Asp Phe Ser Ala Val Ser Arg Tyr Trp
        115                     120                     125

Asp Ala Ser Leu Ala Ala Asn Thr Leu Ala Phe Pro Leu Val Val Val
    130                     135                     140

Val Glu Ala Ala Leu Ile Asn Gln Ala Trp Thr Met Val Ala Phe Trp
145                     150                     155                     160

Pro Arg Ala Ala Lys Ala Ala Cys Ala Cys Ser Ala Val Ile Val
                165                     170                     175

Leu Leu Thr Ile Gly Thr Arg Leu Ala Tyr Thr Ile Val Gln Asn His
            180                     185                     190

Ala Ile Val Thr Ala Val Pro Pro Glu His Phe Leu Trp Ala Ile Gln
        195                     200                     205

Trp Ser Ala Val Met Gly Ala Val Ser Ile Phe Trp Phe Cys Ala Val
    210                     215                     220

Phe Asn Val Lys Leu Val Cys His Leu Val Ala Asn Arg Gly Ile Leu
225                     230                     235                     240

Pro Ser Ile Ser Val Val Asn Pro Met Glu Val Leu Val Met Thr Asn
                245                     250                     255

Gly Thr Leu Met Ile Ile Pro Ser Ile Phe Ala Gly Leu Glu Trp Ala
            260                     265                     270

Lys Phe Thr Asn Phe Glu Ser Gly Ser Leu Thr Leu Thr Ser Val Ile
        275                     280                     285

Ile Ile Leu Pro Leu Gly Thr Leu Ala Ala Gln Arg Ile Ser Gly Gln
    290                     295                     300

Gly Ser Gln Gly Tyr Gln Ala Gly His Leu Phe His Glu Gln Gln Gln
305                     310                     315                     320

Gln Gln Ala Arg Thr Arg Ser Gly Ala Phe Gly Ser Ala Ser Gln Gln
                325                     330                     335

Ser His Pro Thr Asn Lys Val Pro Ser Ser Ile Thr Leu Ser Thr Ser
            340                     345                     350

Gly Thr Pro Ile Thr Pro Gln Ile Ser Ala Gly Ser Arg Pro Glu Leu
        355                     360                     365

Pro Leu Val Asp Arg Ser Glu Arg Leu Asp Pro Ile Asp Leu Glu Leu
370                     375                     380

Gly Arg Ile Asp Ala Phe Arg Gly Ser Ser Asp Phe Ser Pro Ser Thr
385                     390                     395                     400

Ala Arg Pro Lys Arg Met Gln Arg Asp Asn Phe Ala
                405                     410

<210> SEQ ID NO 89
<211> LENGTH: 1239
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
atggatggtt cttctgctcc atcttctcca actccagatc caaccttcga cagattcgcc      60
ggtaacgtca ctttcttctt ggctgaccac atcaccacta cctccgttcc aatgccagtc     120

```
ttgaacgcct actacgacga atccttgtgt actaccatga actacggtgc tcaattaggt    180
gcttgtttag ttatgttggt tgtcgttgtt gctttgaccc cagctgctaa gttggctaga    240
agaccagctt ctgctttgca tttggttggt ttgttgttgt gtgctgttag atccggtttg    300
ttgtttgctt acttcgtctc cccaatctct cacttttacc aagtttgggc tggtgacttc    360
tctgccgttt ccagaagata ctgggacgct tctttggctg ccaacacttt agctttccca    420
ttggttgtcg tcgttgaagc tgctttgatc aaccaagctt ggaccatggt tgctttctgg    480
ccaagagccg ctaaggccgc tgcctgtgct tgttctgctg tcattgtctt gttgactatt    540
ggtactagat tggcctacac tatcgtccaa aaccacgcta ttgttactgc cgtcccacca    600
gaacacttct tgtgggctat tcaatggtcc gctgttatgg gtgctgtttc catcttctgg    660
ttttgtgccg tttcaacgt caagttggtc tgtcacttag tcgctaacag aggtatcttg    720
ccatctatct ctgttgttaa cccaatggaa gtcttggtta tgactaacgg taccttgatg    780
attatcccat ctatcttcgc tggtttggaa tgggctaagt tcaccaactt cgaatccggt    840
tctttgactt tgacttccgt tattattatc ttgccattgg gtactttggc tgcccaacgt    900
atttctggtc aaggttccca aggttaccaa gctggtcact tattccacga caacaacaa    960 caacaagctc gtacccgttc cggtgccttc ggttccgctt ctcaacaatc ccatccaact   1020
aacaaggttc catcctctat taccttgtct acctctggta ctccaattac tccacaaatc   1080
tctgccggtt cccgtccaga attaccattg gttgatagat ccgaacgttt ggacccaatt   1140
gacttggaat tgggtagaat cgatgctttc agaggttctt ccgacttctc tccatccacc   1200
gctagaccaa agcgtatgca acgtgataac ttcgcctag                          1239

<210> SEQ ID NO 90
<211> LENGTH: 360
<212> TYPE: PRT
<213> ORGANISM: Candida lustianiae

<400> SEQUENCE: 90

Met Asn Pro Ala Asp Ile Asn Ile Glu Tyr Thr Leu Gly Asp Thr Ala
1               5                   10                  15

Phe Ser Ser Thr Phe Ala Asp Phe Glu Ala Trp Lys Thr Arg Asn Thr
                20                  25                  30

Gln Phe Ala Ile Val Asn Gly Val Ala Leu Ala Cys Gly Ile Ile Leu
            35                  40                  45

Met Val Val Ser Trp Ile Ile Val Asn Lys Arg Ala Pro Ile Phe
        50                  55                  60

Ala Met Asn Gln Thr Met Leu Val Ile Met Val Ile Lys Ser Ala Met
65                  70                  75                  80

Tyr Leu Lys His Ile Met Gly Pro Leu Asn Ser Leu Thr Phe Arg Phe
                85                  90                  95

Thr Gly Leu Met Glu Glu Ser Trp Ala Pro Tyr Asn Val Tyr Val Thr
                100                 105                 110

Ile Asn Val Leu His Val Leu Val Ala Ala Val Glu Ser Ser Leu
            115                 120                 125

Val Phe Gln Ile His Val Phe Lys Ser Ser Arg Ala Arg Val Ala
        130                 135                 140

Gly Arg Ala Ile Val Ser Ala Met Ser Thr Leu Ala Leu Leu Ile Val
145                 150                 155                 160

Ser Leu Tyr Leu Tyr Ser Thr Val Arg His Ala Gln Thr Leu Arg Ala
                165                 170                 175
```

Glu Leu Ser His Gly Asp Thr Thr Thr Val Glu Pro Trp Val Asp Asn
            180                 185                 190

Val Pro Leu Ile Leu Phe Ser Ala Ser Leu Asn Val Leu Cys Leu Leu
        195                 200                 205

Leu Ala Leu Lys Leu Val Phe Ala Val Arg Thr Arg Arg His Leu Gly
210                 215                 220

Leu Arg Gln Phe Asp Ser Phe His Ile Leu Ile Ile Met Ala Thr Gln
225                 230                 235                 240

Thr Phe Val Ile Pro Ser Ser Leu Val Ile Ala Asn Tyr Arg Tyr Ala
                245                 250                 255

Ser Ser Pro Leu Leu Ser Ser Ile Ser Ile Ile Val Ala Val Cys Asn
            260                 265                 270

Leu Pro Leu Cys Ser Leu Trp Ala Cys Ser Asn Asn Asn Ser Ser Tyr
        275                 280                 285

Pro Thr Ser Ser Gln Asn Thr Ile Leu Ser Arg Tyr Glu Thr Glu Thr
    290                 295                 300

Ser Gln Ala Thr Asp Ala Ser Ser Thr Thr Cys Ala Gly Ile Ala Glu
305                 310                 315                 320

Lys Gly Phe Asp Lys Ser Pro Asp Ser Pro Thr Phe Gly Asp Gln Asp
                325                 330                 335

Ser Val Ser Ile Ser His Ile Leu Asp Ser Leu Glu Lys Asp Val Glu
            340                 345                 350

Gly Val Thr Thr His Arg Leu Thr
        355                 360

<210> SEQ ID NO 91
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
atgaacccag ctgacatcaa catcgaatac accttgggtg atactgcttt ctcttccact      60
ttcgctgatt tcgaagcttg gaaaactaga aacactcaat tcgctattgt caacggtgtc     120
gctttggctt gtggtattat cttgatggtc gtttcttgga ttattattgt taacaagaga     180
gctccaatct tcgctatgaa ccaaactatg ttggttatca tggttattaa gtccgctatg     240
tacttgaagc atatcatggg tccattgaac tccttgacct tccgtttcac cggtttaatg     300
gaagaatcct gggctccata acgtttac gtcactatta acgtcttgca tgttttgttg     360
gtcgctgctg tcgaatcctc tttggtcttc caaatccatg ttgttttcaa gtcttctaga     420
gccagagttg ctggtagagc cattgtttct gctatgtcca ctttggcctt gttgatcgtt     480
tctttgtact tgtactctac tgttagacat gctcaaactt tgcgtgctga attatctcat     540
ggtgacacta ccactgttga accatgggtc gataacgttc cattgatttt gttttccgct     600
tctttgaacg ttttgtgttt gttgttggcc ttgaaattgg ttttcgctgt cagaaccaga     660
agacatttag gtttaagaca attcgactct ttccacatct tgattattat ggccactcaa     720
actttcgtta tcccatcctc tttggtcatc gctaactaca gatacgcttc ttccccattg     780
ttgtcttcca tttccatcat cgtcgccgtc tgtaacttgc cattgtgttc cttgtgggct     840
tgttctaaca caactcttc ctacccaact tcttctcaaa acactatttt gtccagatac     900
gaaactgaaa cctctcaagc tactgacgct tcctctacca cctgtgccgg tattgctgaa     960

```
aagggtttcg acaagtctcc agactctcca actttcggtg accaagactc cgtctctatc   1020
tcccatatct tggactcttt ggaaaaggat gttgaaggtg tcaccaccca tagattgact   1080
tag                                                                 1083
```

<210> SEQ ID NO 92
<211> LENGTH: 419
<212> TYPE: PRT
<213> ORGANISM: Candida tenuis

<400> SEQUENCE: 92

```
Met Asp Ser Tyr Leu Leu Asn His Pro Gly Asp Ile Ser Leu Asn Phe
1               5                   10                  15

Ala Leu Pro Leu Ser Asp Glu Val Tyr Thr Ile Thr Phe Asn Asp Leu
            20                  25                  30

Asp Ser Gln Ser Ser Phe Ser Ile Gln Tyr Leu Val Ile His Ser Cys
        35                  40                  45

Ala Ile Thr Val Cys Leu Thr Leu Leu Val Leu Asn Leu Phe Ile
    50                  55                  60

Arg Asn Lys Lys Thr Pro Val Phe Val Leu Asn Gln Val Ile Leu Phe
65                  70                  75                  80

Phe Ala Ile Val Arg Ser Ser Leu Phe Ile Gly Phe Met Lys Ser Pro
                85                  90                  95

Leu Ser Thr Ile Thr Ala Ser Phe Thr Gly Ile Ile Ser Asp Asp Gln
            100                 105                 110

Lys His Phe Tyr Lys Val Ser Val Ala Ala Asn Ala Ala Leu Ile Ile
        115                 120                 125

Leu Val Met Leu Ile Gln Val Ser Phe Thr Tyr Gln Ile Tyr Ile Ile
    130                 135                 140

Phe Arg Ser Pro Glu Val Arg Lys Phe Gly Val Phe Met Thr Ser Ala
145                 150                 155                 160

Leu Gly Val Leu Met Ala Val Thr Phe Gly Phe Tyr Val Asn Ser Ala
                165                 170                 175

Val Ala Ser Thr Lys Gln Tyr Gln His Ile Phe Tyr Ser Thr Asp Pro
            180                 185                 190

Tyr Ile Met Asp Ser Trp Val Thr Gly Leu Pro Pro Ile Leu Tyr Ser
        195                 200                 205

Ala Ser Val Ile Ala Met Ser Leu Val Leu Val Leu Lys Leu Val Ala
    210                 215                 220

Ala Val Arg Thr Arg Arg Tyr Leu Gly Leu Lys Gln Phe Ser Ser Tyr
225                 230                 235                 240

His Ile Leu Leu Ile Met Phe Thr Gln Thr Leu Phe Val Pro Thr Ile
                245                 250                 255

Leu Thr Ile Leu Ala Tyr Ala Phe Tyr Gly Tyr Asn Asp Ile Leu Ile
            260                 265                 270

His Ile Ser Thr Thr Ile Thr Val Val Leu Leu Pro Phe Thr Ser Ile
        275                 280                 285

Trp Ala Ser Ile Ala Asn Asn Ser Arg Ser Leu Met Ser Ala Ala Ser
    290                 295                 300

Leu Tyr Phe Ser Gly Ser Asn Ser Ser Leu Ser Glu Leu Ser Ser Pro
305                 310                 315                 320

Ser Pro Ser Asp Asn Asp Thr Leu Asn Glu Asn Val Phe Ala Phe Phe
                325                 330                 335

Pro Asp Lys Leu Gln Lys Met Asn Ser Ser Glu Ala Val Ser Ala Val
```

340                 345                 350
Asp Lys Val Val His Asp His Phe Asp Thr Ile Ser Gln Lys Ser
            355                 360                 365

Ile Pro His Asp Ile Leu Glu Ile Leu Gln Gly Asn Glu Gly Gln
        370                 375                 380

Met Lys Glu His Ile Ser Val Tyr Ser Asp Asp Ser Phe Ser Lys Thr
385                 390                 395                 400

Thr Pro Pro Ile Val Gly Gly Asn Leu Leu Ile Thr Asn Thr Asp Ile
                405                 410                 415

Gly Met Lys

<210> SEQ ID NO 93
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
atggactcct acttgttgaa ccatccaggt gacatctctt tgaacttcgc cttgccattg      60
tccgatgaag tctacactat taccttcaac gacttagact ctcaatcttc tttttccatt    120
caatacttgg tcatccactc ttgtgccatt accgtctgtt tgaccttgtt ggttttgttg    180
aacttgttca tcagaaacaa gaagactcca gtcttcgttt tgaaccaagt catcttgttc    240
ttcgctatcg tcagatcttc tttgttcatc ggttttatga agtctccatt gtccaccatc    300
accgcctctt tcaccggtat catttctgat gaccaaaaac acttctacaa ggtctccgtc    360
gctgctaacg ccgctttgat cattttggtc atgttgattc aagtttcttt cacttaccaa    420
atctacatta ttttcagatc cccagaagtt agaaagttcg gtgtcttcat gacctccgcc    480
ttgggtgtct tgatggctgt taccttcggt ttttacgtta actccgctgt cgcttctacc    540
aagcaatacc aacacatctt ctactctacc gacccataca tcatggactc ttgggtcact    600
ggtttgccac caatcttgta ctctgcttcc gtcatcgcta tgtctttggt cttggttttg    660
aagttggtcg ctgctgtcag aaccagaaga tacttgggtt tgaagcaatt ctcctcctac    720
cacatcttgt tgattatgtt cacccaaaac ttgttcgttc aaccatcttt gaccatctta    780
gcttacgctt tctacggtta aacgatatc ttgatccata tttctaccac catcaccgtt    840
gtcttgttgc cattcacctc catttgggct tctatcgcca caactctag atccttgatg    900 tctgccgctt ccttgtactt ctccggttcc aactcctctt tgtctgaatt gtcttctcca    960
tctccatctg ataacgacac tttgaacgaa aacgtcttcg cctttttccc agacaagttg   1020
caaaagatga actcttctga agccgtttct gctgtcgaca aggtcgttgt tcacgaccac   1080
tttgatacca tctcccaaaa gtctatccca cacgacatct ggaaattttt gcaaggtaac   1140
gaaggtggtc aaatgaagga acacatctct gtctactctg atgactcttt ctccaagact   1200
actccaccaa ttgtcggtgg taacttgttg atcaccaaca ccgacatcgg tatgaag     1257

<210> SEQ ID NO 94
<211> LENGTH: 369
<212> TYPE: PRT
<213> ORGANISM: Neosartorya fischeri

<400> SEQUENCE: 94

Met Asn Ser Thr Phe Asp Pro Trp Thr Gln Asn Ile Thr Leu Thr Gln
1               5                   10                  15

Ser Asp Gly Thr Thr Val Ile Ser Ser Leu Ala Leu Ala Asp Asp Tyr
            20                  25                  30

Leu His Tyr Met Ile Arg Leu Gly Ile Asn Tyr Gly Ala Gln Leu Gly
        35                  40                  45

Ala Cys Ala Val Leu Leu Val Leu Leu Leu Thr Arg Pro Glu
 50                  55                  60

Lys Arg Val Ser Ser Val Phe Val Leu Asn Val Ala Ala Leu Leu Ala
 65                  70                  75                  80

Asn Ile Ile Arg Leu Gly Cys Gln Leu Ser Tyr Phe Ser Thr Gly Phe
                85                  90                  95

Ala Arg Met Tyr Ala Leu Leu Ala Gly Asp Phe Ser Arg Val Ser Arg
            100                 105                 110

Gly Ala Tyr Ala Gly Gln Val Met Ala Ser Val Phe Phe Thr Ile Val
            115                 120                 125

Phe Ile Cys Val Glu Ala Ser Leu Val Leu Gln Val Gln Val Val Cys
130                 135                 140

Ser Asn Leu Arg Arg Gln Tyr Arg Ile Leu Leu Gly Ala Ser Thr
145                 150                 155                 160

Leu Ala Ala Leu Val Pro Ile Gly Val Arg Leu Thr Tyr Ser Val Leu
                165                 170                 175

Asn Cys Met Val Ile Met His Ala Gly Thr Met Asp His Leu Asp Trp
            180                 185                 190

Leu Glu Ser Ala Thr Asn Ile Val Thr Thr Val Ser Ile Cys Phe Phe
            195                 200                 205

Cys Ala Val Phe Val Val Lys Leu Gly Leu Ala Ile Lys Met Arg Lys
210                 215                 220

Arg Leu Gly Val Lys Gln Phe Gly Pro Met Arg Val Ile Phe Ile Met
225                 230                 235                 240

Gly Cys Gln Thr Met Thr Ile Pro Ala Ile Phe Ala Ile Cys Gln Tyr
                245                 250                 255

Phe Ser Arg Ile Pro Glu Phe Ser His Asn Val Leu Thr Leu Val Ile
            260                 265                 270

Ile Ser Leu Pro Leu Ser Ser Ile Trp Ala Gly Phe Ala Leu Val Gln
            275                 280                 285

Ala Asn Ser Thr Ala Arg Ser Thr Glu Ser Arg His His Leu Trp Asn
            290                 295                 300

Ile Leu Ser Ser Asp Gly Ala Thr Arg Asp Lys Pro Ser Gln Cys Val
305                 310                 315                 320

Ser Ser Pro Met Thr Ser Pro Thr Thr Cys Tyr Ser Glu Gln Ser
                325                 330                 335

Thr Ser Lys Pro Gln Gln Asp Pro Glu Asn Gly Phe Gly Ile Ser Val
            340                 345                 350

Ala His Asp Ile Ser Ile His Ser Phe Arg Lys Asp Ala His Gly Asp
            355                 360                 365

Ile

<210> SEQ ID NO 95
<211> LENGTH: 1110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95

-continued

```
atgaactcca ccttcgaccc atggacccaa aacattactt tgactcaatc cgacggtacc      60
actgtcatct cctctttggc tttggccgat gactacttgc actacatgat tagattgggt     120
atcaactacg gtgcccaatt gggtgcttgt gctgttttgt tgttggtttt gttattgttg     180
actagaccag aaaagagagt ttcttctgtc ttcgttttga acgtcgctgc tttgttggct     240
aacatcatca gattgggttg tcaattgtcc tacttctcta ccggtttcgc tagaatgtac     300
gccttgttgg ccggtgactt ctccagagtc tctcgtggtg cttacgccgg tcaagttatg     360
gcctccgtct tcttcaccat tgtcttcatt tgtgttgaag cttctttggt tttgcaagtt     420
caagtcgtct gttctaactt gagaagacaa tacagaatct tgttattggg tgcttccact     480
ttggctgcct tggttccaat tggtgttcgt ttgacttact ccgttttaaa ctgtatggtt     540
attatgcacg ctggtactat ggaccacttg gattggttgg aatctgctac caacatcgtt     600
actaccgttt ctatttgttt cttctgtgct gttttcgttg tcaaattagg tttggctatc     660
aagatgagaa agcgtttggg tgtcaaacaa ttcggtccaa tgagagttat cttcatcatg     720
ggttgtcaaa ccatgaccat cccagctatt ttcgctattt gtcaatactt ctctagaatt     780
ccagaatttt ctcataacgt tttgactttg gttatcatct ctttgccatt gtcttctatc     840
tgggccggtt ttgctttggt ccaagccaac tctaccgcca gatctaccga atctagacat     900
catttgtgga acattttgtc ttccgatggt gctaccagag acaagccatc ccaatgtgtt     960
tcttctccaa tgacctctcc aaccactacc tgttactccg aacaatccac ctctaagcca    1020
caacaagacc cagaaaacgg ttttggtatt tctgttgccc acgatatttc catccactct    1080
ttcagaaagg acgcccacgg tgatatttag                                     1110
```

<210> SEQ ID NO 96
<211> LENGTH: 566
<212> TYPE: PRT
<213> ORGANISM: Neurospora crassa

<400> SEQUENCE: 96

Met Ala Ser Ser Ser Pro Pro Ala Asp Ile Phe Ser Gly Ile Thr
1               5                   10                  15

Gln Ser Leu Asn Ser Thr His Ala Thr Leu Thr Leu Pro Ile Pro Pro
            20                  25                  30

Ala Asp Arg Asp His Leu Glu Asn Gln Val Leu Phe Leu Phe Asp Asn
        35                  40                  45

His Gly Gln Leu Leu Asn Val Thr Thr Thr Tyr Ile Asp Ala Phe Asn
    50                  55                  60

Asn Met Leu Val Ser Thr Thr Ile Asn Tyr Ala Thr Gln Ile Gly Ala
65                  70                  75                  80

Thr Phe Ile Met Leu Ala Ile Met Leu Leu Met Thr Pro Arg Arg Arg
                85                  90                  95

Phe Lys Arg Leu Pro Thr Ile Ile Ser Leu Leu Ala Leu Cys Ile Asn
            100                 105                 110

Leu Ile Arg Val Val Leu Leu Ala Leu Phe Phe Pro Ser His Trp Thr
        115                 120                 125

Asp Phe Tyr Val Leu Tyr Ser Gly Asp Trp Gln Phe Val Pro Pro Gly
    130                 135                 140

Asp Met Gln Ile Ser Val Ala Ala Thr Val Leu Ser Ile Pro Val Thr
145                 150                 155                 160

Ala Leu Leu Leu Ser Ala Leu Met Val Gln Ala Trp Ser Met Met Gln
                165                 170                 175

```
Leu Trp Thr Pro Leu Trp Arg Ala Leu Val Leu Val Ser Gly Leu
            180                 185                 190

Leu Ser Leu Val Thr Val Ala Met Ser Phe Ala Asn Cys Ile Phe Gln
        195                 200                 205

Ala Lys Asn Ile Leu Tyr Ala Asp Pro Leu Pro Ser Tyr Trp Val Arg
210                 215                 220

Lys Leu Tyr Leu Ala Leu Thr Thr Gly Ser Ile Ser Trp Phe Thr Phe
225                 230                 235                 240

Leu Phe Met Ile Arg Leu Val Met His Met Trp Thr Asn Arg Ser Ile
                245                 250                 255

Leu Pro Ser Met Lys Gly Leu Lys Ala Met Asp Val Leu Ile Ile Thr
            260                 265                 270

Asn Ser Ile Leu Met Leu Ile Pro Val Leu Phe Ala Gly Leu Glu Phe
        275                 280                 285

Leu Asp Ser Ala Ser Gly Phe Glu Ser Gly Ser Leu Thr Gln Thr Ser
    290                 295                 300

Val Val Ile Val Leu Pro Leu Gly Thr Leu Val Ala Gln Arg Ile Ala
305                 310                 315                 320

Thr Arg Gly Tyr Met Pro Asp Ser Leu Glu Ala Ser Ser Gly Pro Asn
                325                 330                 335

Gly Ser Leu Pro Leu Ser Asn Leu Ser Phe Ala Gly Gly Gly Gly Gly
            340                 345                 350

Gly Ser Gly Gly His Lys Asp Lys Glu Asn Gly Gly Gly Ile Ile Pro
        355                 360                 365

Pro Thr Thr Asn Asn Thr Ala Ala Thr Asn Phe Ser Ser Ile Ala
    370                 375                 380

Cys Ser Gly Ile Ser Cys Leu Pro Lys Val Lys Arg Met Thr Ala Ser
385                 390                 395                 400

Ser Ala Ser Ser Ser Gln Arg Pro Leu Leu Thr Met Thr Asn Ser Thr
                405                 410                 415

Ile Ala Ser Asn Asp Ser Ser Gly Phe Pro Ser Pro Gly Ile His Asn
            420                 425                 430

Thr Thr Thr Thr Thr Thr Gln Tyr Gln Tyr Ser Met Gly Met Asn Met
        435                 440                 445

Pro Asn Phe Pro Pro Val Pro Phe Pro Gly Tyr Gln Ser Arg Thr Thr
    450                 455                 460

Gly Val Thr Ser His Ile Val Ser Asp Gly Arg His His Gln Gly Met
465                 470                 475                 480

Asn Arg His Pro Ser Val Asp His Phe Asp Arg Glu Leu Ala Arg Ile
                485                 490                 495

Asp Asp Glu Asp Asp Gly Tyr Pro Phe Ala Ser Ser Glu Lys Ala
            500                 505                 510

Val Met His Gly Asp Asp Asp Val Glu Arg Gly Arg Arg Arg
    515                 520                 525

Ala Leu Pro Pro Ser Leu Gly Val Arg Val Glu Arg Thr Ile Glu
        530                 535                 540

Thr Arg Ser Glu Glu Arg Met Pro Ser Pro Asp Pro Leu Gly Val Thr
545                 550                 555                 560

Lys Pro Arg Ser Phe Glu
                565

<210> SEQ ID NO 97
<211> LENGTH: 1701
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97

```
atggcgtcct cttcctcacc acctgcagac attttctcag ggatcacgca atcactaaat      60
agtacacacg cgacgcttac actaccgatt ccgccagcgg acagggatca tctggaaaat     120
caagtattat ttttgtttga caatcacggt cagttactta atgtaactac aacttacatt     180
gacgctttta acaatatgct ggtctctact actataaact atgcaacgca aattggagct     240
acttttataa tgctagccat tatgttatta atgactccca aaggaggtt caaacgttta      300
ccaacaatta ttagcttgtt agccttatgt attaatttga tcagggtggt tttgctggcc     360
ctgttttttc cttctcactg gacagacttc tacgtgttgt attccggtga ctggcagttt     420
gtacctccag gggatatgca aatatctgtt gctgctacgg ttttgtctat cccagtgacg     480
gcattattat tgagcgcatt gatggttcaa gcctggtcaa tgatgcaatt atggacacca     540
ctgtggaggg cactagtggt actagtgtcc gggctattgt cactggtaac tgtggcaatg     600
agtttcgcga attgcatttt ccaagcgaaa aatattttgt atgccgaccc tttaccctcc     660
tactgggtca gaaaattgta cttagcatta acgactgggt ctataagttg gttcacattc     720
cttttttatga taagattggt tatgcatatg tggacaaaca gatctatatt accaagcatg    780
aagggtttga aggctatgga tgtattgatt attacgaatt ctatattgat gttaatccca     840
gtgttgtttg caggcttgga atttctggat agtgcctctg gatttgagtc cgggtctttg     900
actcaaacct ctgtagtgat tgtcctgcct ttgggtactt tagtagcaca aagaatagct     960
acgaggggtt acatgcccga tagtctggag gcttctagcg gaccaaatgg ttcattgccg    1020
ttatctaatt taagtttcgc tggaggggggc ggtggtggtt ctggggggaca taagataaa    1080
gaaaacggtg gcggtattat accgcctact acgaacaata ctgctgctac taatttttct    1140
tcatcaatcg cgtgttctgg tatatcttgt ttaccaaaag tcaaagaat gaccgcgagt     1200
tcagcctcaa gtagccagag accgttgttg acaatgacta actcaaccat agcgagtaat    1260
gacagttcag gtttcccttc tcctggcata cataatacca ctactacgac aacacaatac    1320
caatattcca tgggaatgaa catgccgaac tttcctccag tcccgttccc aggttaccag    1380
tcacgtacta ccggtgttac ttcccatatt gtgtccgacg gtagacatca ccagggtatg    1440
aacaggcacc catctgttga ccattttgat agggaacttg ctaggattga tgatgaagat    1500
gacgatggtt acccttcgc atcaagtgaa aaggccgtta tgcacggaga cgatgacgac    1560
gatgtggaaa ggggacgtcg tagagctcta ccaccatcct taggtggagt tagagttgaa    1620
aggacgatcg agaccaggag cgaggaacgt atgccatctc cggacccatt gggtgttacg    1680
aagcctagat cattcgagta g                                             1701
```

<210> SEQ ID NO 98
<211> LENGTH: 397
<212> TYPE: PRT
<213> ORGANISM: Pseudogymnoascus destructans

<400> SEQUENCE: 98

```
Met Ser Thr Ala Asn Val His Leu Pro Ala Asp Phe Asp Pro Thr Arg
1               5                   10                  15

Gln Asn Ile Thr Ile Tyr Thr Pro Asp Gly Thr Pro Val Val Ala Thr
            20                  25                  30
```

```
Leu Pro Met Ile Asn Leu Phe Asn Arg Gln Asn Asn Glu Ile Cys Val
            35                  40                  45

Val Tyr Gly Cys Gln Leu Gly Ala Ser Leu Ile Met Phe Leu Val Val
        50                  55                  60

Leu Leu Thr Thr Arg Val Ser Lys Arg Lys Ser Pro Ile Phe Val Leu
65                  70                  75                  80

Asn Val Leu Ser Leu Ile Ile Ser Cys Leu Arg Ser Leu Leu Gln Ile
                85                  90                  95

Leu Tyr Tyr Ile Gly Pro Trp Thr Glu Ile Tyr Arg Tyr Leu Ser Phe
            100                 105                 110

Asp Tyr Ser Thr Val Pro Ala Ser Ala Tyr Ala Asn Ser Val Ala Ala
        115                 120                 125

Thr Leu Leu Thr Leu Phe Leu Leu Ile Thr Ile Glu Ala Ser Leu Val
    130                 135                 140

Leu Gln Thr Asn Val Val Cys Lys Ser Met Ser Ser His Ile Arg Trp
145                 150                 155                 160

Pro Val Thr Ala Leu Ser Met Val Val Ser Leu Leu Ala Ile Ser Phe
                165                 170                 175

Arg Phe Gly Leu Thr Ile Arg Asn Ile Glu Gly Ile Leu Gly Ala Thr
            180                 185                 190

Val Lys Ser Asp Ser Leu Met Phe Ser Gly Ala Ser Leu Ile Ser Glu
        195                 200                 205

Thr Ala Ser Ile Trp Phe Phe Cys Thr Ile Phe Val Ile Lys Leu Gly
    210                 215                 220

Trp Thr Leu Tyr Gln Arg Lys Lys Met Gly Leu Lys Gln Trp Gly Pro
225                 230                 235                 240

Met Gln Ile Ile Thr Ile Met Ala Gly Cys Thr Met Leu Ile Pro Ser
                245                 250                 255

Leu Phe Thr Val Leu Glu Phe Pro Glu Glu Thr Phe Tyr Glu Ala
            260                 265                 270

Gly Thr Leu Ala Ile Cys Leu Val Ala Ile Leu Leu Pro Leu Ser Ser
    275                 280                 285

Val Trp Ala Ala Ala Ile Asp Gly Asp Pro Val Arg Pro His
        290                 295                 300

Gly Ser Thr Pro Lys Phe Ala Ser Phe Asn Met Gly Ser Asp Tyr Lys
305                 310                 315                 320

Ser Ser Ser Ala His Leu Pro Arg Ser Ile Arg Lys Ala Ser Val Pro
                325                 330                 335

Ala Glu His Leu Ser Arg Thr Ser Glu Glu Leu Gly Asp Asp Gly
            340                 345                 350

Thr Leu Asn Arg Gly Gly Ala Tyr Gly Met Asp Arg Met Ser Gly Ser
    355                 360                 365

Ile Ser Pro Arg Gly Val Arg Ile Glu Arg Thr Tyr Glu Val His Thr
370                 375                 380

Ala Gly Arg Gly Gly Ser Ile Glu Arg Glu Asp Ile Phe
385                 390                 395

<210> SEQ ID NO 99
<211> LENGTH: 1194
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 99

```
atgtccactg ccaacgttca tttaccagct gatttcgatc caactagaca aaacatcact      60
atctataccc cagacggtac cccagttgtt gctaccttgc caatgatcaa tttgtttaac     120
agacaaaaca acgaaatctg tgttgtttac ggttgtcaat gggtgcctc tttaattatg     180
ttcttggttg ttttgttgac caccagagtt tccaagagaa aatctccaat cttcgtcttg     240
aacgttttgt ctttgattat ttcttgttta agatccttgt tgcaaatttt atactatatt     300
ggtccatgga ccgagatcta cagatacttg tctttcgatt actctactgt cccagcttcc     360
gcttacgcta attctgttgc tgccacttta ttaaccttat tcttattgat taccattgaa     420
gcttctttag ttttacaaac taacgttgtc tgcaagtcta tgtcttctca cattcgttgg     480
ccagttactg ctttgtccat ggttgtctct ttattggcta tttcttttag attcggtttg     540
accatccgta acatcgaagg tatcttaggt gctactgtca aatccgactc cttaatgttc     600
tctggtgcct ctttgatctc tgaaactgct tctatctggt tcttctgcac tattttcgtt     660
attaaattgg ttggaccttt gtaccaagaa aagaagatgg gtttgaagca atggggtcca     720
atgcaaatta tcactatcat ggctggttgc accatgttga tcccatcctt gttcactgtt     780
ttggaattct tccctgaaga aacttctac gaggccggta ctttggctat ctgtttggtt     840
gctatttgt tgccattatc ttccgtctgg gctgccgctg ctattgatgg tgatgaacca     900
gtccgtccac atggttctac cccaaaattc gcttctttca acatgggttc cgactacaaa     960
tcttcttctg ctcacttgcc aagatctatt agaaaggcct ccgtcccagc tgaacattta    1020
tctagaactt ctgaagaaga gttaggtgac gacggtactt tgaacagagg tggtgcctac    1080
ggtatggaca gaatgtccgg ttctatctcc cctagaggtg tcagaattga aagaacttac    1140
gaagttcata ccgctggtag aggtggttct atcgagagag aggacatctt ctag          1194
```

<210> SEQ ID NO 100
<211> LENGTH: 296
<212> TYPE: PRT
<213> ORGANISM: Hypocrea jecorina

<400> SEQUENCE: 100

```
Met Ser Ser Phe Asp Pro Tyr Thr Gln Asn Ile Thr Ile Leu Val Ser
1               5                   10                  15

Pro Ser Pro Pro Ile Ser Ile Pro Ile Pro Val Ile Asp Ala Phe
            20                  25                  30

Asn Asp Glu Thr Ala Ser Ile Ile Thr Asn Tyr Ala Ala Gln Leu Gly
        35                  40                  45

Ala Ala Leu Ala Met Leu Leu Val Leu Leu Ala Thr Pro Thr Ala
    50                  55                  60

Arg Leu Leu Arg Ala Asp Gly Pro Ser Leu His Ala Leu Ala Leu
65                  70                  75                  80

Leu Val Cys Val Val Arg Thr Val Leu Leu Ile Tyr Phe Phe Leu Thr
                85                  90                  95

Pro Phe Ser His Phe Tyr Gln Val Trp Thr Gly Asp Phe Ser Gln Val
            100                 105                 110

Pro Ala Trp Asn Tyr Arg Ala Ser Ile Ala Gly Thr Val Leu Ser Thr
        115                 120                 125

Leu Leu Thr Val Val Thr Asp Ala Ala Leu Val Asn Gln Ala Trp Thr
    130                 135                 140

Met Val Ser Leu Phe Ala Pro Arg Thr Lys Arg Ala Val Cys Val Leu
145                 150                 155                 160
```

```
Ser Leu Leu Ile Thr Leu Leu Ala Ile Ser Phe Arg Val Ala Tyr Thr
            165                 170                 175

Val Ile Gln Cys Glu Gly Ile Ala Glu Leu Ala Ala Pro Arg Gln Tyr
        180                 185                 190

Ala Trp Leu Ile Arg Ala Thr Leu Ile Phe Asn Ile Cys Ser Ile Ala
            195                 200                 205

Trp Phe Cys Ala Leu Phe Asn Ser Lys Leu Val Ala His Leu Val Thr
210                 215                 220

Asn Arg Gly Val Leu Pro Ser Arg Arg Ala Met Ser Pro Met Glu Val
225                 230                 235                 240

Leu Ile Met Ala Asn Gly Ile Leu Met Ile Val Pro Val Phe Ala
            245                 250                 255

Ile Leu Glu Trp His His Phe Ile Asn Phe Glu Ala Gly Ser Leu Thr
            260                 265                 270

Pro Thr Ser Ile Ala Ile Ile Leu Pro Leu Ser Ser Leu Ala Ala Gln
            275                 280                 285

Arg Ile Ala Asn Thr Ser Ser Ser
    290                 295

<210> SEQ ID NO 101
<211> LENGTH: 891
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
atgtcttcct tcgacccata cactcaaaac attactattt tggtttctcc atcctctcca      60
ccaatttcca ttccaatccc agttatcgac gctttcaacg acgaaaccgc ttctatcatt     120
actaactacg ccgctcaatt aggtgctgct ttggccatgt tattagtttt gttggccgct     180
actccaaccg ctagattgtt aagagctgat ggtccatcct tgttgcacgc tttggccttg     240
ttagtctgtg tcgtcagaac tgtcttattg atctacttct tcttgacccc attctctcac     300
ttctaccaag tctggaccgg tgacttctct caagttccag cttggaacta cagagcttcc     360
attgctggta ccgttttgtc tactttgttg accgttgtta ccgacgctgc tttggttaac     420
caagcttgga ctatggtttc tttattcgct ccaagaacta gagagccgt ttgtgttttg      480 tccttgttaa tcaccttgtt ggccatttct ttcagagtcg cttacaccgt cattcaatgt    540
gaaggtatcg ctgaattggc tgctccaaga caatacgctt ggttgatcag agccactttg     600
atctttaaca tctgttccat tgcctggttc tgtgctttgt tcaactctaa gttggttgct     660
cacttggtta ccaacagagg tgtcttgcca tcccgtagag ccatgtcccc aatggaagtt     720
ttgattatgg ccaacggtat cttgatgatt gttccagttg ttttcgctat cttggaatgg     780
caccacttca ttaacttcga agctggttct ttaaccccaa cctccatcgc cattatcttg     840
ccattgtcct ctttggccgc caaagaatc gccaacactt cttcctctta g               891

<210> SEQ ID NO 102
<211> LENGTH: 367
<212> TYPE: PRT
<213> ORGANISM: Tuber melanosporum

<400> SEQUENCE: 102

Met Glu Gln Ile Pro Val Tyr Glu Arg Pro Gly Phe Asn Pro His Lys
1               5                   10                  15
```

```
Gln Asn Ile Thr Leu Phe Lys His Asp Gly Ser Thr Val Thr Val Gly
         20                  25                  30

Leu His Glu Leu Asp Ala Met Phe Thr His Ser Ile Arg Val Ala Val
     35                  40                  45

Val Phe Ala Ser Gln Ile Gly Ala Cys Ala Leu Leu Ser Val Ile Val
 50                  55                  60

Ala Met Val Thr Lys Arg Glu Lys Arg Ala Leu Phe Phe Leu His
65                   70                  75                  80

Ile Ile Ser Leu Leu Leu Val Val Arg Ser Val Leu Gln Ile Leu
                 85                  90                  95

Tyr Phe Val Gly Pro Trp Ala Glu Thr Tyr Asn Tyr Val Ala Tyr Tyr
            100                 105                 110

Tyr Glu Asp Ile Pro Leu Ser Asp Lys Leu Ile Ser Ile Trp Ala Gly
        115                 120                 125

Ile Ile Gln Leu Ile Leu Asn Ile Cys Ile Leu Leu Ser Leu Ile Leu
130                 135                 140

Gln Val Arg Val Val Tyr Ala Thr Ser Pro Lys Leu Asn Thr Ile Met
145                 150                 155                 160

Thr Leu Val Ser Cys Val Ile Ala Ser Ile Ser Val Gly Phe Phe
                165                 170                 175

Thr Val Ile Val Gln Ile Ser Glu Ala Ile Leu Asn Gly Val Gly Tyr
            180                 185                 190

Asp Gly Trp Val Tyr Lys Val His Arg Gly Val Phe Ala Gly Ala Ile
        195                 200                 205

Ala Phe Phe Ser Phe Ile Phe Ile Phe Lys Leu Ala Phe Ala Ile Arg
210                 215                 220

Arg Arg Lys Ala Leu Gly Leu Gln Arg Phe Gly Pro Leu Gln Val Ile
225                 230                 235                 240

Phe Ile Met Gly Cys Gln Thr Met Ile Val Pro Ala Ile Phe Ala Thr
                245                 250                 255

Leu Glu Asn Gly Val Gly Phe Glu Gly Met Ser Ser Leu Thr Ala Thr
            260                 265                 270

Leu Ala Val Ile Ser Leu Pro Leu Ser Ser Met Trp Ala Ala Ala Gln
        275                 280                 285

Thr Asp Gly Pro Ser Pro Gln Ser Thr Pro Arg Asp Gly Tyr Arg Arg
290                 295                 300

Phe Ser Thr Arg Arg Ser Ala Leu Asn Arg Ser Asp Pro Ser Gly Gly
305                 310                 315                 320

Arg Ser Val Asp Met Asn Thr Leu Asp Ser Thr Gly Asn Asp Ser Leu
                325                 330                 335

Ala Leu His Val Asp Lys Thr Phe Thr Val Glu Ser Ser Pro Ser Ser
            340                 345                 350

Gln Ser Gln Ala Gly Pro His Lys Glu Arg Gly Phe Glu Phe Ala
        355                 360                 365

<210> SEQ ID NO 103
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
atggagcaaa tcccagtcta cgagcgtcca ggtttcaacc cacacaagca aaacattacc        60
```

```
ttgttcaagc atgatggttc tactgttact gtcggtttgc atgagttgga cgccatgttc     120
actcattcca tcagagttgc tgtcgtcttc gcctctcaaa ttggtgcttg tgctttgttg     180
tctgttatcg ttgctatggt caccaagaga gaaagagac gtgctttgtt cttcttgcac      240
attatttcct tgttgttggt cgttgttcgt tccgtcttgc aaatcttgta cttcgtcggt     300
ccatgggctg aaactataa ttacgtcgcc tactactatg aagacattcc tttgtctgac      360
aaattgattt ccatttgggc tggtattatc caattgattt tgaatatctg tattttgtta     420
tctttgatct tgcaagttcg tgtcgtttac gccacctctc aaaattgaa cactattatg      480 actttagtct cttgtgttat cgcttctatt tctgtcggtt tcttctttac tgtcatcgtt     540
caaatttctg aggctatttt aaacggtgtt ggttacgacg gttgggttta caaagtccat     600
agaggtgtct cgctggtgc tatcgccttc ttctctttca tcttcatctt taagttggcc      660
ttcgctatca gaagaagaaa ggctttgggt ttgcaaagat tcggtccatt gcaagttatc     720
ttcatcatgg gttgtcaaac tatgattgtt ccagctatct ttgctacttt ggaaaacggt     780
gttggtttcg aaggtatgtc ctctttgact gctaccttgg ctgtcatttc cttaccattg     840
tcttctatgt gggccgccgc tcaaaccgac ggtccatctc cacaatccac tccaagagac     900
ggttatagaa gattctctac tcgtagatct gccttgaaca gatctgaccc atctggtggt     960
agatctgttg acatgaacac cttggactct accggtaacg attccttagc tttgcacgtt    1020
gataagactt ttactgttga atcttcccca tcctcccaat ctcaagctgg tccacacaag    1080
gaaagaggtt tcgaattcgc ctag                                            1104
```

<210> SEQ ID NO 104
<211> LENGTH: 527
<212> TYPE: PRT
<213> ORGANISM: Dactylellina haptotyla

<400> SEQUENCE: 104

```
Met Asp His Asn Thr Gln His Phe Asn Arg Pro Glu Tyr Ile Glu Ile
1               5                   10                  15

Pro Val Pro Pro Ser Lys Gly Phe Asn Pro His Thr Asn Pro Ala Phe
            20                  25                  30

Phe Ile Tyr Pro Asp Gly Ser Asn Met Thr Phe Trp Phe Gly Gln Ile
        35                  40                  45

Asp Asp Phe Arg Arg Asp Gln Leu Phe Thr Asn Thr Ile Phe Ser Ile
    50                  55                  60

Gln Ile Gly Ala Ala Leu Val Ile Leu Cys Val Met Phe Cys Val Thr
65                  70                  75                  80

His Ala Asp Lys Arg Lys Thr Ile Val Tyr Leu Leu Asn Val Ser Asn
                85                  90                  95

Leu Phe Val Val Ile Ile Arg Gly Val Phe Phe Val His Tyr Phe Met
            100                 105                 110

Gly Gly Leu Ala Arg Thr Tyr Thr Thr Phe Thr Trp Asp Thr Ser Asp
        115                 120                 125

Val Gln Gln Ser Glu Lys Ala Thr Ser Ile Val Ser Ser Ile Cys Ser
    130                 135                 140

Leu Ile Leu Met Ile Gly Thr Gln Ile Ser Leu Leu Gln Val Arg
145                 150                 155                 160

Ile Cys Tyr Ala Leu Asn Pro Arg Ser Lys Thr Ala Ile Leu Val Thr
                165                 170                 175

Cys Gly Ser Ile Ser Gly Ile Ala Thr Thr Ala Tyr Leu Leu Leu Gly
```

|     |     |     |     | 180 |     |     |     |     | 185 |     |     |     |     | 190 |
| --- | --- | --- | --- | --- | --- | --- | --- | --- | --- | --- | --- | --- | --- | --- |

Ala Tyr Thr Ile Gln Leu Arg Glu Lys Pro Pro Asp Met Lys Phe Met
            195                     200                 205

Lys Trp Ala Lys Pro Val Val Asn Ala Leu Val Ala Leu Ser Ile Val
210                 215                     220

Ser Phe Ser Gly Ile Phe Ser Trp Arg Met Phe Gln Ser Val Arg Asn
225                         230                 235                 240

Arg Arg Arg Met Gly Phe Thr Gly Ile Gly Ser Leu Glu Ser Leu Leu
                245                     250                 255

Ala Ser Gly Phe Gln Cys Leu Val Phe Pro Gly Leu Val Thr Thr Ala
            260                     265                 270

Leu Thr Val Ala Gly Ser Thr Trp Tyr Ile Ala Val Asn Leu Thr Thr
        275                     280                 285

Pro Ser Asp Leu Thr Ala Ile Tyr Asn Cys Ser Ala Phe Phe Ala Tyr
    290                     295                 300

Ala Phe Ser Ile Pro Leu Leu Lys Glu Arg Ala Gln Val Glu Lys Thr
305                 310                     315                 320

Ile Ser Val Val Ile Ala Ile Ala Gly Val Leu Val Ala Tyr Gly
                325                     330                 335

Asp Gly Ala Asp Asp Gly Ser Thr Ser Asn Gly Glu Lys Ala Arg Leu
                340                     345                 350

Gly Gly Asn Val Leu Ile Gly Ile Gly Ser Val Leu Tyr Gly Leu Tyr
            355                     360                 365

Glu Val Leu Tyr Lys Lys Leu Leu Cys Pro Pro Ser Gly Ala Ser Pro
    370                     375                 380

Gly Arg Ser Val Val Phe Ser Asn Thr Val Cys Ala Cys Ile Gly Ala
385                     390                     395                 400

Phe Thr Leu Leu Phe Leu Trp Ile Pro Leu Pro Leu Leu His Trp Ser
                405                     410                 415

Gly Trp Glu Ile Phe Glu Leu Pro Thr Gly Lys Thr Ala Lys Leu Leu
            420                     425                 430

Gly Ile Ser Ile Ala Ala Asn Ala Thr Phe Ser Gly Ser Phe Leu Ile
        435                     440                 445

Leu Ile Ser Leu Thr Gly Pro Val Leu Ser Ser Val Ala Ala Leu Leu
    450                     455                 460

Thr Ile Phe Leu Val Ala Ile Thr Asp Arg Ile Leu Phe Gly Arg Glu
465                     470                     475                 480

Leu Thr Ser Ala Ala Ile Leu Gly Gly Leu Leu Ile Ile Ala Ala Phe
                485                     490                 495

Ala Leu Leu Ser Trp Ala Thr Trp Lys Glu Met Ile Glu Glu Asn Glu
            500                     505                 510

Lys Asp Thr Ile Asp Ser Ile Ser Asp Val Gly Asp His Asp Asp
        515                     520                 525

<210> SEQ ID NO 105
<211> LENGTH: 1584
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
atggaccaca acacccaaca cttcaacaga cctgaataca ttgaaatccc agttccacca     60
tctaagggtt tcaacccaca caccaaccct gctttcttca tctacccaga cggttctaat    120

```
atgaccttttt ggttcggtca aatcgacgat ttcagacgtg accaattatt cactaacacc    180
atctttccca ttcaaattgg tgccgctttg gtcatcttat gtgtcatgtt ttgtgttacc    240
cacgctgata agcgtaaaac cattgtctac ttgttaaacg tttccaactt gttcgttgtt    300
atcattagag gtgttttctt tgttcattac ttcatgggtg gttggccag aacctatacc     360 actttcacct gggatacttc tgatgttcaa caatctgaga aggctacttc cattgtctcc    420
tctatttgtt ctttgatttt gatgatcggt actcaaatct ccttattgtt gcaagtcaga    480
atctgttacg ctttgaaccc aagatccaag accgctatct tggttacttg tggttctatt    540
tccggtattg ctaccactgc ttatttattg ttgggtgctt acactattca attgagagaa    600
aagccaccag acatgaagtt catgaagtgg gctaagccag ttgttaacgc tttggttgcc    660
ttgtccattg tctcctttc tggtattttc tcttggagaa tgttccaatc tgtcagaaac     720
agaagaagaa tgggtttcac tggtatcggt tccttggaat ctttgttggc ttctggtttc    780
caatgtttag tcttccctgg tttggttact accgctttga ccgtcgccgg ttccacttgg    840
tatatcgctg ttaacttaac tactccatct gacttgaccg ctatttacaa ctgttccgct    900
tttttcgctt atgctttctc cattccattg ttaaaggaaa gagctcaagt tgaaaagacc    960
atttctgttg tcattgctat cgctggtgtc ttagtcgttg cttacggtga cggtgctgac   1020
gacggttcca cctctaacgg tgaaaaggct agattgggtg gtaacgtctt gatcggtatc   1080
ggttctgtct tgtatggttt atacgaagtc ttgtataaga agttattatg tccaccatct   1140
ggtgcttccc caggtagatc tgttgttttc tctaataccg tttgtgcttg catcggtgct   1200
ttcactttgt tattcttgtg gatcccattg ccattgttgc actggtccgg ttgggaaatt   1260
tttgaattgc caaccggtaa gactgctaag ttattgggta tttccattgc cgctaacgcc   1320
accttctctg gttctttctt gatcttaatt tctttgactg gtccagtttt gtcctctgtt   1380
gccgccttgt tgaccatttt cttggttgct attactgaca gaattttatt cggtagagaa   1440
ttgacttctg ctgccatttt gggtggtttg ttgatcatcg ctgccttcgc tttgttatct   1500
tgggctactt ggaaggaaat gattgaagag aacgagaagg atactatcga ttccatctct   1560
gacgttggtg accacgatga ctag                                           1584
```

<210> SEQ ID NO 106
<211> LENGTH: 468
<212> TYPE: PRT
<213> ORGANISM: Sporothrix scheckii

<400> SEQUENCE: 106

```
Met Lys Pro Ala Ala Gly Pro Ala Ser Ser Pro Phe Asp Pro Phe Asn
1               5                   10                  15

Gln Thr Phe Tyr Leu Thr Gly Pro Asp Asn Thr Val Pro Val Ser
                20                  25                  30

Val Pro Gln Val Asp Tyr Ile Trp His Tyr Ile Ile Gly Thr Ser Ile
            35                  40                  45

Asn Tyr Gly Ser Gln Ile Gly Ala Cys Leu Leu Met Leu Leu Val Met
        50                  55                  60

Leu Thr Leu Thr Ser Lys Ser Arg Phe Ser Arg Ala Ala Thr Leu Ile
65                  70                  75                  80

Asn Val Ala Ser Leu Leu Ile Gly Val Ile Arg Cys Val Leu Leu Ala
                85                  90                  95

Val Tyr Phe Thr Ser Ser Leu Thr Glu Leu Tyr Ala Leu Phe Val Gly
                100                 105                 110
```

Asp Tyr Ser Gln Val Arg Arg Ser Asp Leu Cys Val Ser Ala Val Ala
        115                 120                 125

Thr Phe Phe Ser Leu Pro Gln Leu Val Leu Ile Glu Ala Ala Leu Phe
    130                 135                 140

Leu Gln Ala Tyr Ser Met Ile Lys Met Trp Pro Ser Leu Trp Arg Ala
145                 150                 155                 160

Val Val Leu Ala Met Ser Val Val Ala Val Cys Ala Ile Gly Phe
                165                 170                 175

Lys Phe Ala Ser Val Val Met Arg Met Arg Ser Thr Leu Thr Leu Asp
                180                 185                 190

Asp Ser Leu Asp Phe Trp Leu Val Glu Val Asp Leu Ala Phe Thr Ala
                195                 200                 205

Thr Thr Ile Phe Trp Phe Cys Phe Ile Tyr Ile Ile Arg Leu Val Ile
    210                 215                 220

His Met Trp Glu Tyr Arg Ser Ile Leu Pro Pro Met Gly Ser Val Ser
225                 230                 235                 240

Ala Met Glu Val Leu Val Met Thr Asn Gly Ala Leu Met Leu Val Pro
                245                 250                 255

Val Ile Phe Ala Ala Ile Glu Ile Asn Gly Leu Ser Ser Phe Glu Ser
                260                 265                 270

Gly Ser Leu Val His Thr Ser Val Ile Val Leu Leu Pro Leu Gly Ser
                275                 280                 285

Leu Ile Ala Gln Ala Met Thr Arg Pro Asp Gly Tyr Val Gln Arg Thr
    290                 295                 300

Asn Thr Ser Gly Ala Ser Gly Ala Ser Gly Ala His Pro Gly Arg Asn
305                 310                 315                 320

Gly Ser Gly His Gly Gly His Gly Gly Ala Tyr Ser Arg Ala Met Thr
                325                 330                 335

Asn Thr Leu Asn Thr Leu Asp Thr Leu Asp Thr Val Asp Ser Lys Thr
                340                 345                 350

Ser Ile Met His His His His His His Arg Asn His Ser Asn Gly
    355                 360                 365

Met Ser Lys Thr Lys Ala Asn Ser Gly Thr Trp Ser His Ala Ser Asp
    370                 375                 380

Ala Asn Ser Thr Asn Ala Met Ile Ser Gly Gly Ile Ala Thr Gln Val
385                 390                 395                 400

Arg Ile Gln Ala Asn Gln Ser Thr Leu Gly Asn Thr Gly Met Ser Gly
                405                 410                 415

Gly Ser Gly Ala Pro Asn Ser His Thr Arg Asn Asn Ser Leu Ala Ala
                420                 425                 430

Met Glu Pro Val Glu Lys Gln Leu His Asp Ile Asp Ala Thr Pro Leu
                435                 440                 445

Ser Ala Ser Asp Cys Arg Val Trp Val Asp Arg Glu Val Glu Val Arg
450                 455                 460

Arg Asp Met Val
465

<210> SEQ ID NO 107
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

```
atgaaacccg ccgctggacc tgcatctagt ccattcgacc catttaacca aacgttttac      60
ctgaccggtc cagataatac cactgtacca gtctcagtcc cacaagttga ctatatctgg     120
cattatatta ttggaacatc catcaactat ggttctcaga tcggagcctg tttacttatg     180
cttcttgtga tgttgacatt gacttcaaag tcaagatttt ctcgtgcggc cactctgatt     240
aacgtagcaa gcttattgat tggagtaatt cgttgtgttc ttttagctgt ctactttact     300
tcttctctaa ctgaattgta tgctctgttc gttggcgatt acagccaggt ccgtaggtct     360
gatctttgtg tctctgctgt ggcaaccttc tttagtctac acaattagt tctaatagaa      420
gctgctttgt ttctacaggc ttatagtatg atcaaaatgt ggccatccct gtggagagca     480
gtggttttag ctatgtcagt ggtggtggct gtgtgtgcaa tcggtttta gttcgcgtcc      540
gttgttatgc gtatgaggtc aacattaaca ttggacgatt ctttggattt ctggctagtg     600
gaagtcgatc tggcttttac agcaactact atttttggt tttgtttcat ctacattata      660
aggttggtta ttcatatgtg ggaatataga agcattttac caccaatggg gtctgtttct     720
gctatggagg ttcttgttat gaccaatgga gcgttgatgt tagttccagt gatttttcgcc    780
gcaatagaaa tcaatggttt atcaagcttt gaatcagggt cactggttca tacatcagtg     840
attgtattat tacctttagg tagcttgata gcgcaagcaa tgacacgtcc agatgggtat     900
gtccaaagaa cgaatacatc tggagcatca ggcgcaagtg gtgcacatcc tggtagaaat     960
ggatccggac acgtggtca tggtggtgcg tactcaagag ccatgactaa taccctaaat     1020
acattggata cattggatac cgtagacagt aagacatcca taatgcatca tcatcatcac    1080
catcatagaa accactcaaa tggcatgagt aagacgaagg caaatagtgg aacatggagc    1140
catgcgtcag atgctaactc caccaatgct atgatcagcg tggtatcgc aactcaagtt     1200
aggattcaag ctaatcagtc aaccttagga aatacgggga tgtccggggg ctctggagcc    1260
cctaattctc atactcgtaa taactcattg gctgctatgg aaccagtgga gaagcaactg    1320
catgatatcg atgccacacc tttaagcgca tctgattgca gggtctgggt tgatcgtgag    1380
gtcgaggtca gagggacat ggtctag                                         1407
```

<210> SEQ ID NO 108
<211> LENGTH: 369
<212> TYPE: PRT
<213> ORGANISM: Yarrowia lipolytica

<400> SEQUENCE: 108

```
Met Gln Leu Pro Pro Arg Pro Asp Phe Asp Ile Ala Thr Leu Val Ala
1               5                  10                  15

Ser Ile Thr Val Pro Glu Thr Glu Leu Val Leu Gly Gln Met Pro Leu
            20                  25                  30

Gly Ala Leu Glu Gln Leu Tyr Gln Asn Arg Leu Arg Leu Ala Ile Leu
        35                  40                  45

Phe Gly Val Arg Val Gly Ala Ala Val Leu Thr Leu Ile Ala Met His
    50                  55                  60

Leu Ile Ser Lys Lys Asn Arg Thr Lys Ile Leu Phe Leu Ala Asn Gln
65                  70                  75                  80

Met Ser Leu Ile Met Leu Ile Ile His Ala Ala Leu Tyr Phe Arg Phe
                85                  90                  95

Leu Leu Gly Pro Phe Ala Ser Met Leu Met Met Val Ala Tyr Ile Val
            100                 105                 110
```

Asp Pro Arg Ser Asn Val Ser Asn Asp Ile Ser Val Ser Val Ala Thr
            115                 120                 125

Asn Val Phe Met Met Leu Met Ile Met Ser Val Gln Leu Ser Leu Ala
130                 135                 140

Val Gln Thr Arg Ser Val Phe His Ala Trp Leu Lys Ser Arg Ile Tyr
145                 150                 155                 160

Val Thr Val Gly Leu Ile Leu Leu Ser Leu Val Val Phe Val Phe Trp
                165                 170                 175

Thr Thr His Thr Ile Val Ser Cys Ile Val Leu Thr His Pro Thr Arg
            180                 185                 190

Asp Leu Pro Ser Met Gly Trp Thr Arg Leu Ala Ser Asp Val Ser Phe
        195                 200                 205

Ala Cys Ser Ile Ser Phe Ala Ser Leu Val Leu Leu Ala Lys Leu Val
    210                 215                 220

Thr Ala Ile Arg Val Arg Lys Thr Leu Gly Lys Lys Pro Leu Gly Tyr
225                 230                 235                 240

Thr Lys Val Leu Val Ile Met Ser Thr Gln Ser Leu Val Val Pro Ser
                245                 250                 255

Ile Leu Ile Ile Val Asn Tyr Ala Leu Pro Glu Lys Asn Ser Trp Ile
            260                 265                 270

Leu Ser Gly Val Ala Tyr Leu Met Val Val Leu Ser Leu Pro Leu Ser
        275                 280                 285

Ser Ile Trp Ala Thr Ala Val His Asp Asp Glu Met Gln Ser Asn Tyr
    290                 295                 300

Leu Leu Ser Ala Leu Lys Asp Gly His Val Gln Pro Ser Glu Ser Lys
305                 310                 315                 320

Leu Lys Thr Val Phe Leu Asn Arg Leu Arg Pro Phe Ser Thr Thr Thr
                325                 330                 335

Asn Arg Asp Asp Glu Ser Ser Val Asp Ser Pro Ala Met Pro Ser Pro
            340                 345                 350

Glu Ser Asp Val Thr Phe Leu Asn Thr Gly Phe Glu Cys Asp Glu Lys
        355                 360                 365

Met

<210> SEQ ID NO 109
<211> LENGTH: 1110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
atgcaattgc caccacgtcc agacttcgac attgccactt tggttgcctc tatcactgtt      60
ccagaaactg aattggtctt gggtcaaatg ccattgggtg ctttagaaca attgtaccaa     120
aacagattgc gtttggctat tttgttcggt gtcagagtcg gtgctgctgt tttgaccttg     180
attgctatgc acttaatctc caagaagaac agaaccaaga tcttgttctt ggctaaccaa     240
atgtctttga tcatgttgat catccatgct gctttgtact tcagattctt gttgggtcca     300
ttcgcctcca tgttgatgat ggttgcttac atcgttgatc aagatctaac cgtctctaac     360
gatatctctg tttctgttgc caccaacgtt tcatgatgt tgatgattat gtccgtccaa     420
ttgtctttgg ctgttcaaac ccgttctgtt ttccacgctt ggttgaagtc tcgtatttac     480
gttaccgttg gtttaatctt gttgtccttg gtcgtcttcg tcttctggac cacccacact     540

```
atcgtttctt gtatcgtttt aacccatcca actagagact tgccatctat ggggttggact    600 agattagctt ctgacgtttc cttcgcttgt tctatctctt tcgcttcttt ggtcttgttg    660
gctaagttgg tcaccgccat cagagttaga aagaccttgg gtaagaagcc attgggttac    720
accaaggttt tggtcatcat gtccactcaa tctttagtcg ttccatctat cttgattatc    780
gttaactacg ctttgccaga aaaaaactct tggatcttgt ctggtgtcgc ttacttgatg    840
gttgttttgt ccttaccatt gtcctccatt tgggctaccg ccgtccatga cgacgaaatg    900
caatccaact acttgttgtc tgccttgaaa gatggtcacg ttcaaccatc cgaatctaag    960
ttgaagactg ttttcttgaa cagattgaga ccattctcta ctaccactaa cagagacgat   1020
gaatcctctg ttgattcccc agccatgcca tctccagaat ctgatgttac cttcttgaac   1080
actggtttcg aatgtgacga aaagatgtag                                    1110
```

<210> SEQ ID NO 110
<211> LENGTH: 471
<212> TYPE: PRT
<213> ORGANISM: Torulaspora delbrueckii

<400> SEQUENCE: 110

```
Met Ser Asp Ser Ala Gln Asn Leu Ser Asp Leu Ala Phe Asn Ser Ser
1               5                   10                  15

Tyr Asn Pro Leu Asp Ser Phe Ile Thr Phe Thr Ser Ile Tyr Gly Asp
            20                  25                  30

Asn Thr Ala Val Lys Phe Ser Val Leu Gln Asp Met Val Asp Val Asn
        35                  40                  45

Thr Asn Glu Ala Ile Val Tyr Gly Thr Arg Cys Gly Ala Ser Val Leu
    50                  55                  60

Thr Gln Ile Ile Met Trp Met Ile Ser Lys Asn Arg Arg Thr Pro Val
65                  70                  75                  80

Phe Ile Ile Asn Gln Val Ser Leu Thr Leu Ile Leu Ile His Ser Ala
                85                  90                  95

Leu Tyr Phe Lys Tyr Leu Leu Ser Gly Phe Ser Val Val Tyr Gly
            100                 105                 110

Leu Thr Ala Phe Pro Gln Leu Ile Lys Pro Gly Asp Leu Arg Ala Phe
        115                 120                 125

Ala Ala Ala Asn Ile Val Met Val Leu Leu Val Ala Ser Ile Glu Ala
    130                 135                 140

Ser Leu Ile Phe Gln Val Lys Val Ile Phe Thr Gly Asp Asn Met Lys
145                 150                 155                 160

Arg Val Gly Leu Ile Leu Thr Ile Ile Cys Thr Cys Met Gly Leu Ala
                165                 170                 175

Thr Val Thr Met Tyr Phe Ile Thr Ala Val Lys Ser Ile Val Ser Leu
            180                 185                 190

Tyr Arg Asp Met Ser Gly Ser Ser Thr Val Leu Tyr Asn Val Ser Leu
        195                 200                 205

Ile Met Leu Ala Ser Ser Ile His Phe Met Ala Leu Ile Leu Val Val
    210                 215                 220

Lys Leu Phe Leu Ala Val Arg Ser Arg Arg Phe Leu Gly Leu Lys Gln
225                 230                 235                 240

Phe Asp Ser Phe His Ile Leu Leu Ile Ile Ser Cys Gln Thr Leu Leu
                245                 250                 255

Val Pro Ser Leu Leu Phe Ile Ile Ala Tyr Ser Phe Pro Ser Ser Lys
            260                 265                 270
```

| | | | | | | | | | | | | | | |
|---|---|---|---|---|---|---|---|---|---|---|---|---|---|---|
|Asn|Ile|Glu|Ser|Leu|Lys|Ala|Ile|Ala|Val|Leu|Thr|Val|Leu|Ser|
| | | |275| | | |280| | | |285| | | |

Leu Pro Leu Ser Ser Met Trp Ala Thr Ala Ala Asn Asn Phe Thr Asn
      290                     295                    300

Ser Ser Ser Ser Gly Ser Asp Ser Ala Pro Thr Asn Gly Gly Phe Tyr
305                  310                     315                 320

Gly Arg Gly Ser Ser Asn Leu Tyr Pro Glu Lys Thr Asp Asn Arg Ser
            325                     330                     335

Pro Lys Gly Ala Arg Asn Ala Leu Tyr Glu Leu Arg Ser Lys Asn Asn
         340                     345                  350

Ala Glu Gly Gln Ala Asp Ile Tyr Thr Val Thr Asp Ile Glu Asn Asp
      355                     360                  365

Ile Phe Asn Asp Leu Ser Lys Pro Val Glu Gln Asn Ile Phe Ser Asp
    370                     375                 380

Val Gln Ile Ile Asp Ser His Ser Leu His Lys Ala Cys Ser Lys Glu
385                  390                     395                 400

Asp Pro Val Met Thr Leu Tyr Thr Pro Asn Thr Ala Ile Glu Gly Glu
             405                     410                  415

Glu Arg Lys Leu Trp Thr Ser Asp Cys Ser Cys Ser Thr Asn Gly Ser
         420                     425                  430

Thr Pro Val Lys Lys Ser Thr Gly Glu Tyr Ala Asn Leu Pro Pro
    435                     440                 445

His Leu Leu Arg Tyr Asp Glu Asn Tyr Asp Glu Glu Ala Gly Gly Arg
    450                     455                 460

Arg Lys Ala Ser Leu Lys Trp
465                  470

<210> SEQ ID NO 111
<211> LENGTH: 1416
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 111

```
atgtctgact ccgcccaaaa cttgtccgat ttggccttca actcttctta taacccattg    60
gactccttta ttacctttac ctctatctac ggtgataaca ctgctgttaa gttctccgtt   120
ttacaagaca tggttgacgt taatactaat gaagccatcg tttacggtac ccgttgtggt   180
gcttctgtct tgacccaaat tatcatgtgg atgatttcta aaaacagaag aaccccagtc   240
tttattatta ccaagttttc tttgactttg attttaattc actctgcctt gtacttcaag   300
tacttgttgt ctggtttcgg ttccgttgtc tacggtttga ctgctttccc acaattgatt   360
aagccaggtg atttgagagc tttcgctgct gctaacatcg ttatggtctt gttggtcgct   420
tctattgaag cttccttaat cttccaagtc aaagttatct tcaccggtga taacatgaag   480
agagtcggtt taatcttgac tattatttgt acttgtatgg gtttagctac tgttaccatg   540
tactttatta ctgccgtcaa gtctattgtc tctttgtacc gtgacatgtc tggttcctcc   600
accgttttat ataacgtttc tttaattatg ttggcttcct ccatccactt tatggctttg   660
atcttggttg tcaaattgtt cttggctgtt agatctagaa gattcttggg tttgaaacaa   720
ttcgattctt tccacatttt tgttgatcat cttgtcaaa ctttgttggt tccatcttta   780
ttattcatta ttgcttactc ttttccatct tctaagaaca ttgaatcttt gaaggctatc   840
gctgttttga ccgtcgtttt gtctttgcca ttgtcttcta tgtgggctac tgctgctaat   900
```

```
aacttcacta actcttcctc ctccggttcc gactccgctc caaccaatgg tggtttctac    960
ggtagaggtt cttccaactt gtatcctgaa aagactgata cagatcccc aaagggtgcc   1020
agaaacgctt tatacgaatt aagatctaag aacaatgctg agggtcaagc tgatatttac   1080
accgttaccg atattgaaaa cgatattttc aacgatttgt ccaagccagt tgagcaaaac   1140
attttctctg atgttcaaat tattgattct cattctttgc ataaggcttg ttctaaagaa   1200
gacccagtca tgactttgta cactccaaac actgctattg aaggtgagga gagaaaattg   1260
tggacttctg actgttcctg ttccactaac ggttccaccc cagttaagaa gaagtccacc   1320
ggtgaatacg ccaatttacc accacactta ttaagatatg atgaaaacta cgatgaagaa   1380
gctggtggta gacgtaaggc ctccttgaaa tggtag                            1416
```

<210> SEQ ID NO 112
<211> LENGTH: 354
<212> TYPE: PRT
<213> ORGANISM: Komagataella pastoris

<400> SEQUENCE: 112

```
Met Glu Glu Tyr Ser Asp Ser Phe Asp Pro Ser Gln Gln Leu Leu Asn
1               5                   10                  15

Phe Thr Ser Leu Tyr Gly Glu Thr Asp Ala Thr Phe Ala Glu Leu Asp
            20                  25                  30

Asp Tyr His Phe Tyr Val Val Lys Tyr Ala Ile Val Tyr Gly Ala Arg
        35                  40                  45

Ile Gly Val Gly Met Phe Cys Thr Leu Met Leu Phe Val Val Ser Lys
    50                  55                  60

Ser Trp Lys Thr Pro Ile Phe Val Leu Asn Gln Ser Ser Leu Ile Leu
65                  70                  75                  80

Leu Ile Ile His Ser Gly Phe Tyr Ile His Tyr Leu Thr Asn Gln Phe
                85                  90                  95

Ser Ser Leu Thr Tyr Met Phe Thr Arg Ile Pro Asn Glu Thr His Ala
            100                 105                 110

Gly Val Asp Leu Arg Ile Asn Val Val Thr Asn Thr Leu Tyr Ala Leu
        115                 120                 125

Leu Ile Leu Ser Ile Glu Ile Ser Leu Ile Tyr Gln Val Phe Val Ile
    130                 135                 140

Phe Lys Gly Val Tyr Glu Asn Ser Leu Arg Trp Ile Val Thr Ile Phe
145                 150                 155                 160

Thr Ala Leu Phe Ala Ala Ala Val Val Ala Ile Asn Phe Tyr Val Thr
                165                 170                 175

Thr Leu Gln Ser Val Ser Met Tyr Asn Ser Asn Val Asp Phe Pro Arg
            180                 185                 190

Trp Ala Ser Asn Val Pro Leu Ile Leu Phe Ala Ser Ser Val Asn Trp
        195                 200                 205

Ala Cys Leu Leu Leu Ser Leu Lys Leu Phe Phe Ala Ile Lys Val Arg
    210                 215                 220

Arg Ser Leu Gly Leu Arg Gln Phe Asp Thr Phe His Ile Leu Ala Ile
225                 230                 235                 240

Met Phe Ser Gln Thr Leu Ile Ile Pro Ser Ile Leu Ile Val Leu Gly
                245                 250                 255

Tyr Thr Gly Thr Arg Asp Arg Asp Ser Leu Ala Ser Leu Gly Phe Leu
            260                 265                 270

Leu Ile Val Val Ser Leu Pro Phe Ser Ser Met Trp Ala Ala Thr Ala
```

```
                275                 280                 285
Asn Asn Ser Asn Ile Pro Thr Ser Thr Gly Ser Phe Ala Trp Lys Asn
            290                 295                 300

Arg Tyr Ser Pro Ser Thr Tyr Ser Asp Asp Thr Thr Ala Val Ser Lys
305                 310                 315                 320

Ser Phe Thr Ile Met Thr Ala Lys Asp Glu Cys Phe Thr Thr Asp Thr
                325                 330                 335

Glu Gly Ser Pro Arg Phe Ile Lys Gly Asp Arg Thr Ser Glu Asp Leu
            340                 345                 350

His Phe

<210> SEQ ID NO 113
<211> LENGTH: 1065
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
atggaagaat actccgactc cttcgaccca tcccaacaat gttgaactt cacttcctta      60 tacggtgaaa ccgatgctac tttcgctgaa ttggacgact accacttcta cgtcgttaag    120
tacgccatcg tttacggtgc cagaattggt gtcggtatgt tttgtacttt gatgttgttc    180 gttgttttcca agtcttggaa gactccaatc ttcgtcttga accaatcttc tttgattttg   240
ttgattattc actccggttt ctacatccac tacttgacca accaattctc ttccttgacc    300
tacatgttca ctagaatccc aaacgaaacc catgctggtg tcgatttgcg tattaacgtc    360
gttaccaaca ccttgtacgc tttgttgatc ttatctattg aaatttcctt aatttaccaa    420
gtcttcgtta tcttcaaagg tgtctacgaa aactctttaa gatggattgt tactattttc    480
accgctttat tcgccgccgc cgtcgttgct attaacttct acgtcactac tttgcaatct    540
gtctctatgt acaactctaa cgttgacttt ccaagatggg cttctaacgt cccattgatc    600
ttgttcgctt cttctgtcaa ctgggcttgt ttgttgttgt ccttgaagtt gttcttcgct    660
atcaaggtta gaagatcttt gggtttgaga caattcgaca cttttcacat cttggccatc    720
atgttctctc aaactttgat tatcccatcc attttgattg tcttgggtta cactggtacc    780
agagacagag actccttggc ttcttttggt ttcttgttga tcgttgtttc tttgccattt    840
tcctctatgt gggctgccac tgctaacaac tccaacatcc aacctctac cggttctttc     900 gcctggaaga acagatactc cccatctact tactccgacg ataccactgc tgtttccaag    960
tccttcacta ttatgaccgc taaggatgaa tgtttcacca ctgataccga aggttctcca    1020
agattcatca gggtgacag aacctccgaa gatttgcact tctag                    1065

<210> SEQ ID NO 114
<211> LENGTH: 14
<212> TYPE: PRT
<213> ORGANISM: Vibrio cholerae

<400> SEQUENCE: 114

Ala Asp Gly Tyr Gly Leu Ala Gly Phe Pro Pro Glu His Arg
1               5                   10

<210> SEQ ID NO 115
<211> LENGTH: 8
<212> TYPE: PRT
<213> ORGANISM: Vibrio cholerae
```

```
<400> SEQUENCE: 115

Ala Asp Ser Arg Pro Pro Asp Glu
1               5

<210> SEQ ID NO 116
<211> LENGTH: 10
<212> TYPE: PRT
<213> ORGANISM: Vibrio cholerae

<400> SEQUENCE: 116

Ala Asp Ser Arg Pro Pro Asp Glu Ile Lys
1               5                   10

<210> SEQ ID NO 117
<211> LENGTH: 12
<212> TYPE: PRT
<213> ORGANISM: Vibrio cholerae

<400> SEQUENCE: 117

Ala Asp Ser Arg Pro Pro Asp Glu Ile Lys Gln Ser
1               5                   10

<210> SEQ ID NO 118
<211> LENGTH: 18
<212> TYPE: PRT
<213> ORGANISM: Vibrio cholerae

<400> SEQUENCE: 118

Ala Asp Ser Arg Pro Pro Asp Glu Ile Lys Gln Ser Gly Gly Leu Met
1               5                   10                  15

Pro Arg

<210> SEQ ID NO 119
<211> LENGTH: 8
<212> TYPE: PRT
<213> ORGANISM: Vibrio cholerae

<400> SEQUENCE: 119

Ala Gly Phe Pro Pro Glu His Arg
1               5

<210> SEQ ID NO 120
<211> LENGTH: 15
<212> TYPE: PRT
<213> ORGANISM: Vibrio cholerae

<400> SEQUENCE: 120

Ala Leu Gly Gly Ile Pro Tyr Ser Gln Ile Tyr Gly Trp Tyr Arg
1               5                   10                  15

<210> SEQ ID NO 121
<211> LENGTH: 17
<212> TYPE: PRT
<213> ORGANISM: Vibrio cholerae

<400> SEQUENCE: 121

Ala Pro Ala Ala Asp Gly Tyr Gly Leu Ala Gly Phe Pro Pro Glu His
1               5                   10                  15

Arg

<210> SEQ ID NO 122
<211> LENGTH: 41
```

<212> TYPE: PRT
<213> ORGANISM: Vibrio cholerae

<400> SEQUENCE: 122

Ala Thr Ala Pro Asn Met Phe Asn Val Asn Asp Val Leu Gly Ala Tyr
1               5                   10                  15

Ser Pro His Pro Asp Glu Gln Glu Val Ser Ala Leu Gly Gly Ile Pro
            20                  25                  30

Tyr Ser Gln Ile Tyr Gly Trp Tyr Arg
        35                  40

<210> SEQ ID NO 123
<211> LENGTH: 27
<212> TYPE: PRT
<213> ORGANISM: Vibrio cholerae

<400> SEQUENCE: 123

Ala Tyr Ser Pro His Pro Asp Glu Gln Glu Val Ser Ala Leu Gly Gly
1               5                   10                  15

Ile Pro Tyr Ser Gln Ile Tyr Gly Trp Tyr Arg
            20                  25

<210> SEQ ID NO 124
<211> LENGTH: 19
<212> TYPE: PRT
<213> ORGANISM: Vibrio cholerae

<400> SEQUENCE: 124

Asp Ile Ala Pro Ala Ala Asp Gly Tyr Gly Leu Ala Gly Phe Pro Pro
1               5                   10                  15

Glu His Arg

<210> SEQ ID NO 125
<211> LENGTH: 26
<212> TYPE: PRT
<213> ORGANISM: Vibrio cholerae

<400> SEQUENCE: 125

Asp Arg Tyr Tyr Ser Asn Leu Asp Ile Ala Pro Ala Ala Asp Gly Tyr
1               5                   10                  15

Gly Leu Ala Gly Phe Pro Pro Glu His Arg
            20                  25

<210> SEQ ID NO 126
<211> LENGTH: 9
<212> TYPE: PRT
<213> ORGANISM: Vibrio cholerae

<400> SEQUENCE: 126

Asp Ser Arg Pro Pro Asp Glu Ile Lys
1               5

<210> SEQ ID NO 127
<211> LENGTH: 31
<212> TYPE: PRT
<213> ORGANISM: Vibrio cholerae

<400> SEQUENCE: 127

Asp Val Leu Gly Ala Tyr Ser Pro His Pro Asp Glu Gln Glu Val Ser
1               5                   10                  15

Ala Leu Gly Gly Ile Pro Tyr Ser Gln Ile Tyr Gly Trp Tyr Arg
            20                  25                  30

<210> SEQ ID NO 128
<211> LENGTH: 10
<212> TYPE: PRT
<213> ORGANISM: Vibrio cholerae

<400> SEQUENCE: 128

Phe Gly Val Leu Asp Glu Gln Leu His Arg
1               5                   10

<210> SEQ ID NO 129
<211> LENGTH: 26
<212> TYPE: PRT
<213> ORGANISM: Vibrio cholerae

<400> SEQUENCE: 129

Phe Leu Asp Glu Tyr Gln Ser Lys Val Lys Arg Gln Ile Phe Ser Gly
1               5                   10                  15

Tyr Gln Ser Asp Ile Asp Thr His Asn Arg
            20                  25

<210> SEQ ID NO 130
<211> LENGTH: 31
<212> TYPE: PRT
<213> ORGANISM: Vibrio cholerae

<400> SEQUENCE: 130

Phe Leu Asp Glu Tyr Gln Ser Lys Val Lys Arg Gln Ile Phe Ser Gly
1               5                   10                  15

Tyr Gln Ser Asp Ile Asp Thr His Asn Arg Ile Lys Asp Glu Leu
            20                  25                  30

<210> SEQ ID NO 131
<211> LENGTH: 35
<212> TYPE: PRT
<213> ORGANISM: Vibrio cholerae

<400> SEQUENCE: 131

Phe Asn Val Asn Asp Val Leu Gly Ala Tyr Ser Pro His Pro Asp Glu
1               5                   10                  15

Gln Glu Val Ser Ala Leu Gly Gly Ile Pro Tyr Ser Gln Ile Tyr Gly
            20                  25                  30

Trp Tyr Arg
        35

<210> SEQ ID NO 132
<211> LENGTH: 28
<212> TYPE: PRT
<213> ORGANISM: Vibrio cholerae

<400> SEQUENCE: 132

Gly Ala Tyr Ser Pro His Pro Asp Glu Gln Glu Val Ser Ala Leu Gly
1               5                   10                  15

Gly Ile Pro Tyr Ser Gln Ile Tyr Gly Trp Tyr Arg
            20                  25

<210> SEQ ID NO 133
<211> LENGTH: 13
<212> TYPE: PRT
<213> ORGANISM: Vibrio cholerae

<400> SEQUENCE: 133

```
Gly Gly Ile Pro Tyr Ser Gln Ile Tyr Gly Trp Tyr Arg
1               5                   10

<210> SEQ ID NO 134
<211> LENGTH: 8
<212> TYPE: PRT
<213> ORGANISM: Vibrio cholerae

<400> SEQUENCE: 134

Gly Gln Ser Glu Tyr Phe Asp Arg
1               5

<210> SEQ ID NO 135
<211> LENGTH: 21
<212> TYPE: PRT
<213> ORGANISM: Vibrio cholerae

<400> SEQUENCE: 135

Gly Gln Ser Glu Tyr Phe Asp Arg Gly Thr Gln Met Asn Ile Asn Leu
1               5                   10                  15

Tyr Asp His Ala Arg
            20

<210> SEQ ID NO 136
<211> LENGTH: 13
<212> TYPE: PRT
<213> ORGANISM: Vibrio cholerae

<400> SEQUENCE: 136

Gly Thr Gln Met Asn Ile Asn Leu Tyr Asp His Ala Arg
1               5                   10

<210> SEQ ID NO 137
<211> LENGTH: 8
<212> TYPE: PRT
<213> ORGANISM: Vibrio cholerae

<400> SEQUENCE: 137

Gly Thr Gln Thr Gly Phe Val Arg
1               5

<210> SEQ ID NO 138
<211> LENGTH: 21
<212> TYPE: PRT
<213> ORGANISM: Vibrio cholerae

<400> SEQUENCE: 138

Gly Thr Gln Thr Gly Phe Val Arg His Asp Asp Gly Tyr Val Ser Thr
1               5                   10                  15

Ser Ile Ser Leu Arg
            20

<210> SEQ ID NO 139
<211> LENGTH: 11
<212> TYPE: PRT
<213> ORGANISM: Vibrio cholerae

<400> SEQUENCE: 139

Gly Tyr Gln Ser Asp Ile Asp Thr His Asn Arg
1               5                   10

<210> SEQ ID NO 140
<211> LENGTH: 29
<212> TYPE: PRT
```

<213> ORGANISM: Vibrio cholerae

<400> SEQUENCE: 140

Gly Tyr Arg Asp Arg Tyr Tyr Ser Asn Leu Asp Ile Ala Pro Ala Ala
1               5                   10                  15

Asp Gly Tyr Gly Leu Ala Gly Phe Pro Pro Glu His Arg
            20                  25

<210> SEQ ID NO 141
<211> LENGTH: 9
<212> TYPE: PRT
<213> ORGANISM: Vibrio cholerae

<400> SEQUENCE: 141

His Asp Asp Gly Tyr Val Ser Thr Ser
1               5

<210> SEQ ID NO 142
<211> LENGTH: 13
<212> TYPE: PRT
<213> ORGANISM: Vibrio cholerae

<400> SEQUENCE: 142

His Asp Asp Gly Tyr Val Ser Thr Ser Ile Ser Leu Arg
1               5                   10

<210> SEQ ID NO 143
<211> LENGTH: 11
<212> TYPE: PRT
<213> ORGANISM: Vibrio cholerae

<400> SEQUENCE: 143

His Phe Gly Val Leu Asp Glu Gln Leu His Arg
1               5                   10

<210> SEQ ID NO 144
<211> LENGTH: 9
<212> TYPE: PRT
<213> ORGANISM: Vibrio cholerae

<400> SEQUENCE: 144

Lys Gln Ser Gly Gly Leu Met Pro Arg
1               5

<210> SEQ ID NO 145
<211> LENGTH: 20
<212> TYPE: PRT
<213> ORGANISM: Vibrio cholerae

<400> SEQUENCE: 145

Leu Asp Ile Ala Pro Ala Ala Asp Gly Tyr Gly Leu Ala Gly Phe Pro
1               5                   10                  15

Pro Glu His Arg
            20

<210> SEQ ID NO 146
<211> LENGTH: 34
<212> TYPE: PRT
<213> ORGANISM: Vibrio cholerae

<400> SEQUENCE: 146

Asn Val Asn Asp Val Leu Gly Ala Tyr Ser Pro His Pro Asp Glu Gln
1               5                   10                  15

```
Glu Val Ser Ala Leu Gly Gly Ile Pro Tyr Ser Gln Ile Tyr Gly Trp
        20                  25                  30
Tyr Arg
```

<210> SEQ ID NO 147
<211> LENGTH: 19
<212> TYPE: PRT
<213> ORGANISM: Vibrio cholerae

<400> SEQUENCE: 147

```
Gln Glu Val Ser Ala Leu Gly Gly Ile Pro Tyr Ser Gln Ile Tyr Gly
1               5                   10                  15
Trp Tyr Arg
```

<210> SEQ ID NO 148
<211> LENGTH: 13
<212> TYPE: PRT
<213> ORGANISM: Vibrio cholerae

<400> SEQUENCE: 148

```
Gln Ile Phe Ser Gly Tyr Gln Ser Asp Ile Asp Thr His
1               5                   10
```

<210> SEQ ID NO 149
<211> LENGTH: 14
<212> TYPE: PRT
<213> ORGANISM: Vibrio cholerae

<400> SEQUENCE: 149

```
Gln Ile Phe Ser Gly Tyr Gln Ser Asp Ile Asp Thr His Asn
1               5                   10
```

<210> SEQ ID NO 150
<211> LENGTH: 15
<212> TYPE: PRT
<213> ORGANISM: Vibrio cholerae

<400> SEQUENCE: 150

```
Gln Ile Phe Ser Gly Tyr Gln Ser Asp Ile Asp Thr His Asn Arg
1               5                   10                  15
```

<210> SEQ ID NO 151
<211> LENGTH: 9
<212> TYPE: PRT
<213> ORGANISM: Vibrio cholerae

<400> SEQUENCE: 151

```
Gln Ser Asp Ile Asp Thr His Asn Arg
1               5
```

<210> SEQ ID NO 152
<211> LENGTH: 8
<212> TYPE: PRT
<213> ORGANISM: Vibrio cholerae

<400> SEQUENCE: 152

```
Gln Ser Gly Gly Leu Met Pro Arg
1               5
```

<210> SEQ ID NO 153
<211> LENGTH: 14
<212> TYPE: PRT
<213> ORGANISM: Vibrio cholerae

<400> SEQUENCE: 153

Arg His Asp Asp Gly Tyr Val Ser Thr Ser Ile Ser Leu Arg
1               5                   10

<210> SEQ ID NO 154
<211> LENGTH: 16
<212> TYPE: PRT
<213> ORGANISM: Vibrio cholerae

<400> SEQUENCE: 154

Arg Gln Ile Phe Ser Gly Tyr Gln Ser Asp Ile Asp Thr His Asn Arg
1               5                   10                  15

<210> SEQ ID NO 155
<211> LENGTH: 13
<212> TYPE: PRT
<213> ORGANISM: Vibrio cholerae

<400> SEQUENCE: 155

Ser Ala His Leu Val Gly Gln Thr Ile Leu Ser Gly His
1               5                   10

<210> SEQ ID NO 156
<211> LENGTH: 16
<212> TYPE: PRT
<213> ORGANISM: Vibrio cholerae

<400> SEQUENCE: 156

Ser Ala His Leu Val Gly Gln Thr Ile Leu Ser Gly His Ser Thr Tyr
1               5                   10                  15

<210> SEQ ID NO 157
<211> LENGTH: 17
<212> TYPE: PRT
<213> ORGANISM: Vibrio cholerae

<400> SEQUENCE: 157

Ser Ala His Leu Val Gly Gln Thr Ile Leu Ser Gly His Ser Thr Tyr
1               5                   10                  15

Tyr

<210> SEQ ID NO 158
<211> LENGTH: 28
<212> TYPE: PRT
<213> ORGANISM: Vibrio cholerae

<400> SEQUENCE: 158

Ser Ala His Leu Val Gly Gln Thr Ile Leu Ser Gly His Ser Thr Tyr
1               5                   10                  15

Tyr Ile Tyr Val Ile Ala Thr Ala Pro Asn Met Phe
            20                  25

<210> SEQ ID NO 159
<211> LENGTH: 8
<212> TYPE: PRT
<213> ORGANISM: Vibrio cholerae

<400> SEQUENCE: 159

Ser Asp Ile Asp Thr His Asn Arg
1               5

<210> SEQ ID NO 160
<211> LENGTH: 12

```
<212> TYPE: PRT
<213> ORGANISM: Vibrio cholerae

<400> SEQUENCE: 160

Ser Gly Tyr Gln Ser Asp Ile Asp Thr His Asn Arg
1               5                   10

<210> SEQ ID NO 161
<211> LENGTH: 22
<212> TYPE: PRT
<213> ORGANISM: Vibrio cholerae

<400> SEQUENCE: 161

Ser Asn Leu Asp Ile Ala Pro Ala Ala Asp Gly Tyr Gly Leu Ala Gly
1               5                   10                  15

Phe Pro Pro Glu His Arg
            20

<210> SEQ ID NO 162
<211> LENGTH: 8
<212> TYPE: PRT
<213> ORGANISM: Vibrio cholerae

<400> SEQUENCE: 162

Ser Gln Ile Tyr Gly Trp Tyr Arg
1               5

<210> SEQ ID NO 163
<211> LENGTH: 16
<212> TYPE: PRT
<213> ORGANISM: Vibrio cholerae

<400> SEQUENCE: 163

Ser Arg Pro Pro Asp Glu Ile Lys Gln Ser Gly Gly Leu Met Pro Arg
1               5                   10                  15

<210> SEQ ID NO 164
<211> LENGTH: 40
<212> TYPE: PRT
<213> ORGANISM: Vibrio cholerae

<400> SEQUENCE: 164

Thr Ala Pro Asn Met Phe Asn Val Asn Asp Val Leu Gly Ala Tyr Ser
1               5                   10                  15

Pro His Pro Asp Glu Gln Glu Val Ser Ala Leu Gly Gly Ile Pro Tyr
            20                  25                  30

Ser Gln Ile Tyr Gly Trp Tyr Arg
            35                  40

<210> SEQ ID NO 165
<211> LENGTH: 43
<212> TYPE: PRT
<213> ORGANISM: Vibrio cholerae

<400> SEQUENCE: 165

Val Ile Ala Thr Ala Pro Asn Met Phe Asn Val Asn Asp Val Leu Gly
1               5                   10                  15

Ala Tyr Ser Pro His Pro Asp Glu Gln Glu Val Ser Ala Leu Gly Gly
            20                  25                  30

Ile Pro Tyr Ser Gln Ile Tyr Gly Trp Tyr Arg
            35                  40
```

```
<210> SEQ ID NO 166
<211> LENGTH: 23
<212> TYPE: PRT
<213> ORGANISM: Vibrio cholerae

<400> SEQUENCE: 166

Val Lys Arg Gln Ile Phe Ser Gly Tyr Gln Ser Asp Ile Asp Thr His
1               5                   10                  15

Asn Arg Ile Lys Asp Glu Leu
            20

<210> SEQ ID NO 167
<211> LENGTH: 8
<212> TYPE: PRT
<213> ORGANISM: Vibrio cholerae

<400> SEQUENCE: 167

Val Leu Asp Glu Gln Leu His Arg
1               5

<210> SEQ ID NO 168
<211> LENGTH: 10
<212> TYPE: PRT
<213> ORGANISM: Vibrio cholerae

<400> SEQUENCE: 168

Tyr Gln Ser Asp Ile Asp Thr His Asn Arg
1               5                   10

<210> SEQ ID NO 169
<211> LENGTH: 23
<212> TYPE: PRT
<213> ORGANISM: Vibrio cholerae

<400> SEQUENCE: 169

Tyr Ser Asn Leu Asp Ile Ala Pro Ala Ala Asp Gly Tyr Gly Leu Ala
1               5                   10                  15

Gly Phe Pro Pro Glu His Arg
            20

<210> SEQ ID NO 170
<211> LENGTH: 26
<212> TYPE: PRT
<213> ORGANISM: Vibrio cholerae

<400> SEQUENCE: 170

Tyr Ser Pro His Pro Asp Glu Gln Glu Val Ser Ala Leu Gly Gly Ile
1               5                   10                  15

Pro Tyr Ser Gln Ile Tyr Gly Trp Tyr Arg
            20                  25

<210> SEQ ID NO 171
<211> LENGTH: 9
<212> TYPE: PRT
<213> ORGANISM: Vibrio cholerae

<400> SEQUENCE: 171

Tyr Ser Gln Ile Tyr Gly Trp Tyr Arg
1               5

<210> SEQ ID NO 172
<211> LENGTH: 17
<212> TYPE: PRT
<213> ORGANISM: Vibrio cholerae
```

<400> SEQUENCE: 172

Tyr Tyr Ser Asn Leu Asp Ile Ala Pro Ala Ala Asp Gly Tyr Gly Leu
1               5                   10                  15

Ala

<210> SEQ ID NO 173
<211> LENGTH: 24
<212> TYPE: PRT
<213> ORGANISM: Vibrio cholerae

<400> SEQUENCE: 173

Tyr Tyr Ser Asn Leu Asp Ile Ala Pro Ala Ala Asp Gly Tyr Gly Leu
1               5                   10                  15

Ala Gly Phe Pro Pro Glu His Arg
            20

<210> SEQ ID NO 174
<211> LENGTH: 9
<212> TYPE: PRT
<213> ORGANISM: Vibrio cholerae

<400> SEQUENCE: 174

Ala Ile Ala Ala Ile Ser Met Ala Asn
1               5

<210> SEQ ID NO 175
<211> LENGTH: 8
<212> TYPE: PRT
<213> ORGANISM: Vibrio cholerae

<400> SEQUENCE: 175

Glu Met Ala Ile Ile Thr Phe Lys
1               5

<210> SEQ ID NO 176
<211> LENGTH: 10
<212> TYPE: PRT
<213> ORGANISM: Vibrio cholerae

<400> SEQUENCE: 176

Phe Ser Tyr Thr Glu Ser Leu Ala Gly Lys
1               5                   10

<210> SEQ ID NO 177
<211> LENGTH: 11
<212> TYPE: PRT
<213> ORGANISM: Vibrio cholerae

<400> SEQUENCE: 177

Ile Phe Ser Tyr Thr Glu Ser Leu Ala Gly Lys
1               5                   10

<210> SEQ ID NO 178
<211> LENGTH: 14
<212> TYPE: PRT
<213> ORGANISM: Vibrio cholerae

<400> SEQUENCE: 178

Asn Asp Lys Ile Phe Ser Tyr Thr Glu Ser Leu Ala Gly Lys
1               5                   10

<210> SEQ ID NO 179

```
<211> LENGTH: 14
<212> TYPE: PRT
<213> ORGANISM: Vibrio cholerae

<400> SEQUENCE: 179

Asn Gly Ala Thr Phe Gln Val Glu Val Pro Gly Ser Gln His
1               5                   10

<210> SEQ ID NO 180
<211> LENGTH: 19
<212> TYPE: PRT
<213> ORGANISM: Vibrio cholerae

<400> SEQUENCE: 180

Asn Gly Ala Thr Phe Gln Val Glu Val Pro Gly Ser Gln His Ile Asp
1               5                   10                  15

Ser Gln Lys

<210> SEQ ID NO 181
<211> LENGTH: 20
<212> TYPE: PRT
<213> ORGANISM: Vibrio cholerae

<400> SEQUENCE: 181

Asn Gly Ala Thr Phe Gln Val Glu Val Pro Gly Ser Gln His Ile Asp
1               5                   10                  15

Ser Gln Lys Lys
            20

<210> SEQ ID NO 182
<211> LENGTH: 10
<212> TYPE: PRT
<213> ORGANISM: Vibrio cholerae

<400> SEQUENCE: 182

Ser Tyr Thr Glu Ser Leu Ala Gly Lys Arg
1               5                   10

<210> SEQ ID NO 183
<211> LENGTH: 12
<212> TYPE: PRT
<213> ORGANISM: Vibrio cholerae

<400> SEQUENCE: 183

Thr Pro His Ala Ile Ala Ala Ile Ser Met Ala Asn
1               5                   10

<210> SEQ ID NO 184
<211> LENGTH: 8
<212> TYPE: PRT
<213> ORGANISM: Vibrio cholerae

<400> SEQUENCE: 184

Tyr Thr Glu Ser Leu Ala Gly Lys
1               5

<210> SEQ ID NO 185
<211> LENGTH: 13
<212> TYPE: PRT
<213> ORGANISM: Saccharomyces cerevisiae

<400> SEQUENCE: 185

Trp His Trp Leu Gln Leu Lys Pro Gly Gln Pro Met Tyr
1               5                   10
```

<210> SEQ ID NO 186
<211> LENGTH: 13
<212> TYPE: PRT
<213> ORGANISM: Candida albicans

<400> SEQUENCE: 186

Gly Phe Arg Leu Thr Asn Phe Gly Tyr Phe Glu Pro Gly
1               5                   10

<210> SEQ ID NO 187
<211> LENGTH: 469
<212> TYPE: PRT
<213> ORGANISM: Candida albicans

<400> SEQUENCE: 187

Met Asn Ile Asn Ser Thr Phe Ile Pro Asp Lys Pro Gly Asp Ile Ile
1               5                   10                  15

Ile Ser Tyr Ser Ile Pro Gly Leu Asp Gln Pro Ile Gln Ile Pro Phe
                20                  25                  30

His Ser Leu Asp Ser Phe Gln Thr Asp Gln Ala Lys Ile Ala Leu Val
            35                  40                  45

Met Gly Ile Thr Ile Gly Ser Cys Ser Met Thr Leu Ile Phe Leu Ile
        50                  55                  60

Ser Ile Met Tyr Lys Thr Asn Lys Leu Thr Asn Leu Lys Leu Lys Leu
65                  70                  75                  80

Lys Leu Lys Tyr Ile Leu Gln Trp Ile Asn Gln Lys Ile Phe Thr Lys
                85                  90                  95

Lys Arg Asn Asp Asn Lys Gln Gln Gln Gln Gln Gln Gln Gln Gln Ile
            100                 105                 110

Glu Ser Ser Ser Tyr Asn Asn Thr Thr Thr Leu Gly Gly Tyr Lys
        115                 120                 125

Leu Phe Leu Phe Tyr Leu Asn Ser Leu Ile Leu Leu Ile Gly Ile Ile
130                 135                 140

Arg Ser Gly Cys Tyr Leu Asn Tyr Asn Leu Gly Pro Leu Asn Ser Leu
145                 150                 155                 160

Ser Phe Val Phe Thr Gly Trp Tyr Asp Gly Ser Ser Phe Ile Ser Ser
                165                 170                 175

Asp Val Thr Asn Gly Phe Lys Cys Ile Leu Tyr Ala Leu Val Glu Ile
            180                 185                 190

Ser Leu Gly Phe Gln Val Tyr Val Met Phe Lys Thr Ser Asn Leu Lys
        195                 200                 205

Ile Trp Gly Ile Met Ala Ser Leu Leu Ser Ile Gly Leu Gly Leu Ile
    210                 215                 220

Val Val Ala Phe Gln Ile Asn Leu Thr Ile Leu Ser His Ile Arg Phe
225                 230                 235                 240

Ser Arg Ala Ile Ser Thr Asn Arg Ser Glu Glu Glu Ser Ser Ser Ser
                245                 250                 255

Leu Ser Ser Asp Ser Val Gly Tyr Val Ile Asn Ser Ile Trp Met Asp
            260                 265                 270

Leu Pro Thr Ile Leu Phe Ser Ile Ser Asn Ile Met Thr Ile Leu
        275                 280                 285

Leu Ile Gly Lys Leu Ile Ile Ala Ile Arg Thr Arg Arg Tyr Leu Gly
    290                 295                 300

Leu Lys Gln Phe Asp Ser Phe His Ile Leu Leu Ile Gly Phe Ser Gln
305                 310                 315                 320

```
Thr Leu Ile Ile Pro Ser Ile Ile Leu Val Val His Tyr Phe Tyr Leu
                325                 330                 335

Ser Gln Asn Lys Asp Ser Leu Leu Gln Gln Ile Ser Leu Leu Leu Ile
            340                 345                 350

Ile Leu Met Leu Pro Leu Ser Ser Leu Trp Ala Gln Thr Ala Asn Asn
        355                 360                 365

Thr His Asn Ile Asn Ser Ser Pro Ser Leu Ser Phe Ile Ser Arg His
    370                 375                 380

His Leu Ser Asp Ser Ser Arg Ser Gly Gly Ser Asn Thr Ile Val Ser
385                 390                 395                 400

Asn Gly Gly Ser Asn Gly Gly Gly Gly Gly Gly Asn Phe Pro Val
                405                 410                 415

Ser Gly Ile Asp Ala Gln Leu Pro Pro Asp Ile Glu Lys Ile Leu His
                420                 425                 430

Glu Asp Asn Asn Tyr Lys Leu Leu Asn Ser Asn Asn Glu Ser Val Asn
            435                 440                 445

Asp Gly Asp Ile Ile Ile Asn Asp Glu Gly Met Ile Thr Lys Gln Ile
        450                 455                 460

Thr Ile Lys Arg Val
465

<210> SEQ ID NO 188
<211> LENGTH: 1410
<212> TYPE: DNA
<213> ORGANISM: Candida albicans

<400> SEQUENCE: 188
atgaatatca attcaacttt catacctgat aaaccaggcg atataattat tagttattca      60
attccaggat tagatcaacc aattcaaatt cctttccatt cattagattc atttcaaacc     120
gatcaagcta aaatagcttt agtcatgggg ataactattg ggagttgttc aatgacatta     180
atttttttga tttctataat gtataaaact aataaattaa caaatttaaa attaaaatta     240
aaattaaaat atatcttgca atggataaat caaaaaatct tcaccaaaaa aaggaatgac     300
aacaaacaac aacaacaaca acaacaacaa caaattgaat catcatcata taacaatact     360
actactacgc tgggggggtta taaattattt ttatttatc ttaattcatt gattttatta     420
attggtatta ttcgatcagg ttgttattta aattataatt taggtccatt aaattcactt     480
agttttgtat ttactggttg gtatgatgga tcatcattta tatcatccga tgtaactaat     540
ggatttaaat gtattttata tgctttagtg gaaatttcat taggtttcca agtttatgtg     600
atgttcaaaa cttcaaattt aaaaatttgg gggataatgg catcattatt atcaattggt     660
ttaggattga ttgttgttgc ctttcaaatc aatttaacaa tttttatctca tattcgattt     720 tcccgggcta tatcaactaa cagaagtgaa gaagaatcat catcatcatt atcatctgat     780
tcggttgggt atgtgattaa ttcaatatgg atggatttac caacaatatt attttccatt     840
agtattaata taatgacaat attattgatt ggtaaactta taattgctat tagaacaaga     900
cgttatttag gattgaaaca atttgatagt ttccatattt tattaattgg tttcagtcaa     960
acattaatta ttccttcaat tattttggtg gttcattatt tttatttatc acaaataaa    1020 gattctttat tacaacaaat tagtcttttta ttgattattt taatgttacc attaagttct    1080
ttatgggctc aaactgctaa taatactcat aatattaatt catctccaag tttatcattc    1140
atatctcgtc atcatctgtc tgatagtagt cgtagtggtg gttccaatac aattgttagt    1200
```

```
aatggtggta gtaatggtgg tggtggtggt ggtgggaatt tccctgtttc aggtattgat    1260
gcacaattac cacctgatat tgaaaaaatc ttacatgaag ataataatta taaattactt    1320
aatagtaata atgaaagtgt aaatgatgga gatattatca ttaatgatga aggtatgatt    1380
actaaacaaa tcaccatcaa aagagtgtag                                    1410
```

<210> SEQ ID NO 189
<211> LENGTH: 13
<212> TYPE: PRT
<213> ORGANISM: Candida glabrata

<400> SEQUENCE: 189

Trp His Trp Val Arg Leu Arg Lys Gly Gln Gly Leu Phe
1               5                   10

<210> SEQ ID NO 190
<211> LENGTH: 417
<212> TYPE: PRT
<213> ORGANISM: Candida glabrata

<400> SEQUENCE: 190

Met Glu Met Gly Tyr Asp Pro Arg Met Tyr Asn Pro Arg Asn Glu Tyr
1               5                   10                  15

Leu Asn Phe Thr Ser Val Tyr Asp Val Asn Asp Thr Ile Arg Phe Ser
                20                  25                  30

Thr Leu Asp Ala Ile Val Lys Gly Leu Leu Arg Ile Ala Ile Val His
            35                  40                  45

Gly Val Arg Leu Gly Ala Ile Phe Met Thr Leu Ile Ile Met Phe Ile
        50                  55                  60

Ser Ser Asn Thr Trp Lys Lys Pro Ile Phe Ile Ile Asn Met Val Ser
65                  70                  75                  80

Leu Met Leu Val Met Ile His Ser Ala Leu Ser Phe His Tyr Leu Leu
                85                  90                  95

Ser Asn Tyr Ser Ser Ile Ser Tyr Ile Leu Thr Gly Phe Pro Gln Leu
            100                 105                 110

Ile Thr Ser Asn Asn Lys Arg Ile Gln Asp Ala Ala Ser Ile Val Gln
        115                 120                 125

Val Leu Leu Val Ala Ala Ile Glu Ala Ser Leu Val Phe Gln Ile His
    130                 135                 140

Val Met Phe Thr Ile Glu Asn Ile Lys Leu Ile Arg Glu Ile Val Leu
145                 150                 155                 160

Ser Ile Ser Ile Ala Met Gly Leu Ala Thr Val Ala Thr Tyr Leu Ala
                165                 170                 175

Ala Ala Ile Lys Leu Ile Arg Gly Leu His Asp Glu Val Met Pro Gln
            180                 185                 190

Thr His Leu Ile Phe Asn Leu Ser Ile Ile Leu Leu Ala Ser Ser Ile
        195                 200                 205

Asn Phe Met Thr Phe Ile Leu Val Ile Lys Leu Phe Phe Ala Ile Arg
    210                 215                 220

Ser Arg Arg Tyr Leu Gly Leu Arg Gln Phe Asp Ala Phe His Ile Leu
225                 230                 235                 240

Leu Ile Met Phe Cys Gln Ser Leu Leu Ile Pro Ser Val Leu Tyr Ile
                245                 250                 255

Ile Val Tyr Ala Val Asp Ser Arg Ser Asn Gln Asp Tyr Leu Ile Pro
            260                 265                 270

Ile Ala Asn Leu Phe Val Val Leu Ser Leu Pro Leu Ser Ser Ile Trp

```
                    275                 280                 285
Ala Asn Thr Ser Asn Asn Ser Ser Arg Ser Pro Lys Tyr Trp Lys Asn
            290                 295                 300

Ser Gln Thr Asn Lys Ser Asn Gly Ser Phe Val Ser Ser Ile Ser Val
305                 310                 315                 320

Asn Ser Asp Ser Gln Asn Pro Leu Tyr Lys Lys Ile Val Arg Phe Thr
                325                 330                 335

Ser Lys Gly Asp Thr Thr Arg Ser Ile Val Ser Asp Ser Thr Leu Ala
            340                 345                 350

Glu Val Gly Lys Tyr Ser Met Gln Asp Val Ser Asn Ser Asn Phe Glu
                355                 360                 365

Cys Arg Asp Leu Asp Phe Glu Lys Val Lys His Thr Cys Glu Asn Phe
            370                 375                 380

Gly Arg Ile Ser Glu Thr Tyr Ser Glu Leu Ser Thr Leu Asp Thr Thr
385                 390                 395                 400

Ala Leu Asn Glu Thr Arg Leu Phe Trp Lys Gln Gln Ser Gln Cys Asp
                405                 410                 415

Lys

<210> SEQ ID NO 191
<211> LENGTH: 1254
<212> TYPE: DNA
<213> ORGANISM: Candida glabrata

<400> SEQUENCE: 191
atggagatgg gctacgatcc aagaatgtat aatccaagaa atgaatactt gaatttcacg      60
tcggtatatg atgtaaatga cacaatcaga ttttcgactc tggacgccat tgtaaaagga     120
ttgcttagaa ttgccattgt tcatggagtt agattgggag caatattcat gacgttaata     180
ataatgttta tctcatcaaa tacatggaaa aaacccatat ttataattaa catggtgtcg     240
ttgatgttag ttatgattca ttccgcactt agcttccatt acctttatc  gaattattct     300 tcaatttctt atatactgac agggtttcct cagttgatta caagcaataa taaacgaatt     360
caagatgcag cgagtatagt ccaagtttta ttggttgctg cgatagaagc atcattggta     420
tttcagattc atgttatgtt tacgattgaa acattaagc ttattagaga aatagtactc      480
tctatatcga tagcaatggg attggcaaca gtggctacat atcttgctgc agcaataaag     540
ctgataagag gactgcatga tgaggtaatg ccacaaacac atcttatttt caatttatct     600
ataatattgc ttgcatcctc cataaatttt atgacattta ttggtcat   taaacttttc     660 ttcgctatta gatctagaag atatctcggt cttcgtcaat tcgatgcttt tcatatttta     720
ttaatcatgt tctgccagtc attattgata ccctcagtat tatatattat agtttacgcg     780
gttgatagca gatctaatca ggattatctg attccaattg ccaatttatt tgttgtttta     840
tctttgccat tatcctctat ctgggctaac acatcaaata actcatccag atctccaaaa     900
tattggaaaa actctcaaac gaataagagc aatgggtctt tgtctcttc  aatatctgtc     960 aatagtgact cacaaaaccc tttgtacaaa aagattgtac gttttacatc aaaaggcgac    1020
actacccgta gtattgtaag tgattcaaca ttagcagagg tgggaaaata ctctatgcaa    1080
gacgttagca attcaaactt tgaatgtcga gaccttgatt ttgagaaggt aaaacatact    1140
tgcgaaaatt ttggcagaat atctgaaaca tatagtgagt taagtacttt agataccact    1200 gcccctcaatg agactcggtt gttttggaaa caacaaagtc agtgtgacaa atag         1254
```

<210> SEQ ID NO 192
<211> LENGTH: 9
<212> TYPE: PRT
<213> ORGANISM: Paracoccidioides brasiliensis

<400> SEQUENCE: 192

Trp Cys Thr Arg Pro Gly Gln Gly Cys
1               5

<210> SEQ ID NO 193
<211> LENGTH: 356
<212> TYPE: PRT
<213> ORGANISM: Paracoccidioides brasiliensis

<400> SEQUENCE: 193

Met Ala Pro Ser Phe Asp Pro Phe Asn Gln Ser Val Val Phe His Lys
1               5                   10                  15

Ala Asp Gly Thr Pro Phe Asn Val Ser Ile His Glu Leu Asp Asp Phe
                20                  25                  30

Val Gln Tyr Asn Thr Lys Val Cys Ile Asn Tyr Ser Ser Gln Leu Gly
            35                  40                  45

Ala Ser Val Ile Ala Gly Leu Met Leu Ala Met Leu Thr His Ser Glu
        50                  55                  60

Lys Arg Arg Leu Pro Val Phe Phe Leu Asn Thr Phe Ala Leu Ala Met
65                  70                  75                  80

Asn Phe Ala Arg Leu Leu Cys Met Thr Ile Tyr Phe Thr Thr Gly Phe
                85                  90                  95

Asn Lys Ser Tyr Ala Tyr Phe Gly Gln Asp Tyr Ser Gln Val Pro Gly
            100                 105                 110

Ser Ala Tyr Ala Ala Ser Val Leu Gly Val Val Phe Thr Thr Leu Leu
        115                 120                 125

Val Ile Ser Met Glu Met Ser Leu Leu Ile Gln Thr Arg Val Val Cys
130                 135                 140

Thr Thr Leu Pro Asp Ile Gln Arg Tyr Leu Leu Met Ala Val Ser Ser
145                 150                 155                 160

Ala Ile Ser Leu Met Ala Ile Gly Phe Arg Leu Gly Leu Met Val Glu
                165                 170                 175

Asn Cys Ile Ala Ile Val Gln Ala Ser Asn Phe Ala Pro Phe Ile Trp
            180                 185                 190

Leu Gln Ser Ala Ser Asn Ile Thr Ile Thr Ile Ser Thr Cys Phe Phe
        195                 200                 205

Ser Ala Val Phe Val Thr Lys Leu Ala Tyr Ala Leu Val Thr Arg Ile
210                 215                 220

Arg Leu Gly Leu Thr Arg Phe Gly Ala Met Gln Val Met Phe Ile Met
225                 230                 235                 240

Ser Cys Gln Thr Met Val Ile Pro Ala Ile Phe Ser Ile Leu Gln Tyr
                245                 250                 255

Pro Leu Pro Lys Tyr Glu Met Asn Ser Asn Leu Phe Thr Leu Val Ala
            260                 265                 270

Ile Phe Leu Pro Leu Ser Ser Leu Trp Ala Ser Val Ala Thr Arg Ser
        275                 280                 285

Ser Phe Glu Thr Ser Ser Ser Gly Arg His Gln Tyr Leu Trp Pro Ser
        290                 295                 300

Glu Gln Ser Asn Asn Val Thr Asn Ser Glu Ile Lys Tyr Gln Val Ser
305                 310                 315                 320

Phe Ser Gln Asn His Thr Thr Leu Arg Ser Gly Gly Ser Val Ala Thr

```
              325                 330                 335
Thr Leu Ser Pro Asp Arg Leu Asp Pro Val Tyr Cys Glu Val Glu Ala
            340                 345                 350

Gly Thr Lys Ala
        355

<210> SEQ ID NO 194
<211> LENGTH: 1071
<212> TYPE: DNA
<213> ORGANISM: Paracoccidioides brasiliensis

<400> SEQUENCE: 194
atggcaccct cattcgaccc cttcaaccaa agcgtggtct tccacaaggc cgacggaact      60
ccattcaacg tctcaatcca tgaactagac gacttcgtgc agtacaacac caaagtctgc    120
atcaactact cttcccagct cggagcatct gtcattgcag gactcatgct tgccatgctg    180
acacactcag aaaagcgtcg tctgccagtt tcttcctaa acacattcgc actggccatg     240
aactttgccc gcctgctctg catgaccatc tacttcacca cgggcttcaa caagtcctat    300
gcctactttg gtcaggatta ctcccaggtg cctgggagcg cctacgcagc ctctgtcttg    360
ggcgttgtct tcaccactct cctggtaatc agcatggaaa tgtccctcct gatccaaaca    420
agggttgtct gcacgaccct tccggatatc caacgttatc tactcatggc agtttcctcc    480
gcgatttccc tgatggccat cgggttccgc cttggcttaa tggttgagaa ctgcattgcc    540
attgtgcagg cgtcgaattt cgcccctttt atctggcttc aaagcgcctc gaacatcacc    600
attacgatca gcacatgttt cttcagtgcc gtctttgtta cgaaattggc atatgcactc    660
gtcactcgta tacgactagg cttgacgagg tttggtgcta tgcaggttat gttcatcatg    720
tcctgccaga ctatggtgat tccagccatc ttctcaattc ccaataccc actccccaag     780 tacgaaatga actccaacct ctttacgctg gtggccattt tcctccctct ttcctcgcta    840
tgggcttcag ttgctacgag atccagtttc gagacgtctc cttccggccg ccatcagtat    900
ctttggccaa gcgaacagag caataacgtc accaattcgg aaattaagta tcaggtcagc    960
ttctctcaga accacactac gttgcggtct ggagggtctg tggccacgac actctccccg   1020
gaccggctcg acccggttta ttgtgaagtt gaagctggca caaaggccta g            1071

<210> SEQ ID NO 195
<211> LENGTH: 10
<212> TYPE: PRT
<213> ORGANISM: Fusarium graminearum

<400> SEQUENCE: 195

Trp Cys Trp Trp Lys Gly Gln Pro Cys Trp
1               5                  10

<210> SEQ ID NO 196
<211> LENGTH: 386
<212> TYPE: PRT
<213> ORGANISM: Fusarium graminearum

<400> SEQUENCE: 196

Met Ser Lys Glu Val Phe Asp Pro Phe Thr Gln Asn Val Thr Phe Phe
1               5                  10                  15

Ala Pro Asp Gly Lys Thr Glu Ile Ser Ile Pro Val Ala Ala Ile Asp
            20                  25                  30

Gln Val Arg Arg Met Met Val Asn Thr Thr Ile Asn Tyr Ala Thr Gln
        35                  40                  45
```

Leu Gly Ala Cys Leu Ile Met Leu Val Val Leu Leu Val Met Val Pro
 50                  55                  60

Lys Glu Lys Phe Arg Arg Pro Phe Met Ile Leu Gln Ile Thr Ser Leu
 65                  70                  75                  80

Val Ile Ser Cys Cys Arg Met Leu Leu Leu Ser Ile Phe His Ser Ser
                 85                  90                  95

Gln Phe Leu Asp Phe Tyr Val Phe Trp Gly Asp Asp His Ser Arg Ile
                100                 105                 110

Pro Arg Ser Ala Tyr Ala Pro Ser Val Ala Gly Asn Thr Met Ser Leu
                115                 120                 125

Cys Leu Val Ile Ser Val Glu Thr Met Leu Met Ser Gln Ala Trp Thr
                130                 135                 140

Met Val Arg Leu Trp Pro Asn Val Trp Lys Tyr Ile Ile Ala Gly Val
145                 150                 155                 160

Ser Leu Ile Val Ser Ile Met Ala Ile Ser Val Arg Leu Ala Tyr Thr
                165                 170                 175

Ile Ile Gln Asn Asn Ala Val Leu Lys Leu Glu Pro Ala Phe His Met
                180                 185                 190

Phe Trp Leu Ile Lys Trp Thr Val Ile Met Asn Val Ala Ser Ile Ser
                195                 200                 205

Trp Trp Cys Ala Ile Phe Asn Ile Lys Leu Val Trp His Leu Ile Ser
210                 215                 220

Asn Arg Gly Ile Leu Pro Ser Tyr Lys Thr Phe Thr Pro Met Glu Val
225                 230                 235                 240

Leu Ile Met Thr Asn Gly Ile Leu Met Ile Ile Pro Val Ile Phe Ala
                245                 250                 255

Ser Leu Glu Trp Ala His Phe Val Asn Phe Glu Ser Ala Ser Leu Thr
                260                 265                 270

Leu Thr Ser Val Ala Val Ile Leu Pro Leu Gly Thr Leu Ala Ala Gln
                275                 280                 285

Arg Ile Ala Ser Ser Ala Pro Ser Ser Ala Asn Ser Thr Gly Ala Ser
                290                 295                 300

Ser Gly Ile Arg Tyr Gly Val Ser Gly Pro Ser Ser Phe Thr Gly Phe
305                 310                 315                 320

Lys Ala Pro Ser Phe Ser Thr Gly Thr Thr Asp Arg Pro His Val Ser
                325                 330                 335

Ile Tyr Ala Arg Cys Glu Ala Gly Thr Ser Ser Arg Glu His Ile Asn
                340                 345                 350

Pro Gln Gly Val Glu Leu Ala Lys Leu Asp Pro Glu Thr Asp His His
                355                 360                 365

Val Arg Val Asp Arg Ala Phe Leu Gln Arg Glu Arg Ile Arg Ala
370                 375                 380

Pro Leu
385

<210> SEQ ID NO 197
<211> LENGTH: 1161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197
atgtctaagg aagttttcga cccattcact caaaacgtta ctttcttcgc tccagacggt      60

-continued

```
aagactgaaa tctctatccc agttgctgct atcgaccaag ttagaagaat gatggttaac    120
actactatca actacgctac tcaattgggt gcttgtttga tcatgttggt tgttttgttg    180
gttatggttc caaaggaaaa gttcagaaga ccattcatga tcttgcaaat cacttctttg    240
gttatctctt gttgtagaat gttgttgttg tctatcttcc actcttctca attcttggac    300
ttctacgttt tctggggtga cgaccactct agaatcccaa gatctgctta cgctccatct    360
gttgctggta acactatgtc tttgtgtttg gttatctctg ttgaaactat gttgatgtct    420
caagcttgga ctatggttag attgtggcca aacgtttgga agtacatcat cgctggtgtt    480
tctttgatcg tttctatcat ggctatctct gttagattgg cttacactat catccaaaac    540
aacgctgttt tgaagttgga accagctttc cacatgttct ggttgatcaa gtggactgtt    600
atcatgaacg ttgcttctat ctcttggtgg tgtgctatct tcaacatcaa gttggtttgg    660
cacttgatct ctaacagagg tatcttgcca tcttacaaga ctttcactcc aatggaagtt    720
ttgatcatga ctaacggtat cttgatgatc atcccagtta tcttcgcttc tttggaatgg    780
gctcacttcg ttaacttcga atctgcttct ttgactttga cttctgttgc tgttatcttg    840
ccattgggta ctttggctgc tcaaagaatc gcttcttctg ctccatcttc tgctaactct    900
actggtgctt cttctggtat cagatacggt gtttctggtc catcttcttt cactggtttc    960
aaggctccat ctttctctac tggtactact gacagaccac acgtttctat ctacgctaga   1020
tgtgaagctg gtacttcttc tagagaacac atcaacccac aaggtgttga attggctaag   1080
ttggacccag aaactgacca ccacgttaga gttgacagag ctttcttgca aagagaagaa   1140
agaatcagag ctccattgta g                                             1161
```

<210> SEQ ID NO 198
<211> LENGTH: 11
<212> TYPE: PRT
<213> ORGANISM: Magnaporthe oryzea

<400> SEQUENCE: 198

```
Gln Trp Cys Pro Arg Arg Gly Gln Pro Cys Trp
1               5                   10
```

<210> SEQ ID NO 199
<211> LENGTH: 415
<212> TYPE: PRT
<213> ORGANISM: Magnaporthe oryzea

<400> SEQUENCE: 199

```
Met Asp Gln Thr Leu Ser Ala Thr Gly Thr Ala Thr Ser Pro Pro Gly
1               5                   10                  15

Pro Ala Leu Thr Val Asp Pro Arg Phe Gln Thr Ile Thr Met Leu Thr
            20                  25                  30

Pro Ala Leu Met Gly Gln Gly Phe Glu Glu Val Gln Thr Thr Pro Ala
        35                  40                  45

Glu Ile Asn Asp Val Tyr Phe Leu Ala Phe Asn Thr Ala Ile Gly Tyr
    50                  55                  60

Ser Thr Gln Ile Gly Ala Cys Phe Ile Met Leu Leu Val Leu Leu Thr
65                  70                  75                  80

Met Thr Ala Lys Ala Arg Phe Ala Arg Ile Pro Thr Ile Ile Asn Thr
                85                  90                  95

Ala Ala Leu Val Val Ser Ile Ile Arg Cys Thr Leu Leu Val Ile Phe
            100                 105                 110
```

```
Phe Thr Ser Thr Met Met Glu Phe Tyr Thr Ile Phe Ser Asp Asp Phe
            115                 120                 125

Ser Phe Val His Pro Asn Asp Ile Arg Arg Ser Val Ala Ala Thr Val
130                 135                 140

Phe Ala Pro Leu Gln Leu Ala Leu Val Glu Ala Ala Leu Met Val Gln
145                 150                 155                 160

Ala Trp Ala Met Val Glu Leu Trp Pro Arg Ala Trp Lys Val Ser Gly
                165                 170                 175

Ile Ala Phe Ser Leu Ile Leu Ala Thr Val Thr Val Ala Phe Lys Cys
            180                 185                 190

Ala Ser Ala Ala Val Thr Val Lys Ser Ala Leu Glu Pro Leu Asp Pro
        195                 200                 205

Arg Pro Tyr Leu Trp Ile Arg Gln Thr Asp Leu Ala Phe Thr Thr Ala
    210                 215                 220

Met Val Thr Trp Phe Cys Phe Leu Phe Asn Val Arg Leu Ile Met His
225                 230                 235                 240

Met Trp Gln Asn Arg Ser Ile Leu Pro Thr Val Lys Gly Leu Ser Pro
                245                 250                 255

Met Glu Val Leu Val Met Ala Asn Gly Leu Leu Met Val Phe Pro Val
            260                 265                 270

Leu Phe Ala Gly Leu Tyr Tyr Gly Asn Phe Gly Gln Phe Glu Ser Ala
        275                 280                 285

Ser Leu Thr Ile Thr Ser Val Val Leu Val Leu Pro Leu Gly Thr Leu
    290                 295                 300

Val Ala Gln Arg Leu Ala Val Asn Asn Thr Val Ala Gly Ser Ser Ala
305                 310                 315                 320

Asn Thr Asp Met Asp Asp Lys Leu Ala Phe Leu Gly Asn Ala Thr Thr
                325                 330                 335

Val Thr Ser Ser Ala Ala Gly Phe Ala Gly Ser Ser Ala Ser Ala Thr
            340                 345                 350

Arg Ser Arg Leu Ala Ser Pro Arg Gln Asn Ser Gln Leu Ser Thr Ser
        355                 360                 365

Val Ser Ala Gly Lys Pro Arg Ala Asp Pro Ile Asp Leu Glu Leu Gln
    370                 375                 380

Arg Ile Asp Asp Glu Asp Asp Phe Ser Arg Ser Gly Ser Ala Gly
385                 390                 395                 400

Gly Val Arg Val Glu Arg Ser Ile Glu Arg Arg Glu Glu Arg Leu
                405                 410                 415

<210> SEQ ID NO 200
<211> LENGTH: 1248
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200
atggaccaaa ctttgtctgc tactggtact gctacttctc caccaggtcc agctttgact      60
gttgacccaa gattccaaac tatcactatg ttgactccag ctttgatggg tcaaggtttc     120
gaagaagttc aaactactcc agctgaaatc aacgacgttt acttcttggc tttcaacact     180
gctatcggtt actctactca aatcggtgct tgtttcatca tgttgttggt tttgttgact     240
atgactgcta aggctagatt cgctagaatc ccaactatca tcaacactgc tgctttggtt     300
gtttctatca tcagatgtac tttgttggtt atcttcttca cttctactat gatggaattc     360
```

```
tacactatct tctctgacga cttctctttc gttcacccaa acgacatcag aagatctgtt      420
gctgctactg ttttcgctcc attgcaattg gctttggttg aagctgcttt gatggttcaa      480
gcttgggcta tggttgaatt gtggccaaga gcttggaagg tttctggtat cgctttctct      540
ttgatcttgg ctactgttac tgttgctttc aagtgtgctt ctgctgctgt tactgttaag      600
tctgctttgg aaccattgga cccaagacca tacttgtgga tcagacaaac tgacttggct      660
ttcactactg ctatggttac ttggttctgt ttcttgttca cgttagatt gatcatgcac       720 atgtggcaaa acagatctat cttgccaact gttaagggtt tgtctccaat ggaagttttg      780
gttatggcta acgtttgtt gatggttttc ccagttttgt tcgctggttt gtactacggt       840
aacttcggtc aattcgaatc tgcttctttg actatcactt ctgttgtttt ggttttgcca      900
ttgggtactt tggttgctca aagattggct gttaacaaca ctgttgctgg ttcttctgct      960
aacactgaca tggacgacaa gttggctttc ttgggtaacg ctactactgt tacttcttct     1020
gctgctggtt tcgctggttc ttctgcttct gctactagat ctagattggc ttctccaaga     1080
caaaactctc aattgtctac ttctgttcct gctggtaagc caagagctga cccaatcgac     1140
ttggaattgc aaagaatcga cgacgaagac gacgacttct ctagatctgg ttctgctggt     1200
ggtgttagag ttgaaagatc tatcgaaaga agagaagaaa gattgtag                  1248
```

<210> SEQ ID NO 201
<211> LENGTH: 9
<212> TYPE: PRT
<213> ORGANISM: Botrytis cinerea

<400> SEQUENCE: 201

Trp Cys Gly Arg Pro Gly Gln Pro Cys
1               5

<210> SEQ ID NO 202
<211> LENGTH: 398
<212> TYPE: PRT
<213> ORGANISM: Botrytis cinerea

<400> SEQUENCE: 202

Met Ala Ser Asn Ser Ser Asn Phe Asp Pro Leu Thr Gln Ser Ile Thr
1               5                   10                  15

Ile Leu Met Ala Asp Gly Ile Thr Thr Val Ser Phe Thr Pro Leu Asp
            20                  25                  30

Ile Asp Phe Phe Tyr Tyr Tyr Asn Val Ala Cys Cys Ile Asn Tyr Gly
        35                  40                  45

Ala Gln Ala Gly Ala Cys Leu Leu Met Phe Phe Val Val Val Val Leu
    50                  55                  60

Thr Lys Ala Val Lys Arg Lys Thr Leu Leu Phe Val Leu Asn Val Leu
65                  70                  75                  80

Ser Leu Ile Phe Gly Phe Leu Arg Ala Met Leu Tyr Ala Ile Tyr Phe
                85                  90                  95

Leu Gln Gly Phe Asn Asp Phe Tyr Ala Ala Phe Thr Phe Asp Phe Ser
            100                 105                 110

Arg Val Pro Arg Ser Ser Tyr Ala Ser Val Ala Gly Ser Val Ile
        115                 120                 125

Pro Leu Cys Met Thr Ile Thr Val Asn Met Ser Leu Tyr Leu Gln Ala
    130                 135                 140

Tyr Thr Val Cys Lys Asn Leu Asp Asp Ile Lys Arg Ile Ile Leu Thr
145                 150                 155                 160

Thr Leu Ser Ala Ile Val Ala Leu Leu Ala Ile Gly Phe Arg Phe Ala
                165                 170                 175

Ala Thr Val Val Asn Ser Val Ala Ile Leu Ala Thr Ser Ala Ser Ser
            180                 185                 190

Val Pro Met Gln Trp Leu Val Lys Gly Thr Leu Val Thr Glu Thr Ile
        195                 200                 205

Ser Ile Trp Phe Phe Ser Leu Ile Phe Thr Gly Lys Leu Val Trp Thr
    210                 215                 220

Leu Tyr Asn Arg Arg Arg Asn Gly Trp Arg Gln Trp Ser Ala Val Arg
225                 230                 235                 240

Ile Leu Ala Ala Met Gly Gly Cys Thr Met Val Ile Pro Ser Ile Phe
                245                 250                 255

Ala Ile Leu Glu Tyr Val Thr Pro Val Ser Phe Pro Glu Ala Gly Ser
            260                 265                 270

Ile Ala Leu Thr Ser Val Ala Leu Leu Pro Ile Ser Ser Leu Trp
        275                 280                 285

Ala Gly Met Val Thr Asp Glu Glu Thr Ser Ala Ile Asp Val Ser Asn
    290                 295                 300

Leu Thr Gly Ser Arg Thr Met Leu Gly Ser Gln Ser Gly Asn Phe Ser
305                 310                 315                 320

Arg Lys Thr His Ala Ser Asp Ile Thr Ala Gln Ser Ser His Leu Asp
                325                 330                 335

Phe Ser Ser Arg Lys Gly Ser Asn Ala Thr Met Met Arg Lys Gly Ser
            340                 345                 350

Asn Ala Met Asp Gln Val Thr Thr Ile Asp Cys Val Val Glu Asp Asn
        355                 360                 365

Gln Ala Asn Arg Gly Leu Arg Asp Ser Thr Glu Met Asp Leu Glu Ala
    370                 375                 380

Met Gly Val Arg Val Asn Lys Ser Tyr Gly Val Gln Lys Ala
385                 390                 395

<210> SEQ ID NO 203
<211> LENGTH: 1197
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
atggcttcta actcttctaa cttcgaccca ttgactcaat ctatcactat cttgatggct      60
gacggtatca ctactgtttc tttcactcca ttggacatcg acttcttcta ctactacaac    120
gttgcttgtt gtatcaacta cggtgctcaa gctggtgctt gtttgttgat gttcttcgtt    180
gttgttgttt tgactaaggc tgttaagaga aagactttgt tgttcgtttt gaacgttttg    240
tctttgatct tcggtttctt gagagctatg ttgtacgcta tctacttctt gcaaggtttc    300
aacgacttct acgctgcttt cactttcgac ttctctagag ttccaagatc ttcttacgct    360
tcttctgttg ctggttctgt tatcccattg tgtatgacta tcactgttaa catgtctttg    420
tacttgcaag cttacactgt ttgtaagaac ttggacgaca tcaagagaat catcttgact    480
actttgtctg ctatcgttgc tttgttggct atcggtttca gattcgctgc tactgttgtt    540
aactctgttg ctatcttggc tacttctgct tcttctgttc caatgcaatg gttggttaag    600
ggtactttgg ttactgaaac tatctctatc tggttcttct ctttgatctt cactggtaag    660

```
ttggtttgga ctttgtacaa cagaagaaga aacggttgga gacaatggtc tgctgttaga      720
atcttggctg ctatgggtgg ttgtactatg gttatcccat ctatcttcgc tatcttggaa      780
tacgttactc cagtttcttt cccagaagct ggttctatcg ctttgacttc tgttgctttg      840
ttgttgccaa tctcttcttt gtgggctggt atggttactg acgaagaaac ttctgctatc      900
gacgtttcta acttgactgg ttctagaact atgttgggtt ctcaatctgg taacttctct      960
agaaagactc acgcttctga catcactgct caatcttctc acttggactt ctcttctaga     1020
aagggttcta acgctactat gatgagaaag ggttctaacg ctatggacca agttactact     1080
atcgactgtg ttgttgaaga caaccaagct aacagaggtt tgagagactc tactgaaatg     1140
gacttggaag ctatgggtgt tagagttaac aagtcttacg gtgttcaaaa ggcttag        1197
```

<210> SEQ ID NO 204
<211> LENGTH: 10
<212> TYPE: PRT
<213> ORGANISM: Aspergillus nidulans

<400> SEQUENCE: 204

Trp Cys Arg Phe Arg Gly Gln Val Cys Gly
1               5                   10

<210> SEQ ID NO 205
<211> LENGTH: 9
<212> TYPE: PRT
<213> ORGANISM: Aspergillus oryzae

<400> SEQUENCE: 205

Trp Cys Ala Leu Pro Gly Gln Gly Cys
1               5

<210> SEQ ID NO 206
<211> LENGTH: 10
<212> TYPE: PRT
<213> ORGANISM: Beauvaria bassiana

<400> SEQUENCE: 206

Trp Cys Met Arg Pro Gly Gln Pro Cys Trp
1               5                   10

<210> SEQ ID NO 207
<211> LENGTH: 14
<212> TYPE: PRT
<213> ORGANISM: Candida lustianiae

<400> SEQUENCE: 207

Lys Trp Lys Trp Ile Lys Phe Arg Asn Thr Asp Val Ile Gly
1               5                   10

<210> SEQ ID NO 208
<211> LENGTH: 13
<212> TYPE: PRT
<213> ORGANISM: Candida tenuis

<400> SEQUENCE: 208

Phe Ser Trp Asn Tyr Arg Leu Lys Trp Gln Pro Ile Ser
1               5                   10

<210> SEQ ID NO 209
<211> LENGTH: 9
<212> TYPE: PRT
<213> ORGANISM: Neosartorya fischeri

<400> SEQUENCE: 209

Trp Cys His Leu Pro Gly Gln Gly Cys
1               5

<210> SEQ ID NO 210
<211> LENGTH: 11
<212> TYPE: PRT
<213> ORGANISM: Neurospora crassa

<400> SEQUENCE: 210

Gln Trp Cys Arg Ile His Gly Gln Ser Cys Trp
1               5                   10

<210> SEQ ID NO 211
<211> LENGTH: 10
<212> TYPE: PRT
<213> ORGANISM: Pseudogymnoascus destructans

<400> SEQUENCE: 211

Phe Cys Trp Arg Pro Gly Gln Pro Cys Gly
1               5                   10

<210> SEQ ID NO 212
<211> LENGTH: 10
<212> TYPE: PRT
<213> ORGANISM: Hypocrea jecorina

<400> SEQUENCE: 212

Trp Cys Tyr Arg Ile Gly Glu Pro Cys Trp
1               5                   10

<210> SEQ ID NO 213
<211> LENGTH: 10
<212> TYPE: PRT
<213> ORGANISM: Tuber melanosporum

<400> SEQUENCE: 213

Trp Thr Pro Arg Pro Gly Arg Gly Ala Tyr
1               5                   10

<210> SEQ ID NO 214
<211> LENGTH: 8
<212> TYPE: PRT
<213> ORGANISM: Dactylellina haptotyla

<400> SEQUENCE: 214

Trp Cys Val Tyr Asn Ser Cys Pro
1               5

<210> SEQ ID NO 215
<211> LENGTH: 10
<212> TYPE: PRT
<213> ORGANISM: Sporothrix scheckii

<400> SEQUENCE: 215

Tyr Cys Pro Leu Lys Gly Gln Ser Cys Trp
1               5                   10

<210> SEQ ID NO 216
<211> LENGTH: 14
<212> TYPE: PRT
<213> ORGANISM: Yarrowia lipolytica

<400> SEQUENCE: 216

Trp Arg Trp Phe Trp Leu Pro Gly Tyr Gly Glu Pro Asn Trp
1               5                   10

<210> SEQ ID NO 217
<211> LENGTH: 11
<212> TYPE: PRT
<213> ORGANISM: Torulaspora delbrueckii

<400> SEQUENCE: 217

Gly Trp Met Arg Leu Arg Leu Gly Gln Pro Leu
1               5                   10

<210> SEQ ID NO 218
<211> LENGTH: 13
<212> TYPE: PRT
<213> ORGANISM: Komagataella pastoris

<400> SEQUENCE: 218

Phe Arg Trp Arg Asn Asn Glu Lys Asn Gln Pro Phe Gly
1               5                   10

<210> SEQ ID NO 219
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Trp His Trp Leu Glu Leu Pro Gly Ser Gln Pro Met Tyr
1               5                   10

<210> SEQ ID NO 220
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Val Glu Val Pro Gly Ser Gln His Ile Asp Ser Lys Lys Ala
1               5                   10

<210> SEQ ID NO 221
<211> LENGTH: 301
<212> TYPE: PRT
<213> ORGANISM: Saccharomyces cerevisiae

<400> SEQUENCE: 221

Met Ser Asp Ala Ala Pro Ser Leu Ser Asn Leu Phe Tyr Asp Pro Thr
1               5                   10                  15

Tyr Asn Pro Gly Gln Ser Thr Ile Asn Tyr Thr Ser Ile Tyr Gly Asn
            20                  25                  30

Gly Ser Thr Ile Thr Phe Asp Glu Leu Gln Gly Leu Val Asn Ser Thr
        35                  40                  45

Val Thr Gln Ala Ile Met Phe Gly Val Arg Cys Gly Ala Ala Ala Leu
    50                  55                  60

Thr Leu Ile Val Met Trp Met Thr Ser Arg Ser Arg Lys Thr Pro Ile
65                  70                  75                  80

Phe Ile Ile Asn Gln Val Ser Leu Phe Leu Ile Leu His Ser Ala
                85                  90                  95

```
Leu Tyr Phe Lys Tyr Leu Leu Ser Asn Tyr Ser Ser Val Thr Tyr Ala
            100                 105                 110

Leu Thr Gly Phe Pro Gln Phe Ile Ser Arg Gly Asp Val His Val Tyr
        115                 120                 125

Gly Ala Thr Asn Ile Ile Gln Val Leu Leu Val Ala Ser Ile Glu Thr
        130                 135                 140

Ser Leu Val Phe Gln Ile Lys Val Ile Phe Thr Gly Asp Asn Phe Lys
145                 150                 155                 160

Arg Ile Gly Leu Met Leu Thr Ser Ile Ser Phe Thr Leu Gly Ile Ala
                165                 170                 175

Thr Val Thr Met Tyr Phe Val Ser Ala Val Lys Gly Met Ile Val Thr
            180                 185                 190

Tyr Asn Asp Val Ser Ala Thr Gln Asp Lys Tyr Phe Asn Ala Ser Thr
        195                 200                 205

Ile Leu Leu Ala Ser Ser Ile Asn Phe Met Ser Phe Val Leu Val Val
    210                 215                 220

Lys Leu Ile Leu Ala Ile Arg Ser Arg Arg Phe Leu Gly Leu Lys Gln
225                 230                 235                 240

Phe Asp Ser Phe His Ile Leu Leu Ile Met Ser Cys Gln Ser Leu Leu
                245                 250                 255

Val Pro Ser Ile Ile Phe Ile Leu Ala Tyr Ser Leu Lys Pro Asn Gln
            260                 265                 270

Gly Thr Asp Val Leu Thr Thr Val Ala Thr Leu Leu Ala Val Leu Ser
        275                 280                 285

Leu Pro Leu Ser Ser Met Trp Ala Thr Ala Ala Asn Asn
290                 295                 300
```